(12) United States Patent
Suri et al.

(10) Patent No.: US 10,544,228 B2
(45) Date of Patent: Jan. 28, 2020

(54) NUCLEIC ACIDS ENCODING ANTIBODY POLYPEPTIDES THAT ANTAGONIZE CD40

(71) Applicants: Bristol-Myers Squibb Company, Princeton, NJ (US); Domantis Limited, Brentford, Middlesex (GB)

(72) Inventors: Anish Suri, Ekeren (BE); Steven Sheriff, Princeton, NJ (US); Suzanne Suchard, Portland, OR (US); Aaron Yamniuk, Lawrenceville, NJ (US); Stanley Krystek, Ringoes, NJ (US); James Tamura, Yardley, PA (US); James Bryson, Langhorne, PA (US); Steven Grant, Swaffham Prior (GB); Philip Drew, Histon (GB)

(73) Assignees: Bristol-Myers Squibb Company, Princeton, NJ (US); Domantis Limited, Brentford, Middlesex (GB)

(*) Notice: Subject to any disclaimer, the term of this patent is extended or adjusted under 35 U.S.C. 154(b) by 288 days.

(21) Appl. No.: 15/259,828

(22) Filed: Sep. 8, 2016

(65) Prior Publication Data

US 2017/0015754 A1    Jan. 19, 2017

Related U.S. Application Data

(62) Division of application No. 14/112,049, filed as application No. PCT/US2012/034519 on Dec. 18, 2013, now Pat. No. 9,475,879.

(60) Provisional application No. 61/477,904, filed on Apr. 21, 2011.

(51) Int. Cl.
| | |
|---|---|
| *C12N 15/13* | (2006.01) |
| *C07K 16/28* | (2006.01) |
| *A61K 39/395* | (2006.01) |
| *A61K 45/06* | (2006.01) |
| *C07K 16/18* | (2006.01) |
| *A61K 39/00* | (2006.01) |

(52) U.S. Cl.
CPC ...... *C07K 16/2878* (2013.01); *A61K 39/3955* (2013.01); *A61K 45/06* (2013.01); *C07K 16/18* (2013.01); *C07K 16/2833* (2013.01); *A61K 2039/505* (2013.01); *C07K 2317/31* (2013.01); *C07K 2317/34* (2013.01); *C07K 2317/56* (2013.01); *C07K 2317/565* (2013.01); *C07K 2317/569* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,182,368 | A | 1/1993 | Ledbetter et al. |
| 5,247,069 | A | 9/1993 | Ledbetter et al. |
| 5,674,492 | A | 10/1997 | Armitage et al. |
| 5,677,165 | A | 10/1997 | de Boer et al. |
| 5,786,456 | A | 7/1998 | Ledbetter et al. |
| 5,849,898 | A | 12/1998 | Seed et al. |
| 5,916,560 | A | 6/1999 | Larsen et al. |
| 6,051,228 | A | 4/2000 | Aruffo et al. |
| 6,056,959 | A | 5/2000 | de Boer et al. |
| 6,376,459 | B1 | 4/2002 | Aruffo et al. |
| 8,669,352 | B2 | 3/2014 | den Hartog et al. |
| 8,828,396 | B2 | 9/2014 | Heusser et al. |
| 9,475,879 | B2 * | 10/2016 | Suri .................. C07K 16/2878 |
| 2006/0062784 | A1 | 3/2006 | Grant et al. |
| 2006/0233797 | A1 | 10/2006 | Gujrathi |
| 2007/0148163 | A1 | 6/2007 | Takahashi et al. |
| 2013/0011405 | A1 | 1/2013 | Long et al. |

FOREIGN PATENT DOCUMENTS

| | | |
|---|---|---|
| AU | 2012245309 C1 | 2/2016 |
| CL | 199900284 | 9/1999 |
| CL | 200700768 | 11/2007 |
| CL | 200701105 | 11/2007 |
| CL | 200701335 | 1/2008 |
| CL | 200901779 | 2/2010 |
| CL | 201202737 | 2/2013 |
| CL | 201301124 | 7/2014 |
| CN | 1922316 A | 2/2007 |
| CN | 101061140 A | 10/2007 |
| EP | 1 707 627 A1 | 10/2006 |
| EP | 2255828 A1 | 12/2010 |
| JP | 2008-513425 A | 5/2008 |
| JP | 2009-022289 A | 2/2009 |
| KR | 2006-0130615 A | 12/2006 |
| KR | 10-2013-7030492 B1 | 5/2017 |
| WO | WO-99/20749 A1 | 4/1999 |
| WO | WO-02/28481 A2 | 4/2002 |
| WO | WO-2003/040170 A2 | 5/2003 |
| WO | WO-2005/044294 A2 | 5/2005 |
| WO | WO-2005/093074 A1 | 10/2005 |
| WO | WO-2006030220 A1 | 3/2006 |
| WO | WO-2006/073443 A2 | 7/2006 |
| WO | WO-2007/085815 A2 | 8/2007 |
| WO | WO-2007/124299 A2 | 11/2007 |
| WO | WO-2008/149143 A2 | 12/2008 |
| WO | WO-2011123489 A2 | 10/2011 |
| WO | WO-2012/145673 A1 | 10/2012 |

OTHER PUBLICATIONS

D'Angelo, Many Routes to an Antibody Heavy-Chain CDR3: Necessary, Yet Insufficient, for Specific Binding, Frontiers in Immunology vol. 9, Article 395 Mar. 2018; doi:10.3389/fimmun.2018.00395. (Year: 2018).*

(Continued)

*Primary Examiner* — Phillip Gambel
(74) *Attorney, Agent, or Firm* — Drinker Biddle & Reath LLP

(57) ABSTRACT

Antibody polypeptides that specifically bind a novel epitope of human CD40 are provided. The antibody polypeptides do not exhibit CD40 agonist activity. The antibody polypeptides are useful in the treatment of diseases involving CD40 activation, such as autoimmune diseases. The antibody polypeptides may be domain antibodies (dAbs) comprising a single $V_L$ or $V_H$ domain. The half-life of the antibody polypeptides may be increased by modifying the antibody polypeptides to be dual specific reagents that can also bind human serum albumin (HSA).

17 Claims, 7 Drawing Sheets

Specification includes a Sequence Listing.

(56) References Cited

OTHER PUBLICATIONS

Peruvian Application No. 2381, Office Action dated Dec. 5, 2017 (with partial English translation/characterization).
Japanese Application No. 2017-000493, Office Action dated Jan. 18, 2018 (with partial English translation/characterization).
A.-C. Malmborg Hager, et al., "Affinity and Epitope Profiling of Mouse Anti-CD40 Monoclonal Antibodies," Scandinavian Journal of Immunology, 2003, 57, pp. 517-524.
Y. Zhuang, et al., "A novel blocking monoclonal antibody recognizing a distinct epitope of human CD40 molecule," Tissue Antigens, 2005, 65, pp. 81-87.
International Preliminary Report on Patentability dated Oct. 31, 2013 for PCT/US2012/034519 filed on Apr. 20, 2012.
Office Action dated Jul. 14, 2014 in New Zealand counterpart Patent Application No. 618025.
English translation of Office Action and Search Report dated Mar. 10, 2015 in Chinese counterpart Patent Application No. 201280030683.4.
English translation of Office Action dated Mar. 10, 2015 in Colombian counterpart Patent Application No. 13.261.140.
English translation of Office Action dated Apr. 28, 2015 in Korean counterpart Patent Application No. 10-2013-7030492.
"Study of HCD122 (Lucatumumab) and Bendamustine Combination Therapy in CD40+ Rituximab-Refractory Follicular Lymphoma," Clinical Trials, Jan. 10, 2012 [online]. [retrieved on Jun. 30, 2015]. Retrieved from the Internet <URL:http://clinicaltrials.gov/show/NCT01275209>.
Adams, et al., "Development of a chimeric anti-CD40 monoclonal antibody that synergizes with LEA29Y to prolong islet allograft survival," *J. Immunol*. 174: 542-50 (2005).
Arkin et al., "An algorithm for protein engineering: Simulations of recursive ensemble mutagenesis", *Proc. Nat'l Acad. Sci. USA* 89:7811-7815 (1992).
Brand et al., "The Mouse Model of Collagen-Induced Arthritis", in *Methods Mol. Med*., vol. 102, Humana Press Inc., Totowa New Jersey, pp. 295-312 (2004).
Blanc et al., "Refinement of severely incomplete structures with maximum likelihood in BUSTER-TNT", *Acta Cryst*. D60: 2210-2221 (2004).
Chapman, et al., "PEGylated antibodies and antibody fragments for improved therapy: a review," *Adv. Drug Deily. Rev*. 54(4):531-45 (2002).
Connolly, "Analytical Molecular Surface Calculation", *J. Appl. Crystallogr*. 16: 548-558 (1983).
Davies et al., "TRAF6 is Required for TRAF2-Dependent CD40 Signal Transduction in Nonhemopoietic Cells", *Mol. Cell Biol*. 25: 9806-19 (2005).
De Winter et al., "Mucosal immunity and inflammation. II. The yin and yang of T cells in intestinal inflammation: pathogenic and protective roles in a mouse colitis model", *Am. J. Physiol*. 276: G1317-1321 (1999).
de Kruif et al., "Rapid selection of cell subpopulation-specific human monoclonal antibodies from a synthetic phage antibody library", *Proc. Natl. Acad. Sci. USA* 92: 3938 (1995).
Emsley et al., "*Coot*: model-building tools for molecular graphics", *Acta Cryst*. D60: 2126-2132 (2004).
Emsley et al., "Features and Development of *Coot*," *Acta Cryst*. D66: 486-501 (2010).
Harrison et al., "Screening of Phage Antibody Libraries", *Meth. Enzymol*. 267: 83-109 (1996).
Hoogenboom et al., "Multi-subunit proteins on the surface of filamentous phage: methodologies for displaying antibody (Fab) heavy and light chains", *Nucleic Acids Res*. 19:4133-4137 (1991).
Kouskoff et al., "Organ-specific disease provoked by systemic autoimmunity", *Cell* 87: 811-822 (1996).
Lawrence et al., "Shape Complementarity at Protein/Protein Interfaces," *J. Mol. Biol*. 234: 946-950 (1993).

Marks et al., "Human antibody fragments specific for human blood group antigens from a phage display library", *BioTechnology* 11: 1145-1149 (1993).
McCoy et al., "*Phaser* crystallographic software", *J. Appl. Crystallogr*. 40: 658-674 (2007).
Pape et al., "Use of adoptive transfer of T-cell-antigen-receptor-transgenic T cell for the study of T-cell activation in vivo", *Immunol. Rev*. 156: 67-78 (1997).
Sheriff et al., "Structure of myohemerythrin in the azidomet state at 1.7/1.3 A resolution", *J. Mol. Biol*. 197: 273-296 (1987).
Sheriff, "Some methods for examining the interactions between two molecules", *Immunomethods* 3: 191-196 (1993).
Tronrud et al., "An efficient general-purpose least-squares refinement program for macromolecular structures", *Acta Cryst*. A43: 489-501 (1987).
Office Action dated Jun. 2, 2015 in Australian counterpart Patent Application No. 2009270726.
English translation of Office Action dated Jul. 29, 2015 in European counterpart Patent Application No. 12717027.2.
An et al., "Crystallographic and Mutational Analysis of the CD40-CD154 Complex and Its Implications for Receptor Activation", The Journal of Biological Chemistry, vol. 286, No. 13, pp. 11226-11235 (Apr. 1, 2011).
English translation of Office Action dated May 29, 2015 in Eurasian counterpart Patent Application No. 201391564.
Qatari Patent Application No. QA/201310/00242_Office Action report dated Sep. 7, 2015 (with partial English translation/characterization).
Thailand Patent Application No. 1301006018_Office Action report dated Sep. 29, 2015 (with partial English translation/characterization).
Chinese counterpart Patent Application No. 201280030683.4, Office Action dated Nov. 16, 2015 (partial English translation/characterization).
Korean counterpart Patent Application No. 10-2013-7030492, Office Action dated Nov. 26, 2015 (with partial English translation/characterization).
New Zealand counterpart Patent Application No. 712771, Office Action dated Oct. 16, 2015.
Taiwanese Application No. 101114258, partial English translation/characterization of Office Action dated Nov. 24, 2015.
An et al., 2011, "Crystallographic and mutational analysis of the CD40-CD154 complex and its implications for receptor activation," J Biol. Chem. 286(13):11226-35.
Japanese Application No. 2014-506589, Office Action dated Feb. 9, 2016 (with partial English translation).
Chilean Application No. 03043-2013, Office Action dated Mar. 27, 2016 (with partial English translation/characterization).
Eurasian Application No. 201391564, Office Action dated Apr. 26, 2016 (with partial English translation/characterization).
Australian Patent Application No. 2012245309 Office Action dated Jun. 2, 2015.
Chilean Patent Application No. 03043-2013 Opposition filed Oct. 10, 2014 (with partial English translation/characterization).
New Zealand Patent Application No. 618025 Office Action dated Sep. 4, 2015.
International Search Report dated Jun. 15, 2012 for PCT/US2012/034519 filed on Apr. 20, 2012.
Israeli Application No. 228720, Office Action dated Apr. 19, 2016 (with partial English translation/characterization).
Written Opinion of the International Searching Authority of PCT/US2012/034519 (dated Oct. 21, 2013).
Rudikoff et al., Proc. Natl. Acad. Sci. USA 79: 1979-1983 (1982).
Colman, Research in Immunology 145: 33-36 (1994).
Kussie et al., J. Immunol. 152: 146-152 (1994).
Chen et al., EMBO J., 14: 2784-2794 (1995).
Korean Application No. 10-2017-7011260, Office Action dated Aug. 15, 2017 (with partial English translation/characterization).
Australian Application No. 2016202672, Office Action dated Nov. 20, 2016.
Chilean Patent Application No. 03043-2013, Office Action dated Jul. 29, 2017 (with partial English translation/characterization).

(56) References Cited

OTHER PUBLICATIONS

Eurasian Application No. 201391564, Office Action dated Nov. 10, 2016 (partial English translation/characterization).
European Application No. 12717027.2, Office Action dated Feb. 8, 2017.
Israeli Application No. 228720, Office Action dated Apr. 6, 2017 (partial English translation/characterization).
Japanese Application No. 2014-506589, Office Action dated Sep. 6, 2016 (with partial English translation/characterization).
Korean Application No. 10-2013-7030492, Office Action dated Sep. 9, 2016 (with partial English translation/characterization).
Malaysian Application No. PI 2013003839, Office Action dated Sep. 30, 2016.
Mexican Application No. MX/a/2013/011966, Office Action with response deadline of Oct. 11, 2016 (partial English translation/characterization).
Mexican Application No. MX/a/2013/011966, Office Action with response deadline of Apr. 7, 2017 (partial English translation/characterization).
Mexican Application No. MX/a/2013/011966, Office Action with response deadline of Jul. 4, 2017 (partial English translation/characterization).
Philippine Application No. 1-2013-502013, Office Action dated Apr. 4, 2017.
Taiwanese Application No. 101114258, Office Action dated Apr. 29, 2016 (partial English translation/characterization).
Taiwanese Application No. 105121984, Search Report dated Jun. 5, 2017 (partial English translation/characterization).
Vietnamese Application No. 1-2013-03601, Office Action dated Dec. 5, 2016 (with partial English translation/characterization).
United Arab Emirates Application No. P1128/13, Search Report and Examination Report with response deadline of May 14, 2017.
European Application No. 18151812.7, Extended European Search Report dated Jun. 18, 2018.
Yamniuk et al., "Functional Antagonism of Human CD40 Achieved by Targeting a Unique Species-Specific Epitope," *J Mol Biol* 428:2860-2879 (2016).
Eurasian Application No. 201391564, Office Action dated Aug. 2, 2017 (with partial English translation/characterization).
Mexican Application No. MX/a/2013/011966, Office Action with response deadline of Dec. 5, 2017 (partial English translation/characterization).
Canadian Application No. 2,833,743, Office Action dated Feb. 20, 2018.
Korean Application No. 10-2017-7011260, Office Action dated Feb. 25, 2018 (with partial English translation/characterization).
Indian Application No. 9863/DELNP/2013, Office Action dated Feb. 22, 2018 (with partial English translation/characterization).
Canadian Application No. 2,833,743, Office Action dated Mar. 19, 2019.
Brazilian Application No. BR112013026828-0, Pre-Examination Office Action dated Apr. 12, 2019 (with partial English translation/characterization).
Vonderheide et al., 2013, "Agonistic CD40 antibodies and cancer therapy," *Clin Cancer Res.* 19(5): 1035-1043.
Jefferis, 2009, "Glycosylation as a strategy to improve antibody-based therapeutics," *Nature Rev Drug Discov.* 8(3): 226-234.
Kasran, et al., "Safety and tolerability of antagonist anti-human CD40 Mab ch5D12 in patients with moderate to severe Crohn's disease," *Alimentary Pharmacology & Therapeutics*, 2005, 22: 111-122.
Byrd JC et al., "Phase I study of the anti-CD40 humanized monoclonal antibody lucatumumab (HCD122) in relapsed chronic lymphocytic leukemia," *Leuk Lymphoma.* Nov. 2012, 53(11):213642; (Author manuscript, PMCID PMC3808981, Oct. 28, 2013).
European Medicines Agency (EMEA). (2007) Guideline on Strategies to identify and mitigate risks for first-in-human clinical trials with investigational medicinal products. EMEA/CH MP/SWP/28367/07.
Winkler, et al., "Changing the Antigen Binding Specificity by Single Point Mutations of an Anti-p24 (HIV-1) Antibody," *The Journal of Immunology*, 2000, vol. 165, No. 8, pp. 4505-4514.
Bai, et al., "A Guide to Rational Dosing of Monoclonal Antibodies," *Clinical Pharmacokinetics*, 2012, vol. 51, No. 2, pp. 119-135.
Vonderheide RH et al., "Clinical activity and immune modulation in cancer patients treated with CP-870,893, a novel CD40 agonist monoclonal antibody," *J Clin Oncol.* 2007, 25(7):876-83.
Walpole et al., "The weight of nations: an estimation of adult human mass," *BMC Public Health*, 2012, 12:439.

\* cited by examiner

FIG. 4

| SEQ ID NO: | | CDR1 | CDR2 | CDR3 |
|---|---|---|---|---|
| SEQ ID NO:9 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCAKLPFYFQEMGQGTLVTVSS |
| SEQ ID NO:10 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCAKLPFYFEHEWGQGTLVTVSS |
| SEQ ID NO:353 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCAKLPFYFESEWGQGTLVTVSS |
| SEQ ID NO:355 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCAKLPFPFSEWGQGTLVTVSS |
| SEQ ID NO:410 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCAKLPQLEHDRGQGTLVTVSS |
| SEQ ID NO:413 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCAKLPQLFQDWGQGTLVTVSS |
| SEQ ID NO:418 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCAKLPTLFQDWGQGTLVTVSS |
| SEQ ID NO:352 | EVQLLESGGGLVQPGGSRRLSCAASGFTFRDY | EMWWVRQAPGKGLERVSA | INPQGTRTYYADSVKGRFTISRDNSKNTLYLQMNSLRAEDTAVYYCAKLPTYFKDWGQGTLVTVSS |
| SEQ ID NO:324 | EVQLLESGGGLVQPGCSRRLSCAASGFTFRDY | EMWWVRQAPGKVLERVSA | INPQGTRTYYADSVKGRFTISRDNSKNTLYLQMNSLRAEDTAVYYCAKLPFTFEDWGQGTLVTVSS |
| SEQ ID NO:334 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCAKLPFTFEDWGQGTLVTVSS |
| SEQ ID NO:317 | EVQLLESGGGLVQPGGSLRLSCAASGFTFRDY | EMWWVRQAPGKGLERVSA | INPQGTRTYYADSVKGRFTISRDNSKNMLYLQMNSLRAEDTAVYYCAKLPFTFEDWGQGTLVTVSS |
| SEQ ID NO:336 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCTKLPFTFEDWGQGTLVTVSS |
| SEQ ID NO:323 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVYYCLKLPFTFEDWGQGTLVTVSS |
| SEQ ID NO:338 | EVQLLESGGGLVQPGGSLRLSCAASGFTFRDY | EMWWVRQAPGKGLERVSA | INPQGTRTYYADSVKGRFTISRDNSKNTLYLQMNSLRAEDTSVHCAKPPFIFGDWGPGTLVTVSS |
| SEQ ID NO:354 | EVQLLESGGGLVQPGGSLRLSCAASGFTFRDY | EMWWVRQAPGKGLERVSA | INPQGTRTYYADSVKGRFTISRDNSKNTLYLQMNSLRADDTAVYHCTKLPFIFEYWGQGTLVTVSN |
| SEQ ID NO:335 | EVQLLESGGGLVQPGGSLRLSCAASGFTFRDY | EMWWVRQAPGKGLERVSA | INPQGTRTYYADSVKGRFTISRDNSKNTLYLQMNSLRAEDTAVHCAKLPMFFEDWGQGTLVTVSS |
| SEQ ID NO:377 | EVQLLESGGGLVQPGGSLRLSCAASGFTFRDY | EMWWVRQAPGKGLERVSA | INPQGTRTYYADSLTYADSVKGRFTISRDNSKNTLYLQMNSLRAEDTAVYYCAKLPFTFEDDWGQGTLVTVSS |
| SEQ ID NO:396 | EVQLLESGGGLVQPGGSLRLSCAASGFTFRDY | EMWWVRQAPGKGLERVSA | INPYGNITYADSVKGRFTISRDNSKNTLYLQMNSLRAEDTAVYYCAKLPFTFEDDWGQGTLVTVSS |
| SEQ ID NO:368 | EVQLLESGGGLVQPGGSLRLSCAASGFTFRDY | EMWWVRQAPGRGLERVSA | INPPGMLTYADSVKGRFTISRDNSKNTLYLQMNSLRAEDTAVYYCAKLPFTEDDWGQGTLVTVSS |
| SEQ ID NO:371 | EVQLLESGGGLVQPGGSLRLSCAASGFTFRDY | EMWWVRQAPGKGLERVSA | INPWGGLTYADSVKGRFTISRDNSKNTLYLQMNSLRAEDTAVYYCAKLPFTFEDDWGQGTLVTVSS |
| SEQ ID NO:373 | EVQLLESGGGLVQPGGSLRLSCAASGFTFRDY | EMWWVRQAPGKGLERVSA | INPWGGLTYADSVKGRFTISRDNSKNTLYLQMNSLRAEDTAVYYCAKLPFTFDDWGQGTLVTVSS |
| SEQ ID NO:392 | EVQLLESGGGLVQPGGSLRLSCAASGFTFRDY | EMWWVRQAPGKGLERVSA | INPWGSHTYADSVKGRFTISRDNSKNTLYLQMNSLRAEDTAVYYCAKLPFTEDDWGQGTLVTVSS |
| SEQ ID NO:380 | EVQLLESGGGLVQPGGSLRLSCAASGFTFRDY | EMWWVRQAPGKGLERVSA | INPWGSLTYADSVKGRFTISRDNSKNTLYLQMNSLRAEDTAVYYCAKLPFTFEDDWGQGTLVTVSS |
| SEQ ID NO:387 | EVQLLESGGGLVQPGGSLRLSCAASGFTFRDY | EMWWVRQAPGKGLERVSA | INPWGQLITYADSVKGRFTISRDNSKNTLYLQMNSLRAEDTAVYYCAKLPFTFEDDWGQGTLVTVSS |
| SEQ ID NO:372 | EVQLLESGGGLVQPGGSLRLSCAASGFTFRDY | EMWWVRQAPGKGLERVSA | INPAGGYTYADSVKGRFTISRDNSKNTLYLQMNSLRAEDTAVYYCAKLPFTFEDWGQGTLVTVSS |
| SEQ ID NO:391 | EVQLLESGGGLVQPGGSLRLSCAASGFTFRDY | EMWWVRQAPGKGLERVSA | INPAGGYTYADSVKGRFTISMGRFTISRDNSKNTLYLQMNSLRAEDTAVYYCAKLPFTFEDDWGQGTLVTVSS |
| SEQ ID NO:401 | EVQLLESGGGLVQPGGSLRLSCAASGFTFRDY | EMWWVRQAPGKGLERVSA | INPQGTRTYYADSVKGRFTISMGRFTISRDNSKNTLYLQMNSLRAEDTAVYYCAKLPFTFEDDWGQGTLVTVSS |
| SEQ ID NO:321 | EVQLLESGGGLVQPGGSLRLSCAASGFTFRDY | EMWWVRQAPGKGLERVSA | INPQGTRTYYADSVMGRFTISRDNSKNTLYLQMNSLRAEDTAVYYCAKLPFTFEDDWGQGTLVTVSS |
| SEQ ID NO:341 | EVQLLESGGGLVQPGGSLRLSCAASGFTFRDY | EMWWVRRAPGKGLERVSA | INPQGTRTYYADSVMGRFTISRDNSKNTLYLQMNSLRAEDTAVYYCAKLPFTFEDDWGQGTLVTVSS |
| SEQ ID NO:325 | EVQLLESGGGLVQPGGSLRLSCAASGFTFAGY | EMWWVRQAPGKGLERVSA | INPQGTRTYYADSVMGRFTISRDNSKNTLYLQMNSLRAEDTAVYYCAKLPFMFEDDRGQGTLVTVSS |
| SEQ ID NO:342 | EVQLLESGGGLVQPGGSLRLSCAASGFTFAGY | ELMWWVRQAPGKGLERVSA | INPQGTRTYYADSVMGRFTISRDNSKNTLYLQMNSLRAEDTAVYYCAKLPFMFEDDRGQGTLVTVSS |
| SEQ ID NO:344 | EVQLLESGGGLVQPGGSLRLSCAASGFTFRDY | EMWWVRQAPGKGLERVSA | INPQGTRTYYADSVMGRFTISRDNSKNTLYLQMNSLRAEDTAVYYCAKLPFTFEDDWGQGTLVTVSS |
| SEQ ID NO:345 | EVQLLESGGGLVQPGGSLRLSCAASGFTFRDY | EMWWVRQAPGKGLERVSA | INPQGTRTYYADSVMGRFTISRDNSKNTLYLQMNSLRAEDTAVYYCAKLPFMFEDDRGQGTLVTVSS |
| SEQ ID NO:332 | EVQLLESGGGLVQPGGSLRLSCAASGFTFRDY | EMWWVRQAPGKGLERVSA | INPQGTRTYYADSVMGRFTISRDNSKNTLYLQMNSLRAEDTAVYYCAKLPFTFEDDWGQGTLVTVSS |

FIG. 5

```
                     CDR1                                        CDR2
BMS3h-37-207  EVQLLESGGGLVQPGGSLRLSCAASGFTFEWYEMQWVRRAPGKKGLEWVSAISGDGYRTYY 60
BMS3h-37-213  EVQLLESGGGLVQPGGSLRLSCAASGFTFEWYEMQWVRRAPGKKGLEWVSAISGDGYRTYY 60
BMS3h-37-212  EVQLLESGGGLVRPGGSLRLSCAASGFTFEWYEMQWVRRAPGKKGLEWVSAISGDGYRTYY 60
BMS3h-37-205  EVQLLESGGGLVQPGGSLRLSCAASGFTFEWYEMQWVRRAPGKKGLEWVSAISGDGYRTYY 60
BMS3h-37-206  EVQLLESGGGLVQPGGSLRLSCAASGFTFEWYEMQWVRRAPGKKGLEWVSAISGDGYRTYY 60
              ************ *********************************************

CDR2                                    CDR3
BMS3h-37-207  ADSVKGRFTISRDNSKNTLYLQMNSLRAEDTAVYYCAKELAFFDYWGRGTLVTVSS 116 (SEQ ID NO: 226)
BMS3h-37-213  ADSVKGRFTISRDNSKNTLYLQMNSLRAEDTAVYYCAKELLFFDYRGRGTLVTVSS 116 (SEQ ID NO: 232)
BMS3h-37-212  ADSVKGRFTISRDNSKNTLYLQMNSLRAEDTAVYYCAKELEFFDYWGRGTLVTVSS 116 (SEQ ID NO: 231)
BMS3h-37-205  ADSVKGRFTISRDNSKNTLYLQMNSLRAEDTAVYYCAKELEYFDYWGRGTLVTVSS 116 (SEQ ID NO: 224)
BMS3h-37-206  ADSVKGRFTISRDNSKNTLYLQMNSLRAEDTAVYYCAKGLEYFDYWGRGTLVTVSS 116 (SEQ ID NO: 225)
              ********************************** *  *** **************
```

FIG. 6

```
                        CDR1                                        CDR2
BMS3h-38-217  EVQLLASGGGLVQPGGSLRLSCAASGFTFEEEEMIWVRQAPGKGLEWVSAISRRGYSTYY 60
BMS3h-38-238  EVQLLASGGGLVQPGGSLRLSCAASGFTFEEEEMIWVRQAPGKGLEWVSAISRSGYSTYY 60
BMS3h-38-228  EVQLLASGGGLVQPGGSLRLSCAASGFTFEEEEMIWVRQAPGKGLEWVSAISRNGFSTYY 60
BMS3h-38-235  EVQLLASGGGLVQPGGSLRLSCAASGFTFEEEEMIWVRQAPGKGLEWVSAISRNGYSTYY 60
BMS3h-38-231  EVQLLASGGGLVQPGGSLRLSCAASGFPFEEEEMIWVRQAPGKGLEWVSAISRQWSTYY 60
BMS3h-38-237  EVQLLASGGGLVQPGGSLRLSCAASGFTFEEEEMIWVRQAPGKGLEWVSAISRQGWSTYY 60
BMS3h-38-218  EVQLLASGGGLVQPGGSLRLSCAASGFTFEEEEMIWVRQAPGKGLEWVSAISRGWSTYY 60
BMS3h-38-215  EVQLLASGGGLVQPGGSLRLSCAASGFTFEEEEMIWVRQAPGKGLEWVSAISRHGWSTYY 60
BMS3h-38-223  EVQLLASGGGLVQPGGSLRLSCAASGFTFEEEEMIWVRQAPGKGLEWVSAISGLGWSTYY 60
BMS3h-38-224  EVQLLASGGGLVQPGGSLRLSCAASGFTFEEEEMIWVRQAPGKGLEWVSAISGSGGSTYY 60
BMS3h-38-225  EVQLLASGGGLVQPGGSLRLSCAASGFTFEEEEMIWVRQAPGKGLEWVSAISGSGGGTYY 60
BMS3h-38-219  EVQLLASGGGLVQPGGSLRLSCAASGFTFEEEEMIWVRQAPGKGLEWVSSISRSGGSTYY 60
              ***************************************:** **  *  ***

CDR2                                 CDR3
BMS3h-38-217  ADSVKGRFTISRDNSKNTLYLQMNSLRAEDTAVYYCGKEPFRYDYWGQGTLVTVSS 116  (SEQ ID NO: 264)
BMS3h-38-238  ADSVKGRFTISRDNSKNTLYLQMNSLRAEDTAVYYCGKEPFRYDYWGQGTLVTVSS 116  (SEQ ID NO: 285)
BMS3h-38-228  ADSVKGRFTISRDNSKNTLYLQMNSLRAEDTAVYYCGKEPFRYDYWGQGTLVTVSS 116  (SEQ ID NO: 275)
BMS3h-38-235  ADSVKGRFTISRDNSKNTLYLQMNSLRAEDTAVYYCGKEPFRYDYWGQGTLVTVSS 116  (SEQ ID NO: 282)
BMS3h-38-231  ADSVKGRFTISRDNSKNTLYLQMNSLRAEDTAVYYCGKEPFRYDYWGQGTLVTVSS 116  (SEQ ID NO: 278)
BMS3h-38-237  ADSVKGRFTISRDNSKNTLYLQMNSLRAEDTAVYYCGKEPFRYDYWGQGTLVTVSS 116  (SEQ ID NO: 284)
BMS3h-38-218  ADSVKGRFTISRDNSKNTLYLQMNSLRAEDTAVYYCGKEPFRYDYWGQGTLVTVSS 116  (SEQ ID NO: 265)
BMS3h-38-215  ADSVKGRFTISRDNSKNTLYLQMNSLRAEDTAVYYCGKEPFRYDYWGQGTLVTVSS 116  (SEQ ID NO: 262)
BMS3h-38-223  ADSVKGRFTISRDNSKNTLYLQMNSLRAEDTAVYYCGKEPFMYDYWGQGTLVTVSS 116  (SEQ ID NO: 270)
BMS3h-38-224  ADSVKGRFTISRDNSKNTLYLQMNSLRAEDTAVYYCGKEPFPYDYWGQGTLVTVSS 116  (SEQ ID NO: 271)
BMS3h-38-225  ADSVKGRFTISRDNSKNTLYLQMNSLRAEDTAVYYCGKEPFRYDYWGQGTLVTVSS 116  (SEQ ID NO: 272)
BMS3h-38-219  ADSVKGRFTISRDNSKNTLYLQMNSLRAEDTAVYYCGKEPFRYDYWGQGTLVTVSS 116  (SEQ ID NO: 266)
              *****************************************  ************
```

FIG. 7

```
                       CDR1                                    CDR2
BMS3h-198-22  EVQLLESGGGLVQPGGSLRLSCAASGFTFAGYEMNWVRQAPGKGLERVSAISGSGGSTYY 60
BMS3h-198-31  EVQLLESGGGLVQPGGSLRLSCAASGFTFAGYEMNWVRQAPGKGLERVSAISGSGGSTYY 60
BMS3h-198-33  EVQLLESGGGLVQPGGSLRLSCAASGFTFAGYEMWWVRQAPGKGLERVSAISGSGGSTYY 60
BMS3h-198-19  EVQLLESGGGLVQPGGSLRLSCAASGFTFAGYELMWVRQAPGKGLERVSAISGSGGSTYY 60
BMS3h-198-38  EVQLLESGGGLVQPGGSLRLSCAASGFTFAGYELNWVRQAPGKGLERVSAISGSGGSTYY 60
BMS3h-198-14  EVQLLESGGGLVQPGGSLRLSCAASGFTFAGYEMWFRQAPGKGLERVSAISGSGGSTYY 60
              ********************************** * ********************

CDR2                                    CDR3
BMS3h-198-22  ADSVKGRFTISRDDSKNTLYLQMNSLRAEDTAVYYCAKEPYSYDYWGHGTLVTVSS 116  (SEQ ID NO: 523)
BMS3h-198-31  ADSVKGRFTISRDNSKNTLYLQMNSLRAEDTAVYHCAKEPYSYDYWGQGTLVTVSS 116  (SEQ ID NO: 532)
BMS3h-198-33  ADSVKGRFTISRDDSKNTLYLQMNSLRAEDTAVYYCAKEPYSYDYWGQGTLVTVSS 116  (SEQ ID NO: 534)
BMS3h-198-19  ADSVKGRFTISRDDSKNTLYLQMNSLRAEDTAVYYCARDPYSFDYRGQGTLVTVSS 116  (SEQ ID NO: 520)
BMS3h-198-38  ADSVKGRFTISRDDSKNTLYLQMNSLRAEDTAVYYCARDPYSFDYWGQGTLVTVSS 116  (SEQ ID NO: 539)
BMS3h-198-14  ADSVKGRFTISRDDTKNTLYLQMNSLRAEDTAVYYCAKDPYSFDYWRQGTLVTVSS 116  (SEQ ID NO: 515)
              ************* ****************** * *** *** ** *********
```

NUCLEIC ACIDS ENCODING ANTIBODY POLYPEPTIDES THAT ANTAGONIZE CD40

CROSS-REFERENCE TO RELATED APPLICATIONS

This application is a divisional of U.S. application Ser. No. 14/112,049, filed Dec. 18, 2013, now U.S. Pat. No. 9,475,879, which is the National Stage of International Application No. PCT/US2012/034519, filed Apr. 20, 2012, and claims the benefit of U.S. Provisional Application No. 61/477,904, filed Apr. 21, 2011, the entire contents of which are herein incorporated by reference.

TECHNICAL FIELD

Antibodies and fragments thereof that target CD40, and do not exhibit CD40 agonist activity, compositions comprising the same, and methods of using the same for treatment of diseases involving CD40 activity are provided.

SEQUENCE LISTING

The instant application contains a Sequence Listing in ASCII format that is hereby incorporated by reference in its entirety. Said ASCII copy, created on Sep. 20, 2016, is named 200896_0004_01_US.txt and is 1, 188, 821 bytes in size.

BACKGROUND

CD40 is a co-stimulatory molecule belonging to the tumor necrosis factor (TNF) receptor superfamily that is present on antigen presenting cells (APC), including dendritic cells, B cells, and macrophages. APCs are activated when CD40 binds its ligand, CD154 (CD40L), on $T_H$ cells. CD40-mediated APC activation is involved in a variety of immune responses, including cytokine production, up-regulation of co-stimulatory molecules (such as CD86), and enhanced antigen presentation and B cell proliferation. CD40 can also be expressed by endothelial cells, smooth muscle cells, fibroblasts, and epithelial cells.

CD40 activation is also involved in a variety of undesired T cell responses related to autoimmunity, transplant rejection, or allergic responses, for example. One strategy for controlling undesirable T cell responses is to target CD40 with an antagonistic antibody. For example, monoclonal antibody HCD122 (Lucatumumab), formerly known as Chiron 1212, is currently in clinical trials for the treatment of certain CD40-mediated inflammatory diseases. See "Study of HCD122 (Lucatumumab) and Bendamustine Combination Therapy in CD40+ Rituximab-Refractory Follicular Lymphoma," Clinical Trials Feeds, on the Internet at hypertext transfer protocol: clinicaltrialsfeeds.org/clinical-trials/show/NCT01275209 (last updated Jan. 11, 2011). Monoclonal antibodies, however, can display agonist activity. For example, the usefulness of the anti-CD40 antibody Chi220 is limited by its weak stimulatory potential. See Adams, et al., "Development of a chimeric anti-CD40 monoclonal antibody that synergizes with LEA29Y to prolong islet allograft survival," *J. Immunol.* 174: 542-50 (2005).

SUMMARY

Anti-CD40 antibody antagonists that do not possess partial agonist activity are still needed in a clinical setting. Novel antibody polypeptides that specifically bind a novel epitope of human CD40 are provided. The CD40 epitope does not overlap the Chi220 epitope, as shown by competition analysis and by the structure derived from co-crystallization of an antibody polypeptide with CD40. The antibody polypeptides advantageously do not exhibit CD40 agonist activity. The antibody polypeptides are useful in the treatment of diseases involving CD40 activation, including autoimmune diseases, transplant rejection, and allergic responses. The antibody polypeptides comprise a variable domain. In one embodiment, the antibody polypeptides are in the form of a domain antibody (dAb) that contains a single variable domain. In another embodiment, the dAbs are bi-specific reagents that comprise a second variable domain that can bind human serum albumin (HSA), for example.

Provided is an antibody polypeptide comprising a first variable domain, where said antibody polypeptide specifically binds an epitope of human CD40, where the epitope comprises the amino acid sequence of SEQ ID NO: 1, where the antibody polypeptide competes with the binding of domain antibody (dAb) BMS3h-56-269 (SEQ ID NO: 417), and where the epitope comprises at least one CD40 amino acid residue selected from the group consisting of Trp109, Leu121, His122, Ser124, Ser156, Ala157, Phe158, Glu159, and His162.

Further provided is an antibody polypeptide where the first variable domain comprises the amino acid sequence of one of the antibody polypeptides selected from the lineage group consisting of BMS3h-37, BMS3h-38, BMS3h-56, and BMS3h-198, and where the first variable domain has an apparent binding constant of 1 pM to 100 nM. Further provided is an antibody polypeptide where the first variable domain has an apparent binding constant of 1 pM to 10 nM.

Also provided is an antibody polypeptide where the amino acid sequence of the first variable domain comprises (a) a CDR1 region which differs from the CDR1 region of BMS3h-56-269 (SEQ ID NO: 417) by up to two amino acids, (b) a CDR2 region which differs from the CDR2 region of BMS3h-56-269 (SEQ ID NO: 417) by up to two amino acids, (c) a CDR3 region which differs from the CDR3 region of BMS3h-56-269 (SEQ ID NO: 417) by up to two amino acids, (d) a FR1 region which differs from the FR1 region of BMS3h-56-269 (SEQ ID NO: 417) by up to two amino acids, (e) a FR2 region which differs from the FR2 region of BMS3h-56-269 (SEQ ID NO: 417) by up to two amino acids, (f) a FR3 region which differs from the FR3 region of BMS3h-56-269 (SEQ ID NO: 417) by up to two amino acids, and (g) a FR4 region which differs from the FR4 region of BMS3h-56-269 (SEQ ID NO: 417) by up to two amino acids.

Also provided is an antibody polypeptide where the amino acid sequence of the first variable domain comprises (a) a CDR1 region which differs from the CDR1 region of BMS3h-56-269 (SEQ ID NO: 417) by up to two amino acids, (b) a CDR2 region which differs from the CDR2 region of BMS3h-56-269 (SEQ ID NO: 417) by up to two amino acids, (c) a CDR3 region which differs from the CDR3 region of BMS3h-56-269 (SEQ ID NO: 417) by up to two amino acids.

Further provided is an antibody polypeptide where the amino acid sequence of the first variable domain differs from the amino acid sequence of BMS3h-56-258 (SEQ ID NO: 10) or BMS3h-56-269 (SEQ ID NO: 417) by up to 10 amino acids.

Further provided is an antibody polypeptide where the amino acid sequence of the first variable domain differs from the amino acid sequence of BMS3h-56-258 (SEQ ID NO: 10) or BMS3h-56-269 (SEQ ID NO: 417) by up to 5 amino acids.

Further provided is an antibody polypeptide where the amino acid sequence of the first variable domain differs from the amino acid sequence of BMS3h-56-258 (SEQ ID NO: 10) or BMS3h-56-269 (SEQ ID NO: 417) by two amino acids.

Further provided is an antibody polypeptide where the amino acid sequence of the first variable domain differs from the amino acid sequence of BMS3h-56-258 (SEQ ID NO: 10) or BMS3h-56-269 (SEQ ID NO: 417) by one amino acid.

Further provided is an antibody polypeptide where the antibody polypeptide is selected from the lineage group of BMS3h-56, and where the amino acid sequence of the first variable domain further comprises: (a) a CDR1 region having a sequence $X_1$-Tyr-Glu-$Y_1$-Trp (SEQ ID NO: 1274), where $X_1$ is Asp or Gly, and $Y_1$ is Met or Leu; (b) a CDR2 region having a sequence Ala-Ile-Asn-Pro-$X_2$-Gly-$Y_2$-$Z_2$-Thr-Tyr-Tyr-Ala-Asp-Ser-Val-$A_2$-Gly (SEQ ID NO: 1275), where $X_2$ is Gln, Tyr, Pro, Trp, or Ala, $Y_2$ is Thr, Ser, Asn, Gly, Met, or Gln, $Z_2$ is Arg, Leu, Tyr, His, or Phe, and $A_2$ is Lys or Met; and (c) a CDR3 region having a sequence $X_3$-Pro-$Y_3$-$Z_3$-Phe-$A_3$-$B_3$ (SEQ ID NO: 1276), where $X_3$ is Leu or Pro, $Y_3$ is Phe, Gln, Thr, or Met, $Z_3$ is Tyr, Pro, Leu, Thr, Ile, Phe, or Met, $A_3$ is Gln, His, Asp, Ser, Lys, Glu, or Gly, and $B_3$ is Glu, Asp, or Tyr.

Further provided is an antibody polypeptide where the amino acid sequence of the first variable domain comprises: (a) a FR1 region having a sequence Glu-Val-Gln-Leu-Leu-Glu-Ser-Gly-Gly-Gly-Leu-Val-Gln-Pro-Gly-Gly-Ser-X-Arg-Leu-Ser-Cys-Ala-Ala-Ser-Gly-Phe-Thr-Phe-$Y_1$ (SEQ ID NO: 1277), where $X_1$ is Leu or Arg, and $Y_1$ is Arg or Ala; (b) a FR2 region having a sequence Trp-Val-Arg-$X_2$-Ala-Pro-Gly-$Y_2$-$Z_2$-Leu-Glu-Arg-Val-Ser (SEQ ID NO: 1278), where $X_2$ is Gln or Arg, $Y_2$ is Lys or Arg, and $Z_2$ is Gly or Val; (c) a FR3 region having a sequence Arg-Phe-Thr-Ile-Ser-Arg-Asp-Asn-Ser-Lys-Asn-$X_3$-Leu-Tyr-Leu-Gln-Met-Asn-Ser-Leu-Arg-Ala-$Y_3$-Asp-Thr-$Z_3$-Val-Tyr-$A_3$-Cys-$B_3$-Lys (SEQ ID NO: 1279), where $X_3$ is Thr or Met, $Y_3$ is Glu or Asp, $Z_3$ is Ala or Ser, $A_3$ is Tyr or His, and $B_3$ is Ala or Thr; and (d) a FR4 region having a sequence $X_4$-Gly-$Y_4$-Gly-Thr-Leu-Val-Thr-Val-Ser-$Z_4$ (SEQ ID NO: 1280), where $X_4$ is Trp or Arg, $Y_4$ is Gln or Pro, and $Z_4$ is Ser or Asn.

Further provided is an antibody polypeptide where the first variable domain comprises the amino acid sequence of BMS3h-56-258 (SEQ ID NO: 10) or BMS3h-56-269 (SEQ ID NO:417).

Further provided is an antibody polypeptide where the antibody polypeptide is selected from the lineage group of BMS3h-37, where the first variable domain comprises the sequence Glu-Val-Gln-Leu-Leu-Glu-Ser-Gly-Gly-Gly-Leu-Val-$X_1$-Pro-Gly-Gly-Ser-Leu-Arg-Leu-Ser-Cys-Ala-Ala-Ser-Gly-Phe-Thr-Phe-Glu-Trp-Tyr-Glu-Met-Gln-Trp-Val-Arg-Arg-Ala-Pro-Gly-Lys-Gly-Leu-Glu-Trp-Val-Ser-Ala-Ile-Ser-Gly-Asp-Gly- Tyr-Arg-Thr-Tyr-Tyr-Ala-Asp-Ser-Val-Lys-Gly-Arg-Phe-Thr-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Ala-Lys-$Y_1$-Leu-$Z_1$-$A_1$-Phe-Asp-Tyr-$B_1$-Gly-Arg-Gly-Thr-Leu-Val-Thr-Val-Ser-Ser (SEQ ID NO: 1281); and where $X_1$ is Gln or Arg; $Y_1$ is Glu or Gly; $Z_1$ is Ala, Leu, or Glu; $A_1$ is Phe or Tyr; and $B_1$ is Trp or Arg.

Also provided is an antibody polypeptide where the antibody polypeptide is selected from the lineage group of BMS3h-38, where the first variable domain comprises the sequence Glu-Val-Gln-Leu-Leu-Ala-Ser-Gly-Gly-Gly-Leu-Val-Gln-Pro-Gly-Gly-Ser-Leu-Arg-Leu-Ser-Cys-Ala-Ala-Ser-Gly-Phe-$X_1$-Phe-Glu-Glu-Glu-Met-Ile-Trp-Val-Arg-Gln-Ala-Pro-Gly-Lys-Gly-Leu-Glu-Trp-Val-Ser-$Y_1$-Ile-Ser-$Z_1$-$A_1$-Gly-$B_1$-$C_1$-Thr-Tyr-Tyr-Ala-Asp-Ser-Val-Lys-Gly-Arg-Phe-Thr-Ile-Ser-Arg-Asp-Asn-Ser-Lys-Asn-Thr-Leu-Tyr-Leu-Gln-Met-Asn-Ser-Leu-Arg-Ala-Glu-Asp-Thr-Ala-Val-Tyr-Tyr-Cys-Gly-Lys-Glu-Pro- Phe-$D_1$-Tyr-Asp-Tyr-Trp-Gly-Gln-Gly-Thr-Leu-Val-Thr-Val-Ser-Ser (SEQ ID NO: 1282); and where $X_1$ is Thr or Pro; $Y_1$ is Ala or Ser; $Z_1$ is Arg or Gly; $A_1$ is Arg, Ser, Asn, Gln, Gly, His, or Leu; $B_1$ is Tyr, Phe, Trp, or Gly; $C_1$ is Ser or Gly; and $D_1$ is Arg, Met, or Pro.

Also provided is an antibody polypeptide where the antibody polypeptide is selected from the lineage group of BMS3h-198, where the first variable domain comprises the sequence Glu-Val-Gln-Leu-Leu-Glu-Ser-Gly-Gly-Gly-Leu-Val-Gln-Pro-Gly-Gly-Ser-Leu-Arg-Leu-Ser-Cys-Ala-Ala-Ser-Gly-Phe-Thr-Phe-Ala-Gly-Try-Glu-$X_1$-Trp-Trp-$Y_1$-Arg-Gln-Ala-Pro-Gly-Lys-Gly-Leu-Glu-Arg-Val-Ser-Ala-Ile-Ser-Gly-Ser-Gly-Gly-Ser-Thr-Tyr-Tyr-Ala-Asp-Ser-Val-Lys-Gly-Arg-Phe-Thr-Ile-Ser-Arg-Asp-$Z_1$-$A_1$-Lys-Asn-Thr-Leu-Tyr-Leu-Gln-Met-Asn-Ser-Leu-Arg-Ala-Glu-Asp-Thr-Ala-Val-Tyr-$B_1$-Cys-Ala-$C_1$-$D_1$-Pro-Tyr-Ser-$E_1$-Asp-Tyr-$F_1$-$G_1$-$H_1$-Gly-Thr-Leu-Val-Thr-Val-Ser-Ser (SEQ ID NO: 1283); and where $X_1$ is Met or Leu; $Y_1$ is Val or Phe; $Z_1$ is Asp or Asn; $A_1$ is Ser or Thr; $B_1$ is Tyr or His; $C_1$ is Lys or Arg; $D_1$ is Asp or Glu; $E_1$ is Tyr or Phe; $F_1$ is Trp or Arg; $G_1$ is Gly or Arg; and $H_1$ is Gln or His.

Further provided is an antibody polypeptide where the antibody polypeptide is a domain antibody (dAb).

Further provided is an antibody polypeptide where the variable domain is fused to an Fc domain.

Further provided is an antibody polypeptide where the antibody polypeptide further comprises a second variable domain that specifically binds a second antigen, where the second antigen is an antigen other than human CD40.

Also provided is an antibody polypeptide where the second antigen is a cluster of differentiation (CD) molecule or a Major Histocompatibility Complex (MHC) Class II molecule.

Also provided is an antibody polypeptide where the second antigen is serum albumin (SA).

Provided is a nucleic acid encoding the antibody polypeptide disclosed herein.

Also provided is a vector comprising the nucleic acid disclosed herein.

Also provided is a host cell comprising the vector disclosed herein.

Provided is a pharmaceutical composition comprising a therapeutically-effective amount of the antibody polypeptide disclosed herein and a pharmaceutically acceptable carrier. Also provided is a pharmaceutical composition further comprising an immunosuppressive/immunomodulatory and/or anti-inflammatory agent.

Provided is a method of treating an immune disease in a patient in need of such treatment, comprising administering to the patient a therapeutically effective amount of the pharmaceutical composition disclosed herein. Also provided is a method where the pharmaceutical composition is administered in combination with an immunosuppressive/immunomodulatory and/or anti-inflammatory agent.

Provided is a method of treating an immune disease where the immune disease is an autoimmune disease or a graft-related disease. Further provided is a method of treating an immune disease where the immune disease is selected from the group consisting of selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus's phenomenon, anaphylaxis, alcohol addiction, and drug addiction.

Also provided is a method of targeting CD40 using a first variable domain that specifically binds an epitope of human CD40 comprising the amino acid sequence of SEQ ID NO: 1, where the antibody polypeptide competes with the binding of domain antibody (dAb) BMS3h-56-269 (SEQ ID NO:417).

Provided is the use in medicine of an antibody polypeptide comprising a first variable domain that specifically binds an epitope of human CD40 comprising the amino acid sequence of SEQ ID NO: 1, wherein the antibody polypeptide competes with the binding of domain antibody (dAb) BMS3h-56-201 (SEQ ID NO: 9), or a pharmaceutically acceptable salt thereof.

Provided is the use of an antibody polypeptide comprising a first variable domain that specifically binds an epitope of human CD40 comprising the amino acid sequence of SEQ ID NO: 1, wherein the antibody polypeptide competes with the binding of domain antibody (dAb) BMS3h-56-201 (SEQ ID NO: 9), or a pharmaceutically acceptable salt thereof, in the preparation of a medicament for treatment of an immune disease. In some embodiments, the pharmaceutical composition is administered in combination with an immunosuppressive/immunomodulatory and/or anti-inflammatory agent. In further embodiments, the immune disease is an autoimmune disease or a graft-related disease. In yet further embodiments, the immune disease is selected from the group consisting of selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus's phenomenon, anaphylaxis, alcohol addiction, and drug addiction.

Provided is an antibody polypeptide comprising a first variable domain that specifically binds an epitope of human CD40 comprising the amino acid sequence of SEQ ID NO: 1, wherein the antibody polypeptide competes with the binding of domain antibody (dAb) BMS3h-56-201 (SEQ ID NO: 9), or a pharmaceutically acceptable salt thereof, for use in the preparation of a medicament for treatment of an immune disease. The medicament can, for example, be administered in combination with an immunosuppressive/immunomodulatory and/or anti-inflammatory agent. The immune disease can be, for example, an autoimmune disease or a graft-related disease. The immune disease can also be selected from the group consisting of selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products, systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, vasculitis, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy. Arthus's phenomenon, anaphylaxis, alcohol addiction, and drug addiction.

BRIEF DESCRIPTION OF THE FIGURES

FIG. 3A shows BMS3h38-2C-P40Br binding to human and cynomolgus B cells; FIG. 3B shows BMS3h38-2C-P40Br binding to human, rhesus, and chimp B cells.

FIG. 4, FIG. 5, FIG. 6, and FIG. 7 show ClustalW2 alignments of representative domain antibody polypeptides from lineages BMS3h-56. BMS3h-37, BMS3h-38, and BMS3h-198, respectively.

DETAILED DESCRIPTION

Figure 1:
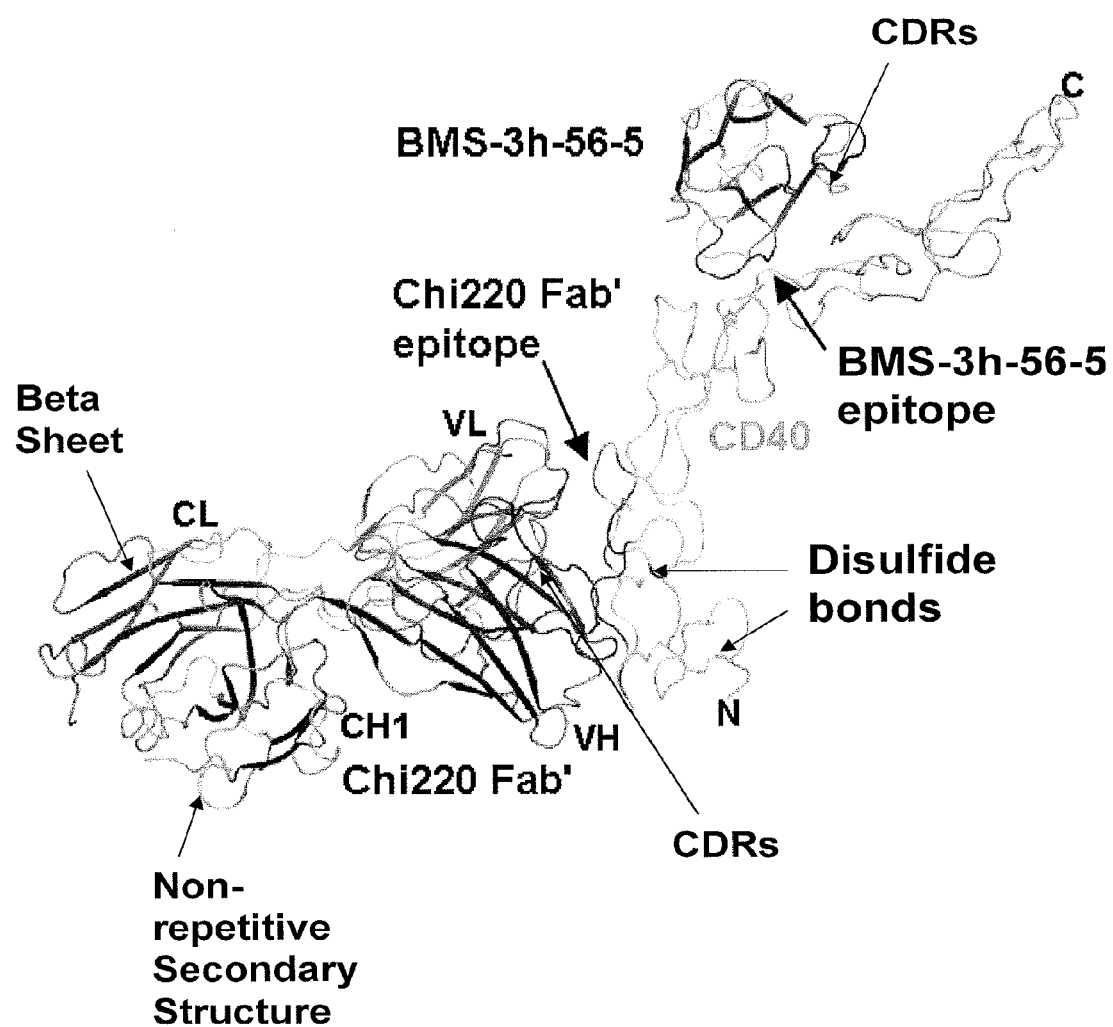
FIG. 1 depicts the binding modes of two different co-crystal structures of human CD40 (SEQ ID NO: 1), one with the dAb BMS3h-56-5 (SEQ ID NO: 321) and one with the Fab' of Chi220 antibody. The BMS3h-56-5 and Chi 220 Fab' molecules are shown as cartoons with β-strands (represented as arrows in the dAb) and non-repetitive secondary structure (represented as loops in th dAb). Complementarity-determining regions (CDRs) are also shown CD40 is also shown as a cartoon with the BMS3h-56-5 epitope residues of human CD40. The Chi220 epitope residues are also shown. Disulfide bonds are also shown The N-terminus (N) and C-terminus (C) of CD40 are labeled.

Antibody polypeptides that specifically bind to human CD40 are provided. The antibody polypeptides do not exhibit CD40 agonist activity, and the antibody polypeptides are useful in the treatment of diseases involving CD40 activation, such as autoimmune diseases. The antibody polypeptides may be selected using a primary screen that utilizes cell binding assays, followed by one or more rounds of error-prone or degenerate oligonucleotide-directed affinity maturation. As a result, a genus of antibody polypeptides that specifically bind a single CD40 epitope are provided.

A "lineage" is a set of related antibody polypeptides that were prepared from a common precursor by error-prone or degenerate oligonucleotide-directed affinity maturation, as disclosed in the examples below, and that are expected to bind the same CD40 epitope. The nomenclature of the antibody polypeptides is used to designate the various lineages. The nomenclature "BMS3h-56," for example, refers to antibody polypeptides of lineage 56, which were raised against human CD40. "Lineage BMS3h-56" antibody polypeptides include BMS3h-56-1 through BMS3h-56-33, and BMS3h-56-202 through BMS3h-56-288.

Accordingly, in one aspect, an antibody polypeptide comprises a variable domain that specifically binds human CD40, where the antibody polypeptide competes with the binding of any one of the domain antibodies (dAbs) listed in TABLE 3. For example, the dAb may belong to a lineage selected from the group consisting of BMS3h-37, BMS3h-38, BMS3h-41, BMS3h-43, BMS3h-56, BMS3h-131, BMS3h-198, and BMS3h-202, such as the dAb BMS3h-56-5, BMS3h-56-201, or BMS3h-56-258, for instance. In another aspect, an antibody polypeptide specifically binds the same human CD40 epitope as any one of the dAbs listed in TABLE 3. For example, the antibody polypeptide may comprise a variable domain that specifically binds the same human CD40 epitope as the dAb BMS3h-56-5, BMS3h-56-201, or BMS3h-56-258, for instance. As disclosed below, the human CD40 epitope may comprise amino acid residue Trp109 of SEQ ID NO: 1, for example.

The antibody polypeptides may be domain antibodies containing a single variable domain. The antibody polypeptides also may comprise additional domains, such as an Fc domain. For instance, the antibody polypeptide may comprise a second variable domain that specifically binds human serum albumin (HSA). Such dual specific antibody polypeptides may have an increased half-life, for example.

In the Sequence Listing, SEQ ID NO: 1 is the amino acid sequence of human CD40; SEQ ID NO: 2 is the amino acid sequence of *Macaca fascicularis* CD40. The amino acid sequence of the domain antibody BMS3h-56-5 is SEQ ID NO: 321.

As used herein, "specific binding" refers to the binding of an antigen by an antibody polypeptide with a dissociation constant ($K_d$) of about 11.1M or lower as measured, for example, by surface plasmon resonance. Suitable assay systems include the BIAcore™ surface plasmon resonance system and BIAcore™ kinetic evaluation software (e.g., version 2.1). The affinity or $K_d$ for a specific binding interaction may be about 500 nM or lower or about 300 nM or lower.

The term "about" will be understood by persons of ordinary skill in the art and will vary to some extent on the context in which it is used. Generally, about encompasses a range of values that are plus/minus 10% of a referenced value.

In accordance with this detailed description, the following abbreviations and definitions apply. It must be noted that as used herein, the singular forms "a", "an", and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

1. CD40 and CD40 Activities

Antibody polypeptides are provided that bind human CD40. CD40 is also known as B-cell surface antigen CD40, Bp50, CD40L receptor, CDw40, CDW40, MGC9013, p50, TNFRSF5, and Tumor necrosis factor receptor superfamily member 5. Relevant structural information for human CD40 can be found, for example, at UniProt Accession Numbers P25942, Q9BYU0, and Q53GN5. "Human CD40" refers to the CD40 comprising the following amino acid sequence:

```
                                           (SEQ ID NO: 1)
MVRLPLQCVL  WGCLLTAVHP  EPPTACREKQ  YLINSQCCSL

CQPGQKLVSD  CTEFTETECL  PCGESEFLDT  WNRETHCHQH

KYCDPNLGLR  VQQKGTSETD  TICTCEEGWH  CTSEACESCV

LHRSCSPGFG  VKQIATGVSD  TICEPCPVGF  FSNVSSAFEK

CHPWTSCETK  DLVVQQAGTN  KTDVVCGPQD  RLRALVVIPI

IFGILFAILL  VLVFIKKVAK  KPTNKAPHPK  QEPQEINFPD

DLPGSNTAAP  VQETLHGCQP  VTQEDGKESR  ISVQERQ.
```

CD40 also has been sequenced in *Mus musculus, Sus scrofa, Bos taunts, Gallus gallus, Canis familiaris, Macaca fascicularis* (cynomolgus monkey), *Ovis aries, Equus caballus*, and *Rattus norvegicus*.

Binding of the present antibody polypeptides to CD40 antagonizes CD40 activity. "CD40 activities" include, but are not limited to, T cell activation (e.g., induction of T cell proliferation or cytokine secretion), macrophage activation (e.g., the induction of reactive oxygen species and nitric oxide in the macrophage), and B cell activation (e.g., B cell proliferation, antibody isotype switching, or differentiation to plasma cells). CD40 activities can be mediated by interaction with other molecules. "CD40 activities" include the functional interaction between CD40 and the following molecules, which are identified by their Uniprot Accession Number is parentheses:

CALR (P27797);
ERP44 (Q9BS26);
FBL (P22087);

POLR2H (P52434);
RFC5 (P40937);
SGK1 (O00141);
SLC30A7 (Q8NEW0);
SLC39A7 (Q92504);
TRAF2 (Q5T1L5);
TRAF3 (Q13114);
TRAF6 (Q9Y4K3);
TXN (Q5T937);
UGGT1 (Q9NYU2); and
USP15 (Q9Y4E8).

For example, a CD40 "activity" includes an interaction with TRAF2. CD40/TRAF2 interaction activates NF-κB and JNK. See Davies et al., *Mol. Cell Biol.* 25: 9806-19 (2005). This CD40 activity thus can be determined by CD40-dependent cellular NF-κB and JNK activation, relative to a reference.

As used herein, the terms "activate," "activates," and "activated" refer to an increase in a given measurable CD40 activity by at least 10% relative to a reference, for example, at least 10%, 25%, 50%, 75%, or even 100%, or more. A CD40 activity is "antagonized" if the activity is reduced by at least 10%, and in an exemplary embodiment, at least about 20%, 30%, 40%, 50%, 60%, 70%, 80%, 90%, 95%, 97%, or even 100% (i.e., no detectable activity), relative to the absence of the antagonist. For example, an antibody polypeptide may antagonize some or all CD40 activity, while not activating CD40. In one embodiment, the antibody polypeptide does not activate B cell proliferation. In another embodiment, the antibody polypeptide does not activate cytokine secretion by T cells, where the cytokine is at least one cytokine selected from the group consisting of IL-2, IL-6, IL-10, IL-13, TNF-α, IFN-γ.

2. The CD40 Epitope

X-ray crystallography of a complex between human CD40 (SEQ ID NO: 1) and the dAb BMS3h-56-5 (SEQ ID NO: 321) was used to reveal an epitope recognized by the antibody polypeptides of the disclosure. Structural models of CD40 and BMS3h-56-5 were fitted to electron density data to yield seven models or versions of the CD40/BMS3h-56-5 complex, which come from three crystallographically independent complexes in one crystal form and four crystallographically independent complexes in a second crystal form. The versions have real space correlation coefficients of about 0.92 for main-chain atoms and 0.80 for side-chain atoms. The CD40 molecule has a certain amount of flexibility in the seven versions, but the overall nature of the CD40/BMS3h-56-5 interaction is retained in all versions. The versions differ in the interaction between the CD40 residue Trp109 and BMS3h-56-5 Trp103 (Kabat Numbering, see below). BMS3h-56-5 Trp103 forms an edge-to-face interaction with CD40 Trp109 in one version, while forming a displaced stacking (i.e., face-to-face) interaction in other versions.

The shape complementarity statistic, Sc, for the seven versions ranges from 0.70-0.77, which shows a higher degree of shape complementarity than for typical antibody/antigen complexes. For example, these values compare to ranges of 0.71-0.76 for four protease/protein inhibitor complexes, 0.70-0.74 for five oligomeric interfaces, and 0.64-0.68 for six antibody/antigen complexes. See Lawrence et al., "Shape Complementarity at Protein/Protein Interfaces," *J. Mol. Biol.* 234: 946-950 (1993).

A model of the human CD40/BMS3H-56-5 complex is shown in FIG. 1. One BMS3h-56-5 dAb binds to one CD40 molecule. The BMS3h-56-5 epitope does not overlap the Chi220 Fab' fragment epitope. All versions of the complex define a set of CD40 residues that contact BMS3h-56-5: Trp109, Leu121, His122, Ser124, Ser156, Ala157, Phe158, Glu159, and His162 (with reference to SEQ ID NO: 1). CD40 residues that contact BMS3h-56-5 in some versions of the complex are Pro85, Asn86, Leu87, Gly88, Glu106, Glu107, Gly108, His110, Thr112, Cys119, Val120, Gln133, Ile134, Ala135. Thr136, Ser155, and Lys160. Val154 is a buried CD40 residue in all versions. Other CD40 residues buried in some versions are Ser118, Arg123, Thr141, Phe151, Asp153, Cys161, and Pro163.

As used herein, the term "in contact" refers to an interatomic distance whose maximum is determined by an atom type distance dependency as defined by Sheriff et al., *J. Mol. Biol.* 197: 273-296 (1987) and Sheriff, *Immunomethods* 3: 191-196 (1993).

As used herein, the term "buried" refers to a residue that has a least one atom with surface area defined by the program MS (Connolly, *J. Appl. Crystallogr.* 16: 548-558 (1983)), a probe sphere of 1.7 Å, and atom type dependent Van der Waals radii as defined by Sheriff, *Immunomethods* 3: 191-196 (1993).

Figure 2:
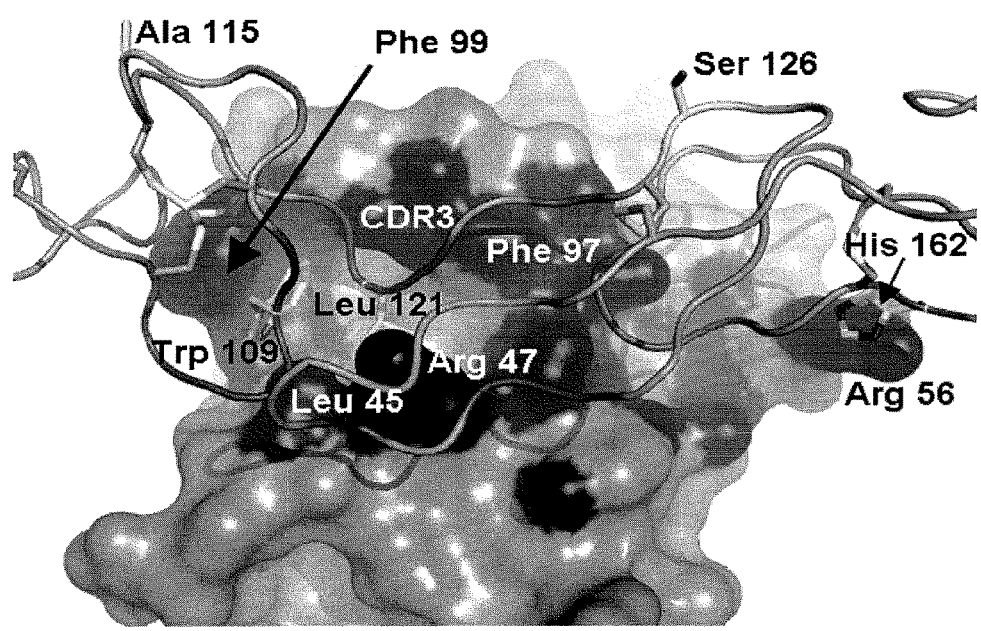
FIG. 2 depicts a space filling model of BMS3h-56-5 (SEQ ID NO: 321) contacting human CD40 (SEQ ID NO: 1), which is shown as a cartoon. Surface residues of the dAb BMS3h-56-5 that contact CD40 are shown. The BMS3h-56-5 CDR3 region and FR-2 residues Leu45, Arg47, Arg56 and Phe99 are labeled. Kabat numbering (Kabat et al., *Sequences of Immunological Interest*, 5$^{th}$ ed., U.S. Dept. Health & Human Services, Washington, D.C. (1991)) is used in this diagram and differs from sequential numbering in that insertion residues are used to keep the residue numbering of the β-strands identical. Thus for BMS3h-56-5, sequential residue 53 becomes residue 52A, sequential residues 84, 85, and 86 become, respectively, 82A, 82B, 82C and Kabat residue number 100 is missing (it would be between sequential residues 103 and 104); CD40 is also represented as a cartoon with non-repetitive secondary structure and the BMS3h-56-5 epitope. CD40 residues that differ between human and *Macaca fascicularis* (cynomolgus monkey), Ala115, Phe99, Ser126, His162, Leu121, and Trp109, are shown in stick representation. CD40 residues that differ between human and cynomolgus monkey that are part of the BMS3h-56-5 epitope are Trp109, Leu121, and His162. CD40 residues Trp109 and Leu121 lie in a cleft between the BMS3h-56-5 CDR3 and FR-2. Mutation of Trp109 either greatly reduces or ablates BMS3h-56-5 activity.

FIG. 2 shows the surface of BMS3h-56-5 (SEQ ID NO: 321) including contacting residues and buried residues. CD40 (SEQ ID NO: 1) is represented as a ribbon diagram with orange representing non-repetitive secondary structure and magenta representing the epitope residues. CD40 residues Trp109, Ala115, Leu121, Ser126, and His162, which are shown, differ in various non-human primate sequences. CD40 residues Ala115 and Ser126 are on the opposite side of the BMS3h-56-5 binding site. Trp109 and Leu121 bind in a cleft that lies between CDR3 and FR-2 (residues Leu45 and Arg47) of BMS3h-56-5. His162 interacts with residues in CDR2 of BMS3h-56-5, especially Lys 56. In summary, the CD40 epitope comprises one or more residues listed in TABLE 1, with reference to the numbering used in SEQ ID NO: 1.

TABLE 1

| CD40 residues contacting BMS3h-56-5: |
| --- |
| Trp109, Leu121, His122, Ser124, Ser156, Ala157, Phe158, Glu159, His162 |

BMS3h-56-5, like the other dAbs listed in TABLE 3, was prepared by a screening and affinity maturation method described in more detail below, using human CD40 as the antigen. It is expected that dAbs created by affinity maturation from a common precursor dAb will bind the same human CD40 epitope. Competition studies described below, for example, indicate that dAbs generated from a common precursor dAb by affinity maturation compete for binding with each other to human CD40. The same competition studies, however, show that the dAbs do not compete with at least the Chi220 or G28-5 antibodies.

3. Antibody Polypeptides

The antibody polypeptides comprise a variable domain. In one embodiment, the antibody polypeptides are in the form of a dAb that contains a single variable domain. Antibody polypeptides may be full-length anti-CD40 immunoglobulin molecules comprising two heavy (H) chains and two light (L) chains interconnected by disulfide bonds. In this embodiment, the amino terminal portion of each chain includes a variable domain ($V_L$ or $V_H$) of about 100-110 amino acids primarily responsible for antigen recognition via the complementarity determining regions (CDRs) contained therein. The carboxy-terminal "half" of each heavy chain defines a constant region (Fc) primarily responsible for effector function.

Antibody polypeptides also may be "fragments" comprising a portion of the full-length anti-CD40 immunoglobulin molecule that comprises a variable domain that specifically binds CD40. Thus, the term "antibody polypeptides" includes an antigen-binding heavy chain, light chain, heavy chain-light chain dimer, Fab fragment, F(ab')₂ fragment, Fv fragment, single chain Fv (scFv), and dAb, for example. The term "antibody polypeptides" thus includes polypeptides made by recombinant engineering and expression, as well as monoclonal antibodies produced by natural recombination and secretion by hybridoma cell clones.

Light chains are classified as kappa (κ) or lambda (λ), and are characterized by a particular constant region, $C_L$, as known in the art. Heavy chains are classified as γ, μ, α, δ, or ε, and define the isotype of an antibody as IgG, IgM, IgA, IgD, or IgE, respectively. The heavy chain constant region is comprised of three domains (CH1, CH2, and CH3) for IgG, IgD, and IgA; and four domains (CH1, CH2, CH3, and CH4) for IgM and IgE. Anti-CD40 antibodies may have a heavy chain constant region selected from any of the immunoglobulin classes (IgA, IgD, IgG, IgM, and IgE).

Each light chain variable domain ($V_L$) and heavy chain variable domain ($V_H$) is composed of three CDRs and four framework regions (FRs), arranged from amino-terminus to carboxy-terminus in the following order: FR1, CDR1, FR2, CDR2, FR3, CDR3, FR4. The three CDRs of the light chain are referred to as "LCDR1, LCDR2, and LCDR3" and the three CDRs of the heavy chain are referred to as "HCDR1, HCDR2, and HCDR3."

As used herein, the term "Fc domain" refers to the constant region antibody sequences comprising CH2 and CH3 constant domains as delimited according to Kabat et al., *Sequences of Immunological Interest,* 5$^{th}$ ed., U.S. Dept. Health & Human Services, Washington, D.C. (1991). The Fc region may be derived from an IgG1 or an IgG4 Fc region, for example. A variable domain may be fused to an Fc domain. In this case, the carboxyl terminus of the variable domain (either a $V_L$ or $V_H$ domain, including dAbs) may be linked or fused to the amino terminus of the Fc CH2 domain. Alternatively, the carboxyl terminus of the variable domain may be linked or fused to the amino terminus of a CH1 domain, which itself is fused to the Fc CH2 domain. The protein may comprise the hinge region between the CH1 and CH2 domains in whole or in part.

The CDRs contain most of the residues that form specific interactions with the antigen. As shown in FIG. 2, for example, CDR2 and CDR3, plus FR4 residue Trp103, form most of the contacts between CD40 and the dAb BMS3h-56-5. For example, the variable domain of an antibody polypeptide comprises CDR1, CDR2, and CDR3 regions that have the same amino acid sequence as the CDR1, CDR2, and CDR3 regions of one of the dAbs listed in TABLE 3 or that each differ from the CDR1, CDR2, and CDR3 regions by one or two amino acids. For example, the antibody polypeptide may comprise CDR1, CDR2, and CDR3 regions that have the same amino acid sequence as the CDR1, CDR2, and CDR3 regions of BMS3h-56-5, BMS3h-56-258, or BMS3h-56-201, for example.

A "domain antibody" (dAb) comprises a single variable ($V_L$ or $V_H$) domain that is capable of specifically and monovalently binding an antigen, such as CD40. For example, a dAb may have a $V_{HH}$ structure, characteristic of a camelid dAb. A "$V_H$ domain" as used herein is meant to include a $V_{HH}$ structure. In another embodiment, the $V_H$ domains of the present invention (including all features and combination of features presented as embodiments herein) are other than $V_{HH}$ domains, dAbs may form homo- or heterodimers in solution. Bivalent anti-CD40 antibodies are believed to exhibit agonist activity because of the ability to cross-link bound CD40 molecules on the cell surface. While not limited by any particular theory, it is believed that monovalent dAbs do not activate CD40, because the dAbs do not cross-link CD40.

As used herein, the term "variable domain" refers to immunoglobulin variable domains defined by Kabat et al., *Sequences of Immunological Interest,* 5$^{th}$ ed., U.S. Dept. Health & Human Services, Washington, D.C. (1991). The numbering and positioning of CDR amino acid residues within the variable domains is in accordance with the well-known Kabat numbering convention. For example, the Kabat numbering for BMS3h-56-5 (SEQ ID NO: 321) is compared in TABLE 2 to the same sequence numbered sequentially. In the Kabat numbering, BMS3h-56-5 has insertion residues 52A, 82A, 82B, 82C, and is missing residue 100. In both numbering systems, the Ser and Thr at the N-terminus that are part of the expression construct are given negative numbers.

TABLE 2

```
            -2-1
             ||
BMS3h-56-5   ST

CDR1
Kabat              10       20       30       40        50
                 -  |    -  |    -  |     -   |    -    |
Sequential         10       20       30       40        50
                 -  |    -  |    -  |     -   |    -    |
BMS3h-56-5   EVQLLESGGGLVQPGGSLRLSCAASGFTFRDYEMWWVRQAPGKGLERVSA CDR2
Kabat              60       70       80              90
              A -   |   -   |   -    | ABC   -        |
Sequential         60       70       80              90       100
                -  |    -  |     -   |    -           |    -   |
BMS3h-56-5   INPQGTRTYYADSVMGRFTISRDNSKNTLYLQMNSLRAEDTAVYYCAKLP CDR3
Kabat        101     110     116
              |   -   |    -|
Sequential          110     119
                -    |   -   |
BMS3h-56-5   FTFDDWGQGTLVTVSSAAA  (SEQ ID NO: 3)
```

The term "human," when applied to antibody polypeptides, means that the antibody polypeptide has a sequence, e.g., FR and/or CH domains, derived from a human immunoglobulin. A sequence is "derived from" a human immunoglobulin coding sequence when the sequence is either: (a) isolated from a human individual or from a cell or cell line from a human individual; (b) isolated from a library of cloned human antibody gene sequences or of human antibody variable domain sequences; or (c) diversified by mutation and selection from one or more of the polypeptides above. An "isolated" compound as used herein means that the compound is removed from at least one component with which the compound is naturally associated with in nature.

Antibody polypeptides can be administered to human patients while largely avoiding the anti-antibody immune response often provoked by the administration of antibodies from other species, e.g., mouse. For example, murine antibodies can be "humanized" by grafting murine CDRs onto a human variable domain FR, according to procedures well known in the art. Human antibodies as disclosed herein, however, can be produced without the need for genetic manipulation of a murine antibody sequence.

Variable domains may comprise one or more framework regions (FR) with the same amino acid sequence as a corresponding framework region encoded by a human germline antibody gene segment. For example, a domain antibody may comprise the $V_H$ germline gene segments DP47, DP45, or DP38, the $V_\kappa$ germline gene segment DPK9, the $J_H$ segment JH4b, or the $J_\kappa$ segment $J_\kappa 1$.

Changes may be made to antibody polypeptide sequences while retaining the ability to bind CD40 specifically. Specifically, the antibody polypeptides (e.g., a dAb) may comprise a variant variable domain that retains the function of specifically binding the same CD40 epitope as the dAb BMS3h-56-5. See TABLE 1. That is, the variant variable domain may bind a human CD40 epitope comprising at least one of Trp109, Leu121, His122, Ser124, Ser156, Ala157, Phe158, Glu159, and His162 of SEQ ID NO: 1. In one embodiment, the variant variable domain epitope may comprise Trp109, Leu121, His122, Ser124, Ser156, Ala157, Phe158, Glu159, and His162. Alternatively, the variant variable domain may specifically bind a CD40 epitope comprising CD40 residue Trp109. In yet another embodiment, the variant variable domain may compete with BMS3h-56-5 for specific binding to CD40. Error-prone affinity maturation, as disclosed in the examples below, provides one exemplary method for making and identifying antibody polypeptides with variant sequences that specifically bind the same CD40 epitope.

For example, a variant variable domain may differ from one of the variable domains listed in TABLE 3 by up to 10 amino acids or any integral value between, where the variant variable domain specifically binds CD40. Alternatively, the variant variable domain may have at least 90% sequence identity (e.g., at least 92%, 95%, or 98% sequence identity) relative to a sequence listed in the present Sequence Listing. Non-identical amino acid residues or amino acids that differ between two sequences may represent amino acid substitutions, additions, or deletions. Residues that differ between two sequences appear as non-identical positions, when the two sequences are aligned by any appropriate amino acid sequence alignment algorithm, such as BLAST.

It is provided that amino acid substitutions may be made to individual FR regions, such that one or more FR comprises up to two amino acid differences relative to the amino acid sequence of the corresponding FR encoded by a human germline antibody gene segment. It is further provided that the variant variable domain may contain one or two amino acid substitutions in one or more CDR. Representative variable domains that specifically bind CD40 are listed in TABLE 3.

ClustalW2 alignments between representative variable domains of antibody polypeptides from lineages BMS3h-56, BMS3h-37, BMS3h-38, and BMS3h-198 are shown in FIG. 4, FIG. 5, FIG. 6, and FIG. 7, respectively. As a general rule, the degree to which an amino acid is conserved in an alignment of related protein sequences is proportional to the relative importance of the amino acid position to the function of the protein. That is, amino acids that are common in all related sequences likely play an important role and cannot be easily substituted. On the other hand, positions that vary between the sequences likely can be substituted with other amino acids or otherwise modified, while maintaining the activity of the protein. The alignments shown in FIG. 4, FIG. 5, FIG. 6, and FIG. 7 and the structural relationships ascertained from FIG. 1 and FIG. 2, for example, can guide the construction of variant antibody polypeptides that specifically bind an epitope of human CD40 comprising the amino acid sequence of SEQ ID NO: 1, wherein the antibody polypeptide competes with the binding of dAb BMS3h-56-201 (SEQ ID NO: 9). Such variant antibody polypeptides include, but are not limited to, those with an amino acid modification corresponding to a substitution, insertion, or deletion with reference to any of the variable domains listed in TABLE 3. Variant antibody polypeptides also include those with an amino acid modification corresponding to an amino acid modification conserved between the sequences listed in TABLE 3.

The information regarding the boundaries of the $V_L$ or $V_H$ domains of heavy and light chain genes may be used to design PCR primers to amplify the variable domain from a cloned heavy or light chain coding sequence encoding an antibody polypeptide known to bind CD40. The amplified variable domain may be inserted into a suitable expression vector, e.g., pHEN-1 (Hoogenboom et al. (1991) *Nucleic Acids Res.* 19:4133-4137) and expressed, either alone or as a fusion with another polypeptide sequence, using techniques well known in the art. Based on the disclosed amino acid and polynucleotide sequences, the fusion protein can be produced and purified using only ordinary skill in any suitable mammalian host cell line, such as CHO, 293, COS, NSO, and the like, followed by purification using one or a combination of methods, including protein A affinity chromatography, ion exchange, reverse phase techniques, or the like.

In one aspect, the antibody polypeptide is a "dual specific" antibody polypeptide comprising a first variable domain that specifically binds human CD40 comprising the amino acid sequence of SEQ ID NO: 1. Dual specific antibody polypeptides comprise a second variable domain that specifically binds a second antigen that is other than human CD40.

In another embodiment, the second antigen may be a cell surface molecule of an immune effector cell or a soluble molecule such as a cytokine, for example. Binding of the dual specificity antibody polypeptide could be used to antagonize CD40 and antagonize a biological activity of the second antigen. Cell surface molecules of immune effector cells include the cluster of differentiation (CD) molecules. Representative CD markers are listed on the Internet at hypertext transfer protocol en.wikipedia.org/wiki/List_of_human_clusters_of_differentiation (last modified on Feb. 22, 2012). Cell surface molecules of immune effector cells also include Major Histocompatibility Complex (MHC)

Class II molecules. Antibodies against these cell surface molecules are known in the art and can be used a source of a variable domain to construct a dual specific antibody polypeptide.

In one embodiment, antibody polypeptides of a dual specific ligand may be linked by an "amino acid linker" or "linker." For example, a dAb may be fused to the N-terminus of an amino acid linker, and another dAb may be fused to the C-terminus of the linker. Although amino acid linkers can be any length and consist of any combination of amino acids, the linker length may be relatively short (e.g., five or fewer amino acids) to reduce interactions between the linked domains. The amino acid composition of the linker also may be adjusted to reduce the number of amino acids with bulky side chains or amino acids likely to introduce secondary structure. Suitable amino acid linkers include, but are not limited to, those up to 3, 4, 5, 6, 7, 10, 15, 20, or 25 amino acids in length. Representative amino acid linker sequences include $(GGGGS)_n$ (SEQ ID NO: 4), where n may be any integer between 1 and 5. Other suitable linker sequences may be selected from the group consisting of AST (SEQ ID NO: 5), TVAAPS (SEQ ID NO: 6), TVA (SEQ ID NO: 7), and ASTSGPS (SEQ ID NO: 8).

The binding of the second antigen can increase the in vivo half-life of the antibody polypeptide. For example, the second variable domain of the dual specific antibody polypeptide may specifically bind serum albumin (SA), e.g., human serum albumin (HSA). The antibody polypeptide formatted to bind HSA can have an increased in vivo t-α ("alpha half-life") or t-β ("beta half-life") half-life relative to the same unformatted antibody polypeptide. The t-α and t-β half-lives measure how quickly a substance is distributed in and eliminated from the body. The linkage to HSA may be accomplished by fusion of the antibody polypeptide with a second variable domain capable of specifically binding HSA, for example. Anti-human serum albumin antibodies are well-known in the art. See, e.g., Abcam®, Human Serum Albumin antibodies ab10241, ab2406, and ab8940, available on the Internet at hypertext transfer protocol www.abcam.com/index.html, or GenWay, ALB antibody, available on the Internet at hypertext transfer protocol www.genwaybio.com. Variable domains that specifically bind HSA can be obtained from any of these antibodies, and then fused to an antibody polypeptide of the disclosure using recombinant techniques that are well known in the art.

Alternatively, the linking of the antibody polypeptide to HSA can be accomplished by directly fusing the antibody polypeptide sequence to an HSA coding sequence using techniques well known to the skilled artisan. The HSA coding sequences can be obtained by PCR using primers derived from the cDNA sequence available at GenBank Accession No. NM000477, for example.

In one embodiment, the tα-half-life of the HSA-linked domain antibody composition is increased by 10% or more. In another embodiment, the tα-half-life of the HSA-linked domain antibody composition is in the range of 0.25 hours to 6 hours. In another embodiment, the tβ-half-life of the HSA-linked domain antibody composition is increased by 10% or more. In another embodiment, the tβ-half-life of the HSA-linked domain antibody composition is in the range of 12 to 48 hours.

In another embodiment, an antibody polypeptide may be formatted to increase its in vivo half-life by PEGylation. In one embodiment, the PEG is covalently linked. In another embodiment, the PEG is linked to the antibody polypeptide at a cysteine or lysine residue. In yet another embodiment, the PEG-linked antibody polypeptide has a hydrodynamic size of at least 24 kD. In yet another embodiment, the total PEG size is from 20 to 60 kD, inclusive. In yet another embodiment, the PEG-linked domain antibody has a hydrodynamic size of at least 200 kD.

PEGylation can be achieved using several PEG attachment moieties including, but not limited to N-hydroxylsuccinimide active ester, succinimidyl propionate, maleimide, vinyl sulfone, or thiol. A PEG polymer can be linked to an antibody polypeptide at either a predetermined position, or can be randomly linked to the domain antibody molecule. PEGylation can also be mediated through a peptide linker attached to a domain antibody. That is, the PEG moiety can be attached to a peptide linker fused to an antibody polypeptide, where the linker provides the site (e.g., a free cysteine or lysine) for PEG attachment. Methods of PEGylating antibodies are well known in the art, as disclosed in Chapman, et al., "PEGylated antibodies and antibody fragments for improved therapy: a review," *Adv. Drug Deliv. Rev.* 54(4):531-45 (2002), for example.

Antibody polypeptides also may be designed to form a dimer, trimer, tetramer, or other multimer. Antibody polypeptides, e.g., dAbs, can be linked to form a multimer by several methods known in the art, including, but not limited to, expression of monomers as a fusion protein, linkage of two or more monomers via a peptide linker between monomers, or by chemically joining monomers after translation, either to each other directly, or through a linker by disulfide bonds, or by linkage to a di-, tri- or multivalent linking moiety (e.g., a multi-arm PEG). In one embodiment, the multimer can bind a single molecule of CD40.

4. Pharmaceutical Compositions and Methods of Treatment

A pharmaceutical composition comprises a therapeutically-effective amount of one or more antibody polypeptides and optionally a pharmaceutically acceptable carrier. Pharmaceutically acceptable carriers include, for example, water, saline, phosphate buffered saline, dextrose, glycerol, ethanol and the like, as well as combinations thereof. Pharmaceutically acceptable carriers can further comprise minor amounts of auxiliary substances, such as wetting or emulsifying agents, preservatives, or buffers that enhance the shelf-life or effectiveness of the fusion protein. The compositions can be formulated to provide quick, sustained, or delayed release of the active ingredient(s) after administration. Suitable pharmaceutical compositions and processes for preparing them are well known in the art. See, e.g., Remington, THE SCIENCE AND PRACTICE OF PHARMACY, A. Gennaro, et al., eds., 21st ed., Mack Publishing Co. (2005).

The pharmaceutical composition further may comprise an immuno-suppressive/immunomodulatory and/or anti-inflammatory agent. A method of treating an immune disease in a patient in need of such treatment may comprise administering to the patient a therapeutically effective amount of the pharmaceutical composition. Antagonizing CD40-mediated T cell activation could inhibit undesired T cell responses occurring during autoimmunity, transplant rejection, or allergic responses, for example. Inhibiting CD40-mediated T cell activation could moderate the progression and/or severity of these diseases.

As used herein, a "patient" means an animal, e.g. mammal, including humans. The patient may be diagnosed with an immune disease. "Treatment" or "treat" or "treating" refers to the process involving alleviating the progression or severity of a symptom, disorder, condition, or disease. An "immune disease" refers to any disease associated with the development of an immune reaction in an individual, including a cellular and/or a humoral immune reaction. Examples of immune diseases include, but are not limited to, inflammation, allergy, autoimmune disease, or graft-related disease. The autoimmune disease may be selected from the group consisting of systemic lupus erythematosus, multiple sclerosis, rheumatoid arthritis, diabetes, psoriasis, scleroderma, atherosclerosis, inflammatory bowel disease, and ulcerative colitis.

Diseases that can be treated by administering the pharmaceutical composition may be selected from the group consisting of Addison's disease, allergies, ankylosing spondylitis, asthma, atherosclerosis, autoimmune diseases of the ear, autoimmune diseases of the eye, autoimmune hepatitis, autoimmune parotitis, colitis, coronary heart disease, Crohn's disease, diabetes, including Type 1 and/or Type 2 diabetes, epididymitis, glomerulonephritis, Graves' disease, Guillain-Barre syndrome, Hashimoto's disease, hemolytic anemia, idiopathic thrombocytopenic purpura, inflammatory bowel disease, immune response to recombinant drug products (e.g., Factor VII in hemophiliacs), systemic lupus erythematosus, male infertility, multiple sclerosis, myasthenia gravis, pemphigus, psoriasis, rheumatic fever, rheumatoid arthritis, sarcoidosis, scleroderma, Sjogren's syndrome, spondyloarthropathies, thyroiditis, transplant rejection, and vasculitis. Autoimmune-mediated conditions include, but are not limited to, conditions in which the tissue affected is the primary target, and in some cases, the secondary target. Such conditions include, but are not limited to, AIDS, atopic allergy, bronchial asthma, eczema, leprosy, schizophrenia, inherited depression, transplantation of tissues and organs, chronic fatigue syndrome, Alzheimer's disease, Parkinson's disease, myocardial infarction, stroke, autism, epilepsy, Arthus' phenomenon, anaphylaxis, alcohol addiction, and drug addiction.

The pharmaceutical composition may be administered alone or in combination therapy, (i.e., simultaneously or sequentially) with an immunosuppressive/immunomodulatory and/or anti-inflammatory agent. Different immune diseases can require use of specific auxiliary compounds useful for treating immune diseases, which can be determined on a patient-to-patient basis. For example, the pharmaceutical composition may be administered in combination with one or more suitable adjuvants, e.g., cytokines (IL-10 and IL-13, for example) or other immune stimulators, e.g., chemokines, tumor-associated antigens, and peptides. Suitable adjuvants are known in the art.

Any suitable method or route can be used to administer the antibody polypeptide or the pharmaceutical composition. Routes of administration include, for example, oral, intravenous, intraperitoneal, subcutaneous, or intramuscular administration. A therapeutically effective dose of administered antibody polypeptide(s) depends on numerous factors, including, for example, the type and severity of the immune disease being treated, the use of combination therapy, the route of administration of the antibody polypeptide(s) or pharmaceutical composition, and the weight of the patient. A non-limiting range for a therapeutically effective amount of a domain antibody is 0.1-20 mg/kg, and in an aspect, 1-10 mg/kg, relative to the body weight of the patient. The dose of antibody polypeptide(s) can be further guided by the amount of antibody polypeptide(s) required for CD40 antagonism in in vitro and/or in vivo models of disease states. Representative models are described below and in the examples.

5. In Vitro and In Vivo Models

The ability of antibody polypeptides of the disclosure to antagonize CD40 can be tested in one of several available in vitro or in vivo model systems. Appropriate animal and cell model systems are described below. Further cell assay systems are described in the examples.

5.1. Inflammatory Bowel Disease (IBD) Models:

IBD is a multifactorial immune disorder of uncertain etiology. Several mouse models of mucosal inflammation that resemble IBD have provided insight into the mechanisms governing both normal and pathological mucosal immune function. IBD models include using the mucosal immunity and inflammation system of De Winter et al., Am. J. Physiol. 276: G1317-1321 (1999). In one aspect, the injection into immunodeficient mice of a subset of CD4(+) T lymphocytes, the CD4(+)CD45RBhigh cells, leads to inflammation of the intestine. Pathogenesis is due in part to the secretion of proinflammatory cytokines. The induction of colitis can be prevented by co-transfer of another CD4(+) subpopulation, the CD4(+)CD45RBlow T cells. This population behaves analogously to the CD4(+)CD45RBhigh population in terms of the acquisition of activation markers and homing to the host intestine. However, their lymphokine profile when activated is different, and anti-inflammatory cytokines secreted and/or induced by CD4(+)CD45RBlow T cells prevent colitis. De Winter et al. provide a description of the adoptive transfer model and the factors that promote and prevent colitis pathogenesis.

5.2. Spontaneous Arthritis Models:

A model of organ-specific disease provoked by systemic autoimmunity is provided by Kouskoff et al., Cell 87: 811-822 (1996). Rheumatoid arthritis (RA) is a chronic joint disease characterized by leukocyte invasion and synoviocyte activation followed by cartilage and bone destruction. Kouskoff et al. disclose a spontaneous mouse model of RA, generated by crossing a T cell receptor (TCR) transgenic line with the NOD strain. All offspring develop a joint disease highly reminiscent of RA in man. The trigger for the murine disorder is chance recognition of a NOD-derived major histocompatibility complex (MHC) class II molecule by the transgenic TCR; progression to arthritis involves CD4+T, B, and probably myeloid cells.

5.3. Collagen Induced Arthritis (CIA) Model:

A mouse model of collagen-induced arthritis is provided by Brand et al., Methods Mol. Med. 102: 295-312 (2004). Collagen-induced arthritis (CIA) is an autoimmune disease that can be elicited in susceptible strains of rodents (rat and mouse) and non-human primates by immunization with type II collagen (CII), the major constituent protein of articular cartilage. After immunization, the animals develop an autoimmune polyarthritis that shares several clinical and histological features with RA. Susceptibility to CIA in rodents is linked to the class II molecules of the major histocompatibility complex (MHC), and the immune response to CII is characterized by both the stimulation of collagen-specific T cells and the production of high titers of antibody specific for both the immunogen (heterologous CII) and the autoantigen (mouse CII). Histologically, murine CIA is characterized by an intense synovitis that corresponds with the clinical onset of arthritis. This experimental data is useful evaluating CIA because of the pathological similarities between CIA and RA.

5.4. Antigen Induced T Cell Proliferation In Vivo Model:

The use of adoptive transfer of T cell receptor (TCR)-transgenic T cells provides an in vivo model for antigen-induced T-cell proliferation. Pape et al., Immunol. Rev. 156: 67-78 (1997) discloses adoptive transfer of TCR-transgenic T cells uniformly expressing an identifiable TCR of a known peptide/MHC specificity. The model can be used to monitor the in vivo behavior of antigen-specific T cells. Naive T cells are initially activated within T-cell zones of secondary lymphoid tissue to proliferate in a B7-dependent manner. If adjuvants or inflammatory cytokines are present during this period, enhanced numbers of T cells accumulate, migrate into B-cell-rich follicles, and acquire the capacity to produce IFN-γ and help B cells produce IgG2a. If inflammation is effectively antagonized, most of the initially activated antigen-specific T cells disappear without entering the follicles, and the survivors are poor producers of IL-2 and IFN-γ.

EXAMPLES

TABLE 3 lists representative anti-human CD40 variable domain amino acid sequences useful for the antibody polypeptides of the disclosure. TABLE 4 discloses representative nucleic acids that encode the variable domain sequences listed in TABLE 3. As is well known in the art, multiple codons can encode the same amino acid. Nucleic acids encoding a protein sequence thus include nucleic acids having codon degeneracy. The antibody polypeptides disclosed in TABLE 3 specifically bind CD40 and were made using the reiterative initial/primary screening and affinity maturation methodologies described in the examples that follow.

TABLE 3

Anti-Human CD40 Variable Domain Amino Acid Sequences

BMS3h-56-201
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFYFQEWGQGTLVTVSS (SEQ ID NO: 9)

BMS3h-56-258
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFYFHEWGQGTLVTVSS (SEQ ID NO: 10)

BMS3h-37
EVQLLESGGGLVQPGGSLRLSCAASGFTFEWYEMQWVRQAPGKGLEWVSAISGDGYRTYYADSVKGRFTISRDNSKNTL
YLQMNSLRAEDTAVYYCAKELGYFDYWGQGTLVTVSS (SEQ ID NO: 11)

BMS3h-38
EVQLLESGGGLVQPGGSLRLSCAASGFTFEEEEMIWVRQAPGKGLEWVSAISGSGGSTYYADSVKGRFTISRDNSKNTL
YLQMNSLRAEDTAVYYCAKEPFRFDYWGQGTLVTVSS (SEQ ID NO: 12)

BMS3h-41
EVQLLESGGGLVQPGGSLRLSCAASGFTFTEYEMIWVRQAPGKGLEWVSSISGNGANTYYADSVKGRFTISRDNSKNTL
YLQMNSLRAEDTAVYYCAKEPLRFDYWGQGTLVTVSS (SEQ ID NO: 13)

BMS3h-43
EVQLLESGGGLVQPGGSLRLSCTASGFTFNMYEMSWVRQAPGKGLEWVSGISRRGFTTYYADSVKGRFTISRDNSKNTL
YLQMNSLRAEDTAVYYCAKEPITYAMRYARFDYWGQGTLVTVSS (SEQ ID NO: 14)

BMS3h-56
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFIFDYWGQGTLVTVSS (SEQ ID NO: 15)

BMS3h-106
EVQLLESGGGLVQPGGSLRLSCAASGFTFSTYHMQWVRQAPGKGLEWVSMIDADGLGTYYADSVKGRFTISRDNSKNTL
YLQMNSLRAEDTAVYYCAKPGPQFGQFDYWGQGTLVTVSS (SEQ ID NO: 16)

BMS3h-107
EVQLLESGGGLVQPGGSLRLSCAASGFTFSGYDMQWVRQAPGKGLEWVSTISASGVFTYYADSVKGRFTTSRDNSKNTL
YLQMNSLRAEDTAVYYCAKYPNRFALNNFDYWGQGTLVTVSS (SEQ ID NO: 17)

BMS3h-131
DIQMTQSPSSLSASVGDRVTITCRANSSILWALAWYQQKPGKAPKLLIESSSGLQSGVPSRFSGSGSGTDFTLTISSLQ
PEDFATYYCVQNAGWPGTFGQGTKVEIKR (SEQ ID NO: 18)

BMS3h-193
DIQMTQSPSSLSASVGDRVTITCRASQTIERRLNWYQQKPGKAPKLLIYLASRLQSGVPSRFSGSGSGTDFTLTISSLQ
PEDFATYYCHQYASPPLTFGQGTKVEIKR (SEQ ID NO: 19)

BMS3h-198
EVQLLESGGGLVQPGGSLRLSCAASGFTFAGYEMWWVRQAPGKGLERVSAISGSGGSTYYADSVKGRFTISRDDSKNTL
YLQMNSLRAEDTAVYYCAKDPYSFDYWGQGTLVTVSS (SEQ ID NO: 20)

BMS3h-202
EVQLLESGGGLVQPGGSLRLSCAASGFTFPTAEMVWVRQAPGKGLEWVSSISASGGSTYYADSVKGRFTISRDNSKNTL
YLQMNSLRAEDTAVYYCAKEPVSYVATFDYWGQGTLVTVSS (SEQ ID NO: 21)

BMS3h-217
DIQMTQSPSSLSASVGDRVTITCRASHFIGTLLSWYQQKPGKAPKLLITYGSLLQSGVPSRFSGSGSGTDFTLTISSLQ
PEDFATYYCGQGVLWPATFGQGTKVEIKR (SEQ ID NO: 22)

BMS3h-1
EVQLLESGGGLVQPGGSLRLSCAASGFTFPKNEMTWVRQAPGKGLEWVSAIESDGQATYYADSVKGRFTISRDNSKNTL
YLQMNSLRAEDTAVYYCAKNRIPDLVFDYWGQGTLVTVSS (SEQ ID NO: 23)

BMS3h-2
EVQLLESGGGLVQPGGSLRLSCAASGFTFDAGAMTWVRQAPGKGLEWVSSIDKEGLSTYYADSVKGRFTISRDNSKNTL
YLQMNSLRAEDTAVYYCAKGRIPGLVFDYWGQGTLVTVSS (SEQ ID NO: 24)

TABLE 3-continued

Anti-Human CD40 Variable Domain Amino Acid Sequences

BMS3h-3
EVQLLESGGGLVQPGGSLRLSCAASGFTFGDAAMTWVRQAPGKGLEWVSAIQPMGDGTYYADSVKGRFTVSRDNSKNTL
YLQMNSLRAEDTAVYYCAKGRIPTLQFDYWGQGTLVTVSS (SEQ ID NO: 25)

BMS3h-4
EVQLLESGGGLVQPGGSLRLSCAASGFTFEDSPMTWVRQAPGKGLEWVSAITSNGYETYYADSVKGRFTISRDNSKNTL
YLQMNSLRAEDTAVYYCAKGRIPTLHFDYWGQGTLVTVSS (SEQ ID NO: 26)

BMS3h-5
EVQLLESGGGLVQPGGSLRLSCAASGFTFDEHDMSWVRQAPGKGLEWVSRIGPDGFHTYYADSVKGRFTISRDNSKNTL
YLQMNSLRAEDTAVYYCAKGRIPTLHFDYWGQGTLVTVSS (SEQ ID NO: 27)

BMS3h-6
EVQLLESGGGLVQPGGSLRLSCAASGFTFGEYHMSWVRQAPGKGLEWVSRITPLGTLTYYADSVKGRFTISRDNSKNTL
YLQMNSLRAEDTAVYYCAKGRIPSLTFDYWGQGTLVTVSS (SEQ ID NO: 28)

BMS3h-7
EVQLLESGGGLVQPGGSLRLSCAASGFTFGTNAMSWVRQAPGKGLEWVSRISPGGDYTYYADSVKGRFTISRDNSKNTL
YLQMNSLRAEDTAVYYCAKGRVPDLLFDYWGQGTLVTVSS (SEQ ID NO: 29)

BMS3h-8
EVQLLESGGGLVQPGGSLRLSCAASGFTFPSEEMSWVRQAPGKGLEWVSRISADGANTYYADSVKGRFTISRDNSKNTL
YLQMNSLRAEDAAVYYCAKGRVPDLLFDYWGQGTLVTVSS (SEQ ID NO: 30)

BMS3h-9
EVQLLESGGGLVQPGGSLRLSCAASGFTFAEDDMTWVRQAPGKGLEWVSRIAVDGDRTYYADSVKGRFTISRDNSKNTL
YLQMNSLRAEDTAVYYCAKGKVPSLHFDYWGQGTLVTVSS (SEQ ID NO: 31)

BMS3h-10
EVQLLESGGGLVQPGGSLRLSCAASGFTFRTMDMSWVRQAPGKGLEWVSRITGDGMNTYYADSVKGRFTISRDNSKNTL
YLQMNSLRAGDTAVYYCAKGVTPDLTFDYWGQGTLVTVSS (SEQ ID NO: 32)

BMS3h-11
EVQLLESGGGLVQPGGSLRLSCAASGFTFERDDMTWVRQAPGKGLEWVSRINAGGVHTYYADSVKGRFTISRDNSKNTL
YLQMNSLRAEDTAVYYCAKGVTPDLTFDYWGQGTLVTVSS (SEQ ID NO: 33)

BMS3h-12
EVQLLESGGGLVQPGGSLRLSCAASGFTFDDDSMTWVRQAPGKGLEWVSRISSDGASTYYADSVKGRFTISRDNSKNTL
YLQMNSLRAEDTAVYYCAKGVTPDLTFDYWGQGTLVTVSS (SEQ ID NO: 34)

BMS3h-13
EVQLLESGGGLVQPGGSLRLSCAASGFTFTEEDMTWVRQAPGKGLEWVSRIDSVGEGTYYADSVKGRFTISRDNSKNTL
YLQMNSLRAEDTAVYYCAKGVTPDLTFDYWGQGTLVTVSS (SEQ ID NO: 35)

BMS3h-14
EVQLLESGGGLVQPGGSLRLSCAASGFTFSDSAMSWVRQAPGKGLEWVSRIDNPGQHTYYADSVKGRFTISRDNSKNTL
YLQMNSLRAEDTAVYYCAKGTVPTLEFDYWGQGTLVTVSS (SEQ ID NO: 36)

BMS3h-15
EVQLLESGGGLVQPGGSLRLSCAASGFTFGQHSMTWVRQAPGKGLEWVSRIDGGGYNTYYADSVKGRFTISRDNSKNTL
YLQMNSLRAEDTAVYYCAKGEVPRLHFDYWGQGTLVTVSS (SEQ ID NO: 37)

BMS3h-16
EVQLLESGGGLVQPGGSLRLSCAASGFTFGQEPMTWVRQAPGKGLEWVSRIAYNGGDTYYADSVKGRFTISRDNSKNTL
YLQMNSLRAEDTAVYYCAKGITPNLTFDYWGQGTLVTVSS (SEQ ID NO: 38)

BMS3h-17
EVQLLESGGGLVQPGGSLRLSCAASGFTFENYPMSWVRQAPGKGLEWVSRINATGSITYYADSVKGRFTISRDNSKNTL
YLQMNSLRAEDTAVYYCAKGVIPHLMFDYWGQGTLVTVSS (SEQ ID NO: 39)

BMS3h-18
EVQLLESGGGLVQPGGSLRLSCAASGFTFRDYDMSWVRQAPGKGLEWVSRITGIGNSTYYADSVKGRFTISRDNSKNTL
YLQMNSLRAEDTAVYYCAQGVVPYLAFDYWGQGTLVTVSS (SEQ ID NO: 40)

BMS3h-19
EVQLLESGGGLVQPGGSLRLSCAASGFTFEADAMTWVRQAPGKGLEWVSRINVDGDRTYYADSVKGRFTISRDNSKNTL
YLQMNSLRAEDTAVYYCAKGTVPTLEFDYWGQGTLVTVSS (SEQ ID NO: 41)

BMS3h-21
EVQLLESGGGLVQPGGSLRLSCAASGFTFDRADMTWVRQAPGKGLEWVSRISGEGKCTYYADSVKGRFTISRDNSKNTL
YLQMNSLRAEDTAVYYCAKGMVPNLVFDYWGQGTLVTVSS (SEQ ID NO: 42)

BMS3h-22
EVQLLESGGGLVQPGGSLRLSCAASGFTFHWEPMSWVRQAPGKGLEWVSRINSSGWDTYYADSVKGRFTISRDNSKNTL
YLQMNSLRAEDTAVYYCAKGMVPNLVFDYWGQGTLVTVSS (SEQ ID NO: 43)

TABLE 3-continued

Anti-Human CD40 Variable Domain Amino Acid Sequences

BMS3h-24
EVQLLESGGGLVQPGGSLRLSCAASGFTFADEPMTWVRQAPGKGLEWVSRIPPEGAPTYYADSVKGRFTISRDNSKNTL
YLQMNSLRAEDTAVYYCAKGITPNLTFDYWGQGTLVTVSS (SEQ ID NO: 44)

BMS3h-26
EVQLLESGGGLVQPGGSLRLSCAASGFTFHNHDMSWVRQAPGKGLEWVSRISRGGLQTYYADSVKGRFTISRDNSKNTL
YLQMNSLRAEDTAVYYCAKGIVPDLHFDYWGQGTLVTVSS (SEQ ID NO: 45)

BMS3h-27
EVQLLESGGGLVQPGGSLRLSCAASGFTFNEYPMSWVRQAPGKGLEWVSRINGDGANTYYADSVKGRFTISRDNSKNTL
YLQMNSLRAEDTAVYYCAKGIIPAMQFDYWGQGTLVTVSS (SEQ ID NO: 46)

BMS3h-28
EVQLLESGGGLVQPGGSLRLSCAASGFTFGDVPMSWVRQAPGKGLEWVSRIDPYGSNTYYADSVKGRFTISRDNSKNTL
YLQMNSLRAEDTAVYYCAKGIMPSLTFDYWGQGTLVTVSS (SEQ ID NO: 47)

BMS3h-29
EVQLLESGGGLVQPGGSLRLSCAASGFTFADYDMSWVRQAPGKGLEWVSRISALGATTYYADSVKGRFTISRDNSKNTL
YLQMNSLRAEDTAVYYCAKGQLPALEFDYWGQGTLVTVSS (SEQ ID NO: 48)

BMS3h-30
EVQLLESGGGLVQPGGSLRLSCAASGFTFKRYYMTWVRQAPGKDLEWVSGIVPSGNRTYYADSVKGRFTISRDNSKNTL
YLQMNSLRAEDTAVYYCAKGRIPDLHFDYWGQGTLVTVSS (SEQ ID NO: 49)

BMS3h-31
EVQLLESGGGLVQPGGSLRLSCAASGFTFADYDMTWVRQAPGKGLEWVSRISPTGGQTYYADSVKGRFTISRDNSKNTL
YLQMNSLRAEDTAVYYCAKGVIPYLSFSPFDYWGQGTLVTVSS (SEQ ID NO: 50)

BMS3h-32
EVQLLESGGGLVQPGGSLRLSCAASGFTFSKYWMGWARQAPGKGLEWVSSIDSHGAGTYYADSVKGRFTISRDNSKNTL
YLQMNSLRVEDTAVYYCAKGAPKFMTTYTFDYWGQGTLVTVSS (SEQ ID NO: 51)

BMS3h-33
EVQLLESGGGLVQPGGSLRLSCAASGFTFLSYPMHWVRQAPGKGLEWVSSIDSRGSVTYYADSVKGRFTISRDNSKNTL
YLQMNSLRAEDTAVYYCAKGHSWTFDYWGQGTLVTVSS (SEQ ID NO: 52)

BMS3h-34
EVQLLESGGGLVQPGGSLRLSCAASGFTFANSNMTWVRQAPGKGLEWVSRINPDGGSTYYADSVKGRFTISRDNSKNTL
YLQMNSLRAEDTAVYYCAEGRIPTLHFDYWGQGTLVTVSS (SEQ ID NO: 53)

BMS3h-35
EVQLLESGGGLVQPGGSLRLSCAASGFTFGPRRMGWVRQAPGKGLEWVSSIDDIGRRTYYADSVKGRFTISRDNSKNTL
YLQMNSLRAEDTAVYYCAEGAQGVLLFDYWGQGTLVTVSS (SEQ ID NO: 54)

BMS3h-36
EVQLLESGGGLVQPGGSLRLSCAASGFTFEDYRMVWVRQAPGKGLEWVSSISTSGELTYYADSVKGRFTISRDNSKNTL
YLQMNSLRAEDTAVYYCAETAGQFFDYWGQGTLVTVSS (SEQ ID NO: 55)

BMS3h-39
EVQLLESGGGLVQPGGSLRLSCAASGFTFPEYEMVWVRQAPGKGLEWVSAISREGRATYYADSVKGRFTISRDNSKNTL
YLQMNNLRAEDTAVYYCAKEPVRFDYWGQGTLVTVSS (SEQ ID NO: 56)

BMS3h-40
EVQLLESGGGLVQPGGSLRLSCAASGFTFSTYEMLWVRQAPGKGLEWVSSISSSGNYTYYADSVKGRFTISRDNSKNTL
YLQMNSLRAEDTAVYYCAKEPLMFDYWGQGTLVTVSS (SEQ ID NO: 57)

BMS3h-42
EVQLLESGGGLVQPGGSLRLSCAASGFTFDTEEMSWVRQAPGKGLEWVSAISPNGAFTFYADSVKGRFTISRDNSKNTL
YLQMNSLRAEDTAVYYCAKEPILFDYWGQGTLVTVSS (SEQ ID NO: 58)

BMS3h-44
EVQLLESGGGLVQPGGSLRLSCAASGFTFGHYDMVWVRQAPGRGLEWVSTINGAGLNTYYADSVKGRFTISRDNSKNTL
YLQMNSLRAEDTAVYYCAQSASRIFDYWGQGTLVTVSS (SEQ ID NO: 59)

BMS3h-45
EVQLLESGGGLVQPGGSLRLSCAASGFTFRSYEMAWVRQAPGKGLEWVSSISTLGTKTYYADSVKGRFTISRDNSKNTL
YLQMNSLRAEDTAVYYCAQSSTHIFDYWGQGTLVTVSS (SEQ ID NO: 60)

BMS3h-46
EVQLLESGGGLVQPGGSLRLSCAASGFTFIRYEMAWVRQAPGKGLEWVSSISSSGWTTYYADSVKGRFTISRDNSKNTL
YLQMNSLRAEDTAVYYCAKSDAHIFDYWGQGTLVTVSS (SEQ ID NO: 61)

BMS3h-47
EVQLLESGGGLVQPGGSLRLSCAASGFTFYAYEMAWVRQAPGKGLEWVSSISDDGTRTYYADSVKGRFTISRDNSKNTL
YLQMNSLRAEDTAVYYCAKDLGQGFDYWGQGTLVTVSS (SEQ ID NO: 62)

TABLE 3-continued

Anti-Human CD40 Variable Domain Amino Acid Sequences

BMS3h-48
EVQLLESGGGLVQPGGSLRLSCAASGFTFADHGMTWVRQAPGKGLEWVSGIGPSGEATYYADSVKGRFTISRDNSKNTL
YLQMNSLRAEDTAVYYCAKDRIPNLVFDYWGQGTLVTVSS (SEQ ID NO: 63)

BMS3h-49
EVQLLESGGGLVQPGGSLRLSCAASGFTFESQDMSWVRQAPGKGLEWVSGISPNGWDTYYADSVKGRFTISRDNSKNTL
YLQMNSLRAEDTAVYYCAKDRSDFDYWGQGTLVTVSS (SEQ ID NO: 64)

BMS3h-50
EVQLLESGGGLVQPGGSLRLSCAASGFTFGDYDMWWVRQAPGKGLEWVSRIRHPGGVTYYADSVKGRFTISRDNSKNTL
YLQMNSLRAEDTAVYYCAKAVPKGFDYWGQGTLVTVSS (SEQ ID NO: 65)

BMS3h-51
EVQLLESGGGLVQPGGSLRLSCAASGFTFRVYWMTWVRQAPGKGLEWVSSIDPQGGMTYYADSVKGRFTISRDNSKNTL
YLQMNSLRAEDTAVYYCAKARIPNLEFDYWGQGTLVTVSS (SEQ ID NO: 66)

BMS3h-52
EVQLLESGGGLVQPGESLRLSCAASGFTFSAYDMTWVRQAPGKGLEWVSRINPTGSYTYYADSVKGRFTISRDNSKNTL
YLQMNSLRAEDTAVYYCAKAKIPNLVFDYWGQGTLVTVSS (SEQ ID NO: 67)

BMS3h-53
EVQLLESGGGLVQPGGSLRLSCAASGFTFADSEMMWVRQAPGKGLEWVSGIAHNGGHTYYADSVKGRFTISRDNSKNTL
YLQMNSLRAEDTAVYYCAKAGHPQQTEAFDYWGQGTLVTVSS (SEQ ID NO: 68)

BMS3h-54
EMQLLESGGGLVQPGGSLRLSCAASGFTFATYDMYWVRQAPGKGLEWVSKISPNGWSTYYADSVKGRFTISRDNSKNTL
YLQMNSLRAEDTAVYYCAKYQTHFDYWGQGTLVTVSS (SEQ ID NO: 69)

BMS3h-55
EVQLLESGGGLVQPGGSLRLSCAASGFTFSVYDMRWVRQAPGKGLEWVSTISSSGTYTYYADSVKGRFTISRDNSKNTL
YLQMNSLRAEDTAVYYCAKYPKNFDYWGQGTLVTVSS (SEQ ID NO: 70)

BMS3h-57
EVQLLESGGGLVQPGGSLRLSCAASGFTFSHEDMTWVRQAPGKGLEWVSSISPNGWDTYYADSVKGRFTISRDNSKNTL
YLQMNSLRAEDTAVYYCAKRTRSKFDYWGQGTLVTVSS (SEQ ID NO: 71)

BMS3h-58
EVQLLESGGGLVQPGGSLRLSCAASGFTFEKYIMGWARQAPGKGLEWVSTIDYWGQHTYYADSVKGRFTISRDNSKNTL
YLQMNSLRAEDTAVYYCAKRSHLIPLQFDYWGQGTLVTVSS (SEQ ID NO: 72)

BMS3h-59
EVQLLESGGGLVQPGGSLRLSCAASGFTFSDYAMGWVRQAPGKGLEWVSTISYVGYYTYYADSVKGRFTISRDNSKNTL
YLQMNSLRAEDTAVYYCAKKALRGEAFTERFDYWGQGTLVTVSS (SEQ ID NO: 73)

BMS3h-60
EVQLLESGGGLVQPGGSLRLSCAASGFTFGPYMMHWVRQAPGKGLEWVSTIEVNGNRTYYADSVKGRFTISRDNSKNTL
YLQMNSLRAEDTAVYYCAKWVGSKTSSDKSFDYWGQGTLVTVSS (SEQ ID NO: 74)

BMS3h-61
EVQLLESGGGLVQPGGSLRLSCAASGFTFGTTEMAWVRQAPGKGLEWVSSIGSAGAWTYYADSVKGRFTISRDNSKNTL
YLQMNSLRAEDTAVYYCAKIGGHPQGQFDYWGQGTLVTVSS (SEQ ID NO: 75)

BMS3h-62
EVQLLESGGGLVQPGGSLRLSCAASGFTFPREWMAWVRQAPGKGLEWVSSIQPMGQTTYYADSVKGRFTISRDNSKNTL
YLQMNSLRAEDTAVYYCAKYSRNKGFFDYWGQGTLVTVSS (SEQ ID NO: 76)

BMS3h-63
EVQLLESGGGLVQPGGSLRLSCAASGFTFTSEYMGWVRQAPGKGLEWVSSIQRYGSTTYYADSVKGRFTISRDNSKNTL
YLQMNSLRAEDTAVYYCAKHESNWETFDYWGQGTLVTVSS (SEQ ID NO: 77)

BMS3h-70
EVQLLESGGGLVQPGGSLRLSCAASGFTFSVYSMQWVRQAPGKGLEWVSAITPNGTRTYYADSVKGRFTISRDNSKNTL
YLQMNSLRAEDTAVYYCAKTLGRGSYPGVDFDYWGQGTLVTVSS (SEQ ID NO: 78)

BMS3h-71
EVQLLESGGGLVQPGGSLRLSCAASGFTFPSYAMTWVRQAPGKGLEWVSRITADGTVTYYADSVKGRFTISRDNSKNTL
YLQMNSLRAEDTAVYYCAKGSIPMLTFDYWGQGTLVTVSS (SEQ ID NO: 79)

BMS3h-72
EVQLLESGGGLVQPGGSLRLSCAASGFTFSTYDMIWVRQAPGKGLEWVSAISPNGTGIVYYADSVKGRFTISRDNSKNTL
YLQMNSLRAEDTAVYYCAKNQSVHHAVFDYWGQGTLVTVSS (SEQ ID NO: 80)

BMS3h-73
EVQLLESGGGLVQPGGSLRLSCAASGFTFENYEMTWVRQAPGKGLEWVSRIAPHGRLTYYADSVKGRFTISRDNSKNTL
YLQMNSLRAEDTAVYYCAKGQIPMLDFDYWGQGTLVTVSS (SEQ ID NO: 81)

TABLE 3-continued

Anti-Human CD40 Variable Domain Amino Acid Sequences

BMS3h-74
EVQLLESGGGLVQPGGSLRLSCAASGFTFSHYMMMWVRQAPGKGLEWVSTISHFGDITYYADSVKGRFTISRDNSKNTL
YLQMNSLRAEDTAVYYCAKNDMVMKNGGFDYWGQGTLVTVSS (SEQ ID NO: 82)

BMS3h-75
EVQLLESGGGLVQPGGSLRLSCAASGFTFERYDMSWVRQAPGKGLEWVSRIDSRGWSTYYADSVKGRFTISRDNSKNTL
YLQMNSLRAEDTAVYYCAKGLVPHLRFDYWGQGTLVTVSS (SEQ ID NO: 83)

BMS3h-76
EVQLLESGGGLVQPGGSLRLSCAASGFTFANAQMTWVRQAPGKGLEWVSRIDAMGDATYYADSVKGRFTISRDNSKNTL
YLQMNSLRAEDTAVYYCAKGKVPSIDYWGQGTLVTVSS (SEQ ID NO: 84)

BMS3h-77
EVQLLESGGGLVQPGGSLRLSCAASGFTFANAQMTWVRQAPGKGLEWVSRIDAMGDATYYADSVKGRFTISRDNSKNTL
YLQMNSLRAEDTAVYYCAKGVIPAFDYWGQGTLVTVSS (SEQ ID NO: 85)

BMS3h-78
EVQLLESGGGLVQPGGSLRLSCAASGFTFQNDRMHWVRQAPGKGLEWVSSISATGGDTYYADSVKGRFTISRDNSKNTL
YLQMNSLRAEDTAVYYCAKQTGTNRFDYWGQGTLVTVSS (SEQ ID NO: 86)

BMS3h-79
EVQLLESGGGLVQPGGSLRLSCAASGFTFNQPYMSWVRQAPGKGLEWVSSIDASGGTTYYADSVKGRFTISRDNSKNTL
YLQMNSLRAEDAAVYYCAKDRIPNLVFDYWGQGTLVTVSS (SEQ ID NO: 87)

BMS3h-80
EVQLLESGGGLVQPGGSLRLSCAASGFTFDNEMTWVRQAPGKGLEWVSRIDGGGYNTYYADSVKGRFTISRDNSKNTL
YLQMNSLRAEDTAVYYCAKGQVPELLFDYWGQGTLVTVSS (SEQ ID NO: 88)

BMS3h-81
EVQLLESGGGLVQPGGSLRLSCAASGFTFVSSNMTWVRQAPGKGLEWVSAISGSGGSTYYADSVKGRFTISRDNSKNTL
YLQMNSLRAEDTAVYYCAKGRIPTLVFDYWGQGTLVTVSS (SEQ ID NO: 89)

BMS3h-82
EVQLLESGGGLVQPGGSLRLSCAASGFTFVSSNMTWVRQAPGKGLEWVSAISGSGGSTYYADSVKGRFTISRDNSKNTL
YLQMNSLRAEDTAVYYCAKDRIPNLVFDYWGQGTLVTVSS (SEQ ID NO: 90)

BMS3h-83
EVQLLESGGGLVQPGGSLRLSCAASGFTFSDDSMSWVRQAPGKGLEWVSRINDAGSSTYYADSVKGRFTISRDNSKNTL
YLQMNSLRAEDTAVYYCAKGTIPLLEFDYWGQGTLVTVSS (SEQ ID NO: 91)

BMS3h-84
EMQLLESGGGLVQPGGSLRLSCAASGFTFVSDTMSWVRQAPGKGLEWVSRIDGTGGDTYYADSVKGRFTISRDNSKNTL
YLQMNSLRAGDTAVYYCAKGLIPDLQFDYWGQGTLVTVSS (SEQ ID NO: 92)

BMS3h-85
EVQLLESGGGLVQPGGSLRLSCAASGFTFDEEEMTWVRQAPGKGLEWVSRIIGGGHETYYADSVKGRFTISRDNSKNTL
YLQMNSLRAEDTAVYYCAKGTIPLLEFDYWGQGTLVTVSS (SEQ ID NO: 93)

BMS3h-86
EVQLLESGGGLVQPGGSLRLSCAASGFTFDNEMTWVRQAPGKDLEWVSRITERGDVTYYADSVKGRFTISRDNSKNTL
YLQMNSLRAEDTAVYYCAKGTVPTLEFDYWGQGTLVTVSS (SEQ ID NO: 94)

BMS3h-87
EVQLLESGGGLVQPGGSLRLSCAASGFTFDEEEMTWVRQAPGKGLEWVSRIIGGGHETYYADSVKGRFTISRDNSKNTL
YLQMNSLRAEDTAVYYCAKGTVPTLEFDYWGQGTLVTVSS (SEQ ID NO: 95)

BMS3h-88
EVQLLESGGGLVQPGGSLRLSCAASGFTFHETEMTWVRQAPGKGLEWVSAINRLGQDTYYADSVKGRFTISRDNSKNTL
YLQMNSLRAEDTAVYYCAKGRIPGLVFDYWGQGTLVTVSS (SEQ ID NO: 96)

BMS3h-89
EVQLLESGGGLVQPGGSLRLSCAASGFTFSDDSMSWVRQAPGKGLEWVSRINDAGSSTYYADSVKGRFTISRDNSKNTL
YLQMNSLRAEDTAVYYCAKGTVPTLEFDYWGQGTLVTVSS (SEQ ID NO: 97)

BMS3h-90
EVQLLESGGGLVQPGGSLRLSCAASGFTFDNEMTWVRQAPGKDLEWVSRITERGDVTYYADSVKGRFTISRDNSKNTL
YLQMNSLRAEDTAVYYCAKGRIPTLVFDYWGQGTLVTVSS (SEQ ID NO: 98)

BMS3h-91
EVQLLESGGGLVQPGGSLRLSCAASGFTFSDDSMSWVRQAPGKGLEWVSRINDAGSSTYYADSVKGRFTISRDNSKNTL
YLQMNSLRAEDTAVYYCAKGITPNLTFDYWGQGTLVTVSS (SEQ ID NO: 99)

BMS3h-92
EVQLLESGGGLVQPGGSLRLSCAASGFTFADEPMTWVRQAPGKGLEWVSRIPPEGAPTYYADSVKGRFTISRDNSKNTL
YLQMNSLRAEDTAVYYCAKGLIPDLQFDYWGQGTLVTVSS (SEQ ID NO: 100)

TABLE 3-continued

Anti-Human CD40 Variable Domain Amino Acid Sequences

BMS3h-93
EVQLLESGGGLVQPGGSLRLSCAASGFTFQDSDMTWVRQAPGKGLEWVSAIAAPGGSTYYADSVKGRFTISRDNSKNTL
YLQMNSLRAEDTAVYYCAKDRIPNLRFDYWGQGTLVTVSS (SEQ ID NO: 101)

BMS3h-94
EVQLLESGGGLVQPGGSLRLSCAASGFTFVSDTMSWVRQAPGKGLEWVSRIDGTGGDTYYADSVKGRFTISRDNSKNTL
YLQMNSLRAEDTAVYYCAKGQVPELLFDYWGQGTLVTVSS (SEQ ID NO: 102)

BMS3h-95
EVQLLESGGGLVQPGGSLRLSCAASGFTFQDSDMTWVRQAPGKGLEWVSAIAAPGGSTYYADSVKGRFTISRDNSKNTL
YLQMNSLRAEDTAVYYCAKDRIPNLVFDYWGQGTLVTVSS (SEQ ID NO: 103)

BMS3h-96
EVQLLESGGGLVQPGGSLRLSCAAAGFTFDLAEMTWVRQAPGKGLEWVSRIDEDGASTYYADSVKGRFTISRDNSKNTL
YLQMNSLRAEDAAVYYCAEGVIPSLTFDYWGQGTLVTVSS (SEQ ID NO: 104)

BMS3h-97
EVQLLESGGGLVQPGGSLRLSCAASGFTFTDKHMSWVRQAPGKGLEWVSRISPDGTYTYYADSVKGRFTISRDNSKNTL
YLQMNSLRAEDAAVYYCAEGVIPSLTFDYWGQGTLVTVSS (SEQ ID NO: 105)

BMS3h-98
EVQLLESGGGLVQPGGSLRLSCAASGFTFAEDDMTWVRQAPGKGLEWVSRIAVDGDRTYYADSVKGRFTISRDNSKNTL
YLQMNSLRTEDTAVYYCAKGKTPHLVFDYWGQGTLVTVSS (SEQ ID NO: 106)

BMS3h-99
EVQLLESGGGLVQPGGSLRLSCAAAGFTFDLAEMTWVRQAPGKGLEWVSRIDEDGASTYYADSVKGRFTISRDNSKNTL
YLQMNSLRAEDTAVYYCAKGQVPALVFDYWGQGTLVTVSS (SEQ ID NO: 107)

BMS3h-100
EVQLLESGGGLVQPGGSLRLSCAASGFTFEDSMMSWVRQAPGKGLEWVSRIDPGGAQTYYADSVKGRFTISRDNSKNTL
YLQMNSLRAEDTAVYYCAKGVTPDLTFDYWGQGTLVTVSS (SEQ ID NO: 108)

BMS3h-101
EVQLLESGGGLVQPGGSLRLSCAASGFTFEHADMSWVRQASGKGLEWVSRIDNSGQSTYYADSVKGRFTISRDNSKNTL
YLQMNSLRAEDTAVYYCAKGVTPDLTFDYWGQGTLVTVSS (SEQ ID NO: 109)

BMS3h-102
EVQLLESGGGLVQPGGSLRLSCAASGFTFSEAEMNWVRQAPGKGLEWVSRITTDGDSTYYADSVKGRFTISRDNSKNTL
YLQMNSLRAEDTAVYYCAKGRIPTLHFDYWGQGTLVTVSS (SEQ ID NO: 110)

BMS3h-103
EVQLLESGGGLVQPGGSLRLSCAASGFTFDDSDMTWVRQAPGKSLEWVSYIRGDDDETYYADSVKGRFTISRDNSKNTL
YLQMNSLRAEDTAVYYCAKNRIPDLVFDYWGQGTLVTVSS (SEQ ID NO: 111)

BMS3h-108
EVQLLESGGGLVQPGGSLRLSCAASGFTFNVADMQWVRQAPGKGLEWVSSISPNGWDTYYADSVKGRFTISRDNSKNTL
YLQMNSLRAEDTAVYYCAKHASTEGPTAFDYWGQGTLVTVSS (SEQ ID NO: 112)

BMS3h-109
EVQLLESGGGLVQPGGSLRLSCAASGFTFGPYDMGWVRQAPGKGLEWVSWISAHGSFTYYADSVKGRFTISRDNSKNTL
YLQMNSLRAEDTAVYYCAKWPYKFDYWGQGTLVTVSS (SEQ ID NO: 113)

BMS3h-110
EVQLLESGGGLVQPGGSLRLSCAASGFTFGSGSMSWVRQAPGKGLEWVSRIGSNGADTYYADSVKGRFTISRDNSKNTL
YLQMNSLRAEDTAVYYCAKGMVPNLVFDYWGQGTLVTVSS (SEQ ID NO: 114)

BMS3h-111
EVQLLESGGGLVQPGGSLRLSCAASGFTFNRFDMTWVRQAPGKGLEWVSAISGSGGSTYYADSVKGRFTISRDNSKNTL
YLQMNSLRAEDTAVYYCAKDRIPNLVFDYWGQGTLVTVSS (SEQ ID NO: 115)

BMS3h-112
EVQLLESGGGLVQPGGSLRLSCAASGFTFGESDMKWVRQAPGKGLEWVSSISPNGWDTYYADSVKGRFTISRDNSKNTL
YLQMNSLRAEDTAVYYCAKSPSSRLKFDYWGQGTLVTVSS (SEQ ID NO: 116)

BMS3h-139
EVQLLESGGGLVQPGGSLRLSCAASGFTFDSSEMSWVRQAPGKGLEWVSSIENQGGATYYADSVKGRFTISRDNSKNTL
YLQMNSLRAEDTAVYYCAKDRIPNLVFDYWGQGTLVTVSS (SEQ ID NO: 117)

BMS3h-140
EVQLLESGGGLVQPGGSLRLSCAASGFTLDAYPMYWVRQAPGKGLEWVSWIASGGGATYYADSVKGRFTISRDNSKNTL
YLQMNSLRAEDTAVYYCAKRTKNFDYWGQGTLVTVSS (SEQ ID NO: 118)

BMS3h-141
EVQLLESGGGLVQPGGSLRLSCAASGFTFMSYSMAWVRQAPGKGLEWVSGITSNGNRTYYADSVKGRFTISRDNSKNTL
YLQMNSLRAEDTAVYYCAKSTGANSRNFDYWGQGTLVTVSS (SEQ ID NO: 119)

TABLE 3-continued

Anti-Human CD40 Variable Domain Amino Acid Sequences

BMS3h-142
EVQLLESGGGLVQPGGSLRLSCAASGFTFEGYLMSWVRQAPGKGLEWVSSIAANGMQTYYADSVKGRFTISRDNSKNTL
YLQMNSLRAEDTAVYYCAKKPRGIWDGDFDYWGQGTLVTVSS (SEQ ID NO: 120)

BMS3h-143
EVQLLESGGGLVQPGGSLRLSCAASGFTFHESTMTWVRQAPGKGLEWVSTIRHPGEFTYYADSVKGRFTISRDNSKNTL
YLQMNSLRAGDTAVYYCAKGLIPDLQFDYWGQGTLVTVSS (SEQ ID NO: 121)

BMS3h-144
EVQLLESGGGLVQPGGSLRLSCAASGFTFAMYSMSWVRQAPGKGLEWVSSIAPPGGRTYYADSVKGRFTISRDNSKNTL
YLQMNSLRAEDTAVYYCAKQSLTGYSRSFDYWGQGTLVTVSS (SEQ ID NO: 122)

BMS3h-145
EVQLLESGGGLVQPGGSLRLSCAASGFTFSQNPMSWVRHAPGKGLEWVSTIPANGRPTSYADSVKGRFTISRDNSKNTL
YLQMNSLRAEDTAVYYCAKYSQQPGRRFDYWGQGTLVTVSS (SEQ ID NO: 123)

BMS3h-146
EVQLLESGGGLVQPGGSLRLSCAASGFTFANYHMTWVRQAPGKGLEWVSSIPDSGKQTYYADSVKGRFTISRDNSKNTL
YLQMNSLRAEDTAVYYCAKGRIPSLLFDYWGQGTLVTVSS (SEQ ID NO: 124)

BMS3h-147
EVQLLESGGGLVQPGGSLRLSCAASGFTFAQYHMRWVRQAPGKGLEWVSTINDIGSNTYYADSVKGRFTISRDNSKNTL
YLQMNSLRAEDTAVYYCAKVGGRGSFSFDYWGQGTLVTVSS (SEQ ID NO: 125)

BMS3h-148
EVQLLESGGGLVQPGGSLRLSCAASGFTFSSYDMKWVRQAPGKGLEWVSTISASGVFTYYADSVKGRFTISRDNSKNTL
YLQMNSLRAEDTAVYYCAKREHAGQPPFDYWGQGTLVTVSS (SEQ ID NO: 126)

BMS3h-149
EVQLLESGGGLVQPGGSLRLSCAASGFTFNGYAMSWVRQAPGKGLEWVSTINANGKYTYYADSVKGRFTISRDNSKNTL
YLQMNSLRAEDTAVYYCAKKLTLASNYFDYWGQGTLVTVSS (SEQ ID NO: 127)

BMS3h-150
EVQLLESGGGLVQPGGSLRLSCAASGFTFMDYDMKWVRQAPGKGLEWVSSITALGKKTYYADSVKGRFTISRDNSKNTL
YLQMNSLRAEDTAVYYCAKDSVKYPLNLFDYWGQGTLVTVSS (SEQ ID NO: 128)

BMS3h-151
EVQLLESGGGLVQPGGSLRLSCAASGFTFPHYTMAWVRQAPGKGLEWVSSIQSPGWRTYYADSVKGRFTISRDNSKNTL
YLQMNSLRAEDTAVYYCAKYGDGLPLTFDYWGQGTLVTVSS (SEQ ID NO: 129)

BMS3h-167
EVQLLESGGGLVQPGGSLRLSCAASGFTFSGTPMSWVRQAPGKGLEWVSRIGDEGQETYYADSVKGRFTISRDNSKNTL
YLQMNSLRAEDTAVYYCAKGVTPDLTFDYWGQGTLVTVSS (SEQ ID NO: 130)

BMS3h-168
EVQLLESGGGLVQPGGSLRLSCAASGFTFSSSSMSWVRQAPGKGLEWVSAIGSDGPSTYYADSVKGRFTISRDNSKNTL
YLQMNSLRAEDTAVYYCAKGRIPTLHFDYWGQGTLVTVSS (SEQ ID NO: 131)

BMS3h-169
EVQLLESGGGLVQPGGSLRLSCAASGFTFNPGEMTWVRQAPGKGLEWVSSIDGSGSSTYYADSVKGRFTISRDNSKNTL
YLQMNSLRADDTAVYYCAKGRIPTLHFDYWGQGTLVTVSS (SEQ ID NO: 132)

BMS3h-170
EVQLLESGGGLVQPGGSLRLSCAASGFTFPESMMGWVRQAPGKGLEWVSSIGYPGATTYYADSVKGRFTISRDNSKNTL
YLQMNSLRAEDTAVYYCAKGGSRDDNFDYWGQGTLVTVSS (SEQ ID NO: 133)

BMS3h-171
EVQLLESGGGLVQPGGSLRLSCAASGFTFGQHSMHWVRQAPGKGLEWVSSISVPGPKTYYADSVKGRFTISRDNSKNTL
YLQMNSLRAEDTAVYYCAKSLRDLRPGDSKSFDYWGQGTLVTVSS (SEQ ID NO: 134)

BMS3h-197
EVQLLESGGGLVQPGGSLRLSCAASGFTFGSAAMDWVRQAPGKGLEWVSSINDMGSNTYYADSVKGRFTISRDNSKNTL
YLQMNSLRAEDTAVYYCAKQGGRFDYWGQGTLVTVSS (SEQ ID NO: 135)

BMS3h-199
EVQLLESGGGLVQPGGSLRLSCAASGFTFGYDRMAWVRQAPGKGLEWVSSIDGPGGATYYADSVKGRFTISRDNSKNTL
YLQMNSLRAEDTAVYYCAEGRRVPDFDYWGQGTLVTVSS (SEQ ID NO: 136)

BMS3h-200
EVQLLESGGGLVQPGGSLRLSCAASGFTFGEYEMTWVRQAPGKGLEWVSRIDPFGSETYYADSVKGRFTISRDNSKNTL
YLQMNSLRAEDTAVYYCAEGVVPDLNFDYWGQGTLVTVSS (SEQ ID NO: 137)

BMS3h-201
EVQLLESGGGLVQPGGSLRLSCAASGFTFDKYVMGWVRQAPGKGLEWVSTIGSYGGATYYADSVKGRFTISRDNSKNTL
YLQMNSLRAEDTAVYYCAKRLTLSATKFDYWGQGTLVTVSS (SEQ ID NO: 138)

TABLE 3-continued

Anti-Human CD40 Variable Domain Amino Acid Sequences

BMS3h-203
EVQLLESGGGLVQPGGSLRLSCAASGFTFEDYVMGWVRQAPGKGLEWVSTIAHRGDITYYADSVKGRFTISRDNSKNTL
YLQMNSLRAEDTAVYYCAKRRRLSDYRFDYWGQGTLVTVSS (SEQ ID NO: 139)

BMS3h-204
EVQLLESGGGLVQPGGSLRLSCAASGFTFGQFDMYWVRQAPGKGLEWVSAISPAGTGTYYADSVKGRFTISRDNSKNTL
YLQMNSLRAEDTAVYYCAKAGDRSSLFDYRGQGTLVTVSS (SEQ ID NO: 140)

BMS3h-205
EVQLLESGGGLVQPGGSLRLSCAASGFTFKDTGMTWVRQAPGKGLEWVSSISSYGRDTYYADSVKGRFTISRDNSKNTL
YLQMNSLRAEDAAVYYCAKLNAALGFDYWGQGTLVTVSS (SEQ ID NO: 141)

BMS3h-206
EVQLLESGGGLVQPGGSLRLSCAASGFTFGPYPMSWVRQAPGKGLEWVSGINAPGTRTYYADSVKGRFTISRDNSKNTL
YLQMNSLRAEDTAVYYCAQQMSSGVFDYWGQGTLVTVSS (SEQ ID NO: 142)

BMS3h-207
EVQLLESGGGLVQPGGSLRLSCAASGFTFSNQDMTWVRQAPGKGLEWVSSIDSSGQLTYYADSVKGRFTISRDNSKNTL
YLQMNSLRAEDTAVYYCAKVKSLARFDYWGQGTLVTVSS (SEQ ID NO: 143)

BMS3h-208
EVQLLESGGGLVQPGGSLRLSCAASGFTFPESDMKWVRQAPGKGLEWVSSISPNGWDTYYADSVKGRFTISRDNSKNTL
YLQMNSLRAEDTAVYYCAKPAQVLFDYWGQGTLVTVSS (SEQ ID NO: 144)

BMS3h-209
EVQLLESGGGLVQPGGSLRLSCAASGFTFEQYVMGWVRQAPGKGLEWVSTIGTSGKYTYYADSVKGRFTISRDNSKNTL
YLQMNSLRAEDTAVYYCAQRRSLTRVHFDYWGQGTLVTVSS (SEQ ID NO: 145)

BMS3h-210
EVQLLESGGGLVQPGGSLRLSCAASGFTFGVEHMSWVRQAPGKGLEWVSAITGDGDRTYYADSVKGRFTISRDNSKNTL
YLQMNSLRAEDTAVYYCAKTVSWNGRFDYWGQGTLVTVSS (SEQ ID NO: 146)

BMS3h-211
EVQLLESGGGLVQPGGSLRLSCAASGFTFAWYNMGWVRQAPGKGLEWVSRIAPSGIITYYADSVKGRFTISRDNSKNTL
YLQMNSLRAEDTAVYYCAKGLRGKFDYWGQGTLVTVSS (SEQ ID NO: 147)

BMS3h-212
EVQLLESGGGLVQPGGSLRLSCAASGFTFSNYEMRWVRQAPGKGLEWVSSISSAGTDTYYADSVKGRFTISRDNSKNTL
YLQMNSLRAEDTAVYYCAKQSLNFDYWGQGTLVTVSS (SEQ ID NO: 148)

BMS3h-213
EVQLLESGGGLVQPGGSLRLSCVASGFTFDEEPMTWVRQAPGKGLEWVSIIDPGGGATYYADSVKGRFTISRDNSKNTL
YLQMNSLRAEDTAVYYCAKSNSMFDYWGQGTLVTVSS (SEQ ID NO: 149)

BMS3h-214
EVQLLESGGGLVQPGGSLRLSCAASGFTFSAYPMHWVRQAPGKGLEWVSSIASSGITTYYADSVKGRFTISRDNSKNTL
YLQMNSLRAEDTAVYYCAKFTRLHFPAQFDYWGQGTLVTVSS (SEQ ID NO: 150)

BMS3h-215
EVQLLESGGGLVQPGGSLRLSCAASGFTFADYAMGWVRQAPGKGLEWVSRISPEGSRTYYADSVKGRFTISRDNSKNTL
YLQMNSLRAEDTAVYYCAKLRPYASKFDYWGQGTLVTVSS (SEQ ID NO: 151)

BMS3h-230
EVQLLESGGGLVQPGGSLRLSCAASGFTFRPYDMGWVRQAPGKGLEWVSTISHQGNRTYYADSVKGRFTISRDNSKNTL
YLQMNSLRAEDTAVYYCAKVSHHFDYWGQGTLVTVSS (SEQ ID NO: 152)

BMS3h-231
EVQLLESGGGLVQPGGSLRLSCAASGFTFSAYNMWWARQAPGKGLEWVSWINSTGSRTYYADSVKGRFTISRDNSKNTL
YLQMNSLRAEDTAVYYCAKNWHRGRFDYWGQGTLVTVSS (SEQ ID NO: 153)

BMS3h-232
EVQLLESGGGLVQPGGSLRLSCAASGFTFDRYRMGWVRQAPGKGLEWVSTINRLGQSTYYADSVKGRFTISRDNSKNTL
YLQMNSLRAEDTAVYYCAKVKKHKFDYWGQGTLVTVSS (SEQ ID NO: 154)

BMS3h-233
EVQLLESGGGLVQPGGSLRLSCAASGFTFAHYNMRWVRQAPGKGLEWVSTITKTGFRTYYADSVKGRFTISRDNSKNTL
YLQMNSLRAEDTAVYYCAKAGQFDFDYWGQGTLVTVSS (SEQ ID NO: 155)

BMS3h-234
EVQLLESGGGLVQPGGSLRLSCAASGFTFYPYSMHWVRQAPGKGLEWVSTIDGSGMFTYYADSVKGRFTISRDNSKNTL
YLQMNSLRAEDTAVYYCAEDSLKASFDYWGQGTLVTVSS (SEQ ID NO: 156)

BMS3h-235
EVQLLESGGGLVQPGGSLRLSCAASGFTFPLYGMWWVRQAPGKGLEWVSYIGPYGHTTYYADSVKGRFTISRDNSKNTL
YLQMNSLRAEDTAVYYCAKKRKKKFDYWGQGTLVTVSS (SEQ ID NO: 157)

TABLE 3-continued

Anti-Human CD40 Variable Domain Amino Acid Sequences

BMS3h-236
EVQLLESGGGLVQPGGSLRLSCAASGFTFPRYRMSWVRQAPGKGLEWVSSITPYGAHTYYADSVKGRFTISRDNSKNTL
YLQMNSLRAEDTAVYYCAKYGKWYFDYWGQGTLVTVSS (SEQ ID NO: 158)

BMS3h-237
EVQLLESGGGLVQPGGSLRLSCAASGFTFNEYAMRWVRQAPGKGLEWVSTIDRLGLHTYYADSVKGRFTISRDNSKNTL
YLQMNSLRAEDTAVYYCAKSGPFTFDYWGQGTLVTVSS (SEQ ID NO: 159)

BMS3h-238
EVQLLESGGGLVQPGGSLRLSCAASGFTFERYNMRWVRQAPGKGLEWVSTIDRLGLATYYADSVKGRFTISRDNSKNTL
YLQMNSLRAEDTAVYYCAKAGSWSFDYWGQGTLVTVSS (SEQ ID NO: 160)

BMS3h-239
EVQLLESGGGLVQPGGSLRLSCAASGFTFGIYDMKWVRQAPGKGLEWVSTISSSGTHTYYADSVKGRFTISRDNSKNTL
YLQMNSLRAEDTAVYYCAKYPQPYPFDYWGQGTLVTVSS (SEQ ID NO: 161)

BMS3h-240
EVQLLESGGGLVQPGGSLRLSCAASGFTFWVYDMRWVRQAPGKGLEWVSTISATGVHTYYADSVKGRFTISRDNSKNTL
YLQMNSLRAEDTAVYYCAKYPPAGRFDYWGQGTLVTVSS (SEQ ID NO: 162)

BMS3h-241
EVQLLESGGGLVQPGGSLRLSCAASGFTFSTYDMIWVRQAPGKGLEWVSAISPNGTGTYYADSVKGRFTISRDNSKNTL
YLQMNSLRAEDTAVYYCAKPPQVNTEFDYRGQGTLVTVSS (SEQ ID NO: 163)

BMS3h-243
EVQLLESGGGLVQPGGSLRLSCAASGFTFEKEDMGWVRQAPGKGLEWVSHISPNGYATYYADSVKGRFTISRDNSKNTL
YLQMNSLRAEDTAVYYCAKSWSSFDYWGQGTLVTVSS (SEQ ID NO: 164)

BMS3h-244
EVQLLESGGGLVQPGGSLRLSCAASGFTFSATPMEWARQAPGKGLEWVSTISESGYSTYYADSVKGRFTISRDNSKNTL
YLQMNSLRAEDTAVYYCAKWNSTTGFDYWGQGTLVTVSS (SEQ ID NO: 165)

BMS3h-245
EVQLLESGGGLVQPGGSLRLSCAASGFTFNTVDMEWVRQAPGKGLEWVSSISPNGWDTYYADSVKGRFTISRDNSKNTL
YLQMNSLRAEDTAVYYCAEAPHRAFDYWGQGTLVTVSS (SEQ ID NO: 166)

BMS3h-246
EVQLLESGGGLVQPGGSLRLSCAASGFTFEDKEMSWVRQAPGKGLEWVSRIDALGDSTYYADSVKGRFTISRDNSKNTL
YLQMNSLRAEDTAVYYCAEGMVPRLKFDYWGQGTLVTVSS (SEQ ID NO: 167)

BMS3h-247
EVQLLESGGGLVQPGGSLRLSCAASGFTFSDHSMMWVRQAPGKGLEWVSDIEPHGVHTYYADSVKGRFTISRDNSKNTL
YLQMNSLRAEDTAVYYCANPTFDYWGQGTLVTVSS (SEQ ID NO: 168)

BMS3h-248
EVQLLESGGGLVQPGGSLRLSCAASGFTFSPHTMHWVRQAPGKGLEWVSGIGPDGTTTYYADSVKGRFTISRDNSKNTL
YLQMNSLRAEDTAVYYCAKRSYSWDRGWTFDYWGQGTLVTVSS (SEQ ID NO: 169)

BMS3h-249
EVQLLESGGGLVQPGGSLRLSCAASGFTFYASDMKWVRQAPGKGLEWVSSISPNGWDTYYADSVKGRFTISRDNSKNTL
YLQMNSLRAEDTAVYYCAKADYTYHSFDYWGQGTLVTVSS (SEQ ID NO: 170)

BMS3h-250
EVQLLESGGGLVQPGGSLRLSCAASGFTFAHYNMRWVRQAPGKGLEWVSTITKTGFRTYYADSVKGRFTISRDNSKNTL
YLQMNSLRAEDTAVYYCAKAGQFDFDYWGQGTLVTVSS (SEQ ID NO: 171)

BMS3h-251
EVQLLESGGGLVQPGGSLRLSCAASGFTFSHYHMGWARQAPGKGLEWVSVIGPRGISTYYADSVKGRFTISRDNSKNTL
YLQMNSLRAEDTAVYYCAKSPSRHRFDYWGQGTLVTVSS (SEQ ID NO: 172)

BMS3h-252
EVQLLESGGGLVQPGGSLRLSCAASGFTFNEYAMRWVRQAPGKGLEWVSTIDRLGLHTYYADSVKGRFTISRDNSKNTL
YLQMNSLRAEDTAVYYCAKSGPFTFDYWGQGTLVTVSS (SEQ ID NO: 173)

BMS3h-253
EVQLLESGGGLVQPGGSLRLSCAASGFTFGNYSMKWARQAPGKGLEWVSTITPDGWYTYYADSVKGRFTISRDNSKNTL
YLQMNSLRAEDTAVYYCAKVGDAVWGWIGGFDYWGQGTLVTVSS (SEQ ID NO: 174)

BMS3h-254
EVQLLESGGGLVQPGGSLRLSCAASGFTFGDYGMKWVRQAPGKGLEWVSAITSNGDFTYYADSVKGRFTISRDNSKNTL
YLQMNSLRAEDTAVYYCAKSLYKFDYWGQGTLVTVSS (SEQ ID NO: 175)

BMS3h-255
EVQLLESGGGLVQPGGSLRLSCAGSGFTFPTYKMGWVRQAPGKGLEWVSFIDYWGWRTYYADSVKGRFTISRDNSKNTL
YLQMNSLRAEDTAVYYCAKSPYSWTHDSPHFDYWGQGTLVTVSS (SEQ ID NO: 176)

TABLE 3-continued

Anti-Human CD40 Variable Domain Amino Acid Sequences

BMS3h-256
EVQLLESGGGLVQPGGSLRLSCAASGFTFRPYTMCWARQAPGKGLEWVSCISDAGSFTYYADSVKGRFTISRDNSKNTL
YLQMNSLRAEDTAVYYCAKRMSSFDYWGQGTLVTVSS (SEQ ID NO: 177)

BMS3h-257
EVQLLESGGGLVQPGGSLRLSCAASGFTFQNYQMAWVRQAPGKGLEWVSTISGTGKNTYYADSVKGRFTISRDNSKNTL
YLQMNSLRAEDTAVYYCAKTPQNYFSVRRFDYWGQGTLVTVSS (SEQ ID NO: 178)

BMS3h-258
EVQLLESGGGLVQPGGSLRLSCAASGFTFGAYTMGWVRQAPGKGLEWVSKISTSGGQTYYADSVKGRFTISRDNSKNTL
YLQMNSLRAEDTAVYYCAKPLNWWAFDYWGQGTLVTVSS (SEQ ID NO: 179)

BMS3h-272
EVQLLESGGGLVQPGGSLRLSCAASGFTFNAYPMTWVRQAPGKGLEWVSRIDGYGRHTYYADSVKGRFTISRDNSKNTL
YLQMNSLRAEDTAVYYCAKGIIPNFDYWGQGTLVTVSS (SEQ ID NO: 180)

BMS3h-273
EVQLLESGGGLVQPGGSLRLSCAASGFTFGAVDMTWVRQAPGKGLEWVSAISPSGSATYYADSVKGRFTISRDNSKNTL
YLQMNSLRAEDTAVYYCAKGRVPDLGFDYWGQGTLVTVSS (SEQ ID NO: 181)

BMS3h-274
EVQLLESGGGLVQPGGSLRLSCAASGFTFDSYAMGWARQAPGKGLEWVSAIGAKGLSTYYADSVKGRFTISRDNSKNTL
YLQMNSLRAEDTAVYYCAKAARGKFDYWGQGTLVTVSS (SEQ ID NO: 182)

BMS3h-275
EVQLLESGGGLVQPGGSLRLSCAASGFTFTRYQMGWVRQAPGKGLEWVSVINVWGSSTYYADSVKGRFTISRDNSKNTL
YLQMNSLRAEDTAVYYCAKMSGKFAYWGQGTLVTVSS (SEQ ID NO: 183)

BMS3h-276
EVQLLESGGGLVQPGGSLRLSCAASGFTFGNYSMMWVRQAPGKGLEWVSTIIPAGTSTYYADSVKGRFTISRDNSKNTL
YLQMNSLRAEDTAVYYCAKPSIRLFDYWGQGTLVTVSS (SEQ ID NO: 184)

BMS3h-279
EVQLLESGGGLVQPGGSLRLSCAASGFTFGAYDMGWVRQAPGKGLEWVSWISPNGYDTYYADSVKGRFTISRDNSKNTL
YLQMNSLRAEDTAVYYCAKGGVKFDYWGQGTLVTVSS (SEQ ID NO: 185)

BMS3h-282
EVQLLESGGGLVQPGGSLRLSCAASGFTFVWYEMAWVRQAPGKGLEWVSTIQADGEQTYYADSVKGRFTISRDNSKNTL
YLQMNSLRAEDTAVYYCAKASYALVYPPEEFDYWGQGTLVTVSS (SEQ ID NO: 186)

BMS3h-287
EVQLLESGGGLVQPGGSLRLSCAASGFTFTNYRMSWVRQAPGKGLEWVSAIDDLGVSTYYADSVKGRFTISRDNSKNTL
YLQMNSLRAEDTAVYYCAKWRLKNSQPTDFDYWGQGTLVTVSS (SEQ ID NO: 187)

BMS3h-292
EVQLLESGGGLVQPGGSLRLSCAASGFTFDQAHMWWVRQAPGKGLEWVSFINPSGYYTYYADSVKGRFTISRDNSKNTL
YLQMNSLRAEDTAVYYCAKPSLSPSSFDYWGQGTLVTVSS (SEQ ID NO: 188)

BMS3h-293
EVQLLESGGGLVQPGGSLRLSCAASGFTFETGQMGWARQAPGKGLEWVSNIDGSGTYTYYADSVKGRFTISRDNSKNTL
YLQMNSLRAEDTAVYYCAKSTQNYRFDYWGQGTLVTVSS (SEQ ID NO: 189)

BMS3h-296
EVQLLESGGGLVQPGGSLRLSCAASGFTFGAYPMYWVRQAPGKGLEWVSSIHKDGRITYYADSVKGRFTISRDNSKNTL
YLQMNSLRAEDTAVYYCAKQGTPVDGFDYWGQGTLVTVSS (SEQ ID NO: 190)

BMS3h-297
EVQLLESGGGLVQPGGSLRLSCAASGFTFPDEGMTWVRQAPGKGLEWVSTIETGGTVTYYADSVKGRFTISRDNSKNTL
YLQMNSLRAEDTAVYYCAKMDGSGTWQTFDYWGQGTLVTVSS (SEQ ID NO: 191)

BMS3h-298
EVQLLESGGGLVQPGGSLRLSCAASGFTFDSLGMGWARQAPGKGLEWVSYIRAEGAYTYYADSVKGRFTISRDNSKNTL
YLQMNSLRAEDTAVYYCAKYLADSDYWGQGTLVTVSS (SEQ ID NO: 192)

BMS3h-299
EVQLLESGGGLVQPGGSLRLSCAASGFTFSESYMEWVRQAPGKGLEWVSGIDHIGGGTYYADSVKGRFTISRDNSKNTL
YLQMNSLRAEDTAVYYCAKDDGRGGSMFDYWGQGTLVTVSS (SEQ ID NO: 193)

BMS3h-300
EVQLLESGGGLVQPGGSLRLSCAASGFTFSGGYMWWVRQAPGKGLEWVSSIGASGAYTYYADSVKGRFTISRDNSKNTL
YLQMNSLRAEDTAVYYCAKTGGRLDYWGQGTLVTVSS (SEQ ID NO: 194)

BMS3h-301
EVQLLESGGGLVQPGGSLRLSCAASGFTFDEGHMGWVRQAPGKDLEWVSYIGSLGLHTYYADSVKGRFTISRDNSKNTL
YLQMNSLRAEDTAVYYCAKREFSNGGFDYWGQGTLVTVSS (SEQ ID NO: 195)

TABLE 3-continued

Anti-Human CD40 Variable Domain Amino Acid Sequences

BMS3h-302
EVQLLESGGGLVQPGGSLRLSCAASGFTFKTSPMYWVRQAPGKGLEWVSSIDRTGGHTYYADSVKGRFTISRDNSKNTL
YLQMNSLRAEDTAVYYCAKQALLTDAKRFDYWGQGTLVTVSS (SEQ ID NO: 196)

BMS3h-303
EVQLLESGGGLVQPGGSLRLSCAASGFTFDGRDMVWVRQAPGKGLEWVSAISPSGLDTYYADSVKGRFTISRDNSKNTL
YLQMNSLRAEDTAVYYCAERPQMLVTNFDYWGQGTLVTVSS (SEQ ID NO: 197)

BMS3h-304
EVQLLESGGGLVQPGGSLRLSCAASGFTFGNDPMSWVRQAPGKGLEWVSGIGREGDSTYYADSVKGRFTISRDNSKNTL
YLQMNSLRAEDTAVYYCAKDSMRHQPFDYWGQGTLVTVSS (SEQ ID NO: 198)

BMS3h-305
EVQLLESGGGLVQPGGSLRLSCAASGFTFDETYMKWVRQAPGKGLEWVSAIGASGADTYYADSVKGRFTISRDNSKNTL
YLQMNSLRAEDTAVYYCAKFTHLNGRFDYWGQGTLVTVSS (SEQ ID NO: 199)

BMS3h-306
EVQLLESGGGLVQPGGSLRLSCAASGFTFGGWPMGWVRQAPGKGLEWVSGIDIDGAPTYYADSVKGRFTISRDNSKNTL
YLQMNSLRAEDTAVYYCAKEEAGSWSFDYWGQGTLVTVSS (SEQ ID NO: 200)

BMS3h-307
EVQLLESGGGLVQPGGSLRLSCAASGFTFSDQAMWWARQAPGKGLEWVSFIQGDGGFTYYADSVKGRFTISRDNSKNTL
YLQMNSLRAEDTAVYYCAKPSKPFDYWGQGTLVTVSS (SEQ ID NO: 201)

BMS3h-308
EVQLLESGGGLVQPGGSLRLSCAASGFTFETGQMGWARQAPGKGLEWVSNIDGSGTYTYYADSVKGRFTISRDNSKNTL
YLQMNSLRAEDTAVYYCAKAVRNFAFDYWGQGTLVTVSS (SEQ ID NO: 202)

BMS3h-309
EVQLLESGGGLVQPGGSLRLSCAASGFTFSGHDMSWVRQAPGKGLEWVSAISPHGTHTYYADSVKGRFTISRDNSKNTL
YLQMNSLRAEDTAVYYCAKGIRGWIGHDTQPFDYWGQGTLVTVSS (SEQ ID NO: 203)

BMS3h-310
EVQLLESGGGLVQPGGSLRLSCAASGFTFESKDMLWVRQAPGKGLEWVSSISSDGTHTYYADSVKGRFTISRDNSKNTL
YLQMNSLRAEDTAVYYCAQELGGSWQFDYWGQGTLVTVSS (SEQ ID NO: 204)

BMS3h-311
EVQLLESGGGLVQPGGSLRLSCAASGFTFADRDMVWVRQAPGKGLEWVSGIGASGTSTYYADSVKGRFTISRDNSKNTL
YLQMNSLRAEDAAVYYCAKGGTGPTDLWDFDYWGQGTLVTVSS (SEQ ID NO: 205)

BMS3h-312
EVQLLESGGGLVQPGGSLRLSCAASGFTFDDEKMLWVRQAPGKGLEWVSSISVSGLHTYYADSVKGRFTISRDNSKNTL
YLQMNSLRAEDTAVYYCAKEEAGSWSFDYWGQGTLVTVSS (SEQ ID NO: 206)

BMS3h-313
EVQLLESGGGLVQPGGSLRLSCAASGFTFGQERMIWVRQAPGKGLEWVSDISASGGTTYYADSVKGRFTISRDNSKNTL
YLQMNSLRAEDTAVYYCAKEEAGSWSFDYWGQGTLVTVSS (SEQ ID NO: 207)

BMS3h-37-1
EVQLLESGGGLVQPGGSLRLSCAASGFTFEWYEMQWVRQAPGKGLEWVSAISGDGYRTYYADSVKGRFTISRDNSMNTL
YLQMNSLRAEDTAVYYCAKELGYFDYRGRGTLVTVSS (SEQ ID NO: 208)

BMS3h-37-2
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELGYFDYWGRGTLVTVSS (SEQ ID NO: 209)

BMS3h-37-3
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELGYFDYRVQGTLVTVSS (SEQ ID NO: 210)

BMS3h-37-4
EVQLLESGGGLVQPGGSLRLSCAASGFTFEWYEMQWVRKAPGKGLEWVSAISGDGYRTYYADSVKGRFTISRDNSKNTL
YLQMNSLRAEDTAVYYCAKELGYFDYWGRGTLVTVSS (SEQ ID NO: 211)

BMS3h-37-5
EVQLLESGGGLVQPGGSLRLSCAASGFTFEWYEMQWVRQAPGKGLEWISAISGDGYRTYYADSVKGRFTISRDNSKNTL
YLQMNSLRAEDTAVYYCAKELGYFDYRVQGTLVTVSS (SEQ ID NO: 212)

BMS3h-37-6
EVQLLESGGGLVQPGGSLRLSCAASGFTFEWYEMQWVRRAPGKGLEWVSAISGDGYRTYYADSVKGRFTISRDNSENTL
YLQMNSLRAEDTAVYYCAKELGYFDYWGRGTLVTVSS (SEQ ID NO: 213)

BMS3h-37-7
EVQLLETGGGLVQPGGSLRLSCAASGFTFEWYEMQWVRRAPGKGLEWVSAISGDGYRTYYADSVKGRFTISRDNSKNTL
YLQMDSLRAEDTAVYYCAKELGYFDYWGRGTLVTVTS (SEQ ID NO: 214)

TABLE 3-continued

Anti-Human CD40 Variable Domain Amino Acid Sequences

BMS3h-37-8
EVQLLESGGGLVQPGGSLRLSCAASGFTFEWYEMQWVRQAPGKGLEWVSAISGDGYRTYYADSVKGRFTISRDNSKNTL
YLQMNSLRAEDTAVYYCAKELGYFHYWGRGTLVTVSS (SEQ ID NO: 215)

BMS3h-37-9
EVQLLESGGGLVQPGGSLRLSCVASGFTFEWYEMQWVRQAPGNGLEWISAISGDGYRTYYADSVKGRFTISRDNSKNTL
YLQMNSLRAEDTAVYYCAKELGYFDYWGRGTLVTVSS (SEQ ID NO: 216)

BMS3h-37-10
EVQLLESGGGLVQPGGSLRLSCAASGFTFEWYEMQWVRRAPGKGLEWVSAISGDGYRTYYADSVKGRFTISRDNSKNTL
YLLMNSLRAEDTAVYYCAKELGYFDYWGRGTLVTVSS (SEQ ID NO: 217)

BMS3h-37-11
EVQLLESGGGLVQPGGSLRLSCAASGFTFEWYEMQWVRKAPGKGLEWVSAISGDGYRTYYADSVKGRFTISRDNSKNTL
YLQMNSLRAEDTAVYYCAKELGYFDYRGRGTLVTVSS (SEQ ID NO: 218)

BMS3h-37-12
EVQLLESGGGLVQPGGSMRLSCAASGFTFEWYEMQWVRRAPGKGLEWVSAISGDGYRTYYADSVKGRFTISRDNSKNTL
YLQMNSLRAEDTAVYYCAKELGYFDYRGRGTLVTVSS (SEQ ID NO: 219)

BMS3h-37-201
EVQLLESGGGLVQPGGSLRLSCAASGFTFEWYEMQWVRRAPGKGLEWVSMISGDGYRTYYADSVKGRFTISRDNSKNTL
YLQMNSLRAEDTAVYYCAKELGYFDYWGRGTLVTVSS (SEQ ID NO: 220)

BMS3h-37-202
EVQLLESGGGLVQPGGSLRLSCAASGFTFEWYEMQWVRRAPGKGLEWVSAISGDGWRTYYADSVKGRFTISRDNSKNTL
YLQMNSLRAEDTAVYYCAKELGYFDYWGRGTLVTVSS (SEQ ID NO: 221)

BMS3h-37-203
EVQLLESGGGLVQPGGSLRLSCAASGFTFGWYEMQWVRRAPGKGLEWVSAISGDGYRTYYADSVKGRFTISRDNSKNTL
YLQMNSLRAEDTAVYYCAKELLYFDYWGRGTLVTVSS (SEQ ID NO: 222)

BMS3h-37-204
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELGFFDYWGRGTLVTVSS (SEQ ID NO: 223)

BMS3h-37-205
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELEYFDYWGRGTLVTVSS (SEQ ID NO: 224)

BMS3h-37-206
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKGLEYFDYWGRGTLVTVSS (SEQ ID NO: 225)

BMS3h-37-207
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELAFFDYWGRGTLVTVSS (SEQ ID NO: 226)

BMS3h-37-208
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELLYFDYWGRGTLVTVSS (SEQ ID NO: 227)

BMS3h-37-209
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELEFFDYWGRGTLVTVSS (SEQ ID NO: 228)

BMS3h-37-210
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELQFFDYWGRGTLVTVSS (SEQ ID NO: 229)

BMS3h-37-211
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELLFFDYWGRGTLVTVSS (SEQ ID NO: 230)

BMS3h-37-212
EVQLLESGGGLVRPGGSLRLSCAASGFTFEWYEMQWVRRAPGKGLEWVSAISGDGYRTYYADSVKGRFTISRDNSKNTL
YLQMNSLRAEDTAVYYCAKELEFFDYWGRGTLVTVSS (SEQ ID NO: 231)

BMS3h-37-213
EVQLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELLFFDYRGRGTLVTVSS (SEQ ID NO: 232)

BMS3h-37-214
EVQLLESGGGLVQPGGSLRLSCAASGFIFEWYEMQWVRRAPGKGLEWVSAISGDGYRTYYADSVKGRFTISRDNSKNTL
YLQMNSLRAEDTAVYYCAKNLEYFDYWGRGTLVTVSS (SEQ ID NO: 233)

TABLE 3-continued

Anti-Human CD40 Variable Domain Amino Acid Sequences

BMS3h-37-215
EVRLLESGGGLVQPGGSLRLSCAASGFTFEWYEMQWVRRAPGKGLEWVSAISGDGYRTYYADSVKGRFTISRDNSKNTL
YLQMNSLRAEDTAVYYCAKELQFFDYWGRGTLVTVSS (SEQ ID NO: 234)

BMS3h-38-1
EVQLLGSGGGLVQPGGSLRLSCAASGFTFEEEEMIWVRQAPGKGLEWVSAISGSGGSTYYADSVKGRFTISRDNSKNTL
YLQMNSLRAEDTAVYYCSKEPFRFDYWGQGTLVTVSS (SEQ ID NO: 235)

BMS3h-38-2
EVQLLASGGGLVQPGGSLRLSCAASGFTFEEEEMIWVRQAPGKGLEWVSAISGSGGSTYYADSVKGRFTISRDNSKNTL
YLQMNSLRAEDTAVYYCGKEPFRYDYWGQGTLVTVSS (SEQ ID NO: 236)

BMS3h-38-3
EVQLLASGGGLVQPGGSLRLSCAASGFTFEEEEMIWVRQAPGKGLEWISAISGSGGSTYYADSVKGRFTISRDNSKNTL
YLQMNSLRAEDTAVYYCGKEPFRFDYWGQGTLVTVSS (SEQ ID NO: 237)

BMS3h-38-4
EVQLLDPGGGLVQPGGSLRLSCAASGFTFGKEEMIWVRQAPGKGLEWVSSISGSGGSTYYADSVKGRFTISRDNSRNTL
YLQMNSLRAEDTAVYYCGKEPFRFDYWGQGTLVTVSS (SEQ ID NO: 238)

BMS3h-38-5
EVQLLGSGGGLVQPGGSLRLSCAASGFTFEEEEMIWVRQAPGKGLEWVSAISGSGGSTYYADSVKGRFTISRDNSKNTL
YLQMNSLRAEDTAVYYCGKEPFRFDYWGQGTLVTVSS (SEQ ID NO: 239)

BMS3h-38-6
EVQLLEPGGGLVQPGGSLRLSCAASGFTFEEEEMIWVRQAPGKGLEWVSAISGSGGSTYYADSVKGRFTISRDNSKNTL
YLLMNSLRAEDTAVYYCSKEPFRFDYWGQGALVTVSS (SEQ ID NO: 240)

BMS3h-38-7
EVQLLDPGGGLVQPGGSLRLSCAASGFTFGKEEMIWVRQAPGKGLEWVSSISGSGGSTYYADSVKGRFTISRDNSKNTL
YLQMNSLRAEDTAVYYCAKEPLRFDYWGQGTLVTVSS (SEQ ID NO: 241)

BMS3h-38-8
EVQLLESGGGLVQPGGSLRLSCAASGFTFEEEEMIWVRQAPGKGLEWISAISGSGGSTYYADSVKGRFTIHRDNSKNTL
YLQMNSLRAEDTAVYYCSKEPFRFDYRGLGTLVTVSS (SEQ ID NO: 242)

BMS3h-38-9
EVQLLDPGGGLVQPGGSLRLSCAASGFTFGKEEMIWVRQAPGKGLEWVSSISGSGGSTYYADSVKGRFTISRDNSRNTL
YLQMNSLRAEDTAVYYCAKEPLRFDYWGQGTLVTVSS (SEQ ID NO: 243)

BMS3h-38-10
EVQLLDSGGGFVQPGGSLRLSCAASGFTFEEEEMIWVRQAPGKGLEWISAISGSGGSTYYADSVKGRFTISRDNSKNTL
YLQMNSLRAEDTAVYYCAKEPFRFDYWGQGTLVTVSS (SEQ ID NO: 244)

BMS3h-38-11
EVQLLDPGGGLVQPGGSLRLSCAASGFTFEEEEMIWVRQAPGKGLEWISAISGSGGSTYYADSVKGRFTISRDNSNNTL
YLQMNSLRAEDTAVYYCGREPFRFDYWGQGTLVTVSS (SEQ ID NO: 245)

BMS3h-38-12
EVRLLESGEGLVQPGGSLRLSCAASGFTFEEEEMIWVRQAPGKGLEWVSAISGSGGSTYYADSVKGRFTISRDNSKNTL
YLQMNSLRAEDTAVYYCGKEPFRFDYWGQGTLVTVSS (SEQ ID NO: 246)

BMS3h-38-13
EVQQLESGGGLVQPGGSLRLSCAASGFTFEEEEMIWVRQAPGKGLEWVSAISGSGGSTYYADSVKGRFTISRDNSKNTL
YLQMNSLRAEDTAVYYCGKEPFRFDYWGQGTLVTVSS (SEQ ID NO: 247)

BMS3h-38-201
EVQLLASGGGLVQPGGSLRLSCAASGFTFEEEEMIWVRQAPGKGLEWVSAISGSGGSTYYADSVKGRFTISRDNSKNTL
YLQMNSLRAEDTAVYYCGKEPFYYDYWGQGTLVTVSS (SEQ ID NO: 248)

BMS3h-38-202
EVQLLASGGGLVQPGGSLRLSCAASGFTFEEEEMIWVRQAPGKGLEWVSAISGSGGSTYYADSVKGRFTISRDNSKNTL
YLQMNSLRAEDTAVYYCGKEPFYFDYWGQGTLVTVSS (SEQ ID NO: 249)

BMS3h-38-203
EVQLLASGGGLVQPGGSLRLSCAASGFTFEEKEMIWVRQAPGKGLEWVSAISGSGGSTYYADSVKGRFTISRDNSKNTL
YLQMNSLRAEDTAVYYCGKEPFFYDYWGQGTLVTVSS (SEQ ID NO: 250)

BMS3h-38-204
EVQLLASGGGLVQPGGSLRLSCAASGFTFPQEEMIWVRQAPGKGLEWVSAISGSGGSTYYADSVKGRFTISRDNSKNTL
YLQMNSLRAEDTAVYYCGKEPFRYDYWGQGTLVTVSS (SEQ ID NO: 251)

BMS3h-38-205
EVQLLASGGGLVQPGGSLRLSCAASGFTFFAAEMIWVRQAPGKGLEWVSAISGSGGSTYYADSVKGRFTISRDNSKNTL
YLQMNSLRAEDTAVYYCGKEPFRYDYWGQGTLVTVSS (SEQ ID NO: 252)

TABLE 3-continued

Anti-Human CD40 Variable Domain Amino Acid Sequences

BMS3h-38-206
EVQLLASGGGLVQPGGSLRLSCAASGFTFEEEEMIWVRQAPGKGLEWVSAISRPGTSTYYADSVKGRFTISRDNSKNTL
YLQMNSLRAEDTAVYYCGKEPFRYDYWGQGTLVTVSS (SEQ ID NO: 253)

BMS3h-38-207
EVQLLASGGGLVQPGGSLRLSCAASGFTFEEEEMIWVRQAPGKGLEWVSAISRMGFSTYYADSVKGRFTISRDNSKNTL
YLQMNSLRAEDTAVYYCGKEPFRYDYWGQGTLVTVSS (SEQ ID NO: 254)

BMS3h-38-208
EVQLLASGGGLVQPGGSLRLSCAASGFTFEEEEMIWVRQAPGKGLEWVSAISRWGHSTYYADSVKGRFTISRDNSKNTL
YLQMNSLRAEDTAVYYCGKEPFRYDYWGQGTLVTVSS (SEQ ID NO: 255)

BMS3h-38-209
EVQLLASGGGLVQPGGSLRLSCAASGFTFEEEEMIWVRQAPGKGLEWVSAISRLGWSTYYADSVKGRFTISRDNSKNTL
YLQMNSLRAEDTAVYYCGKEPFRYDYWGQGTLVTVSS (SEQ ID NO: 256)

BMS3h-38-210
EVQLLASGGGLVQPGGSLRLSCAASGFTFEEEEMIWVRQAPGKGLEWVSAISRWGASTYYADSVKGRFTISRDNSKNTL
YLQMNSLRAEDTAVYYCGKEPFRYDYWGQGTLVTVSS (SEQ ID NO: 257)

BMS3h-38-211
EVQLLASGGGLVQPGGSLRLSCAASGFTFEEEEMIWVRQAPGKGLEWVSAISRQGGSTYYADSVKGRFTISRDNSKNTL
YLQMNSLRAEDTAVYYCGKEPFRYDYWGQGTLVTVSS (SEQ ID NO: 258)

BMS3h-38-212
EVQLLASGGGLVQPGGSLRLSCAASGFTFEEEEMIWVRQAPGKGLEWVSAISVSGWSTYYADSVKGRFTISRDNSKNTL
YLQMNSLRAEDTAVYYCGKEPFRYDYWGQGTLVTVSS (SEQ ID NO: 259)

BMS3h-38-213
EVQLLASGGGLVQPGGSLRLSCAASGFTFEEEEMIWVRQAPGKGLEWVSAISRWGWSTYYADSVKGRFTISRDNSKNTL
YLQMNSLRAEDTAVYYCGKEPFRYDYWGQGTLVTVSS (SEQ ID NO: 260)

BMS3h-38-214
EVQLLASGGGLVQPGGSLRLSCAASGFTFEEEEMIWVRQAPGKGLEWVSAISRNGLSTYYADSVKGRFTISRDNSKNTL
YLQMNSLRAEDTAVYYCGKEPFRYDYWGQGTLVTVSS (SEQ ID NO: 261)

BMS3h-38-215
EVQLLASGGGLVQPGGSLRLSCAASGFTFEEEEMIWVRQAPGKGLEWVSAISGLGWSTYYADSVKGRFTISRDNSKNTL
YLQMNSLRAEDTAVYYCGKEPFRYDYWGQGTLVTVSS (SEQ ID NO: 262)

BMS3h-38-216
EVQLLASGGGLVQPGGSLRLSCAASGFTFEEEEMIWVRQAPGKGLEWVSAISALGWSTYYADSVKGRFTISRDNSKNTL
YLQMNSLRAEDTAVYYCGKEPFRYDYWGQGTLVTVSS (SEQ ID NO: 263)

BMS3h-38-217
EVQLLASGGGLVQPGGSLRLSCAASGFTFEEEEMIWVRQAPGKGLEWVSAISRRGYSTYYADSVKGRFTISRDNSKNTL
YLQMNSLRAEDTAVYYCGKEPFRYDYWGQGTLVTVSS (SEQ ID NO: 264)

BMS3h-38-218
EVQLLASGGGLVQPGGSLRLSCAASGFTFEEEEMIWVRQAPGKGLEWVSAISRHGWSTYYADSVKGRFTISRDNSKNTL
YLQMNSLRAEDTAVYYCGKEPFRYDYWGQGTLVTVSS (SEQ ID NO: 265)

BMS3h-38-219
EVQLLASGGGLVQPGGSLRLSCAASGFTFEEEEMIWVRQAPGKGLEWVSSISRSGGSTYYADSVKGRFTISRDNSKNTL
YLQMNSLRAEDTAVYYCGKEPFRYDYWGQGTLVTVSS (SEQ ID NO: 266)

BMS3h-38-220
EVQLLASGGGLVQPGGSLRLSCAASGFTFEEEEMIWVRQAPGKGLEWVSAISRIGNSTYYADSVKGRFTISRDNSKNTL
YLQMNSLRAEDTAVYYCGKEPFRYDYWGQGTLVTVSS (SEQ ID NO: 267)

BMS3h-38-221
EVQLLASGGGLVQPGGSLRLSCAASGFTFEEEEMIWVRQAPGKGLEWVSAISGHGWSTYYADSVKGRFTISRDNSKNTL
YLQMNSLRAEDTAVYYCGKEPFRYDYWGQGTLVTVSS (SEQ ID NO: 268)

BMS3h-38-222
EVQLLASGGGLVQPGGSLRLSCAASGFTFEEEEMIWVRQAPGKGLEWVSAISRWGGSTYYADSVKGRFTISRDNSKNTL
YLQMNSLRAEDTAVYYCGKEPFRYDYWGQGTLVTVSS (SEQ ID NO: 269)

BMS3h-38-223
EVQLLASGGGLVQPGGSLRLSCAASGFTFEEEEMIWVRQAPGKGLEWVSAISGSGGSTYYADSVKGRFTISRDNSKNTL
YLQMNSLRAEDTAVYYCGKEPFMYDYWGQGTLVTVSS (SEQ ID NO: 270)

BMS3h-38-224
EVQLLASGGGLVQPGGSLRLSCAASGFTFEEEEMIWVRQAPGKGLEWVSAISGSGGSTYYADSVKGRFTISRDNSKNTL
YLQMNSLRAEDTAVYYCGKEPFPYDYWGQGTLVTVSS (SEQ ID NO: 271)

TABLE 3-continued

Anti-Human CD40 Variable Domain Amino Acid Sequences

BMS3h-38-225
EVQLLASGGGLVQPGGSLRLSCAASGFTFEEEEMIWVRQAPGKGLEWVSAISGSGGGTYYADSVKGRFTISRDNSKNTL
YLQMNSLRAEDTAVYYCGKEPFRYDYWGQGTLVTVSS (SEQ ID NO: 272)

BMS3h-38-226
EVQLLASGGGLVQPGGSLRLSCAASGFTFEEEEMIWVRQAPGKGLEWVSAISGSGGSTYYADSVKGRFTISRDNSKNTL
YLQMNSLRAEDTAVYYCGKEPLYYDYWGQGTLVTVSS (SEQ ID NO: 273)

BMS3h-38-227
EVQLLASGGGLVQPGGSLRLSCAASGFTFEEEEMIWVRQAPGKGLEWVSAISGSGGSTYYADSVKGRFTISRDNSKNTL
YLQMNSLRAEDTAVYYCGKEPMYYDYWGQGTLVTVSS (SEQ ID NO: 274)

BMS3h-38-228
EVQLLASGGGLVQPGGSLRLSCAASGFTFEEEEMIWVRQAPGKGLEWVSAISRNGFSTYYADSVKGRFTISRDNSKNTL
YLQMNSLRAEDTAVYYCGKEPFRYDYWGQGTLVTVSS (SEQ ID NO: 275)

BMS3h-38-229
EVQLLASGGGLVQPGGSLRLSCAASGFTFEEEEMIWVRQAPGKGLEWVSAISRTGGSTYYADSVKGRFTISRDNSKNTL
YLQMNSLRAEDTAVYYCGKEPFRYDYWGQGTLVTVSS (SEQ ID NO: 276)

BMS3h-38-230
EVQLLASGGGLVQPGGSLRLSCAASGFTFEEEEMIWVRQAPGKGLEWVSAISREGGSTYYADSVKGRFTISRDNSKNTL
YLQMNSLRAEDTAVYYCGKEPFRYDYWGQGTLVTVSS (SEQ ID NO: 277)

BMS3h-38-231
EVQLLASGGGLVQPGGSLRLSCAASGFPFEEEEMIWVRQAPGKGLEWVSAISRQGWSTYYADSVKGRFTISRDNSKNTL
YLQMNSLRAEDTAVYYCGKEPFRYDYWGQGTLVTVSS (SEQ ID NO: 278)

BMS3h-38-232
EVQLLASGGGLVQPGGSLRLSCAASGFTFEEEEMIWVRQAPGKGLEWVSAISRGGGSTYYADSVKGRFTISRDNSKNTL
YLQMNSLRAEDTAVYYCGKEPFRYDYWGQGTLVTVSS (SEQ ID NO: 279)

BMS3h-38-233
EVQLLASGGGLVQPGGSLRLSCAASGFTFEEEEMIWVRQAPGKGLEWVSAISRTGYSTYYADSVKGRFTISRDNSKNTL
YLQMNSLRAEDTAVYYCGKEPFRYDYWGQGTLVTVSS (SEQ ID NO: 280)

BMS3h-38-234
EVQLLASGGGLVQPGGSLRLSCAASGFTFEEEEMIWVRQAPGKGLEWVSAISRNGRSTYYADSVKGRFTISRDNSKNTL
YLQMNSLRAEDTAVYYCGKEPFRYDYWGQGTLVTVSS (SEQ ID NO: 281)

BMS3h-38-235
EVQLLASGGGLVQPGGSLRLSCAASGFTFEEEEMIWVRQAPGKGLEWVSAISRNGYSTYYADSVKGRFTISRDNSKNTL
YLQMNSLRAEDTAVYYCGKEPFRYDYWGQGTLVTVSS (SEQ ID NO: 282)

BMS3h-38-236
EVQLLASGGGLVQPGGSLRLSCAASGFTFEEEEMIWVRQAPGKGLEWVSAISRKGSSTYYADSVKGRFTISRDNSKNTL
YLQMNSLRAEDTAVYYCGKEPFRYDYWGQGTLVTVSS (SEQ ID NO: 283)

BMS3h-38-237
EVQLLASGGGLVQPGGSLRLSCAASGFTFEEEEMIWVRQAPGKGLEWVSAISRGGWSTYYADSVKGRFTISRDNSKNTL
YLQMNSLRAEDTAVYYCGKEPFRYDYWGQGTLVTVSS (SEQ ID NO: 284)

BMS3h-38-238
EVQLLASGGGLVQPGGSLRLSCAASGFTFEEEEMIWVRQAPGKGLEWVSAISRSGYSTYYADSVKGRFTISRDNSKNTL
YLQMNSLRAEDTAVYYCGKEPFRYDYWGQGTLVTVSS (SEQ ID NO: 285)

BMS3h-38-239
EVQLLASGGGLVQPGGSLRLSCAASGFTFEEEEMIWVRQAPGKGLEWVSAISRNGMSTYYADSVKGRFTISRDNSKNTL
YLQMNSLRAEDTAVYYCGKEPFRYDYWGQGTLVTVSS (SEQ ID NO: 286)

BMS3h-38-240
EVQLLESGGGLVQPGGSLRLSCAASGFTFEEEEMIWVRQAPGKGLEWVSAISRNGYSTYYADSVKGRFTISRDNSKNTL
YLQMNSLRAEDTAVYYCGKEPFRYDYWGQGTLVTVSS (SEQ ID NO: 287)

BMS3h-41-1
EVQLLESGEGLVQPGGSLRLSCAASGFTFTEHEMIWVRQAPGKGLEWVSSISGNGANTYYADSVKGRFTISRDNSKNTL
YLQMNSLRPEDTAVYYCAKEPLRFDYWGQGTLVTVSS (SEQ ID NO: 288)

BMS3h-41-2
EVQLLESGGGLVQPGGSLRLSCAASGSTFTEYEMIWVRQAPGKGLEWISSISGNGANTYYADSVKGRFTISRDNSKNTL
YLQMNSLRAEDTAVYFCAKEPLRFDYRGQGTLVTVSS (SEQ ID NO: 289)

BMS3h-41-3
EVQLLEPGGGLVQPGGSLRLSCAASGFTFTEYEMIWVRKAPGKGMEWVSSISGNGANTYYADSVKGRFTISRDNSKNML
YLQMNSLRAEDTAVYYCAKEPLRFGYWGQGTLVTVSS (SEQ ID NO: 290)

TABLE 3-continued

Anti-Human CD40 Variable Domain Amino Acid Sequences

BMS3h-41-4
EVQLLDSGGGLVQPGGSLRLSCAASGFTFTEYEMIWVRQAPGKGLEWVSSISGNGANTYYADSVKGRFTISRDNSKNTL
YLQMNSLRAEDTAVYYCAKEPLRFDYWGRGTLVTVSS (SEQ ID NO: 291)

BMS3h-41-5
EVQLLGSGGGLVQPGGSLRLSCAASGFTFTEYEMIWVRQAPGKSLEWVSSISGNGANTYYADSVKGRFTISRDNSKNTL
YLQMNSLRAEDTAVYYCAKEPLRYDDWGQGTLVTVSS (SEQ ID NO: 292)

BMS3h-41-6
EVQPLESGGGLVQPGGSLRLSCSASGFTFNEYEMIWVRQAPGKGLEWVSSISGNGANTYYADSVKGRFTISRDNSKNTL
YLQMNSLRAEDTAVYYCAKEPLRFDYWGQGTLVTVSS (SEQ ID NO: 293)

BMS3h-41-7
EVQLLESGEGLVQPGGSLRLSCAASGFTFAEYEMIWVRQAPGKGLEWVSSISGNGANTYYADSVKGRFTISRDNSKNTL
YLQMNSLRAEDTAVYYCAKEPLRFDYWGQGTLVTVSS (SEQ ID NO: 294)

BMS3h-41-8
EVQLLDPGGGLVQPGGSLRLSCAASGFTFTESEMIWVRQAPGKGLEWVSSISGNGANTYYADSVKGRFTISRDNSKNTL
YLQMNSLRAEDTAVYYCAKEPLRFDYWGQGTLVTVSS (SEQ ID NO: 295)

BMS3h-41-9
EVQLLEPGGGLVQPGGSLRLSCAASGFTFTEYEMIWVRKAPGKGMEWVSSISGNGANTYYADSVKGRFTISRDNSKNTL
YLQMNSLRPEDTAVYYCAKEPLRFDDWGQGTLVTVSS (SEQ ID NO: 296)

BMS3h-41-10
EVQLLESGVGLVQPGGSLRLSCAASGFTFTEYEMIWVRKAPGKGLEWVSSISGNGANTYYADSVKGRFTISRDNSKNTL
YLQMNSLRAEDTAVYYCAKEPLRFDNWGQGTLVTVSS (SEQ ID NO: 297)

BMS3h-41-11
EVQLLESRGGLVQPGGSLRLSCAASGFTFTEHEMIWVRQAPGKGLEWVSSISGNGANTYYADSVKGRFSVSRDNSKNTL
YLQMNSLRAEDTAVYYCAKEPLRFDYWGQGTLVTVSS (SEQ ID NO: 298)

BMS3h-41-12
EVQPLESGGGLVQPGGSLRLSCAASGFTFTEYEMIWVRQAPGKGLEWVSSISGNGANTYYADSVKGRFTISRDNSKNTL
YLQMNSLRAEDTAVYYCAKEPLRFDYWGQGTLVTVSS (SEQ ID NO: 299)

BMS3h-41-13
EVQLLESAGGLVQPGGSLRLSCAASGFTFAEYEMIWVRQAPGKGLEWVSSISGNGANTYYADSVKGRFTISRDNSKNTL
YLQMNSLRAEDTAVYYCAKEPLRFDYWGQGALVTVSS (SEQ ID NO: 300)

BMS3h-41-14
EVQLLEPGGGLVQPGGSLRLSCAASGFTFTEYEMIWVRQAPGKGLEWVSSISGNGANTYYADSVKGRFTISRDNSKNTL
YLQMNSLRAEDTAVYYCAKEPLRFDNWGQGTLVTVSS (SEQ ID NO: 301)

BMS3h-43-1
EVQLLESGGGLVQPGGSLRLSCTASGFTFNMYEMSWVRQAPGKGLEWVSGISRRGFTTYYADSVKGRFTISRDNSKNTL
YLQMNSLRAEDTAVYYCAKEPITYDLRYARFDYSGQGTLVTVSS (SEQ ID NO: 302)

BMS3h-43-2
EEQLLESGGGLVQPGGSLRLSCTASGFTFNMYEMSWVRQAPGKGLEWVSGISRRGFTTYYADSVKGRFTISRDNSKNTL
YLQMNSLRAEDTAVYYCAKEPITYATRYARFDYWGQGTLVTVSS (SEQ ID NO: 303)

BMS3h-43-3
EVQLLESGGGLVQPGGSLRLSCTASGFTFNMYEMSWVRQAPGKGLEWVSGISRRGFTTYYADSVKGRFTISRDNFKNTL
YLQMNSLRAEDTAVYYCAKEPITYDMRYARFDYGGQGTLVTVSS (SEQ ID NO: 304)

BMS3h-43-4
EVQLLESGGGLVQPGGSLRLSCTASGFTFNMYEMSWVRQAPGKGLEWVSGISRRGFTTYYADSVKGRFTISRDNSKNTL
YLQMNSLRAEDTAVYYCAKEPITYDMRYARFDNWGQGTLVTVSN (SEQ ID NO: 305)

BMS3h-43-5
EVQLLESGGGLVQPGGSLRLSCTASGFTFNTYEMSWVRQAPGKGLEWVSGIGRRGFTTYYADSVKGRFTISRDNSKNTL
YLQMNSLRAEDTAVYYCAKEPITYDLRYARFDYSGQGTLVTVSS (SEQ ID NO: 306)

BMS3h-43-6
EVQLMESGGGLVQPGGSLRLSCTASGFSFNMYEMSWVRQAPGKGLEWVSGISRRGYTTYYADSVKGRFTISRDNSKNTL
YLQMNSLRAEDTAVYYCAKEPITYDMRYARFDYWGRGTLVTVSS (SEQ ID NO: 307)

BMS3h-43-7
EVQLLESGGGLVQPGGSLRLSCTASGFAFNMYEMSWVRQAPGKGLEWVSGISRHGFTTYYADSVKGRFTVSRDNSKNTL
YLQMNSLRAEDTAVYYCAKEPITYDMRYARSDYWGQGTLVTVSS (SEQ ID NO: 308)

BMS3h-43-8
EVQLLESGGGLVQPGGSLRLSCTASGFTFNMYEMSWVRQAPGKGLEWVSGISRRGFTTYYADSVKGRFTISRDNSKNTL
YLQMNSLRAEDTAVYFCAKEPITYDMRYARSDYWGQGTLVTVSS (SEQ ID NO: 309)

TABLE 3-continued

Anti-Human CD40 Variable Domain Amino Acid Sequences

BMS3h-43-9
EVQLLESGGGLVQPGGSLRLSCTASGFTFNMYEMSWVRQAPGKGLEWVSGISRRGFTTYYADSVKGRFTISRDNSKNTL
YLQMNSLRAEDTAVYYCAKEPITYSMRYARFDYSGLGTMVTVSS (SEQ ID NO: 310)

BMS3h-43-10
EVQLLESGGGLVQPGGSLRLSCTASGFTFNMYEMSWVRQAPGKGLEWVSGISRRGFTTYYADSVKGRFTISRDNSKNTL
YLQMNSLRAEDTAVYYCAKEPITYDMRYARFDYSGQGTLVTVSS (SEQ ID NO: 311)

BMS3h-43-11
EVQLLESGGGLVQPGGSLRLSCTASGFTFNMYEMSWVRKAPGKGLEWVSGISRHGFTTYYADSVKGRFTISRDNSKNTL
YLQMNSLRAEDTAVYYCAKEPITYDMRYARFDYWGQGTLVTVSS (SEQ ID NO: 312)

BMS3h-43-12
EVQLFESGGGLVQPGGSLRLSCTASGFTFNMYEMSWVRQAPGKGLEWVSGISRRGFTTYYADSVKGRFTISRDNSKNTL
YLQMNSLRAEDTAVYYCAKEPITYDMRYARFDYWGRGTLVTVSS (SEQ ID NO: 313)

BMS3h-43-13
EVQLLESGGGLVQPGGSLRLSCTASGFTFNMYEMSWVRQAPGKGLEWVSGISRRGFTTYYADSVKGRFTISRDNSKNTL
YLQMNSLRAEDTAVYYCAKEPITYDMRYARFDYWGRGTLVTVSS (SEQ ID NO: 314)

BMS3h-43-14
EVQLLESGGGSVQPGGSLRLSCTASGFSFNMYEMSWVRQAPGKGLEWVSGISRRGFTTYYADSVKGRFTISRDNSKNTL
YLQMNSLRAEDTAVYYCAKEPITYDMRYARFDYWGQGTLVTVSG (SEQ ID NO: 315)

BMS3h-43-15
EVQLLESGGGLVQPGGSLRLSCTASGFTFNMYEMSWVRKAPGKGLEWVSGISRRGFTTYYADSVKGRFTISRDNSKNTL
YLQMNSLRAEDTAVYYCAKEPITYDMRYARFDYWGQGTLVTVSS (SEQ ID NO: 316)

BMS3h-56-1
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFTFEDWGQGTLVTVSS (SEQ ID NO: 317)

BMS3h-56-2
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFTFDDWGQGTLVTVSS (SEQ ID NO: 318)

BMS3h-56-3
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCTKLPFIFEYWGQGTLVTVSS (SEQ ID NO: 319)

BMS3h-56-4
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFMFDDRGQGTLVTVSS (SEQ ID NO: 320)

BMS3h-56-5
EVQLLESGGGLVQPGGSLRLSCAASGFTFRDYEMWWVRQAPGKGLERVSAINPQGTRTYYADSVMGRFTISRDNSKNTL
YLQMNSLRAEDTAVYYCAKLPFTFDDWGQGTLVTVSS (SEQ ID NO: 321)

BMS3h-56-6
EVQLLESGGGLVQPGGSLRLSCAASGFSFRDYEMWWVRQAPGKGLERVSAINPQGTRTYYADSVKGRFTISRDNSKNTL
YLQMNSLRAEDTAVYYCAKLPFIFDNRGQGTLVTVSS (SEQ ID NO: 322)

BMS3h-56-7
EVQLLESGGGLVQPGGSLRLSCAASGFTFRDYEMWWVRQAPGKGLERVSAINPQGTRTYYADSVKGRFTISRDNSKNTL
YLQMNSLRAEDTSVYHCAKPPFIFGDWGPGTLVTVSS (SEQ ID NO: 323)

BMS3h-56-8
EVQLLESGGGLVQPGGSRRLSCAASGFTFRDYEMWWVRQAPGKGLERVSAINPQGTRTYYADSVKGRFTISRDNSKNTL
YLQMNSLRAEDTAVYYCAKLPFTFEDWGQGTLVTVSS (SEQ ID NO: 324)

BMS3h-56-9
EVQLLESGGGLVQPGGSLRLSCAASGFTFRDYEMWWVRQAPGKGLERVSAINPQGTRTYYADSVMGRFTISRDNSKNTL
YLQMNSLRAEDTAVYYCAKLPFMFDDRGQGTLVTVSS (SEQ ID NO: 325)

BMS3h-56-10
EVQLLESGGGLVQPGGSLRLSCAASGFTFRDYEMWWVRQAPGKVLERVSAINPQGTRTYYADSVKGRFTISRDNSKNML
YLQMNSLRAEDTAVYYCAKLPFMFDDRGQGTLVTVSS (SEQ ID NO: 326)

BMS3h-56-11
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFMFDDRGQGTLVTVSS (SEQ ID NO: 327)

BMS3h-56-12
EVQLLESGGGLIQPGGSLRLSCAASGFTFRDYEMWWVRQAPGKGLERVSAINPQGTRTYYADSVKGRFTISRDNSKNTL
YLQMNSLRAEDTAVYYCLKLPFIFDYWGQGTLVTVSS (SEQ ID NO: 328)

TABLE 3-continued

Anti-Human CD40 Variable Domain Amino Acid Sequences

BMS3h-56-13
EVQLLESGGGLVQPGGSLRLSCAASGFTFRDYEMWWVRQAPGKGLERVSAINPQGTRTYYADSVKGRFTISRDNSKNTL
YLQMNSLRADDTAVYHCTKLPFIFDYWGQGTLVTVSS (SEQ ID NO: 329)

BMS3h-56-14
EVQLLESGGGLVQPGGSLRLSCAASGFTFRDYEMWWVRQAPGMVLERVSAINPQGTRTYYADSVKGRFTISRDNSKNTL
YLQMNSLRAEDTAVYYCAKLPFFFDSRGQGTLVTVSS (SEQ ID NO: 330)

BMS3h-56-15
EVQLLESGGGLVQPGGSLRLSCAASGFTFRDYEMWWVRRAPGKGLERVSAINPQGTRTYYADSVKGRFTISRDNSKNTL
YLQMNSLRAEDTAVYYCAKLPFTFEDWGQGTLVTVSS (SEQ ID NO: 331)

BMS3h-56-16
EVQLLESGGGLVQPGGSLRLSCAASGFTFRDYEMWWVRQAPGKGLERVSAINPQGTRTYYADSVMGRFTISRDNSKNTL
YLQMNSLRAEDTAVYYCAKLPFTFEDWGQGTLVTVSS (SEQ ID NO: 332)

BMS3h-56-17
EVQLLESGGGLVQPGGSLRLSCAASGFSFRDYEMWWYRQAPGKGLERVSAINPQGTRTYYADSVKGRFTISRDNSKNTL
YLQMNSLRAEDTAVYYCAKLPFTFEDWGQGTLVTVSS (SEQ ID NO: 333)

BMS3h-56-18
EVQLLESGGGLVQPGGSLRLSCAASGFTFRDYEMWWVRQAPGKVLERVSAINPQGTRTYYADSVKGRFTISRDNSKNML
YLQMNSLRAEDTAVYYCAKLPFTFEDWGQGTLVTVSS (SEQ ID NO: 334)

BMS3h-56-19
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYHCAKLPFTFEDWGQGTLVTVSS (SEQ ID NO: 335)

BMS3h-56-20
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCTKLPFTFEDWGQGTLVTVSS (SEQ ID NO: 336)

BMS3h-56-21
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCLKLPFTFEDWGQGTLVTVSS (SEQ ID NO: 337)

BMS3h-56-22
EVQLLESGGGLVQPGGSLRLSCAASGFTFRDYEMWWVRQAPGKGLERVSAINPQGTRTYYADSVKGRFTISRDNSKNTL
YLQMNSLRADDTAVYHCTKLPFIFEYWGQGTLVTVSS (SEQ ID NO: 338)

BMS3h-56-23
EVQLLESGGGLVQPGGSLRLSCAASGFTFRDYEMWWVRQAPGKGLERVSAINPQGTRTYYADSVMGRFTISRDNSKNTL
YLQMNSLRAEDTAVYYCAKEPYSFDSWGQGTLVTVSS (SEQ ID NO: 339)

BMS3h-56-24
EVQLLESGGGLVQPGGSLRLSCAASGFTFRDYEMWWVRQAPGKGLERVSAINPQGTRTYYADSVMGRFTISRDNSKNTL
YLQMNSLRAEDTAVYHCAKEPYSYDYWGQGTLVTVSS (SEQ ID NO: 340)

BMS3h-56-25
EVQLLESGGGLVQPGGSLRLSCAASGFTFRDYEMWWVRRAPGKGLERVSAINPQGTRTYYADSVMGRFTISRDNSKNTL
YLQMNSLRAEDTAVYYCAKLPFTFDDWGQGTLVTVSS (SEQ ID NO: 341)

BMS3h-56-26
EVQLLESGGGLVQPGGSLRLSCAASGFTFRDYEMWWVRRAPGKGLERVSAINPQGTRTYYADSVMGRFTISRDNSKNTL
YLQMNSLRAEDTAVYYCAKLPFMFDDRGQGTLVTVSS (SEQ ID NO: 342)

BMS3h-56-27
EVQLLESGGGLVQPGGSLRLSCAASGFTFRDYEMWWVRQAPGKGLERVSAINPQGTRTYYADSVMGRFTISRDNSKNTL
YLQMNSLRAEDTAVYYCAKLPFMFDDRGQGTLVTVSS (SEQ ID NO: 343)

BMS3h-56-28
EVQLLESGGGLVQPGGSLRLSCAASGFTFAGYELWWVRQAPGKGLERVSAINPQGTRTYYADSVMGRFTISRDNSKNTL
YLQMNSLRAEDTAVYYCAKLPFTFDDWGQGTLVTVSS (SEQ ID NO: 344)

BMS3h-56-29
EVQLLESGGGLVQPGGSLRLSCAASGFTFAGYELWWVRQAPGKGLERVSAINPQGTRTYYADSVMGRFTISRDNSKNTL
YLQMNSLRAEDTAVYYCAKLPFMFDDRGQGTLVTVSS (SEQ ID NO: 345)

BMS3h-56-30
EVQLLESGGGLVQPGGSLRLSCAASGFTFAGYEMWWFRQAPGKGLERVSAINPQGTRTYYADSVMGRFTISRDNSKNTL
YLQMNSLRAEDTAVYYCAKLPFTFDDWGQGTLVTVSS (SEQ ID NO: 346)

BMS3h-56-31
EVQLLESGGGLVQPGGSLRLSCAASGFTFAGYEMWWFRQAPGKGLERVSAINPQGTRTYYADSVMGRFTISRDNSKNTL
YLQMNSLRAEDTAVYYCAKLPFMFDDRGQGTLVTVSS (SEQ ID NO: 347)

TABLE 3-continued

Anti-Human CD40 Variable Domain Amino Acid Sequences

BMS3h-56-32
EVQLLESGGGLVQPGGSLRLSCAASGFTFRDYEMWWVRQAPGKGLEWVSAINPQGTRTYYADSVMGRFTISRDNSKNTL
YLQMNSLRAEDTAVYYCAKLPFTFDDWGQGTLVTVSS (SEQ ID NO: 348)

BMS3h-56-33
EVQLLESGGGLVQPGGSLRLSCAASGFTFRDYEMWWVRQAPGKGLEWVSAINPQGTRTYYADSVMGRFTISRDNSKNTL
YLQMNSLRAEDTAVYYCAKLPFMFDDRGQGTLVTVSS (SEQ ID NO: 349)

BMS3h-56-202
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPTYFSDRGQGTLVTVSS (SEQ ID NO: 350)

BMS3h-56-203
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFFFEEWGQGTLVTVSS (SEQ ID NO: 351)

BMS3h-56-204
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPTYFKDWGQGTLVTVSS (SEQ ID NO: 352)

BMS3h-56-205
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFYFSEWGQGTLVTVSS (SEQ ID NO: 353)

BMS3h-56-206
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYHCAKLPMFFEDWGQGTLVTVSN (SEQ ID NO: 354)

BMS3h-56-207
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFPFSEWGQGTLVTVSS (SEQ ID NO: 355)

BMS3h-56-208
EVQLLESGGGLVQPGGSLRLSCAASGFTFRDYEMWWVRQAPGKGLERVSAINPQGTRTYYADSVKGRFTISRDNSKNTL
YLQMDSLRAEDTAVYYCAKLPFYFSEWGQGTLVTVSS (SEQ ID NO: 356)

BMS3h-56-209
EVQLLESGGGLVQPGGSLRLSCAASGFTFRDYEMWWVRQAPGKGLERVSAINPYGNLTYYADSVKGRFTISRDNSKNTL
YLQMNSLRAEDTAVYYCAKLPFTFEDWGQGTLVTVSS (SEQ ID NO: 357)

BMS3h-56-210
EVQLLESGGGLVQPGGSLRLSCAASGFTFRDYEMWWVRQAPGKGLERVSAINPPGTLTYYADSVKGRFTISRDNSKNTL
YLQMNSLRAEDTAVYYCAKLPFTFEDRGQGTLVTVSS (SEQ ID NO: 358)

BMS3h-56-211
EVQLLESGGGLVQPGGSLRLSCAASGFTFRDYEMWWVRQAPGKGLERVSAINPWGGLTYYADSVKGRFTISRDNSKNTL
YLQMNSLRAEDTAVYYCAKLPFTFEDWGQGTLVTVSS (SEQ ID NO: 359)

BMS3h-56-212
EVQLLESGGGLVQPGGSLRLSCAASGFTFRDYEMWWVRQAPGKGLERVSAINPMGGFTYYADSVKGRFTISRDNSKNTL
YLQMNSLRAEDTAVYYCAKLPFTFEDWGQGTLVTVSS (SEQ ID NO: 360)

BMS3h-56-213
EVQLLESGGGLVQPGGSLRLSCAASGFTFRDYEMWWVRQAPGKGLERVSAINPWGSHTYYADSVKGRFTISRDNSKNTL
YLQMNSLRAEDTAVYYCAKLPFTFEDWGQGTLVTVSS (SEQ ID NO: 361)

BMS3h-56-214
EVQLLESGGGLVQPGGSLRLSCAASGFTFRDYEMWWVRQAPGKGLERVSAINPSGGLTYYADSVKGRFTISRDNSKNTL
YLQMNSLRAEDTAVYYCAKLPFTFDDRGQGTLVTVSS (SEQ ID NO: 362)

BMS3h-56-215
EVQLLESGGGLVQPGGSLRLSCAASGFTFRDYEMWWVRQAPGKGLERVSAINPHGSLTYYADSVKGRFTISRDNSKNTL
YLQMNSLRAEDTAVYYCAKLPFTFDDWGQGTLVTVSS (SEQ ID NO: 363)

BMS3h-56-216
EVQLLESGGGLVQPGGSLRLSCAASGFTFRDYEMWWVRQAPGKGLERVSAINPAGRLTYYADSVKGRFTISRDNSKNTL
YLQMNSLRAEDTAVYYCAKLPFTFEDWGQGTLVTVSS (SEQ ID NO: 364)

BMS3h-56-217
EVQLLESGGGLVQPGGSLRLSCAASGFTFRDYEMWWVRQAPGKGLERVSAINPWGSLTYYADSVKGRFTISRDNSKNTL
YLQMNSLRAEDTAVYYCAKLPFTFEDWGQGTLVTVSS (SEQ ID NO: 365)

BMS3h-56-218
EVQLLESGGGLVQPGGSLRLSCAASGFTFPDYEMWWVRQAPGKGLERVSAINPQGTRTYYADSVKGRFTISRDNSKNTL
YLQMNSLRAEDTAVYHCAKLPFTFDDWGQGTLVTVSS (SEQ ID NO: 366)

TABLE 3-continued

Anti-Human CD40 Variable Domain Amino Acid Sequences

BMS3h-56-219
EVQLLESGGGLVQPGGSLRLSCADSGFTFPPVEMWWVRQAPGKGLERVSAINPQGTRTYYADSVKGRFTISRDNSKNTL
YLQMNSLRAEDTAVYYCAKLPFTFEDWGQGTLVTVSS (SEQ ID NO: 367)

BMS3h-56-220
EVQLLESGGGLVQPGGSLRLSCAASGFTFRDYEMWWVRQAPGKGLERVSAINPYGGLTYYADSVKGRFTISRDNSKNTL
YLQMNSLRAEDTAVYYCAKLPFTFDDWGQGTLVTVSS (SEQ ID NO: 368)

BMS3h-56-221
EVQLLESGGGLVQPGGSLRLSCAASGFTFRDYEMWWVRQAPGKGLERVSAINPWGNHTYYADSVKGRFTISRDNSKNTL
YLQMNSLRAEDTAVYYCAKLPFTFEDWGQGTLVTVSS (SEQ ID NO: 369)

BMS3h-56-222
EVQLLESGGGLVQPGGSLRLSCAASGFTFRDYEMWWVRQAPGKGLERVSAINPHGGYTYYADSVKGRFTISRDNSKNTL
YLQMNSLRAEDTAVYYCAKLPFTFDDWGQGTLVTVSS (SEQ ID NO: 370)

BMS3h-56-223
EVQLLESGGGLVQPGGSLRLSCAASGFTFRDYEMWWVRQAPGRGLERVSAINPPGMLTYYADSVKGRFTISRDNSKNTL
YLQMNSLRAEDTAVYYCAKLPFTFDDWGQGTLVTVSS (SEQ ID NO: 371)

BMS3h-56-224
EVQLLESGGGLVQPGGSLRLSCAASGFTFRDYEMWWVRQAPGKGLERVSAINPWGQLTYYADSVKGRFTISRDNSKNTL
YLQMNSLRAEDTAVYYCAKLPFTFDDWGQGTLVTVSS (SEQ ID NO: 372)

BMS3h-56-225
EVQLLESGGGLVQPGGSLRLSCAASGFTFRDYEMWWVRQAPGKGLERVSAINPWGGYTYYADSVKGRFTISRDNSKNTL
YLQMNSLRAEDTAVYYCAKLPFTFDDWGQGTLVTVSS (SEQ ID NO: 373)

BMS3h-56-226
EVQLLESGGGLVQPGGSLRLSCAASGFTFRDYEMWWVRQAPGKGLERVSAINPSGGLTYYADSVKGRFTISRDNSKNTL
YLQMNSLRAEDTAVYYCAKLPFTFDDWGQGTLVTVSS (SEQ ID NO: 374)

BMS3h-56-227
EVQLLESGGGLVQPGGSLRLSCAASGFTFRDYEMWWVRQAPGKGLERVSAINPSGGLTYYADSVKGRFTISRDNSKNTL
YLQMNSLRAEDTAVYYCAKLPFTFDDWGQGTLVTVSS (SEQ ID NO: 375)

BMS3h-56-228
EVQLLESGGGLVQPGGSLRLSCAASGFTFRDYEMWWVRQAPGKGLERVSAINPSGTLTYYADSVKGRFTISRDNSKNTL
YLQMNSLRAEDTAVYYCAKLPFTFDDWGQGTLVTVSS (SEQ ID NO: 376)

BMS3h-56-229
EVQLLESGGGLVQPGGSLRLSCAASGFTFRDYEMWWVRQAPGKGLERVSAINPYGSLTYYADSVKGRFTISRDNSKNTL
YLQMNSLRAEDTAVYYCAKLPFTFDDWGQGTLVTVSS (SEQ ID NO: 377)

BMS3h-56-230
EVQLLESGGGLVQPGGSLRLSCAASGFTFRDYEMWWVRQAPGKGLERVSAINPWGGYTYYADSVKGRFTISRDNSKNTL
YLQMNSLRAEDTAVYYCAKLPFTFDDWGQGTLVTVSS (SEQ ID NO: 378)

BMS3h-56-231
EVQLLESGGGLVQPGGSLRLSCAASGFTFRDYEMWWVRQAPGKGLERVSAINPQGGLTYYADSVKGRFTISRDNSKNTL
YLQMNSLRAEDTAVYYCAKLPFTFEDWGQGTLVTVSS (SEQ ID NO: 379)

BMS3h-56-232
EVQLLESGGGLVQPGGSLRLSCAASGFTFRDYEMWWVRQAPGKGLERVSAINPWGSHTYYADSVKGRFTISRDNSKNTL
YLQMNSLRAEDTAVYYCAKLPFTFDDWGQGTLVTVSS (SEQ ID NO: 380)

BMS3h-56-233
EVQLLESGGGLVQPGGSLRLSCAASGFTFRDYEMWWVRQAPGKGLERVSAINPWGTLTYYADSVKGRFTISRDNSRNTL
YLQMNSLRAEDTAVYYCAKLPFTFDDWGQGTLVTVSS (SEQ ID NO: 381)

BMS3h-56-234
EVQLLESGGGLVQPGGSLRLSCAASGFTFRDYEMWWVRQAPGKGLERVSAINPNGRLTYYADSVKGRFTISRDNSKNTL
YLQMNSLRAEDTAVYYCAKLPFTFADWGQGTLVTVSS (SEQ ID NO: 382)

BMS3h-56-235
EVQLLESGGGLVQPGGSLRLSCAASGFTFRDYEMWWVRQAPGKGLERVSAINPWGQLTYYADSVKGRFTISRDNSKNTL
YLQMNSLRAEDTAVYYCAKLPFTFDDWGQGTLVTVSS (SEQ ID NO: 383)

BMS3h-56-236
EVQLLESGGGLVQPGGSLRLSCAASGFTFRDYEMWWVRQAPGKGLERVSAINPHGGLTYYADSVKGRFTISRDNSKNTL
YLQMNSLRAEDTAVYYCAKLPFTFDDWGQGTLVTVSS (SEQ ID NO: 384)

BMS3h-56-237
EVQLLESGGGLVQPGGSLRLSCAASGFTFRDYEMWWVRQAPGKGLERVSAINPAGMLTYYADSVKGRFTISRDNSKNTL
YLQMNSLRAEDTAVYYCAKLPFTFDDWGQGTLVTVSS (SEQ ID NO: 385)

TABLE 3-continued

Anti-Human CD40 Variable Domain Amino Acid Sequences

BMS3h-56-238
EVQLLESGGGLVQPGGSLRLSCAASGFTFRDYEMWWVRQAPGKGLERVSAINPHGTLTYYADSVKGRFTISRDNSKNTL
YLQMNSLRAEDTAVYYCAKLPFTFEDWGQGTLVTVSS (SEQ ID NO: 386)

BMS3h-56-239
EVQLLESGGGLVQPGGSLRLSCAASGFTFRDYEMWWVRQAPGKGLERVSAINPWGSLTYYADSVKGRFTISRDNSKNTL
YLQMNSLRAEDTAVYYCAKLPFTFDDWGQGTLVTVSS (SEQ ID NO: 387)

BMS3h-56-240
EVQLLESGGGLVQPGGSLRLSCAASGFTFRDYEMWWVRQAPGKGLERVSAINPYGGLTYYADSVKGRFTISRDNSKNTL
YLQMNSLRAEDTAVYYCAKLPFTFEDWGQGTLVTVSS (SEQ ID NO: 388)

BMS3h-56-241
EVQLLESGGGLVQPGGSLRLSCAASGFTFRDYEMWWVRQAPGKGLERVSAINPAGFLTYYADSVKGRFTISRDNSKNTL
YLQMNSLRAEDTAVYYCAKLPFTFEDWGQGTLVTVSS (SEQ ID NO: 389)

BMS3h-56-242
EVQLLESGGGLVRPGGSLRLSCAASGFTFRDYEMWWVRQAPGKGLERVSAINPYGGLTYYADSVKGRFTISRDNSKNTL
YLQMNSLRAEDTAVYYCAKLPFTFEDWGQGTLVTVSS (SEQ ID NO: 390)

BMS3h-56-243
EVQLLESGGGLVQPGGSLRLSCAASGFTFRDYEMWWVRQAPGKGLERVSAINPWGGFTYYADSVKGRFTISRDNSKNTL
YLQMNSLRAEDTAVYYCAKLPFTFEDWGQGTLVTVSS (SEQ ID NO: 391)

BMS3h-56-244
EVQLLESGGGLVQPGGSLRLSCAASGFTFRDYEMWWVRQAPGKGLERVSAINPWGGLTYYADSVKGRFTISRDNSKNTL
YLQMNSLRAEDTAVYYCAKLPFTFDDWGQGTLVTVSS (SEQ ID NO: 392)

BMS3h-56-245
EVQLLESGGGLVQPGGSLRLSCAASGFTFRDYEMWWVRQAPGKGLERVSAINPYGGLTYYADSVKGRFTISRDNSKNTL
YLQMDSLRAEDTAVYYCAKLPFTFEDWGQGTLVTVSS (SEQ ID NO: 393)

BMS3h-56-246
EVQLLESGGGLVQPGGSLRLSCAASGFTFRDYEMWWVRQAPGKGLERVSAINPWGTLTYYADSVKGRFTISRDNSKNTL
YLQMNSLRAEDTAVYYCAKLPFTFEDWGQGTLVTVSS (SEQ ID NO: 394)

BMS3h-56-247
EVQLLESGGGLVQPGGSLRLSCAASGFTFRDYEMWWVRQAPGKGLERVSAINPWGGYTYYADSVKGRFTISRDNSKNTL
YLQMNSLRAEDTAVYYCAKLPFTFEDWGRGTLVTVSS (SEQ ID NO: 395)

BMS3h-56-248
EVQLLESGGGLVQPGGSLRLSCAASGFTFRDYEMWWVRQAPGKGLERVSAINPYGNLTYYADSVKGRFTISRDNSKNTL
YLQMNSLRAEDTAVYYCAKLPFTFDDWGQGTLVTVSS (SEQ ID NO: 396)

BMS3h-56-249
EVQLLESGGGLVQPGGSLRLSCAASGFTFRDYEMWWVRQAPGKGLERVSAINPHGGFTYYADSVKGRFTISRDNSKNTL
YLQMNSLRAEDTAVYYCAKLPFTFEDWGQGTLVTVSS (SEQ ID NO: 397)

BMS3h-56-250
EVQLLESGGGLVQPGGSLRLSCAASGFTFRDYEMWWVRQAPGKGLERVSAINPAGFYTYYADSVKGRFTISRDNSKNTL
YLQMNSLRAEDTAVYYCAKLPFTFDDWGQGTLVTVSS (SEQ ID NO: 398)

BMS3h-56-251
EVQLLESGGGLVQPGGSLRLSCAASGFTFRDYEMWWVRQAPGKGLERVSAINPAGGLTYYADSVKGRFTISRDNSKNTL
YLQMNSLRAEDTAVYYCAKLPFTFDDWGQGTLVTVSS (SEQ ID NO: 399)

BMS3h-56-252
EVQLLESGGGLVQPGGSLRLSCAASGFAFRDYEMWWVRQAPGKGLERVSAINPHGSLTYYADSVKGRFTISRDNSKNTL
YLQMNSLRAEDTAVYYCAKLPFTFEDWGQGTLVTVSS (SEQ ID NO: 400)

BMS3h-56-253
EVQLLESGGGLVQPGGSLRLSCAASGFTFRDYEMWWVRQAPGKGLERVSAINPAGGYTYYADSVKGRFTISRDNSKNTL
YLQMNSLRAEDTAVYHCAKLPFTFEDWGQGTLVTVSS (SEQ ID NO: 401)

BMS3h-56-254
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFWFTEWGQGTLVTVSS (SEQ ID NO: 402)

BMS3h-56-255
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFMFSDRGQGTLVTVSS (SEQ ID NO: 403)

BMS3h-56-256
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFLFQEWGQGTLVTVSS (SEQ ID NO: 404)

TABLE 3-continued

Anti-Human CD40 Variable Domain Amino Acid Sequences

BMS3h-56-257
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPTRFEDWGQGTLVTVSS (SEQ ID NO: 405)

BMS3h-56-258
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFYFHEWGQGTLVTVSS (SEQ ID NO: 406)

BMS3h-56-259
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCGKEPFRYDYWGQGTLVTVSS (SEQ ID NO: 407)

BMS3h-56-260
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPTFFKDWGQGTLVTVSS (SEQ ID NO: 408)

BMS3h-56-261
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFFFQEWGQGTLVTVSS (SEQ ID NO: 409)

BMS3h-56-262
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPQLFHDRGQGTLVTVSS (SEQ ID NO: 410)

BMS3h-56-263
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPQLFEDWGQGTLVTVSS (SEQ ID NO: 411)

BMS3h-56-264
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYHCAKLPFGFSEWGQGTLVTVSS (SEQ ID NO: 412)

BMS3h-56-265
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPQLFQDWGQGTLVTVSS (SEQ ID NO: 413)

BMS3h-56-266
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFFFHEWGQGTLVTVSS (SEQ ID NO: 414)

BMS3h-56-267
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPHYFKDWGQGTLVTVSS (SEQ ID NO: 415)

BMS3h-56-268
EVQLLESGGGLVQSGGSLRLSCAASGFTFRDYEMWWVRQAPGKGLERVSAINPQGTRTYYADSVKGRFTISRDNSKNTL
YLQMNSLRAEDTAVYYCAKLPFYFEEWGQGTLVTVSS (SEQ ID NO: 416)

BMS3h-56-269
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFRFSDRGQGTLVTVSS (SEQ ID NO: 417)

BMS3h-56-270
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPTLFQDWGQGTLVTVSS (SEQ ID NO: 418)

BMS3h-56-271
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFYFSEWGQGTLVTVSN (SEQ ID NO: 419)

BMS3h-56-272
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYYCAKLPFWFQEWGQGTLVTVSS (SEQ ID NO: 420)

BMS3h-56-273
EVQLLESGGGLVQPGGSLRLSCAASGFTFRDYEMWWVRQAPGKGLERVSAINPWGSLTYYADSVKGRFTISRDNSKNTL
YLQMNSLRAEDTAVYYCAKLPFYFQEWGQGTLVTVSS (SEQ ID NO: 421)

BMS3h-56-274
EVQLLESGGGLVQPGGSLRLSCAASGFTFRDYEMWWVRQAPGKGLERVSAINPWGSLTYYADSVKGRFTISRDNSKNTL
YLQMNSLRAEDTAVYHCAKLPMFFEDWGQGTLVTVSN (SEQ ID NO: 422)

BMS3h-56-275
EVQLLESGGGLVQPGGSLRLSCAASGFTFRDYEMWWVRQAPGKGLERVSAINPWGSLTYYADSVKGRFTISRDNSKNTL
YLQMNSLRAEDTAVYYCAKLPFYFHEWGQGTLVTVSS (SEQ ID NO: 423)

TABLE 3-continued

Anti-Human CD40 Variable Domain Amino Acid Sequences

BMS3h-56-276
EVQLLESGGGLVQPGGSLRLSCAASGFTFRDYEMWWVRQAPGKGLERVSAINPWGSLTYYADSVKGRFTISRDNSKNTL
YLQMNSLRAEDTAVYYCAKLPFFFQEWGQGTLVTVSS (SEQ ID NO: 424)

BMS3h-56-277
EVQLLESGGGLVQPGGSLRLSCAASGFTFRDYEMWWVRQAPGKGLERVSAINPWGSLTYYADSVKGRFTISRDNSKNTL
YLQMNSLRAEDTAVYYCAKLPFFFHEWGQGTLVTVSS (SEQ ID NO: 425)

BMS3h-56-278
EVQLLESGGGLVQPGGSLRLSCAASGFTFRDYEMWWVRQAPGKGLERVSAINPWGGFTYYADSVKGRFTISRDNSKNTL
YLQMNSLRAEDTAVYYCAKLPFYFQEWGQGTLVTVSS (SEQ ID NO: 426)

BMS3h-56-279
EVQLLESGGGLVQPGGSLRLSCAASGFTFRDYEMWWVRQAPGKGLERVSAINPWGGFTYYADSVKGRFTISRDNSKNTL
YLQMNSLRAEDTAVYHCAKLPMFFEDWGQGTLVTVSN (SEQ ID NO: 427)

BMS3h-56-280
EVQLLESGGGLVQPGGSLRLSCAASGFTFRDYEMWWVRQAPGKGLERVSAINPWGGFTYYADSVKGRFTISRDNSKNTL
YLQMNSLRAEDTAVYYCAKLPFYFHEWGQGTLVTVSS (SEQ ID NO: 428)

BMS3h-56-281
EVQLLESGGGLVQPGGSLRLSCAASGFTFRDYEMWWVRQAPGKGLERVSAINPWGGFTYYADSVKGRFTISRDNSKNTL
YLQMNSLRAEDTAVYYCAKLPFFFQEWGQGTLVTVSS (SEQ ID NO: 429)

BMS3h-56-282
EVQLLESGGGLVQPGGSLRLSCAASGFTFRDYEMWWVRQAPGKGLERVSAINPWGGFTYYADSVKGRFTISRDNSKNTL
YLQMNSLRAEDTAVYYCAKLPFFFHEWGQGTLVTVSS (SEQ ID NO: 430)

BMS3h-56-283
EVQLLESGGGLVQPGGSLRLSCAASGFTFRDYEMWWVRQAPGKGLERVSAINPWGGLTYYADSVKGRFTISRDNSKNTL
YLQMNSLRAEDTAVYYCAKLPFYFQEWGQGTLVTVSS (SEQ ID NO: 431)

BMS3h-56-284
EVQLLESGGGLVQPGGSLRLSCAASGFTFRDYEMWWVRQAPGKGLERVSAINPWGGLTYYADSVKGRFTISRDNSKNTL
YLQMNSLRAEDTAVYHCAKLPMFFEDWGQGTLVTVSN (SEQ ID NO: 432)

BMS3h-56-285
EVQLLESGGGLVQPGGSLRLSCAASGFTFRDYEMWWVRQAPGKGLERVSAINPWGGLTYYADSVKGRFTISRDNSKNTL
YLQMNSLRAEDTAVYYCAKLPFYFHEWGQGTLVTVSS (SEQ ID NO: 433)

BMS3h-56-286
EVQLLESGGGLVQPGGSLRLSCAASGFTFRDYEMWWVRQAPGKGLERVSAINPWGGLTYYADSVKGRFTISRDNSKNTL
YLQMNSLRAEDTAVYYCAKLPFFFQEWGQGTLVTVSS (SEQ ID NO: 434)

BMS3h-56-287
EVQLLESGGGLVQPGGSLRLSCAASGFTFRDYEMWWVRQAPGKGLERVSAINPWGGLTYYADSVKGRFTISRDNSKNTL
YLQMNSLRAEDTAVYYCAKLPFFFHEWGQGTLVTVSS (SEQ ID NO: 435)

BMS3h-56-288
EVQLLESGGGLVQPGGSLRLSCAASGFTFRDYEMWWVRQAPGKGLERVSAINPQGTRTYYADSVKGRFTISRDNSKNTL
YLQMNSLRAEDTAVYHCAKLPMFFEDWGQGTLVTVSS (SEQ ID NO: 436)

BMS3h-106-1
EVQLLETGGGLVQPGGSLRLSCAASGFTFSTYHMQWVRRAPGKGLEWVSMIDADGLGTYYADPVKGRFTISRDNSKNTL
YLQMNSLRAKDTAVYYCARPGPQFGQFDYLGQGTLVTVSS (SEQ ID NO: 437)

BMS3h-106-2
EVQLFESGGGLVQTGGSLRLSCAASGFTFSTYHMQWVRQAPGKGLEWVSMIDADGLGKYYADPVKGRFTISRDNSKNTL
YLQMNSLRAEDTAVYYCVKPGPQFGQYDYWGQGTLVTVSS (SEQ ID NO: 438)

BMS3h-107-1
EVQLLESGGGLVQPGGSLRLSCSASGFTFSGYDMQWVRQAPGKGLEWVSTISASGVYTYYADSVKGRFTISRDNSKNTL
YLQMNSLRAEDTAVYYCAKYPNRFALNSFDYRGRGTLVTVSS (SEQ ID NO: 439)

BMS3h-107-2
EVQLLESGGGLVQPGGSLRLSCAASGFTFSGYDMQWVRQAPGRGLEWVSTISASGVYTYYTDSVKGRFTTSRDNSKNTL
YLQMNSLRAEDTAVYYCTKYPNRFARNNFDYWGQGTLVTVSS (SEQ ID NO: 440)

BMS3h-131-1
DILMTQSPSSLSASVGDRVTITCRANSSILWALAWYQQKPGEAPKLLIESSGLQSGVPSRFSGSGSGTDFTLTISSLQ
PEDFATYYCVQNAVWPGTFSQGTKVEIKR (SEQ ID NO: 441)

BMS3h-131-2
DIQMTQSPSSLSASVGDRVTITCRADSSILWALAWYQQKPGKAPKLLIESSGLQSGVPSRFSGSGSGTDFTLTISSLQ
PEDFATYYCVQNAVWPGTFGQGTKVEIKR (SEQ ID NO: 442)

TABLE 3-continued

Anti-Human CD40 Variable Domain Amino Acid Sequences

BMS3h-131-3
DIQMTVSPSSLSASVGDRVTITCRADSSILWALAWYQQKPGKAPKLLIESSSGLQSGVPSRFSGSGSGTDFTLTISSLQ
PEDFATYYCVQNAVWPGTFGQGTKVEIKR (SEQ ID NO: 443)

BMS3h-131-4
DIQMTQSPSSLSASVGDRVTITCRANSSILWALAWYQQKPGKAPKLLIESSSGLQSGVPSRFSGSGSGTDFTLTISSLQ
PEDFATYYCVQNAVWPGTFDQGTKVEIKR (SEQ ID NO: 444)

BMS3h-131-5
DIQMTQSPSSLSASVGDRVTITCRANSSILWALAWYQQKPGKAPKLLIESSTGLQSGVPSRFSGSGSGTDFTLTISSLQ
PEDFATYYCVQNAVWPGTFGQGTKVEIKR (SEQ ID NO: 445)

BMS3h-131-6
DIQMTVSPSSLSASVGDRVTITCRANSSILWALAWYQQKPGKAPKLLIESSSGLQSGVPSRFSGSGSGTDFTLTISSLQ
PEDFATYYCVQNAVWPGTFGQGTKVEIKR (SEQ ID NO: 446)

BMS3h-131-7
DIQMTQSPSSLSASVGDRVTITCRADSSILWALAWYQQKPGKAPKLLIESSSGLQSGVPSRFSGSGSGTDFTLTISSLQ
PEDFATYYCVQNAVWPGTFDQGTKVEIKR (SEQ ID NO: 447)

BMS3h-131-8
DIQMTQSPSSLSASVGDRVTITCRANSSILWALAWYQQKPGKAPELLIESSSGLQSGVPSRFSGSGSGTDFTLTISSLQ
PEDFATYYCVQNAVWPGTFGQGTKVEIKR (SEQ ID NO: 448)

BMS3h-131-9
DIQMTQSPSSLSASVGDRVTITCRANSSILWALAWYQQKPGKAPKLLIESSSGLQSGVPSRFSGSGSGTDFTLTISSLQ
PEDFATYYCVQNAVWPGTFGQGTKVENKR (SEQ ID NO: 449)

BMS3h-131-10
DIQMTQSPSSLSASVGDRVTITCRANSSILWALAWYQQKPGKAPKLLIESSSGLQSGVPSRFSGSGSGTDFTLTISSLQ
PEDFATYYCVQNAVWPGTFGQGTKVEIKR (SEQ ID NO: 450)

BMS3h-131-11
DIQMTQSPSSLSASVGDRVTITCRANSSILWALAWYQQKPGKAPKLLIESSSGLQSGIPSRFSGSGSGTDFTLTISSLQ
PEDFATYYCVQNAVWPGTFGQGTKVEIKR (SEQ ID NO: 451)

BMS3h-131-12
DIQMTQSPSSLSASVGDRVTITCRANSSILWALAWYQQKPGKAPKLLIESSSGLQSGVPSRFSGSGSGTDFTLTISSLQ
PEDFATYYCVQNAVWPGTFGQGTKVEIKR (SEQ ID NO: 452)

BMS3h-131-13
DILLTQSPSSLSASVGDRVTITCRANSSILWALAWYQQKPGKAPKLLIESSSGLQSGVPSRFSGSGSGTDFTLTISSLQ
PEDFATYYCVQNAVWPGTFGQGTKVEIKR (SEQ ID NO: 453)

BMS3h-131-14
DIQMTQSPSSLSASVGDRVTITCRANSSILWALAWYQQKPGKAPKLLIESSSGLQSGVPSRFSGSGTGTDFTLTISGLQ
PEDFATYYCVQNAVWPGTFDQGTKVEIKR (SEQ ID NO: 454)

BMS3h-131-15
DIQMTQSPSSLSASVGDRVTIPCRANSSILWALAWYQQKPGKAPKLLIESSSGLQSGVPSRFSGSASGTDFTLTISSLQ
PEDFATYYCVQNAVWPGTFGQGTKVEIKR (SEQ ID NO: 455)

BMS3h-193-1
DIQMAQSPSSLSASVGDRVTITCRASQTIERRLNWYQQKPGKAPKLLIYLASRLQSGVPSRFSGSGSGTDFTLTISSLQ
PEDFATYYCHQYASPPLTLGQGTKVEIKR (SEQ ID NO: 456)

BMS3h-193-2
DIQMTQSPSSLSASVGDSVTITCRASQTIERRLNWYQQKPGEAPKLLIYLASRLQSGVPSRFSGSGSGTDFTLTISSLQ
PEDFATYYCHQYASPPLTFGQGTNVEIKR (SEQ ID NO: 457)

BMS3h-193-3
DIQMTQSPSSLSASVGDRVTITCRASQTIERRLNWYQQKPGKAPKLLIYLASRLQSGVPSRFSGSGSGTDFTLTISSLQ
PEDFAAYYCHQYESPPLTFGQGTKVEIKR (SEQ ID NO: 458)

BMS3h-193-4
DIQMTQSPSSLSASVGDRVTITCRASRTIERRLNWYQQKPGKAPKLLIYLASRLQSGVPSRFSGSGSGTDFTLTISSLQ
PEDFATYYCHQYESPPLTFGQGTKVEIKR (SEQ ID NO: 459)

BMS3h-193-5
DIQMTQSPSSLSASVGERVTITCRASQTIERRLNWYQQKPGKAPKLLIYLASRLQSGVPSRFSGSGSGTDFTLTISNLQ
PEDSATYYCHQYASPPLTLGQGTKVEIKR (SEQ ID NO: 460)

BMS3h-193-6
DIQMTQSPSSLSASVGDRVTITCRASQTIERRLNWYQQKPGKAPKLLIYLASRLQSGVPSRFSGSGSGTDFTLTISSLQ
PEDFATYYCHQYASPPLTLGQGTKVEIKR (SEQ ID NO: 461)

TABLE 3-continued

Anti-Human CD40 Variable Domain Amino Acid Sequences

BMS3h-193-7
DIQITQSPSSLSASVGDRVTITCRASQTIERRLNWYQQKPGKDPKLLIYLASRLQSGVPSRFSGSGSGTDFTLTISSLQ
PEDFATYYCHQYESPPLTFGQGTKVEIKR (SEQ ID NO: 462)

BMS3h-193-8
DIQMTQSPSSLSASVGDRVTITCRASQTIERRLNWYQQKPGEAPKLLIYLASRLQSGVPSRFSGSGSGTDFTLTISSLQ
PEDFATYYCHQYESPPLTFGQGTKVEIKW (SEQ ID NO: 463)

BMS3h-193-9
DIQLTQSPSSLSASVGDRVTITCRASQTIERRLNWYQQKPGKAPKLLIYLASRLQSGVPSRFSGSGSGTEFTLTISSLQ
PEDFATYYCHQYESPPLTFGQGTKVEIKR (SEQ ID NO: 464)

BMS3h-193-10
DIQMSQSPSTLSASVGDRVTITCRASQTIERRLNWYQQKPGKAPKLLIYLASRLQSGVPSRFSGSGSGTDFTLTISSLQ
PEDFATYYCHQYESPPLMFGQGTKVEIKR (SEQ ID NO: 465)

BMS3h-193-11
DIQMTQSPSSLSASVGDRVTITCRASQTIERRLNWYQQKPGKDPKLLIYLASRLQSGVPSRFSGSGSGTDFTLTISSLQ
PEDFATYYCHQYESPPLTFGQGTKVEIKR (SEQ ID NO: 466)

BMS3h-193-12
DIQMTQSPSSLSASVGDRVTITCRASQTIERRLNWYQQKPGKAPKLLIYLASRLQSGVPSRFSGSGSGTDFTLTISSLQ
PEDFATYYCHQYESPPLTFGQGTKVEIKR (SEQ ID NO: 467)

BMS3h-193-13
DIQMTQSPSSLFASVGDRVTITCRASQTIERRLNWYQQKPGKAPKLLIYLASRLQSGVPSRFSGSGSGTDFTLTISSLQ
PEDFATYYCHQYESPPLTFGQGTKVEIKR (SEQ ID NO: 468)

BMS3h-193-14
DIQMTQYPSSLSASVGDRVTITCRASQSIERRLNWYQQKPGEAPKLLIYLASRLQSGVPSRFSGSGSGTDFTLTISSLQ
PEDFATYYCHQYESPPLTFGQGTKVEIKR (SEQ ID NO: 469)

BMS3h-193-15
DIQMTQSPSSLSASVGDRVTITCRASRTIERRLNWYQQKPGKAPKLLIYLASRLQSGVPSRFSGSGSGTDFTLTISSLQ
PEDFATYYCHPYESPPLTFGQGTKVEIKR (SEQ ID NO: 470)

BMS3h-193-16
DIQMTQSPSSLSASVGDRVTITCRASQAIERRLNWYQQKPGKAPKLLIYLASRLQSGVPSRFSGSGSGTDFTLTISSLQ
PEDFATYYCHQYASPPLTLGQGTKVEIKR (SEQ ID NO: 471)

BMS3h-193-17
NIQMTQSPSSLSASVGDRVTITCRASQAIERRLNWYQQKPGKAPKLLIYLASRLQSGVPSRFSGSGSGTDFTLTISSLQ
PEDFATYYCHQYESPPLTFGQGTKVEIKR (SEQ ID NO: 472)

BMS3h-193-18
DIQMTQSPSSLSASVGDRVTITCRASQTIGRRLNWYQQKPGKAPKLLIYLASRLQSGVPSRFSGSGSGSDFTLTISSLQ
PEDFATYYCHQYESPPLTFGQGTKVEIKR (SEQ ID NO: 473)

BMS3h-193-19
DIQMTQSPSSLSASVGDRVTITCRASQTIERRLNWYQQKPGKAPKLLIYLASRLQSGVPSRFSGSGSGTEFTLTISSLQ
PEDFATYYCHQYESPPLTFGQGTKVEIKR (SEQ ID NO: 474)

BMS3h-193-20
DIQMTQTPSSLSASVGDRVTITCRASQTIERRLNWYQQKPGEAPKLLIYLASRLQSGVPSRFSGSGSGTDFTLTISSLQ
PEDFATYYCHQYESPPLTFGQGTKVKIKR (SEQ ID NO: 475)

BMS3h-193-21
DIQMTQSPSSLSASVGDSVTITCRASQTIERRLNWYQQKPGKAPKLLIYLASRLQSGVPSRFSGSGSGTDFTLTISSLQ
PEDFATYYCHQYESPPLTFGQGTKVEIKR (SEQ ID NO: 476)

BMS3h-193-22
HIQMTQSPSSLSASVGDRVTITCRASQTIERRLNWYQQKPGKAPKLLIYLASRLQSGVPSRFSGSGSGTDFTLTISSLQ
PEDFATYYCHQYESPPLTFGQGTKVEIKR (SEQ ID NO: 477)

BMS3h-193-23
DVQMTQSPSSLSASVGDRVTITCRASQTIERRLNWYQQKPGEAPKLLIYLTSRLQSGVPSRFSGSGSGTDFTLTISSLQ
PEDFATYYCHQYASPPLTFGQGTKVEIKR (SEQ ID NO: 478)

BMS3h-193-24
DIQMTQSPSSLSASVGDRVTITCRASQTIERRLNWYQQKPGKAPKLLIYLASRLQSGVPSRFSGSGSGTDFTLTISSLQ
PEDFATYYCHQYESPPLTFGQGTKVVIKR (SEQ ID NO: 479)

BMS3h-193-25
DIQMTQSPSSLSASVGDRVTITCRASQTIERRLNWYQQKPGKAPRLLIYLATRLQSGVPSRFSGSGSGTDFTLTISSLQ
PEDFATYYCHQYESPPLTFGQGTKVEIKR (SEQ ID NO: 480)

TABLE 3-continued

Anti-Human CD40 Variable Domain Amino Acid Sequences

BMS3h-193-26
DIQMTQSPSSLSASVGDRVTITCRASQPIERRLNWYQQKPGKAPKLLIYLASRLQSGVPSRFSGSGSGTDFTLTISSLQ
PEDFATYYCHQYESPPLTFGQGTKVEIKR (SEQ ID NO: 481)

BMS3h-193-27
DIQMTQSPSSLSASVGDRVTITCRASQTIGRRLNWYQQKPGKAPKLLIYLASRLQSGVPSRFSGSGSGTDFTLTISSLQ
PEDFATYYCHQYESPPLTFGQGTKVEIKR (SEQ ID NO: 482)

BMS3h-193-28
DIQMTQSPSSLSASVGDRVTITCRASQSIERRLNWYQQKPGKAPKLLIYLASRLQSGVPSRFSGSGSGTDFTLTISSLQ
PEDFATYYCHQYESPPLTFGQGTKVEIIR (SEQ ID NO: 483)

BMS3h-193-29
DIQMTQSPSSLSASVGDRVTITCRASQTIERRLNWYQQKPGKAPKLLIYLATRLQSGVPSRFSGSGSGTDFTLTISSLQ
PEDFATYYCHQYESPPLTFGQGTKVEIKR (SEQ ID NO: 484)

BMS3h-193-30
DIQMTQSPSSLSASVGDRVTITCRASQSIERRLNWYQQKPGKAPKLLIYLASRLQSGVPSRFSGSGSGTDFTLTISSLQ
PEDFATYYCHQYESPPLTFGQGTKVEIKR (SEQ ID NO: 485)

BMS3h-193-2501
DIQMTQSPSSLSASVGDRVTITCRASQTIERRLNWYQQKPGKAPRLLIYLATRLQSGVPSRFSGSGSGTDFTLTISSLQ
PEDFATYYCHQFEHPPLTFGQGTKVEIKR (SEQ ID NO: 486)

BMS3h-193-2502
DIQMTQSPSSLSASVGDRVTITCRASFPIDRRLNWYQQKPGKAPRLLIYLATRLQSGVPSRFSGSGSGTDFTLTISSLQ
PEDFATYYCHQYESPPLTFGQGTKVEIKR (SEQ ID NO: 487)

BMS3h-193-2503
DIQMTQSPSSLSASVGDRVTITCRASSTIGRRLNWYQQKPGKAPRLLIYLATRLQSGVPSRFSGSGSGTDFTLTISSLQ
PEDFATYYCHQYESPPLTFGQGTKVEIKR (SEQ ID NO: 488)

BMS3h-193-2504
DIQMTQSPSSLSASVGDRVTITCRASSQIGRRLNWYQQKPGKAPRLLIYLATRLQSGVPSRFSGSGSGTDFTLTISSLQ
PEDFATYYCHQYESPPLTFGQGTKVEIKR (SEQ ID NO: 489)

BMS3h-193-2505
DIQMTQSPSSLSASVGDRVTITCRASERIGRRLNWYQQKPGKAPRLLIYLATRLQSGVPSRFSGSGSGTDFTLTISSLQ
PEDFATYYCHQYESPPLTFGQGTKVEIKR (SEQ ID NO: 490)

BMS3h-193-2506
DIQMTQSPSSLSASVGDRVTITCRASQQIGRRLNWYQQKPGKAPRLLIYLATRLQSGVPSRFSGSGSGTDFTLTISSLQ
PEDFATYYCHQYESPPLTFGQGTKVEIKR (SEQ ID NO: 491)

BMS3h-193-2507
DIQMTQSPSSLSASVGDRVTITCRASQPIARRLNWYQQKPGKAPRLLIYLATRLQSGVPSRFSGSGSGTDFTLTISSLQ
PEDFATYYCHQYESPPLTFGQGTKVEIKR (SEQ ID NO: 492)

BMS3h-193-2508
DIQMTQSPSSLSASVGDRVTITCRASGNIGRRLNWYQQKPGKAPRLLIYLATRLQSGVPSRFSGSGSGTDFTLTISSLQ
PEDFATYYCHQYESPPLTFGQGTKVEIKR (SEQ ID NO: 493)

BMS3h-193-2509
DIQMTQSPSSLSASVGDRVTITCRASRNIDRRLNWYQQKPGKAPRLLIYLATRLQSGVPSRFSGSGSGTDFTLTISSLQ
PEDFATYYCHQYESPPLTFGQGTKVEIKR (SEQ ID NO: 494)

BMS3h-193-2510
DIQMTQSPSSLSASVGDRVTITCRASQSIGRRLNWYQQKPGKAPRLLIYLATRLQSGVPSRFSGSGSGTDFTLTISSLQ
PEDFATYYCHQYESPPLTFGQGTKVEIKR (SEQ ID NO: 495)

BMS3h-193-2511
DIQMTQSPSSLSASVGDRVTITCRASQNIGTRLNWYQQKPGKAPRLLIYLATRLQSGVPSRFSGSGSGTDFTLTISSLQ
PEDFATYYCHQYESPPLTFGQGTKVEIKR (SEQ ID NO: 496)

BMS3h-193-2512
DIQMTQSPSSLSASVGDRVTITCRASEVIGRRLNWYQQKPGKAPRLLIYLATRLQSGVPSRFSGSGSGTDFTLTISSLQ
PEDFATYYCHQYESPPLTFGQGTKVEIKR (SEQ ID NO: 497)

BMS3h-193-2513
DIQMTQSPSSLSASVGDRVTITCRASEAIGRRLNWYQQKPGKAPRLLIYLATRLQSGVPSRFSGSGSGTDFTLTISSLQ
PEDFATYYCHQYESPPLTFGQGTKVEIKR (SEQ ID NO: 498)

BMS3h-193-2514
DIQMTQSPSSLSASVGDRVTITCRASTSIARRLNWYQQKPGKAPRLLIYLATRLQSGVPSRFSGSGSGTDFTLTISSLQ
PEDFATYYCHQYESPPLTFGQGTKVEIKR (SEQ ID NO: 499)

TABLE 3-continued

Anti-Human CD40 Variable Domain Amino Acid Sequences

BMS3h-193-2515
DIQMTQSPSSLSASVGDRVTITCRASLNIGRRLNWYQQKPGKAPRLLIYLATRLQSGVPSRFSGSGSGTDFTLTISSLQ
PEDFATYYCHQYESPPLTFGQGTKVEIKR (SEQ ID NO: 500)

BMS3h-193-2516
DIQMTQSPSSLSASVGDRVTITCRASQTIERRLNWYQQKPGKAPRLLIYLSSKLQSGVPSRFSGSGSGTDFTLTISSLQ
PEDFATYYCHQYESPPLTFGQGTKVEIKR (SEQ ID NO: 501)

BMS3h-198-1
EVQLLESGGGLVQPGGSLRLSCAASGSTIAGYEMWWVRQAPGKGLERVSAISGSGGSTYYADSVKGRFTISRDDSKNTL
YLQMNSLRAEDTAVYYCARDPYSFDYWGQGTLVTVSS (SEQ ID NO: 502)

BMS3h-198-2
EVQPLESGGGLVQPGGSLRLSCAASGFTFAGYEMWWVRQAPGKGLERISAISGSGGSTYYADSVKGRFTISRDDSKNTL
YLQMNSLRAEDTAVYYCARDPYSFDYWGQGTLVTVSS (SEQ ID NO: 503)

BMS3h-198-3
EVQLLESGGGSVQPGGSLRLSCAATGSTFAGYEMWWVRQAPGKGLERVSAISGSGGSTYYADSVKGRFTISRDDSKNTL
YLQMNSLRAEDTAVYYCARDPYSYDYWGQGTLVSVSS (SEQ ID NO: 504)

BMS3h-198-4
EVQLLESGGGLVQPGGSLRLSCAASGLTFAGYEMWWVRQAPGKGLERVSAISGSGGSTYYADSVKGRFTISRDDSKNTL
YLQMNSLRAEDTAVYHCARDPYSFDYWGQGTLVTVSS (SEQ ID NO: 505)

BMS3h-198-5
EVQLLESGGGLVQPGGSLRLSCAASGFTFAGYEMWWVRQAPGKGLERVSAISGSGGSTYYADSVKGRFTISRDDSKNTL
YLQMNSLRAEDTAVYHCAKEPYSYDYWGQGTLVTVSS (SEQ ID NO: 506)

BMS3h-198-6
EVQLLESGGGLVQPGGSLRLSCAASGSTFAGYEMWWVRQAPGKGLERVSAISGSGGSTYYADSVKGRFTISRDDSKNTL
YLQMNSLRPEDTAVYYCVKDPYSFDYWGQGTLVTVSS (SEQ ID NO: 507)

BMS3h-198-7
EVQLLESGGGLVQPGGSLRLSCAASGSTIAGYEMWWVRQAPGKGLERVSAISGSGGSTYYADSVKGRFTISRDDSKNTL
YLQMNSLRAEDTAVYYCARDPYSFDYWGQGTPVTVSS (SEQ ID NO: 508)

BMS3h-198-8
EVQLMESGGGLVQPGGSLRLSCAASGSTFAGYEMWWYRQAPGKGLERVSAISGSGRSTYYADSVKGRFTISRDDSKNTL
YLQMNSLRAEDTAVYYCAKDPYSFDYWGQGTLVTVSS (SEQ ID NO: 509)

BMS3h-198-9
EVQLLESGGGLVQPGGSLRLSCAASGFTFAGYEMWWVRQAPGKGLERVSAISGSGGSTYYADSVKGRFTISRDDSKNTL
YLQMNSLRAEDTAVYYCAKEPYSFDYWGQGTLVTVSS (SEQ ID NO: 510)

BMS3h-198-10
EVQLLESGGGLVQPGGSLRLSCAASGSTIAGYEMWWVRQAPGKGLERVSAISGSGGSTYYADSVKGRFTISRDDSKNTL
YLQMNSLRAEDTAVYYCAKDPYSFDYWGQGTLVTVSS (SEQ ID NO: 511)

BMS3h-198-11
EVQLLESGGGLVQPGGSLRLSCAASGFTFAGYEMWWVRQAPGKGLERVSAISGSGGSTYYADSVKGRFTISRDDSKNTL
YLQMNSLRAEDTAVYYCARDPYSFDYWGQGTLVSVSS (SEQ ID NO: 512)

BMS3h-198-12
EVQLLESGGGLVQPGGSLRLSCAASGFTIAGYEMWWVRQAPGKGLERVSAISGSGGSTYYADSVKGRFTISRDDSKNTL
YLQMNSLRAEDTAVYYCAKDPYSFDYWGQGTLVTVSS (SEQ ID NO: 513)

BMS3h-198-13
EVQLLESGGGLVQPGGSLRLSCAASGFTFAGYEMWWVRQAPGKGLERVSAISGSGGSTYYADSVKGRFTITRDDSKNTL
YLQMNSLRAEDTAVYYCAKEPYSFDYWGQGTLVTVSS (SEQ ID NO: 514)

BMS3h-198-14
EVQLLESGGGLVQPGGSLRLSCAASGFTFAGYEMWWFRQAPGKGLERVSAISGSGGSTYYADSVKGRFTISRDDTKNTL
YLQMNSLRAEDTAVYYCAKDPYSFDYWRQGTLVTVSS (SEQ ID NO: 515)

BMS3h-198-15
EVQLLESGGGLVQPGGSLRLSCAASGSTFAGYEVWWVRQAPGKGLERVSAISGSGGSTYYADSVKGRFTISRDDSKNTL
YLQMNSLRAEDTAVYYCARDPYSFDYWGQGTLVTVSS (SEQ ID NO: 516)

BMS3h-198-16
EVQLLESGGGLVQPGGSLRLSCAASGSTFAGYEMWWVRQAPGKGLERISAISGSGGSTYYADSVKGRFTISRDDSKNTL
YLKMNSLRAEDTAVYYCAKDPYSFDYWGQGTLVTVSS (SEQ ID NO: 517)

BMS3h-198-17
EVQLLESGGGLVQPGGSLRLSCAASGFTFAGYEMWWVRQAPGKGLERVSAISGSGGSTYYADSVKGRFTISRDDSKNTL
YLQMNSLRAEDTAVYYCARDPYSFDYWGQGTLVTVSS (SEQ ID NO: 518)

TABLE 3-continued

Anti-Human CD40 Variable Domain Amino Acid Sequences

BMS3h-198-18
EVQLLESGGGLVQPGGSLRLSCAASGLTFAGYEMWWVRRAPGKGLERVAAISGSGGSTYYADSVKGRFTISRDDSKNTL
YLQMNSLRAEDTAVYYCARDPYSFDYWGQGTLVTVSS (SEQ ID NO: 519)

BMS3h-198-19
EVQLLESGGGLVQPGGSLRLSCAASGFTFAGYELWWVRQAPGKGLERVSAISGSGGSTYYADSVKGRFTISRDDSKNTL
YLQMNSLRAEDTAVYYCARDPYSFDYRGQGTLVTVSS (SEQ ID NO: 520)

BMS3h-198-20
EVQLLESGGGLVQPGGSLRLSCAAPGFTLAGYEMWWVRQAPGKGLERVSAISGSGGSTYYADSVKGRFTISRDDSKNTL
YLQMNSLRAEDTAVYYCAKEPYSFDYWGQGTLVTVSS (SEQ ID NO: 521)

BMS3h-198-21
EVQLLESGGGLVQPGGSLRLSCAASGLTFAGYEMWWVRRAPGKGLERVSAISGSGGSTYYADSVKGRFTTSRDDSKNTL
YLQMNSLRAEDTAVYYCARDPYSFDYWGRGTLVTVSS (SEQ ID NO: 522)

BMS3h-198-22
EVQLLESGGGLVQPGGSLRLSCAASGFTFAGYEMWWVRQAPGKGLERVSAISGSGGSTYYADSVKGRFTISRDDSKNTL
YLQMNSLRAEDTAVYYCAKEPYSYDYWGHGTLVTVSS (SEQ ID NO: 523)

BMS3h-198-23
EVQPLESGGGLVQPGGSLRLSCAASGFTFAGYEMWWVRQAPGKGLERVSAISGSGGNTYYADSVKGRFTISRDDSKNTL
YLQMNSLRAEDTGVYYCARDPYSFDYWGQGTLVTVSS (SEQ ID NO: 524)

BMS3h-198-24
EVQLLESGGGLVQPGGSLRLSCAASGFTFAGYEMWWVRQAPGKGLERVSAISGSGGSTYYADSVKGRFTISRDDSKNTL
YLQMNSLRAEDTAVYYCAKEPYSFDSWGQGTLVTVSS (SEQ ID NO: 525)

BMS3h-198-25
EAQLLESGGGLVQPGGSLRLSCAASGLTFAGYEMWWVRQAPGKGLERVSAISGSGGSTYYADSVKGRFTISRDDSKNTL
YLQMNSLRAEDTAVYYCARDPYSFDYWGQGTLVTVSS (SEQ ID NO: 526)

BMS3h-198-26
EVQLLESGGGLVQPGGSLRLSCAASGSTFAGYEMWWVRQAPGKGLERVSAISGSGGSTYYADSVKGRFSISRDDSKNTL
YLQMNSLRAEDTAVYYCAKEPYSFDHWGQGTLVTVSS (SEQ ID NO: 527)

BMS3h-198-27
EVQLLESGGGLVQPGGSLRLSCAASGSTFAGYEMWWVRRAPGKGLERVSAISGSGGSTYYADSVKGRFTISRDDSKNTL
YLQMNSLRAEDTAVYYCARDPYSFDYWGQGTLVTVSS (SEQ ID NO: 528)

BMS3h-198-28
EVQLLESGGGLVQPGGSLRLSCAASGFTFAGYEMWWFRQAPGKGLERVSAISGSGGSTYYADSVKGRFTISRDDSKNTL
YLQMNSLRAEDTAVYYCAKDPYSFDNWGQGTLVTVSS (SEQ ID NO: 529)

BMS3h-198-29
EVQLLESGGGLVEPGGSLRLSCAASGFTFAGYEMWWVRQAPGKGLERVSAISGSGGSTYYADSVKGRFTISRDDSKNTL
YLQMNSLRAEDTAVYYCAKEPYSFDHRGQGTLVTVSS (SEQ ID NO: 530)

BMS3h-198-30
EVQLLESGGGLVQPGGSLRLSCAASGYTFAGYEMWWVRQAPGKGLERVSAISGSGGSTYYADSVKGRFTISRDDSKNTL
YLQMNSLRAEDTAVYYCAKEPYSFDHRGQGTLVTVSS (SEQ ID NO: 531)

BMS3h-198-31
EVQLLESGGGLVQPGGSLRLSCAASGFTFAGYEMWWVRQAPGKGLERVSAISGSGGSTYYADSVKGRFTISRDNSKNTL
YLQMNSLRAEDTAVYHCAKEPYSYDYWGQGTLVTVSS (SEQ ID NO: 532)

BMS3h-198-32
EVQLLESGGGLVQPGGSLRLSCAASGFTFAGYEMWWFRQAPGKGLERVSAISGSGGSTYYADSVKGRFTISRDNSKNTL
YLQMNSLRAEDTAVYYCAKDPYSFDNWGQGTLVTVSS (SEQ ID NO: 533)

BMS3h-198-33
EVQLLESGGGLVQPGGSLRLSCAASGFTFAGYEMWWVRQAPGKGLERVSAISGSGGSTYYADSVKGRFTISRDDSKNTL
YLQMNSLRAEDTAVYYCAKEPYSYDYWGQGTLVTVSS (SEQ ID NO: 534)

BMS3h-198-34
EVQLLESGGGLVQPGGSLRLSCAASGFTFAGYEMWWVRQAPGKGLERVSAISGSGGSTYYADSVKGRFTISRDDSKNTL
YLQMNSLRAEDTAVYYCAKDPYSFDNWGQGTLVTVSS (SEQ ID NO: 535)

BMS3h-198-35
EVQLLESGGGLVQPGGSLRLSCAASGFTFAGYEMWWVRQAPGKGLEWVSAISGSGGSTYYADSVKGRFTISRDDSKNTL
YLQMNSLRAEDTAVYHCAKEPYSYDYWGQGTLVTVSS (SEQ ID NO: 536)

BMS3h-198-36
EVQLLESGGGLVQPGGSLRLSCAASGFTFAGYEMWWFRQAPGKGLEWVSAISGSGGSTYYADSVKGRFTISRDDSKNTL
YLQMNSLRAEDTAVYYCAKDPYSFDNWGQGTLVTVSS (SEQ ID NO: 537)

TABLE 3-continued

Anti-Human CD40 Variable Domain Amino Acid Sequences

BMS3h-198-37
EVQLLESGGGLVQPGGSLRLSCAASGFTFAGYELWWVRQAPGKGLERVSAISGSGGSTYYADSVKGRFTISRDDSKNTL
YLQMNSLRAEDTAVYYCAKDPYSFDYRGQGTLVTVSS (SEQ ID NO: 538)

BMS3h-198-38
EVQLLESGGGLVQPGGSLRLSCAASGFTFAGYELWWVRQAPGKGLERVSAISGSGGSTYYADSVKGRFTISRDDSKNTL
YLQMNSLRAEDTAVYYCARDPYSFDYWGQGTLVTVSS (SEQ ID NO: 539)

BMS3h-202-1
EVQLLESGGGLVQPGGSLRLSCAASGFTFPTAEMLWVRKAPGKGLEWVSSISASGGSTYYADSVKGRFTISRDNSKNTL
YLQMNSLRAEDTAVYYCAKEPVSYVATFDYWGQGTLVTVSS (SEQ ID NO: 540)

BMS3h-202-2
EVQLLVSGGGLVQPGGSLRLSCAASGFTFPTAEMLWVRQAPGKGPEWVSSISASGGSTYYADSVKGRFTISRDNSKNTL
YLQMNSLRAEDTAVYYCAKEPVSYVATFDYWGQGTLVTVSS (SEQ ID NO: 541)

BMS3h-202-3
EVQLLESGGGLVQPGGSLRLSCAASGFTFPTAEMVWVRKAPGMGLEWVSSISASGGYTYYADSVKGRFTISRDNSKNML
YLQMNSLRAEDTAVYYCAKEPVSYVATFDYWGQGALVTVTS (SEQ ID NO: 542)

BMS3h-202-4
EVQLLVSGGGLVQPGGSLRLSCAASGFTFPTAEMVWVRQAPGKGLEWVSSISASGGSTYYADSVKGRFSISRDDSKNTL
YLQMNSLRAEDTAVYYCAKEPVSYVATFDYWGHGALVTVSS (SEQ ID NO: 543)

BMS3h-202-5
EVQLLESGGGLVQPGGSLRLSCAASGFTFPTAEMLWVRQAPGKGLEWVSSISASGGSTYYADSVKGRFTISRDNSKNTL
YLQMNSLRAEDTAVYYCAKEPVSYVATFDYWGQGTLVTVSS (SEQ ID NO: 544)

BMS3h-202-6
EAQLLESGGGLVQPGGSLRLSCAASGFTFPTAEMVWVRQAPGKGLEWISSISASGGSTYYADSVKGRFTISRDNSKNTL
YLQLNSLRAEDTAVYYCAKEPVSYVATFDYWGRGTLVTVSS (SEQ ID NO: 545)

BMS3h-202-7
EVQLLESGGGLVQPGGSLRLSCAASGFTFPTAEMLWVRQAPGKGLEWVSSISASGGSTYYADSVKGRFTISRDNSKSTL
YLQMNSLRAEDTAVYYCAKEPVSYVATFDYWGPGALVTVSS (SEQ ID NO: 546)

BMS3h-202-8
EVQLLESGGGLVQPGGSLRLSCAASGFTFPTAEMLWVRKAPGKGLEWVSSISASGGSTYYADSVKGRFTISRDNSKNTL
FLQMNSLRAEDTAVYYCAKEPVSYVATFDYWGQGTLVTVSS (SEQ ID NO: 547)

BMS3h-202-9
EVQLLESGGGLVQPGGSLRLSCAASGFTFPTAEMLWVRQAPGKGLEWVSSISASGGSTYYADSVKGRFTISRDNSKNTL
YLQMNSLRAEDTAVYYCAKEPVSYVATFDYWGPGALVTVSS (SEQ ID NO: 548)

BMS3h-202-10
EVQLLESGGGLVQPGGSLRLSCAASGFTFPTAEMLWVRQAPGKGLEWVSSISASGGSTYYADSVKGRFTISRDNSKNTL
YLQMNSLRAEDTAVYYCAKEPVYYVATFDYWGQGTLVTVSS (SEQ ID NO: 549)

BMS3h-202-11
EVQLLESGGGLVQPGGSLRLSCAASGFTFPTAEMLWVRKAPGKGLEWVSSISASGGSTYYADSVKGRFTISRDNSKNTL
YLQMNSLRAEDAAVYYCAKEPVSYVATFDYWGQGTLVTVSS (SEQ ID NO: 550)

BMS3h-217-1
NIQMTQSPSSLSASVGDRVTITCRASHFIGTLLTWYQHKPGKAPKLLITYGSLLQSGVPSRFSGSGSGTDFTLTISSLQ
PEDFATYYCGQGVLWPATFGQGTKVEIKR (SEQ ID NO: 551)

BMS3h-217-2
DIQMTQSPSSLSASVGDRVTITCRASHFIGTLLSWYQQKPRKAPKLLITYGSLLQSGVPSRFSGSGSGTDFTLTISSLH
PEDFATYYCGQGVLWPPTFGQGTKVEIKR (SEQ ID NO: 552)

BMS3h-217-3
DIQMTQSPSSLTASVGDRVTITCRASHFIGTLLSWYQQKPGKAPKLLVTYGSLLQSGVPSRFSGSGSGTDFTLTISNLQ
PEDFATYYCGQGVLWPPTFGQGTKVENIR (SEQ ID NO: 553)

BMS3h-217-4
DIQMTQSPSSLSASVGDRVTITCRASHFIATLLSWYQQKPGKAPKLLITYGSLLQSGVPSRFSGSGSGTDFTLTISSLQ
PEDFATYYCGQGVLWPPTFGQGTKVEIKR (SEQ ID NO: 554)

BMS3h-217-5
DIQMTQSPSFLSASVGDRVTITCRASHFIATLLSWYQQKPGKAPKLLITYGSLLQSGVPSRFSGSGSGTDFTLTISSLQ
PEDFATYYCGQGVLWPPTFGQGTKVEIKR (SEQ ID NO: 555)

BMS3h-217-6
DIQMTQSPSSLSASVGDRVTITCRASHFIGTLLSWYQQKPGKATKLLITYGSLLQSGVPSRFSGSGSGTDFTLTISSLQ
PEDFATYYCGQGVLWPPTFGQGTKVEIKR (SEQ ID NO: 556)

TABLE 3-continued

Anti-Human CD40 Variable Domain Amino Acid Sequences

BMS3h-217-7
DIQMTQSPSSLSASVGDRVTITCRASHFIGSLLSWYQHKPGKAPKLLITYGSLLQSGVPSRFSGSGSGTDFTLTISSLQ
PEDFATYYCGQGVLWPATFGQGTKVEIKR (SEQ ID NO: 557)

BMS3h-217-8
DIQMTQSPSSLSASVGDRVTITCRASHFIGTLLSWYQHKPGKAPKLLITYGSLLQSGVPSRFSGSGSGTDFTLTISSLQ
PEDFATYYCGQGVLWPATFGQGTKVEIKR (SEQ ID NO: 558)

BMS3h-217-9
DIQMTQSPSSLSASVGDRVTITCRASHFIGTLLSWYQHKPGKAPKLLITYGSMLQSGVPSRFSGSGSGTDFTLTISSLQ
PEDFATYYCGQGVLWPATFGQGTKVEIKR (SEQ ID NO: 559)

BMS3h-217-10
DIQMTQSPSSLSASVGDRVTITCRASHFIGTLLSWYQHKPGKAPKLLITYGSLLQSGVPSRFSGSGSGTEFTLTISSLQ
PEDFATYYCGQGVLWPATFGQGTKVEIKR (SEQ ID NO: 560)

BMS3h-217-11
DIQMTQSPSSLTASVGDRVTITCRASHFIGTLLSWYQHKPGKAPKLLITYGSLLQSGVPSRFSGSGSGTEFTLTISSLQ
PEDFATYYCGQGVLWPATFGQGTKVEIKR (SEQ ID NO: 561)

BMS3h-217-12
NIQMTQSPSSLSASVGDRVTITCRASHFIGTLLSWYQHKPGKAPKLLITYGSLLQSGVPSRFSGSGSGTDFTLTISSLQ
PEDFATYYCGQGVLWPATFGQGTKVEIKR (SEQ ID NO: 562)

BMS3h-217-13
DIQMTQSPSSLSASVGDRVTINCRASHFIGTLLSWYQHKPGKAPKLLITYGSLLQSGVPSRFSGSGSGTDFTLTISSLQ
PEDFATYYCGQGVLWPATFGQGTKVEIKR (SEQ ID NO: 563)

BMS3h-217-14
DIQLTQSPSSLSASVGDRVTITCRASHFIGTLLSWYQQKPGKATKLLITYGSLLQSGVPSRFSGSGSGTDFTLTISSLQ
PEDFATYYCGQGVLWPPTFGQGTKVEIKR (SEQ ID NO: 564)

BMS3h-217-15
DIQMTQSPSSLYASVGDRVTITCRVSHFIGTLLSWYQQKPGKAPKLLITYGSLLQSGVPSRFSGSGSGTDFTLSISSLQ
PEDFATYYCGQGVLWPPTFGQGTKVEIKQ (SEQ ID NO: 565)

BMS3h-217-16
DIQMTQSPSSLSASVGDRVTITCRASHFIGTLLSWYQQKPRKAPKLLITYGSLLQSGVPSRFSGSGSGTDFTLTISSLQ
PEDFATYYCGQGVLWPPTFGQGTKVEIKR (SEQ ID NO: 566)

BMS3h-217-17
DIQIIQSPSSLSASVGDRVTITCRASHFIGTLLSWYQQKPGKAPKLLITYGSLLQSGVPSRFSGSGSGTDFTLTISSLQ
PEDFATYYCGQGVLWPPTFGQGTKVEIKR (SEQ ID NO: 567)

BMS3h-217-18
DIQMTQSPSSLSASVGDRVTITCRASHFIGTLLSWYQLKPGKAPKLLITYGSLLQSGVPSRFSGSGSGTDFTLTISSLQ
PEDFATYYCGQGVLWPATFGQGTKVEIKR (SEQ ID NO: 568)

BMS3h-217-19
DIQMTQSPSSLSASVGDRVTITCRASHFIGTLLSWYQLKPGKAPKLLITYGSWLQSGVPSRFSGSGSGTDFTLTISSLQ
PEDFATYYCGQGVLWPATFGQGTKVENKR (SEQ ID NO: 569)

BMS3h-217-20
DIQMTQSPSSLSASVGDRVTITCRASHFIGTLLSWYQLKPGKAPKLLITYGSLLQRGVPSRFSGSGSGTDFTLTISSLQ
PEDFATYYCGQGVLWPATFGQGTKVEIKR (SEQ ID NO: 570)

BMS3h-217-21
DIQMTQAPSSLSASVGDRVTITCRASHFIGTLLSWYQLKPGKAPKLLITYGSLLQSGVPSRFSGSGSGTDFTLTISSLQ
PEDFATYYCGQGVLWPATFGQGTKVENKR (SEQ ID NO: 571)

BMS3h-217-22
DIQMTQSPSSLSASVGDRVTITCRASHFIGSLLSWYQQKPGKAPKLLITYGSLLQSGVPSRFSGSGSGTDFALTISSLQ
PEDFATYYCGQGVLWPATFGQGTKVEIKR (SEQ ID NO: 572)

BMS3h-217-23
DIQMTQSPSSLSASVGDRVTITCRASHFIGSLLSWYQVKPGKAPKLLITYGSLLQSGVPSRFSGSGSGTDFTLTISSLQ
PEDFATYYCGQGVLWPATFGQGTTVEIKR (SEQ ID NO: 573)

BMS3h-217-24
DILMTQSPSSLSASVGDRVTITCRASHFIGSLLSWYQQKPGKAPKLLITYGSLLQSGVPSRFSGSGSGTDFTLTISSLQ
PEDFATYYCGQGVLWPATFGQGTKVEIKR (SEQ ID NO: 574)

BMS3h-217-25
DIQMTQSPSSLSASVGDRVTITCRASHFIGTLVSWYQQKPGKAPKLLITYGSLLQSGVPSRFSGSGSGTDFTLTISSLQ
PEDFATYYCGQGVLWPATYGQGTKVEIKR (SEQ ID NO: 575)

TABLE 3-continued

Anti-Human CD40 Variable Domain Amino Acid Sequences

BMS3h-217-26
DIQMTQSPSSLSASVGDRVTITCRASHFIGTLVSWYQQKPGKAPKLLITYGSLLQSGVPSRFSGSGSGTDFTLTISSLQ
PEDFATYYCGQGVLWPATFGQGTKVENKR (SEQ ID NO: 576)

BMS3h-217-27
DIKMTQSPSSLSASVGDRVTITCRASHFIGTLVSWYQQKPGKAPKLLITYGSMLQSGVPSRFSGSGSGTDFTLTISSLQ
PEDFATYYCGQGVLWPATFGQGTKVEIKR (SEQ ID NO: 577)

BMS3h-217-28
DIQMTQSPSSLSASVGDRVTITCQASHFIGTLVSWYQQKPGKAPKLLITYGSLLQSGVPSRFSGSGSGTDFTLTISSLQ
PEDFATYYCGQGVLWPATFGQGTKVEIKR (SEQ ID NO: 578)

BMS3h-217-29
DIQMTQSPSSLSASVGDRVTITCRASHFIGTLLSWYQQKPGKAPKLLITYGSWLQSGVPSRFSGSGSGTDFTLTISSLQ
PEDFATYYCGQGVLWPATFGQGTKVEIKR (SEQ ID NO: 579)

BMS3h-217-30
DIQMTQSPSSLSASVGDRVTITCRASHFIGTLLSWYQLKPGKAPKLLITYGSWLQSGVPSRFSGSGSGTDFTLTISSLQ
PEDFATYYCGQGVLWPATFGQGTKVEIKR (SEQ ID NO: 580)

BMS3h-217-31
DIQMTQSPSSLSASVGDRVTITCRASHFIGTLLSWYQQKPGKAPKLLITYGSLLQSGVPSRFSGSGEGTDFTLTISSLQ
PEDFATYYCGQEVLWPATFGQGTKVEIKR (SEQ ID NO: 581)

BMS3h-217-32
DIQMTQSPSSLSASVGDRVSITCRASHFIGTLLSWYQQKPGKAPKLLITYGSLLQSGVPSRFSGSGEGTDFTLTISSLQ
PEDLATYYCGQEVLWPATFGQGTKVEIKR (SEQ ID NO: 582)

BMS3h-217-33
DIQMTQSPSSLSASVGDRVTITCQASHFIGTLLSWYQQKPGKAPKLLITYGSLLQSGVPSRFSGSGEGTDFTLTISSLQ
PEDFATYYCGQEVLWPATFGQGTKVEIKR (SEQ ID NO: 583)

BMS3h-217-34
DIQMTQSPSSLSASVGDRVTITCRASHFIGTLLSWYQQKPGKAPKLLITYGSLLQSGVPSRFSGSGFGTEFTLTIGSLQ
PEDFATYYCGQGVLWPATFGQGTKVEIKR (SEQ ID NO: 584)

BMS3h-217-35
DIQMTQSPSSLSASVGDRVTITCRASHFIGTLLSWYQQKPGKATKLLITYGSLLQSGVPSRFSGSGSGTDFTLTISSLQ
PEDFATYYCGQGVLWPPTFGQGTKVEIKR (SEQ ID NO: 585)

BMS3h-217-2301
DIQMTQSPSSLSASVGDRVTITCRASHFIASLLSWYQVKPGKAPKLLITYGSLLQSGVPSRFSGSGSGTDFTLTISSLQ
PEDFATYYCGQGVLWPATFGQGTTVEIKR (SEQ ID NO: 586)

BMS3h-217-2302
DIQMTQSPSSLSASVGDRVTITCRASHFIAQLLSWYQVKPGKAPKLLITYGSLLQSGVPSRFSGSGSGTDFTLTISSLQ
PEDFATYYCGQGVLWPATFGQGTTVEIKR (SEQ ID NO: 587)

BMS3h-217-2303
DIQMTQSPSSLSASVGDRVTITCRASHFIAQLLSWYQVKPGKAPKLLITYGSLLQSGVPSRFSGSGSGTDFTLTISSLQ
PEDFATYYCGQGVLWPATFGQGTTVEIRR (SEQ ID NO: 588)

BMS3h-217-2304
DIQMTQSPSSLSASVGDRVTITCRASHYIASLLSWYQVKPGKAPKLLITYGSLLQSGAPSRFSGSGSGTDFTLTISSLQ
PEDFATYYCGQGVLWPATFGQGTTVEIKR (SEQ ID NO: 589)

BMS3h-217-2305
DIQMTQSPSSLSASVGDRVTITCRASHFIGSLLSWYQVKPGKAPKLLITWASYLQSGVPSRFSGSGSGTDFTLTISSLQ
PEDFATYYCGQGVLWPATFGQGTTVEIKR (SEQ ID NO: 590)

BMS3h-217-2306
DIQMTQSPSSLSASVGDRVTITCRASHFIGSLLSWYQVKPGKAPKLLITWTSYLQSGVPSRFSGSGSGTDFTLTISSLQ
PEDFATYYCGQGVLWPATFGQGTTVEIKR (SEQ ID NO: 591)

BMS3h-217-2307
DIQMTQSPSSLSASVGDRVTITCRASHFIGSLLSWYQVKPGKAPKLLITWSSYLQSGVPSRFSGSGSGTDFTLTISSLQ
PEDFATYYCGQGVLWPATFGQGTTVEIKR (SEQ ID NO: 592)

BMS3h-217-2308
DIQMTQSPSSLSASVGDRVTITCRASHFIGSLLSWYQVKPGKAPKLLITWGSWLQSGVPSRFSGSGSGTDFTLTISSLQ
PEDFATYYCGQGVLWPATFGQGTTVEIKR (SEQ ID NO: 593)

BMS3h-217-2309
DIQMTQSPSSLSASVGDRVTITCRASHFIGSLLSWYQVKPGKAPKLLITWASWLQSGVPSRFSGSGSGTDFTLTISSLQ
PEDFATYYCGQGVLWPATFGQGTTVEIKR (SEQ ID NO: 594)

TABLE 3-continued

Anti-Human CD40 Variable Domain Amino Acid Sequences

BMS3h-217-2310
DIQMTQSPSSLSASVGDRVTITCRASHFIGSLLSWYQVKPGKAPKLLITWSSWLQSGVPSRFSGSGSGTDFTLTISSLQ
PEDFATYYCGQGVLWPATFGQGTTVEIKR (SEQ ID NO: 595)

BMS3h-217-2311
DIQMTQSPSSLSASVGDRVTITCRASHWIAQLLSWYWKPGKAPKLLITYGSLLQSGVPSRFSGSGSGTDFTLTISSLQ
PEDFATYYCGQGVLWPATFGQGTTVEIKR (SEQ ID NO: 596)

BMS3h-217-2312
DIQMTQSPSSLSASVGDRVTITCRASHFIGSLLRWYQVKPGKAPKLLITYGSLLQSGVPSRFSGSGSGTDFTLTISSLQ
PEDFATYYCGQGVLWPATFGQGTTVEIKR (SEQ ID NO: 597)

BMS3h-217-2313
DIQMTQSPSSLSASVGDRVTITCRASHRIAQLLSWYQVKPGKAPKLLITYGSLLQSGVPSRFSGSGSGTDFTLTISSLQ
PEDFATYYCGQGVLWPATFGQGTTVEIKR (SEQ ID NO: 598)

BMS3h-217-2314
DIQMTQSPSSLSASVGDRVTITCRASHYIASLLSWYQVKPGKAPKLLITYGSLLQSGVPSRFSGSGSGTDFTLTISSLQ
PEDFATYYCGQGVLWPATFGQGTTVEIKR (SEQ ID NO: 599)

BMS3h-217-2315
DIQMTQSPSSLSASVGDRVTITCRASHFIGSLLSWYQVKPGKAPKLLIREGSLLQSGVPSRFSGSGSGTDFTLTISSLQ
PEDFATYYCGQGVLWPATFGQGTTVEIKR (SEQ ID NO: 600)

BMS3h-217-2316
DIQMTQSPSSLSASVGDRVTITCRASHFIGSLLSWYQVKPGKAPKLLITYKSYLQSGVPSRFSGSGSGTDFTLTISSLQ
PEDFATYYCGQGVLWPATFGQGTTVEIKR (SEQ ID NO: 601)

BMS3h-217-2317
DIQMTQSPSSLSASVGDRVTITCRASHFIGSLLSWYQVKPGKAPKLLITWGSYLQSGVPSRFSGSGSGTDFTLTISSLQ
PEDFATYYCGQGVLWPATFGQGTTVEIKR (SEQ ID NO: 602)

BMS3h-217-2318
DIQMTQSPSSLSASVGDRVTITCRASHFIWGPLSWYQVKPGKAPKLLITYGSLLQSGVPSRFSGSGSGTDFTLTISSLQ
PEDSATYYCGQGVLWPATFGQGTTVEIKR (SEQ ID NO: 603)

BMS3h-217-2319
DIQMTQSPSSLSASVGDRVTITCRASHWIATLLSWYQVKPGKAPKLLITYGSLLQSGVPSRFSGSGSGTDFTLTISSLQ
PEDFATYYCGQGVLWPATFGQGTTVEIKR (SEQ ID NO: 604)

BMS3h-217-2320
DIQMTQSPSSLSASVGDRVTITCRASHFIWGPLSWYQVKPGKAPKLLITYGSLLQSGVPSRFSGSGSGTDFTLTISSLQ
PEDFATYYCGQGVLWPATFGQGTTVEIKR (SEQ ID NO: 605)

BMS3h-217-2321
DIQMTQSPSSLSASVGDRVTITCRASHFIGSLLNWYQVKPGKAPKLLITYGSLLQSGVPSRFSGSGSGTDFTLTISSLQ
PEDFATYYCGQGVLWPATFGQGTTVEIKR (SEQ ID NO: 606)

BMS3h-217-2322
GIQMTQSPSSLSASVGDRVTITCRASHFIGSLLSWYQVKPGKAPKLLITYGSWLQSGVPSRFSGSGSGTDFTLTISSLQ
PEDFATYYCGQGVLWPATFGQGTTVEIKR (SEQ ID NO: 607)

TABLE 4

Human Anti-CD40 Variable Domain Encoding Nucleotide Sequences

BMS3h-56-201
GAGGTGCAGCTGTTGGAGTCCGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTACTTTCAGGAGT
GGGGTCAGGGAACCCTGGTCACCGTCTCGAGC (SEQ ID NO: 608)

BMS3h-56-258
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTACTTTCACGAGT
GGGGTCAGGGAACCCTGGTCACCGTCTCGAGC (SEQ ID NO: 609)

TABLE 4-continued

Human Anti-CD40 Variable Domain Encoding Nucleotide Sequences

BMS3h-37
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCAGGCTCCAGGGAAGGGTCTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACT
GGGGTCAGGGAACCCTGGTCACCGTCTCGAGC (SEQ ID NO: 610)

BMS3h-38
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGGAGGAGGAGATGATTTGGGTCCGCCAGGCTCCAGGGAAGGGTCTAGAGTGGGTCTCAGCTATTAGTGG
TAGTGGTGGTAGCACATACTACGCAGACTCCGTGAAAGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGTTTCGTTTTGACTACT
GGGGTCAGGGAACCCTGGTCACCGTCTCGAGC (SEQ ID NO: 611)

BMS3h-41
GAGGTGCAGCTGTTGGAGTCTGGGGGAGGCTTGGTACAGCCTGGGGGGTCCCTGCGTCTCTCCTGTGCAGCCTCCGGAT
TCACCTTTACTGAGTATGAGATGATTTGGGTCCGCCAGGCTCCAGGGAAGGGTCTGGAGTGGGTCTCATCTATTTCGGG
TAATGGTGCTAATACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGCTTAGGTTTGACTACT
GGGGTCAGGGAACCCTGGTCACCGTCTCGAGC (SEQ ID NO: 612)

BMS3h-43
GAGGTGCAGCTGTTGGAGTCTGGGGGAGGCTTGGTACAGCCTGGGGGGTCCCTGCGTCTCTCCTGTACAGCCTCCGGAT
TCACCTTTAATATGTATGAGATGTCGTGGGTCCGCCAGGCTCCAGGGAAGGGTCTAGAGTGGGTCTCAGGTATTAGTAG
GCGTGGTTTTACTACATACTACGCAGACTCCGTGAAAGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGCTATGA
GGTATGCGCGTTTTGACTACTGGGGTCAGGGAACCCTGGTCACCGTCTCGAGC (SEQ ID NO: 613)

BMS3h-56
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGTGGGTCTCAGCTATTAATCC
GCAGGGTACGCGTACATACTACGCAGACTCCGTGAAAGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTATTTTTGACTACT
GGGGTCAGGGAACCCTGGTCACCGTCTCGAGC (SEQ ID NO: 614)

BMS3h-106
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGACTTATCATATGCAGTGGGTCCGCCAGGCTCCAGGGAAGGGTCTGGAGTGGGTCTCAATGATTGATGC
GGATGGTCTTGGGACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAACCGGGTCCGCAGTTTGGTCAGT
TTGACTACTGGGGTCAGGGAACCCTGGTCACCGTCTCGAGC (SEQ ID NO: 615)

BMS3h-107
GAGGTGCAGCTGTTGGAGTCTGGGGGAGGCTTGGTACAGCCTGGGGGGTCCCTGCGTCTCTCCTGTGCAGCTTCCGGAT
TCACCTTTTCGGGGTATGATATGCAGTGGGTCCGCCAGGCTCCAGGGAAGGGTCTAGAGTGGGTCTCAACGATTAGTGC
GTCGGGTGTTTTTACATACTACGCAGACTCCGTGAAAGGCCGGTTCACCACCTCCCGCGACAATTCCAAGAACACGCTG
TATCTGCAAATGAACAGCCTGCGTGCCGAGGACACCGCGGTATATTACTGTGCGAAATATCCTAATCGTTTTGCGCTTA
ATAATTTTGACTACTGGGGTCAGGGAACCCTGGTCACCGTCTCGAGC (SEQ ID NO: 616)

BMS3h-131
GACATCCAGATGACCCAGTCTCCATCCTCCCTGTCTGCATCTGTAGGAGACCGTGTCACCATCACTTGCCGGGCAAATA
GTTCTATTTTGTGGGCGTTAGCTTGGTACCAGCAGAAACCAGGGAAAGCCCCTAAGCTCCTGATCGAGAGTTCTTCCGG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGGTTGGCCTGGTACGTTCGGCCAAGGGACCAAGGTGGAAA
TCAAACGG (SEQ ID NO: 617)

BMS3h-193
GACATCCAGATGACCCAGTCTCCATCCTCCCTGTCTGCATCTGTAGGAGACCGTGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGCGAGTCCACCTTTGACGTTCGGCCAAGGGACCAAAGTGGAAA
TCAAACGG (SEQ ID NO: 618)

BMS3h-198
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAAGGCCGGTTCACCATCTCCCGCGACGATTCCAAGAACACGCTG
TATCTGCAAATGAACAGCCTGCGTGCCGAGGATACCGCGGTATATTACTGTGCGAAAGATCCTTATAGTTTTGACTACT
GGGGTCAGGGAACCCTGGTCACCGTCTCGAGC (SEQ ID NO: 619)

BMS3h-202
GAGGTGCAGCTGTTGGAGTCTGGGGGAGGCTTGGTACAGCCTGGGGGGTCCCTGCGTCTCTCCTGTGCAGCCTCCGGAT
TCACCTTTCCGACTGCTGAGATGGTGTGGGTCCGCCAGGCTCCAGGGAAGGGTCTAGAGTGGGTCTCATCTATTTCGGC
TAGTGGTGGTTCTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGGTGAGTTATGTGGCGA
CGTTTGACTACTGGGGTCAGGGAACCCTGGTCACCGTCTCGAGC (SEQ ID NO: 620)

TABLE 4-continued

Human Anti-CD40 Variable Domain Encoding Nucleotide Sequences

BMS3h-217
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCAGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 621)

BMS3h-1
GAGGTGCAGCTGTTGGAGTCTGGGGGAGGCTTGGTACAGCCTGGGGGGTCCCTGCGTCTCTCCTGTGCAGCCTCCGGAT
TCACCTTTCCGAAGAATGAGATGACGTGGGTCCGCCAGGCTCCAGGGAAGGGTCTAGAGTGGGTCTCAGCGATTGAGTC
GGATGGTCAGGCTACATACTACGCAGACTCCGTGAAGGGCCGGTTCACCATCTCCCGCGACAATTCCAAGAACACGCTG
TATCTGCAAATGAACAGCCTGCGTGCTGAGGACACCGCGGTATATTACTGTGCGAAAAATCGGATTCCTGATCTTGTGT
TTGACTACTGGGGTCAGGGAACCCTGGTCACCGTCTCGAGC (SEQ ID NO: 622)

BMS3h-2
GAGGTGCAGCTGTTGGAGTCTGGGGGAGGCTTGGTACAGCCTGGGGGGTCCCTGCGTCTCTCCTGTGCAGCCTCCGGAT
TCACCTTTGATGCTGGGCTATGACGTGGGTCCGCCAGGCTCCAGGGAAGGGTCTCATCTATTGATAA
GGAGGGTCTGTCTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGGTAGGATTCCTGGGCTGGTTT
TTGACTACTGGGGTCAGGGAACCCTGGTCACCGTCTCGAGC (SEQ ID NO: 623)

BMS3h-3
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTGATGCGGCGATGACTTGGGTCCGCCAGGCTCCAGGGAAGGGTCTAGAGTGGGTCTCAGCGATTCAGCC
TATGGGTGATGGTACATACTACGCAGACTCCGTGAAGGGCCGGTTCACCGTCTCCCGCGACAATTCCAAGAACACGCTG
TATCTGCAAATGAACAGCCTGCGTGCCGAGGACACCGCGGTATATTACTGTGCGAAAGGGCGTATTCCTACTCTTCAGT
TTGACTACTGGGGTCAGGGAACCCTGGTCACCGTCTCGAGC (SEQ ID NO: 624)

BMS3h-4
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGGATTCGCTATGACTTGGGTCCGCCAGGCTCCAGGGAAGGGTCTAGAGTGGGTCTCAGCTATTACTTC
GAATGGTTATGAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGCGTATTCCTACTCTTCATT
TTGACTACTGGGGTCAGGGAACCCTGGTCACCGTCTCGAGC (SEQ ID NO: 625)

BMS3h-5
GAGGTGCAGCTGTTGGAGTCTGGGGGAGGCTTGGTACAGCCTGGGGGGTCCCTGCGTCTCTCCTGTGCAGCCTCCGGAT
TCACCTTTGATGAGCATGATATGAGTTGGGTCCGCCAGGCTCCAGGGAAGGGTCTAGAGTGGGTCTCACGTATTGGTCC
GGATGGTTTTCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGCGTATTCCTACTCTTCATT
TTGACTACTGGGGTCAGGGAACCCTGGTCACCGTCTCGAGC (SEQ ID NO: 626)

BMS3h-6
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTGAGTATCATATGTCTTGGGTCCGCCAGGCTCCAGGGAAGGGTCTAGAGTGGGTCTCAAGGATTACTCC
TCTTGGTACGCTTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGCGTATTCCTTCGCTTACGT
TTGACTACTGGGGTCAGGGAACCCTGGTCACCGTCTCGAGC (SEQ ID NO: 627)

BMS3h-7
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTACGAATGCGATGAGTTGGGTCCGCCAGGCTCCAGGGAAGGGTCTGGAGTGGGTCTCAAGGATTTCGCC
GGGTGGTGATTATACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTGTATTACTGTGCGAAAGGGCGTGTTCCGGATCTGCTTT
TTGACTACTGGGGTCAGGGAACCCTGGTCACCGTCTCGAGC (SEQ ID NO: 628)

BMS3h-8
GAGGTGCAGCTGTTGGAGTCTGGGGGAGGCTTGGTACAGCCTGGGGGGTCCCTGCGTCTCTCCTGTGCAGCCTCCGGAT
TCACCTTTCCGTCTGAGGAGATGTCTTGGGTCCGCCAGGCTCCAGGGAAGGGTCTAGAGTGGGTCTCAAGGATTTCGGC
TGATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACGCCGCGGTATATTACTGTGCGAAAGGGCGTGTTCCGGATCTGCTTT
TTGACTACTGGGGTCAGGGAACCCTGGTCACCGTCTCGAGC (SEQ ID NO: 629)

BMS3h-9
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGAGGATGATATGACTTGGGTCCGCCAGGCTCCAGGGAAGGGTCTAGAGTGGGTCTCACGTATTGCGGT
TGATGGTGATCGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTAAGGTTCCGTCTCTTCATT
TTGACTACTGGGGTCAGGGAACCCTGGTCACCGTCTCGAGC (SEQ ID NO: 630)

BMS3h-10
GAGGTGCAGCTGTTGGAGTCTGGGGGAGGCTTGGTACAGCCTGGGGGATCCCTGCGTCTCTCCTGTGCAGCCTCCGGAT
TCACCTTTAGGACGATGGATATGTCTTGGGTCCGCCAGGCTCCAGGGAAGGGTCTAGAGTGGGTCTCACGTATTACGGG
TGATGGTATGAATACATACTACGCAGACTCCGTGAAGGGCCGGTTCACCATCTCCCGCGACAATTCCAAGAACACGCTG
TATCTGCAAATGAACAGCCTGCGTGCCGGGACACCGCGGTATATTACTGTGCGAAAGGGGTGACTCCGGATTTGACTT
TTGACTACTGGGGTCAGGGAACCCTGGTCACCGTCTCGAGC (SEQ ID NO: 631)

TABLE 4-continued

Human Anti-CD40 Variable Domain Encoding Nucleotide Sequences

BMS3h-11
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGCGTGATGATATGACGTGGGTCCGCCAGGCTCCAGGGAAGGGTCTAGAGTGGGTCTCACGTATTAATGC
TGGGGGTGTGCATACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGGGGTGACTCCGGATTTGACTT
TTGACTACTGGGGTCAGGGAACCCTGGTCACCGTCTCGAGC (SEQ ID NO: 632)

BMS3h-12
GAGGTGCAGCTGTTGGAGTCTGGGGGAGGCTTGGTACAGCCTGGGGGGTCCCTGCGTCTCTCCTGTGCAGCCTCCGGAT
TCACCTTTGATGATGATTCTATGACGTGGGTCCGCCAGGCTCCAGGGAAGGGTCTAGAGTGGGTCTCACGGATTTCGAG
TGATGGTGCGAGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGGTGACTCCGGATTTGACTT
TTGACTACTGGGGTCAGGGAACCCTGGTCACCGTCTCGAGC (SEQ ID NO: 633)

BMS3h-13
GAGGTGCAGCTGTTGGAGTCTGGGGGAGGCTTGGTACAGCCTGGGGGGTCCCTGCGTCTCTCCTGTGCAGCCTCCGGAT
TCACCTTTACTGAGGAGGATATGACGTGGGTCCGCCAGGCTCCAGGGAAGGGTCTAGAGTGGGTCTCACGTATTGATAG
TGTTGGTGAGGGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGGTGACTCCGGATTTGACTT
TTGACTACTGGGGTCAGGGAACCCTGGTCACCGTCTCGAGC (SEQ ID NO: 634)

BMS3h-14
GAGGTGCAGCTGTTGGAGTCTGGGGGAGGCTTGGTACAGCCTGGGGGGTCCCTGCGTCTCTCCTGTGCAGCCTCCGGAT
TCACCTTTTCTGATTCGGCGATGAGTTGGGTCCGCCAGGCTCCAGGGAAGGGTCTAGAGTGGGTCTCACGGATTGATAA
TCCTGGTCAGCATACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGGTACTGTTCCTACGCTGGAGT
TTGACTACTGGGGTCAGGGAACCCTGGTCACCGTCTCGAGC (SEQ ID NO: 635)

BMS3h-15
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGCAGCATAGTATGACTTGGGTCCGCCAGGCTCCAGGGAAGGGTCTAGAGTGGGTCTCACGTATTGATGG
TGGGGGTTATAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGGAGGTTCCTCGTCTTCATT
TTGACTACTGGGGTCAGGGAACCCTGGTCACCGTCTCGAGC (SEQ ID NO: 636)

BMS3h-16
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTCAGGAGCCTATGACTTGGGTCCGCCAGGCTCCAGGGAAGGGTCTAGAGTGGGTCTCACGGATTGCGTA
TAATGGTGGTGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATTACTCCTAATTTGACTT
TTGACTACTGGGGTCAGGGAACCCTGGTCACCGTCTCGAGC (SEQ ID NO: 637)

BMS3h-17
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGAATTATCCGATGTCTTGGGTCCGCCAGGCTCCAGGGAAGGGTCTAGAGTGGGTCTCACGTATTAATGC
TACGGGTTCTATTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGGTTATTCCTCATTTGATGT
TTGACTACTGGGGTCAGGGAACCCTGGTCACCGTCTCGAGC (SEQ ID NO: 638)

BMS3h-18
GAGGTGCAGCTGTTGGAGTCTGGGGGAGGCTTGGTACAGCCTGGGGGGTCCCTGCGTCTCTCCTGTGCAGCCTCCGGAT
TCACCTTTCGTGATTATGATATGAGTTGGGTCCGCCAGGCTCCAGGGAAGGGTCTAGAGTGGGTCTCACGTATTACTGG
TACTGGTAATAGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGCAAGGGGTGGTGCCGTATCTTGCTT
TTGACTACTGGGGTCAGGGAACCCTGGTCACCGTCTCGAGC (SEQ ID NO: 639)

BMS3h-19
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGGCTGATGCGATGACGTGGGTCCGCCAGGCTCCAGGGAAGGGTCTAGAGTGGGTCTCAAGGATTAATGT
GGATGGTGATCGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTACTGTTCCTACGCTGGAGT
TTGACTACTGGGGTCAGGGAACCCTGGTCACCGTCTCGAGC (SEQ ID NO: 640)

BMS3h-21
GAGGTGCAGCTGTTGGAGTCTGGGGGAGGCTTGGTACAGCCTGGGGGGTCCCTGCGTCTCTCCTGTGCAGCCTCCGGAT
TCACCTTTGATCGGGCGGATATGACGTGGGTCCGCCAGGCTCCAGGGAAGGGTCTAGAGTGGGTCTCAAGGATTCGGG
GGAGGGTAAGTGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATGGTTCCTAATTTGGTTT
TTGACTACTGGGGTCAGGGAACCCTGGTCACCGTCTCGAGC (SEQ ID NO: 641)

BMS3h-22
GAGGTGCAGCTGTTGGAGTCTGGGGGAGGCTTGGTACAGCCTGGGGGGTCCCTGCGTCTCTCCTGTGCAGCCTCCGGAT
TCACCTTTCATTGGGAGCCGATGTCTTGGGTCCGCCAGGCTCCGGGGAAGGGTCTAGAGTGGGTCTCACGTATTAATTC
TTCTGGTTGGGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATGGTTCCTAATTTGGTTT
TTGACTACTGGGGTCAGGGAACCCTGGTCACCGTCTCGAGC (SEQ ID NO: 642)

TABLE 4-continued

Human Anti-CD40 Variable Domain Encoding Nucleotide Sequences

BMS3h-24
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGATGAGCCGATGACTTGGGTCCGCCAGGCTCCAGGGAAGGGTCTAGAGTGGGTCTCACGTATTCCTCC
TGAGGGTGCTCCGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATTACTCCTAATTTGACTT
TTGACTACTGGGGTCAGGGAACCCTGGTCACCGTCTCGAGC (SEQ ID NO: 643)

BMS3h-26
GAGGTGCAGCTGTTGGAGTCTGGGGGAGGCTTGGTACAGCCTGGGGGGTCCCTGCGTCTCTCCTGTGCAGCCTCCGGAT
TCACCTTTCATAATCATGATATGTCTTGGGTCCGCCAGGCTCCAGGGAAGGGTCTAGAGTGGGTCTCACGTATTAGTCG
GGGTGGTCTTCAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATTGTGCCGGATCTGCATT
TTGACTACTGGGGTCAGGGAACCCTGGTCACCGTCTCGAGC (SEQ ID NO: 644)

BMS3h-27
GAGGTGCAGCTGTTGGAGTCTGGGGGAGGCTTGGTACAGCCTGGGGGGTCCCTGCGTCTCTCCTGTGCAGCCTCCGGAT
TCACCTTTAATGAGTATCCTATGTCGTGGGTCCGCCAGGCTCCAGGGAAGGGTCTAGAGTGGGTCTCACGTATTAATGG
GGATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATTATTCCGGCTATGCAGT
TTGACTACTGGGGTCAGGGAACCCTGGTCACCGTCTCGAGC (SEQ ID NO: 645)

BMS3h-28
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGGATGTGCCTATGTCGTGGGTCCGCCAGGCTCCAGGGAAGGGTCTAGAGTGGGTCTCAAGGATTGATCC
TTATGGTTCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTATTATGCCTAGTCTTACTT
TTGACTACTGGGGTCAGGGAACCCTGGTCACCGTCTCGAGC (SEQ ID NO: 646)

BMS3h-29
GAGGTGCAGCTGTTGGAGTCTGGGGGAGGCTTGGTACAGCCTGGGGGGTCCCTGCGTCTCTCCTGTGCAGCCTCCGGAT
TCACCTTTGCGGATTATGATATGTCTTGGGTCCGCCAGGCTCCAGGGAAGGGTCTAGAGTGGGTCTCACGTATTTCGGC
GCTTGGTGCTACTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTCAGCTTCCGGCGTTGGAGT
TTGACTACTGGGGTCAGGGAACCCTGGTCACCGTCTCGAGC (SEQ ID NO: 647)

BMS3h-30
GAGGTGCAGCTGTTGGAGTCTGGGGGAGGCTTGGTACAGCCTGGGGGGTCCCTGCGTCTCTCCTGTGCAGCCTCCGGAT
TCACCTTTAAGCGTTATTATATGACTTGGGTCCGCCAGGCTCCAGGGAAGGATCTAGAGTGGGTCTCAGGTATTGTTCC
TTCTGGTAATAGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTAGGATTCCGGATCTGCATT
TTGACTACTGGGGTCAGGGAACCCTGGTCACCGTCTCGAGC (SEQ ID NO: 648)

BMS3h-31
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGATTATGATATGACTTGGGTCCGCCAGGCTCCAGGGAAGGGTCTAGAGTGGGTCTCAAGGATTTCTCC
GACGGGTGGGCAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTGTTATTCCGTATTTGTCTT
TTTCTCCGTTTGACTACTGGGGTCAGGGAACCCTGGTCACCGTCTCGAGC (SEQ ID NO: 649)

BMS3h-32
GAGGTGCAGCTGTTGGAGTCTGGGGGAGGCTTGGTACAGCCTGGGGGGTCCCTGCGTCTCTCCTGTGCAGCCTCCGGAT
TCACCTTTTCTAAGTATTGGATGGGTTGGGCCCGCCAGGCTCCAGGGAAGGGTCTAGAGTGGGTCTCATCGATTGATTC
GCATGGTGCTGGTACATACTACGCAGACTCCGTGAAGGGCCGGTTCACCATCTCCCGCGACAATTCCAAGAACACGCTG
TATCTGCAAATGAACAGCCTGCGTGTCGAGGACACCGCGGTATATTACTGTGCGAAAGGTGCTCCTAAGTTTATGACTA
CGTATACGTTTGACTACTGGGGTCAGGGAACCCTGGTCACCGTCTCGAGC (SEQ ID NO: 650)

BMS3h-33
GAGGTGCAGCTGTTGGAGTCTGGGGGAGGCTTGGTACAGCCTGGGGGGTCCCTGCGTCTCTCCTGTGCAGCCTCCGGAT
TCACCTTTTTGTCTTATCCGATGCATTGGGTCCGCCAGGCTCCAGGGAAGGGTCTAGAGTGGGTCTCATCGATTGATTC
GAGGGGTTCGGTTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTCATAGTTGGACGTTTGACT
ACTGGGGTCAGGGAACCCTGGTCACCGTCTCGAGC (SEQ ID NO: 651)

BMS3h-34
GAGGTGCAGCTGTTGGAGTCTGGGGGAGGCTTGGTACAGCCTGGGGGGTCCCTGCGTCTCTCCTGTGCAGCCTCCGGAT
TCACCTTTGCGAATAGTAATATGACTTGGGTCCGCCAGGCTCCAGGGAAGGGTCTAGAGTGGGTCTCACGTATTAATCC
GGATGGTGGGTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGGAAGGGCGTATTCCTACTCTTCATT
TTGACTACTGGGGTCAGGGAACCCTGGTCACCGTCTCGAGC (SEQ ID NO: 652)

BMS3h-35
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGCCGAGGAGGATGGGTTGGGTCCGCCAGGCTCCAGGGAAGGGTCTAGAGTGGGTCTCATCGATTGATGA
TATTGGTCGTAGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGGAAGGGGCGCAGGGTGTGTTGTTGT
TTGACTACTGGGGTCAGGGAACCCTGGTCACCGTCTCGAGC (SEQ ID NO: 653)

TABLE 4-continued

Human Anti-CD40 Variable Domain Encoding Nucleotide Sequences

BMS3h-36
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGGATTATAGGATGGTTTGGGTCCGCCAGGCTCCAGGGAAGGGTCTAGAGTGGGTCTCATCGATTTCTAC
TTCTGGTGAGCTGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGGAAACGGCGGGTCAGTTTTTTGACT
ACTGGGGTCAGGGAACCCTGGTCACCGTCTCGAGC (SEQ ID NO: 654)

BMS3h-39
GAGGTGCAGCTGTTGGAGTCTGGGGGAGGCTTGGTACAGCCTGGGGGGTCCCTGCGTCTCTCCTGTGCAGCCTCCGGAT
TCACCTTTCCGGAGTATGAGATGGTTTGGGTCCGCCAGGCTCCAGGGAAGGGTCTGGAGTGGGTCTCAGCGATTTCGCG
TGAGGGTCGGGCTACATACTACGCAGACTCCGTGAAGGGCCGGTTCACCATCTCCCGCGACAATTCCAAGAACACGCTG
TATCTGCAAATGAACAACCTGCGTGCCGAGGATACCGCGGTATATTACTGTGCGAAAGAGCCTGTTCGTTTTGACTACT
GGGGTCAGGGAACCCTGGTCACCGTCTCGAGC (SEQ ID NO: 655)

BMS3h-40
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGACTTATGAGATGCTTTGGGTCCGCCAGGCTCCAGGGAAGGGTCTAGAGTGGGTCTCATCTATTTCTTC
TTCTGGTAATTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGCTGATGTTTGACTACT
GGGGTCAGGGAACCCTGGTCACCGTCTCGAGC (SEQ ID NO: 656)

BMS3h-42
GAGGTGCAGCTGTTGGAGTCTGGGGGAGGCTTGGTACAGCCTGGGGGGTCCCTGCGTCTCTCCTGTGCAGCCTCCGGAT
TCACCTTTGATACTGAGGAGATGAGTTGGGTCCGCCAGGCTCCAGGGAAGGGTCTAGAGTGGGTCTCAGCGATTAGTCC
TAATGGTGCTTTTACATTCTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCTATTCTGTTTGACTACT
GGGGTCAGGGAACCCTGGTCACCGTCTCGAGC (SEQ ID NO: 657)

BMS3h-44
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTCATTATGATATGGTTTGGGTCCGCCAGGCTCCAGGGAAGGGGTCTAGAGTGGGTCTCAACTATTAATGG
TGCTGGTCTGAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGCAAAGTGCTAGTCGTATTTTTGACT
ACTGGGGTCAGGGAACCCTGGTCACCGTCTCGAGC (SEQ ID NO: 658)

BMS3h-45
GAGGTGCAGCTGTTGGAGTCTGGGGGAGGCTTGGTACAGCCTGGGGGGTCCCTGCGTCTCTCCTGTGCAGCCTCCGGAT
TCACCTTTAGGAGTTATGAGATGGCGTGGGTCCGCCAGGCTCCAGGGAAGGGTCTAGAGTGGGTCTCATCTATTAGTAC
TCTGGGTACGAAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGCAATCTTCTACTCATATTTTTGACT
ACTGGGGTCAGGGAACCCTGGTCACCGTCTCGAGC (SEQ ID NO: 659)

BMS3h-46
GAGGTGCAGCTGTTGGAGTCTGGGGGAGGCTTGGTACAGCCTGGGGGGTCCCTGCGTCTCTCCTGTGCAGCCTCCGGAT
TCACCTTTATTAGGTATGAGATGGCTTGGGTCCGCCAGGCTCCAGGGAAGGGTCTAGAGTGGGTCTCAAGTATTTCGTC
GTCTGGTTGGACGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAAGTGATGCTCATATTTTTGACT
ACTGGGGTCAGGGAACCCTGGTCACCGTCTCGAGC (SEQ ID NO: 660)

BMS3h-47
GAGGTGCAGCTGTTGGAGTCTGGGGGAGGCTTGGTACAGCCTGGGGGGTCCCTGCGTCTCTCCTGTGCAGCCTCCGGAT
TCACCTTTTATGCTTATGAGATGGCTTGGGTCCGCCAGGCTCCAGGGAAGGGTCTAGAGTGGGTCTCATCTATTTCGGA
TGATGGTACGCGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGATCGGGGCAGGGGTTTGACT
ACTGGGGTCAGGGAACCCTGGTCACCGTCTCGAGC (SEQ ID NO: 661)

BMS3h-48
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGATCATGGGATGACGTGGGTCCGCCAGGCTCCAGGGAAGGGTCTAGAGTGGGTCTCAGGGATTGGTCC
GTCTGGTGAGGCGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGATCGTATTCCTAATCTTGTGT
TTGACTACTGGGGTCAGGGAACCCTGGTCACCGTCTCGAGC (SEQ ID NO: 662)

BMS3h-49
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTCTCAGGATATGTCTTGGGTCCGCCAGGCTCCAGGGAAGGGTCTAGAGTGGGTCTCAGGTATTAGTCC
GAATGGTTGGGATACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGATAGGTCTGATTTTGACTACT
GGGGTCAGGGAACCCTGGTCACCGTCTCGAGC (SEQ ID NO: 663)

BMS3h-50
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGATTATGATATGTGGTGGGTCCGCCAGGCTCCAGGGAAGGGTCTAGAGTGGGTCTCAAGGATTCGTCA
TCCGGGTGGTGTTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGCTGTTCCTAAGGGTTTTGACT
ACTGGGGTCAGGGAACCCTGGTCACCGTCTCGAGC (SEQ ID NO: 664)

TABLE 4-continued

Human Anti-CD40 Variable Domain Encoding Nucleotide Sequences

BMS3h-51
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGTTTATTGGATGACTTGGGTCCGCCAGGCTCCAGGGAAGGGTCTAGAGTGGGTCTCATCTATTGATCC
GCAGGGTGGGATGACATACTACGCAGACTCCGTGAAGGGCCGGTTCACCATCTCTCGCGACAATTCCAAGAACACGCTG
TATCTGCAAATGAACAGCCTGCGTGCCGAGGATACCGCGGTATATTACTGTGCGAAAGCGCGTATTCCTAATTTGGAGT
TTGACTACTGGGGTCAGGGAACCCTGGTCACCGTCTCGAGC (SEQ ID NO: 665)

BMS3h-52
GAGGTGCAGCTGTTGGAGTCTGGGGGAGGCTTGGTACAGCCTGGGGAGTCCCTGCGTCTCTCCTGTGCAGCCTCCGGAT
TCACCTTTAGTGCTTATGATATGACGTGGGTCCGCCAGGCTCCAGGGAAGGGTCTTGAGTGGGTCTCACGTATTAATCC
GACGGGTTCTTATACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGCTAAGATTCCGAATTTGGTTT
TTGACTACTGGGGTCAGGGAACCCTGGTCACCGTCTCGAGC (SEQ ID NO: 666)

BMS3h-53
GAGGTGCAGCTGTTGGAGTCTGGGGGAGGCTTGGTACAGCCTGGGGGTCCCTGCGTCTCTCCTGTGCAGCCTCCGGAT
TCACCTTTGCGGATAGTGAGATGATGTGGGTCCGCCAGGCTCCAGGGAAGGGTCTAGAGTGGGTCTCAGGTATTGCGCA
TAATGGTGGGCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGCTGGTCATCCTCAGCAGACTG
AGGCTTTTGACTACTGGGGTCAGGGAACCCTGGTCACCGTCTCGAGC (SEQ ID NO: 667)

BMS3h-54
GAGATGCAGCTGTTGGAGTCTGGGGGAGGCTTGGTACAGCCTGGGGGTCCCTGCGTCTCTCCTGTGCAGCCTCCGGAT
TCACCTTTGCTACTTATGATATGTATTGGGTCCGCCAGGCTCCAGGGAAGGGTCTAGAGTGGGTCTCAAAGATTTCTCC
GAATGGTTGGAGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATATCAGACGCATTTTGACTACT
GGGGTCAGGGAACCCTGGTCACCGTCTCGAGC (SEQ ID NO: 668)

BMS3h-55
GAGGTGCAGCTGTTGGAGTCTGGGGGAGGCTTGGTACAGCCTGGGGGGTCCCTGCGTCTCTCCTGTGCAGCCTCCGGAT
TCACCTTTAGTGTTTATGATATGAGGTGGGTCCGCCAGGCTCCAGGGAAGGGTCTAGAGTGGGTCTCAACGATTTCTTC
TTCGGGTACGTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATATCCTAAGAATTTTGACTACT
GGGGTCAGGGAACCCTGGTCACCGTCTCGAGC (SEQ ID NO: 669)

BMS3h-57
GAGGTGCAGCTGTTGGAGTCTGGGGGAGGCTTGGTACAGCCTGGGGGTCCCTGCGTCTCTCCTGTGCAGCCTCCGGAT
TCACCTTTTCTCATGAGGATATGACTTGGGTCCGCCAGGCTCCAGGGAAGGGTCTAGAGTGGGTCTCAAGTATTAGTCC
GAATGGTTGGGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACGTACTAGGAGTAAGTTTGACT
ACTGGGGTCAGGGAACCCTGGTCACCGTCTCGAGC (SEQ ID NO: 670)

BMS3h-58
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGAAGTATATTATGGGTTGGGCCCGCCAGGCTCCAGGGAAGGGTCTAGAGTGGGTCTCAACGATTGATTA
TTGGGGTCAGCATACATACTACGCAGACTCCGTGAAGGGCCGGTTCACTATCTCCCGCGACAATTCCAAGAACACGCTG
TATCTGCAAATGAACAGCCTGCGTGCCGAGGACACCGCGGTATATTACTGTGCGAAACGTAGTCATCTTATTCCTCTGC
AGTTTGACTACTGGGGTCAGGGAACCCTGGTCACCGTCTCGAGC (SEQ ID NO: 671)

BMS3h-59
GAGGTGCAGCTGTTGGAGTCTGGGGGAGGCTTGGTACAGCCTGGGGGTCCCTGCGTCTCTCCTGTGCAGCCTCCGGAT
TCACCTTTTCTGATTATGCGATGGGTGGGTCCGCCAGGCTCCAGGGAAGGGTCTGGAGTGGGTCTCAACGATTTCGTA
TGTGGGTTATTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAAGGCTCTGCGGGGGAGGCGT
TTACGGAGCGTTTTGACTACTGGGGTCAGGGAACCCTGGTCACCGTCTCGAGC (SEQ ID NO: 672)

BMS3h-60
GAGGTGCAGCTGTTGGAGTCTGGGGGAGGCTTGGTACAGCCTGGGGGTCCCTGCGTCTCTCCTGTGCAGCCTCCGGAT
TCACCTTTGGTCCGTATATGATGCATTGGGTCCGCCAGGCTCCAGGGAAGGGTCTAGAGTGGGTCTCAACGATTGAGGT
TAATGGTAATAGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATGGGTTGGTTCGAAGACGTCGT
CGGATAAGAGTTTTGACTACTGGGGTCAGGGAACCCTGGTCACCGTCTCGAGC (SEQ ID NO: 673)

BMS3h-61
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTACGACGGAGATGGCTTGGGTCCGCCAGGCTCCAGGGAAGGGTCTAGAGTGGGTCTCAAGTATTGGTAG
TGCTGGTGCTTGGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAATTGGTGGGCATCCTCAGGGTC
AGTTTGACTACTGGGGTCAGGGAACCCTGGTCACCGTCTCGAGC (SEQ ID NO: 674)

BMS3h-62
GAGGTGCAGCTGTTGGAGTCTGGGGGAGGCTTGGTACAGCCTGGGGGTCCCTGCGCCTCTCCTGTGCAGCCTCCGGAT
TCACCTTTCCTAGGGAGTGGATGGCTTGGGTCCGCCAGGCTCCAGGGAAGGGTCTAGAGTGGGTCTCAAGTATTCAGCC
TATGGGTCAGATACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAATATTCTCGGAATAAGGGGTTTT
TTGACTACTGGGGTCAGGGAACCCTGGTCACCGTCTCGAGC (SEQ ID NO: 675)

TABLE 4-continued

Human Anti-CD40 Variable Domain Encoding Nucleotide Sequences

BMS3h-63
GAGGTGCAGCTGTTGGAGTCTGGGGGAGGCTTGGTACAGCCTGGGGGGTCCCTGCGTCTCTCCTGTGCAGCCTCCGGAT
TCACCTTTACGAGTGAGTATATGGGGTGGGTCCGCCAGGCTCCAGGGAAGGGTCTAGAGTGGGTCTCATCTATTCAGAG
GTATGGTAGTACGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACATGAGTCTAATTGGGAGACTT
TTGACTACTGGGGTCAGGGAACCCTGGTCACCGTCTCGAGC (SEQ ID NO: 676)

BMS3h-70
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGGTGTATAGTATGCAGTGGGTCCGCCAGGCTCCAGGGAAGGGTCTAGAGTGGGTCTCAGCGATTACTCC
TAATGGTACTCGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAACTCTTGGTCGGGGTTCTTATC
CTGGTGTTGATTTTGACTACTGGGGTCAGGGAACCCTGGTCACCGTCTCGAGC (SEQ ID NO: 677)

BMS3h-71
GAGGTGCAGCTGTTGGAGTCTGGGGGAGGCTTGGTACAGCCTGGGGGGTCCCTGCGTCTCTCCTGTGCAGCCTCCGGAT
TCACCTTTCCGAGTTATGCTATGACGTGGGTCCGCCAGGCTCCAGGGAAGGGTCTGGAGTGGGTCTCACGTATTACGGC
GGATGGTACTGTTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTTCTATTCCGATGCTTACGT
TTGACTACTGGGGTCAGGGAACCCTGGTCACCGTCTCGAGC (SEQ ID NO: 678)

BMS3h-72
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGACTTATGATATGATTTGGGTCCGCCAGGCTCCAGGGAAGGGTCTAGAGTGGGTCTCAGCTATTTCTCC
TAATGGTACTGGTATATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAATCAGAGTGTTCATCATGCTG
TTTTTGACTACTGGGGTCAGGGAACCCTGGTCACCGTCTCGAGC (SEQ ID NO: 679)

BMS3h-73
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGAATTATGAGATGACGTGGGTCCGCCAGGCTCCAGGGAAGGGTCTAGAGTGGGTCTCACGTATTGCGCC
GCATGGTCGGCTTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGGTCAGATTCCGATGCTTGATT
TTGACTACTGGGGTCAGGGAACCCTGGTCACCGTCTCGAGC (SEQ ID NO: 680)

BMS3h-74
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGCATTATATGATGATGTGGGTCCGCCAGGCTCCAGGGAAGGGTCTAGAGTGGGTCTCAACGATTTCTCA
TTTTGGTGATATTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAAATGATATGGTGATGAAGAATG
GGGGGTTTGACTACTGGGGTCAGGGAACCCTGGTCACCGTCTCGAGC (SEQ ID NO: 681)

BMS3h-75
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGAGGTATGATATGAGTTGGGTCCGCCAGGCTCCAGGGAAGGGTCTAGAGTGGGTCTCACGTATTGATTC
GCGGGGTTGGTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTTGGTGCCGCATCTGAGGT
TTGACTACTGGGGTCAGGGAACCCTGGTCACCGTCTCGAGC (SEQ ID NO: 682)

BMS3h-76
GAGGTGCAGCTGTTGGAGTCTGGGGGAGGCTTGGTACAGCCTGGGGGGTCCCTGCGTCTCTCCTGTGCAGCCTCCGGAT
TCACCTTTGCGAATGCGCAGATGACTTGGGTCCGCCAGGCTCCAGGGAAGGGTCTAGAGTGGGTCTCAAGGATTGATGC
TATGGGTGATGCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTAAGGTTCCGAGTATTGACT
ACTGGGGTCAGGGAACCCTGGTCACCGTCTCGAGC (SEQ ID NO: 683)

BMS3h-77
GAGGTGCAGCTGTTGGAGTCTGGGGGAGGCTTGGTACAGCCTGGGGGGTCCCTGCGTCTCTCCTGTGCAGCCTCCGGAT
TCACCTTTGCGAATGCGCAGATGACTTGGGTCCGCCAGGCTCCAGGGAAGGGTCTAGAGTGGGTCTCAAGGATTGATGC
TATGGGTGATGCTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGGTGTTATTCCGGCGTTTGACT
ACTGGGGTCAGGGAACCCTGGTCACCGTCTCGAGC (SEQ ID NO: 684)

BMS3h-78
GAGGTGCAGCTGTTGGAGTCTGGGGGAGGCTTGGTACAGCCTGGGGGGTCCCTGCGTCTCTCCTGTGCAGCCTCCGGAT
TCACCTTTCAGAATGATCGGATGCATTGGGTCCGCCAGGCTCCAGGGAAGGGTCTAGAGTGGGTCTCATCGATTTCTGC
TACTGGTGGTGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACAGAGGGTACGAATCGTTTTG
ACTACTGGGGTCAGGGAACCCTGGTCACCGTCTCGAGC (SEQ ID NO: 685)

BMS3h-79
GAGGTGCAGCTGTTGGAGTCTGGGGGAGGCTTGGTACAGCCTGGGGGGTCCCTGCGTCTCTCCTGTGCAGCCTCCGGAT
TCACCTTTAATCAGCCTTATATGTCGTGGGTCCGCCAGGCTCCAGGGAAGGGTCTGGAGTGGGTCTCATCTATTGATGC
TTCGGGTGGTACTACATACTACGCAGACTCCGTGAAGGGCCGGTTCACCATCTCCCGCGACAATTCCAAGAACACGCTG
TATCTGCAAATGAACAGCCTGCGTGCCGAGGACGCCGCGGTATATTACTGTGCGAAAGATCGTATTCCTAATCTTGTGT
TTGACTACTGGGGTCAGGGAACCCTGGTCACCGTCTCGAGC (SEQ ID NO: 686)

TABLE 4-continued

Human Anti-CD40 Variable Domain Encoding Nucleotide Sequences

BMS3h-80
GAGGTGCAGCTGTTGGAGTCTGGGGGAGGCTTGGTACAGCCTGGGGGGTCCCTGCGTCTCTCCTGTGCAGCCTCCGGAT
TCACCTTTGATAATGAGAATATGACTTGGGTCCGCCAGGCTCCAGGGAAGGGTCTAGAGTGGGTCTCACGTATTGATGG
TGGGGGTTATAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGCAGGTTCCTGAGCTGCTGT
TTGACTACTGGGGTCAGGGAACCCTGGTCACCGTCTCGAGC (SEQ ID NO: 687)

BMS3h-81
GAGGTGCAGCTGTTGGAGTCTGGGGGAGGCTTGGTACAGCCTGGGGGGTCCCTGCGTCTCTCCTGTGCAGCCTCCGGAT
TCACCTTTGTTTCGTCGAATATGACTTGGGTCCGCCAGGCTCCAGGGAAGGGTCTAGAGTGGGTCTCAGCTATTAGTGG
TAGTGGTGGTAGCACATACTATGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTCGGATTCCTACGTTGGTGT
TTGACTACTGGGGTCAGGGAACCCTGGTCACCGTCTCGAGC (SEQ ID NO: 688)

BMS3h-82
GAGGTGCAGCTGTTGGAGTCTGGGGGAGGCTTGGTACAGCCTGGGGGGTCCCTGCGTCTCTCCTGTGCAGCCTCCGGAT
TCACCTTTGTTTCGTCGAATATGACTTGGGTCCGCCAGGCTCCAGGGAAGGGTCTAGAGTGGGTCTCAGCTATTAGTGG
TAGTGGTGGTAGCACATACTATGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGATCGTATTCCTAATCTTGTGT
TTGACTACTGGGGTCAGGGAACCCTGGTCACCGTCTCGAGC (SEQ ID NO: 689)

BMS3h-83
GAGGTGCAGCTGTTGGAGTCTGGGGGAGGCTTGGTACAGCCTGGGGGGTCCCTGCGTCTCTCCTGTGCAGCCTCCGGAT
TCACCTTTTCTGATGATTCGATGAGTTGGGTCCGCCAGGCTCCAGGGAAGGGTCTAGAGTGGGTCTCACGTATTAATGA
TGCTGGTAGTTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTACTATTCCTCTTCTGGAGT
TTGACTACTGGGGTCAGGGAACCCTGGTCACCGTCTCGAGC (SEQ ID NO: 690)

BMS3h-84
GAGATGCAGCTGTTGGAGTCTGGGGGAGGCTTGGTACAGCCTGGGGGGTCCCTGCGTCTCTCCTGTGCAGCCTCCGGAT
TCACCTTTGTTTCGGATACTATGAGTTGGGTCCGCCAGGCTCCAGGGAAGGGTCTAGAGTGGGTCTCACGTATTGATGG
GACTGGTGGTGATACATACTACGCAGACTCCGTGAAGGGCCGGTTCACCATCTCCCGCGACAATTCCAAGAACACGCTG
TATCTGCAAATGAACAGCCTGCGTGCCGGGGACACCGCGGTATATTACTGTGCGAAAGGGCTTATTCCTGATCTTCAGT
TTGACTACTGGGGTCAGGGAACCCTGGTCACCGTCTCGAGC (SEQ ID NO: 691)

BMS3h-85
GAGGTGCAGCTGTTGGAGTCTGGGGGAGGCTTGGTACAGCCTGGGGGGTCCCTGCGTCTCTCCTGTGCAGCCTCCGGAT
TCACCTTTGATGAGGAGGAGATGACGTGGGTCCGCCAGGCTCCAGGGAAGGGTCTAGAGTGGGTCTCACGTATTATTGG
TGGTGGTCATGAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTACTATTCCTCTTCTGGAGT
TTGACTACTGGGGTCAGGGAACCCTGGTCACCGTCTCGAGC (SEQ ID NO: 692)

BMS3h-86
GAGGTGCAGCTGTTGGAGTCTGGGGGAGGCTTGGTACAGCCTGGGGGGTCCCTGCGTCTCTCCTGTGCAGCCTCCGGAT
TCACCTTTGATAATGAGAATATGACTTGGGTCCGCCAGGCTCCAGGGAAGGATCTAGAGTGGGTCTCACGGATTACTGA
GAGGGGTGATGTGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTACTGTTCCTACGCTGGAGT
TTGACTACTGGGGTCAGGGAACCCTGGTCACCGTCTCGAGC (SEQ ID NO: 693)

BMS3h-87
GAGGTGCAGCTGTTGGAGTCTGGGGGAGGCTTGGTACAGCCTGGGGGGTCCCTGCGTCTCTCCTGTGCAGCCTCCGGAT
TCACCTTTGATGAGGAGGAGATGACGTGGGTCCGCCAGGCTCCAGGGAAGGGTCTAGAGTGGGTCTCACGTATTATTGG
TGGTGGTCATGAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTACTGTTCCTACGCTGGAGT
TTGACTACTGGGGTCAGGGAACCCTGGTCACCGTCTCGAGC (SEQ ID NO: 694)

BMS3h-88
GAGGTGCAGCTGTTGGAGTCTGGGGGAGGCTTGGTACAGCCTGGGGGGTCCCTGCGTCTCTCCTGTGCAGCCTCCGGAT
TCACCTTTCATGAGACGGAGATGACGTGGGTCCGCCAGGCTCCAGGGAAGGGTCTAGAGTGGGTCTCAGCTATTAATCG
GCTGGGTCAGGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTAGGATTCCTGGGCTGGTTT
TTGACTACTGGGGTCAGGGAACCCTGGTCACCGTCTCGAGC (SEQ ID NO: 695)

BMS3h-89
GAGGTGCAGCTGTTGGAGTCTGGGGGAGGCTTGGTACAGCCTGGGGGGTCCCTGCGTCTCTCCTGTGCAGCCTCCGGAT
TCACCTTTTCTGATGATTCGATGAGTTGGGTCCGCCAGGCTCCAGGGAAGGGTCTAGAGTGGGTCTCACGTATTAATGA
TGCTGGTAGTTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTACTGTTCCTACGCTGGAGT
TTGACTACTGGGGTCAGGGAACCCTGGTCACCGTCTCGAGC (SEQ ID NO: 696)

BMS3h-90
GAGGTGCAGCTGTTGGAGTCTGGGGGAGGCTTGGTACAGCCTGGGGGGTCCCTGCGTCTCTCCTGTGCAGCCTCCGGAT
TCACCTTTGATAATGAGAATATGACTTGGGTCCGCCAGGCTCCAGGGAAGGATCTAGAGTGGGTCTCACGGATTACTGA
GAGGGGTGATGTGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTCGGATTCCTACGTTGGTGT
TTGACTACTGGGGTCAGGGAACCCTGGTCACCGTCTCGAGC (SEQ ID NO: 697)

TABLE 4-continued

Human Anti-CD40 Variable Domain Encoding Nucleotide Sequences

BMS3h-91
GAGGTGCAGCTGTTGGAGTCTGGGGGAGGCTTGGTACAGCCTGGGGGGTCCCTGCGTCTCTCCTGTGCAGCCTCCGGAT
TCACCTTTTCTGATGATTCGATGAGTTGGGTCCGCCAGGCTCCAGGGAAGGGTCTAGAGTGGGTCTCACGTATTAATGA
TGCTGGTAGTTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATTACTCCTAATTTGACTT
TTGACTACTGGGGTCAGGGAACCCTGGTCACCGTCTCGAGC (SEQ ID NO: 698)

BMS3h-92
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGATGAGCCGATGACTTGGGTCCGCCAGGCTCCAGGGAAGGGTCTAGAGTGGGTCTCACGTATTCCTCC
TGAGGGTGTTCCGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGCTTATTCCTGATCTTCAGT
TTGACTACTGGGGTCAGGGAACCCTGGTCACCGTCTCGAGC (SEQ ID NO: 699)

BMS3h-93
GAGGTGCAGCTGTTGGAGTCTGGGGGAGGCTTGGTACAGCCTGGGGGGTCCCTGCGTCTCTCCTGTGCAGCCTCCGGAT
TCACCTTTCAGGATAGTGATATGACGTGGGTCCGCCAGGCTCCAGGGAAGGGTCTAGAGTGGGTCTCAGCTATTGCTGC
GCCTGGTGGTAGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGATCGTATTCCTAATCTTAGGT
TTGACTACTGGGGTCAGGGAACCCTGGTCACCGTCTCGAGC (SEQ ID NO: 700)

BMS3h-94
GAGGTGCAGCTGTTGGAGTCTGGGGGAGGCTTGGTACAGCCTGGGGGGTCCCTGCGTCTCTCCTGTGCAGCCTCCGGAT
TCACCTTTGTTTCGGATACTATGAGTTGGGTCCGCCAGGCTCCAGGGAAGGGTCTAGAGTGGGTCTCACGTATTGATGG
GACTGGTGGTGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGCAGGTTCCTGAGCTGCTGT
TTGACTACTGGGGTCAGGGAACCCTGGTCACCGTCTCGAGC (SEQ ID NO: 701)

BMS3h-95
GAGGTGCAGCTGTTGGAGTCTGGGGGAGGCTTGGTACAGCCTGGGGGGTCCCTGCGTCTCTCCTGTGCAGCCTCCGGAT
TCACCTTTCAGGATAGTGATATGACGTGGGTCCGCCAGGCTCCAGGGAAGGGTCTAGAGTGGGTCTCAGCTATTGCTGC
GCCTGGTGGTAGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGATCGTATTCCTAATCTTGTGT
TTGACTACTGGGGTCAGGGAACCCTGGTCACCGTCTCGAGC (SEQ ID NO: 702)

BMS3h-96
GAGGTGCAGCTGTTGGAGTCTGGGGGAGGCTTGGTACAGCCTGGGGGGTCCCTGCGTCTCTCCTGTGCAGCCGCCGGAT
TCACCTTTGATCTGGCGGAGATGACTTGGGTCCGCCAGGCTCCAGGGAAGGGTCTAGAGTGGGTCTCACGTATTGATGA
GGATGGTGCTTCTACATACTACGCAGACTCCGTGAAGGGCCGGTTCACCATCTCCCGCGACAATTCCAAGAACACGCTG
TATCTGCAAATGAACAGCCTGCGTGCCGAGGACGCCGCGGTATATTACTGTGCGGAAGGTGTTATTCCGTCTCTGACTT
TTGACTACTGGGGTCAGGGAACCCTGGTCACCGTCTCGAGC (SEQ ID NO: 703)

BMS3h-97
GAGGTGCAGCTGTTGGAGTCTGGGGGAGGCTTGGTACAGCCTGGGGGGTCCCTGCGTCTCTCCTGTGCAGCCTCCGGAT
TCACCTTTACTGATAAGCATATGAGTTGGGTCCGCCAGGCTCCAGGGAAGGGTCTAGAGTGGGTCTCACGGATTTCGCC
TGATGGTACGTATACATACTACGCAGACTCCGTGAAGGGCCGGTTCACCATCTCCCGCGACAATTCCAAGAACACGCTG
TATCTGCAAATGAACAGCCTGCGTGCCGAGGACGCCGCGGTATATTACTGTGCGGAAGGTGTTATTCCGTCTCTGACTT
TTGACTACTGGGGTCAGGGAACCCTGGTCACCGTCTCGAGC (SEQ ID NO: 704)

BMS3h-98
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGAGGATGATATGACTTGGGTCCGCCAGGCTCCAGGGAAGGGTCTAGAGTGGGTCTCACGTATTGCGGT
TGATGGTGATCGGACATACTACGCAGACTCCGTGAAGGGCCGGTTCACCATCTCCCGCGACAATTCCAAGAACACGCTG
TATCTGCAAATGAACAGCCTGCGTACCGAGGACACCGCGGTATATTACTGTGCGAAAGGGAAGACGCCGCATCTTGTGT
TTGACTACTGGGGTCAGGGAACCCTGGTCACCGTCTCGAGC (SEQ ID NO: 705)

BMS3h-99
GAGGTGCAGCTGTTGGAGTCTGGGGGAGGCTTGGTACAGCCTGGGGGGTCCCTGCGTCTCTCCTGTGCAGCCGCCGGAT
TCACCTTTGATCTGGCGGAGATGACTTGGGTCCGCCAGGCTCCAGGGAAGGGTCTAGAGTGGGTCTCACGTATTGATGA
GGATGGTGCTTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGTCAGGTTCCTGCTTTGGTTT
TTGACTACTGGGGTCAGGGAACCCTGGTCACCGTCTCGAGC (SEQ ID NO: 706)

BMS3h-100
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGGATTCGATGATGTCGTGGGTCCGCCAGGCGCCAGGGAAGGGTCTAGAGTGGGTCTCACGGATTGATCC
TGGGGGTGCTCAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGGTGACTCCGGATTTGACTT
TTGACTACTGGGGTCAGGGAACCCTGGTCACCGTCTCGAGC (SEQ ID NO: 707)

BMS3h-101
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGCATGCGGATATGAGTTGGGTCCGCCAGGCTTCAGGGAAGGGTCTAGAGTGGGTCTCACGTATTGATAA
TAGTGGTCAGTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGGTGACTCCGGATTTGACGT
TTGACTACTGGGGTCAGGGAACCCTGGTCACCGTCTCGAGC (SEQ ID NO: 708)

TABLE 4-continued

Human Anti-CD40 Variable Domain Encoding Nucleotide Sequences

BMS3h-102
GAGGTGCAGCTGTTGGAGTCTGGGGGAGGCTTGGTACAGCCTGGGGGGTCCCTGCGTCTCTCCTGTGCAGCCTCCGGAT
TCACCTTTAGTGAGGCGGAGATGAATTGGGTCCGCCAGGCTCCAGGGAAGGGTCTAGAGTGGGTCTCACGTATTACGAC
GGATGGTGATTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGCGTATTCCTACTCTTCATT
TTGACTACTGGGGTCAGGGAACCCTGGTCACCGTCTCGAGC (SEQ ID NO: 709)

BMS3h-103
GAGGTGCAGCTGTTGGAGTCTGGGGGAGGCTTGGTACAGCCTGGGGGGTCCCTGCGTCTCTCCTGTGCAGCCTCAGGAT
TCACCTTTGATGATAGTGATATGACTTGGGTCCGCCAGGCTCCAGGGAAGGAGTCTAGAGTGGGTCTCATATATTCGGGG
TGATGATGATGAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAATCGGATTCCTGATCTTGTGT
TTGACTACTGGGGTCAGGGAACCCTGGTCACCGTCTCGAGC (SEQ ID NO: 710)

BMS3h-108
GAGGTGCAGCTGTTGGAGTCTGGGGGAGGCTTGGTACAGCCTGGGGGGTCCCTGCGTCTCTCCTGTGCAGCCTCCGGAT
TCACCTTTAATGTGGCGGATATGCAGTGGGTCCGCCAGGCTCCAGGGAAGGGTCTAGAGTGGGTCTCAAGTATTAGTCC
GAATGGTTGGGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACATGCTTCTACGGAGGGGCCGA
CTGCTTTTGACTACTGGGGTCAGGGAACCCTGGTCACCGTCTCGAGC (SEQ ID NO: 711)

BMS3h-109
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGCCGTATGATATGGGTGGGTCCGCCAGGCTCCAGGGAAGGGTCTGGAGTGGGTCTCATGGATTTCTGC
TCATGGTTCGTTTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAATGGCCTTATAAGTTTGACTACT
GGGGTCAGGGAACCCTGGTCACCGTCTCGAGC (SEQ ID NO: 712)

BMS3h-110
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGAGTGGGTCTATGAGTTGGGTCCGCCAGGCTCCAGGGAAGGGTCTAGAGTGGGTCTCACGGATTGGTAG
TAATGGTGCGGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATGGTTCCTAATTTGGTTT
TTGACTACTGGGGTCAGGGAACCCTGGTCACCGTCTCGAGC (SEQ ID NO: 713)

BMS3h-111
GAGGTGCAGCTGTTGGAGTCTGGGGGAGGCTTGGTACAGCCTGGGGGGTCCCTGCGTCTCTCCTGTGCAGCCTCCGGAT
TCACCTTTAATCGTTTTGATATGACGTGGGTCCGCCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGATCGTATTCCTAATCTTGTGT
TTGACTACTGGGGTCAGGGAACCCTGGTCACCGTCTCGAGC (SEQ ID NO: 714)

BMS3h-112
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGGAGAGTGATATGAAGTGGGTCCGCCAGGCTCCAGGGAAGGGTCTAGAGTGGGTCTCAAGTATTAGTCC
GAATGGTTGGGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATCTCCTTCTTCTCGTCTTAAGT
TTGACTACTGGGGTCAGGGAACCCTGGTCACCGTCTCGAGC (SEQ ID NO: 715)

BMS3h-139
GAGGTGCAGCTGTTGGAGTCTGGGGGAGGCTTGGTACAGCCTGGGGGGTCCCTGCGTCTCTCCTGTGCAGCCTCCGGAT
TCACCTTTGATAGTAGTGAGATGAGTTGGGTCCGCCAGGCTCCAGGGAAGGGTCTAGAGTGGGTCTCATCGATTGAGAA
TCAGGGTGGTGCGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGATCGTATTCCTAATCTTGTGT
TTGACTACTGGGGTCAGGGAACCCTGGTCACCGTCTCGAGC (SEQ ID NO: 716)

BMS3h-140
GAGGTGCAGCTGTTGGAGTCTGGGGGAGGCTTGGTACAGCCTGGGGGGTCCCTGCGTCTCTCCTGTGCAGCCTCCGGAT
TCACCCTTGATGCGTATCCTATGTATTGGGTCCGCCAGGCTCCAGGGAAGGGTCTAGAGTGGGTCTCATGGATTGCTTC
GGGTGGTGGTGCGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACGTACGAAGAATTTTGACTACT
GGGGTCAGGGAACCCTGGTCACCGTCTCGAGC (SEQ ID NO: 717)

BMS3h-141
GAGGTGCAGCTGTTGGAGTCTGGGGGAGGCTTGGTACAGCCTGGGGGGTCCCTGCGTCTCTCCTGTGCAGCCTCCGGAT
TCACCTTTATGAGTTATTCTATGGCTTGGGTCCGCCAGGCTCCAGGGAAGGGTCTAGAGTGGGTCTCAGGGATTACTTC
TAATGGTAATCGGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAATCGACTGGGGCTAATAGTAGGA
ATTTTGACTACTGGGGTCAGGGAACCCTGGTCACCGTCTCGAGC (SEQ ID NO: 718)

BMS3h-142
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGGGGTATCTGATGTCGTGGGTCCGCCAGGCTCCAGGGAAGGGTCTAGAGTGGGTCTCAAGTATTGCGGC
TAATGGTATGCAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAAGCCGAGGGGTATTTGGGATG
GGGATTTTGACTACTGGGGTCAGGGAACCCTGGTCACCGTCTCGAGC (SEQ ID NO: 719)

TABLE 4-continued

Human Anti-CD40 Variable Domain Encoding Nucleotide Sequences

BMS3h-143
GAGGTGCAGCTGTTGGAGTCTGGGGGAGGCTTGGTACAGCCTGGGGGGTCCCTGCGTCTCTCCTGTGCAGCCTCCGGAT
TCACCTTTCATGAGTCTACGATGACGTGGGTCCGCCAGGCTCCAGGGAAGGGTCTAGAGTGGGTCTCAACTATTCGGCA
TCCGGGTGAGTTTACATACTACGCAGACTCCGTGAAGGGCCGGTTCACCATCTCCCGCGACAATTCCAAGAACACGCTG
TATCTGCAAATGAACAGCCTGCGTGCCGGGGACACCGCGGTATATTACTGTGCGAAAGGGCTTATTCCTGATCTTCAGT
TTGACTACTGGGGTCAGGGAACCCTGGTCACCGTCTCGAGC (SEQ ID NO: 720)

BMS3h-144
GAGGTGCAGCTGTTGGAGTCTGGGGGAGGCTTGGTACAGCCTGGGGGTCCCTGCGTCTCTCCTGTGCAGCCTCCGGAT
TCACCTTTGCGATGTATAGTATGAGTTGGGTCCGCCAGGCTCCAGGGAAGGGTCTAGAGTGGGTCTCATCGATTGCGCC
GCCGGGTGGTAGGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACAGTCGCTGACGGGGTATAGTA
GGTCTTTTGACTACTGGGGTCAGGGAACCCTGGTCACCGTCTCGAGC (SEQ ID NO: 721)

BMS3h-145
GAGGTGCAGCTGTTGGAGTCTGGGGGAGGCTTGGTACAGCCTGGGGGTCCCTGCGTCTCTCCTGTGCAGCCTCCGGAT
TCACCTTTTCGCAGAATCCGATGTCGTGGGTCCGCCACGCTCCAGGGAAGGGTCTAGAGTGGGTCTCAACGATTCCTGC
GAATGGTCGTCCTACATCCTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAATATAGTCAGCAGCCGGGTCGTC
GGTTTGACTACTGGGGTCAGGGAACCCTGGTCACCGTCTCGAGC (SEQ ID NO: 722)

BMS3h-146
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTAATTATCATATGACGTGGGTCCGCCAGGCTCCAGGGAAGGGTCTAGAGTGGGTCTCATCGATTCCTGA
TAGTGGTAAGCAGACATACTACGCAGACTCCGTGAAGGGCCGGTTCACCATCTCCCGCGACAATTCCAAGAACACGCTG
TATCTACAAATGAACAGCCTGCGTGCCGAGGACACCGCGGTATATTACTGTGCGAAAGGTAGGATTCCGTCTCTTCTTT
TTGACTACTGGGGTCAGGGAACCCTGGTCACCGTCTCGAGC (SEQ ID NO: 723)

BMS3h-147
GAGGTGCAGCTGTTGGAGTCTGGGGGAGGCTTGGTACAGCCTGGGGGTCCCTGCGTCTCTCCTGTGCAGCCTCCGGAT
TCACCTTTGCGCAGTATCATATGCGTTGGGTCCGCCAGGCTCCAGGGAAGGGTCTAGAGTGGGTCTCAACGATTAATGA
TATTGGTAGTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGTTGGGGGCGGGGGAGTTTTT
CTTTTGACTACTGGGGTCAGGGAACCCTGGTCACCGTCTCGAGC (SEQ ID NO: 724)

BMS3h-148
GAGGTGCAGCTGTTGGAGTCTGGGGGAGGCTTGGTACAGCCTGGGGGTCCCTGCGTCTCTCCTGTGCAGCCTCCGGAT
TCACCTTTTCTTCGTATGATATGAAGTGGGTCCGCCAGGCTCCAGGGAAGGGTCTAGAGTGGGTCTCAACGATTAGTGC
GTCTGGTGTGTTTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACGGGAGCATGCGGGTCAGCCGC
CTTTTGACTACTGGGGTCAGGGAACCCTGGTCACCGTCTCGAGC (SEQ ID NO: 725)

BMS3h-149
GAGGTGCAGCTGTTGGAGTCTGGGGGAGGCTTGGTACAGCCTGGGGGGTCCCTGCGTCTCTCCTGTGCAGCCTCCGGAT
TCACCTTTAATGGTTATGCTATGAGTTGGGTCCGCCAGGCTCCAGGGAAGGGTCTAGAGTGGGTCTCAACTATTAATGC
TAATGGTAAGTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAAGTTGACTCTTGCTTCTAATT
ATTTTGACTACTGGGGTCAGGGAACCCTGGTCACCGTCTCGAGC (SEQ ID NO: 726)

BMS3h-150
GAGGTGCAGCTGTTGGAGTCTGGGGGAGGCTTGGTACAGCCTGGGGGTCCCTGCGTCTCTCCTGTGCAGCCTCCGGAT
TCACCTTTATGGATTATGATATGAAGTGGGTCCGCCAGGCTCCAGGGAAGGGTCTAGAGTGGGTCTCAAGTATTACTGC
GCTTGGTAAGAAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGATAGTGTTAAGTATCCTCTTA
ATCTTTTTGACTACTGGGGTCAGGGAACCCTGGTCACCGTCTCGAGC (SEQ ID NO: 727)

BMS3h-151
GAGGTGCAGCTGTTGGAGTCTGGGGGAGGCTTGGTACAGCCTGGGGGTCCCTGCGTCTCTCCTGTGCAGCCTCCGGAT
TCACCTTTCCGCATTATACGATGGCGTGGGTCCGCCAGGCTCCAGGGAAGGGTCTGGAGTGGGTCTCATCTATTCAGTC
GCCTGGTTGGCGGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAATATGGGGATGGTCTTCCTTTGA
CTTTTGACTACTGGGGTCAGGGAACCCTGGTCACCGTCTCGAGC (SEQ ID NO: 728)

BMS3h-167
GAGGTGCAGCTGTTGGAGTCTGGGGGAGGCTTGGTACAGCCTGGGGGGTCCCTGCGTCTCTCCTGTGCAGCCTCCGGAT
TCACCTTTAGTGGTACGCCGATGTCTTGGGTCCGCCAGGCTCCAGGGAAGGGTCTAGAGTGGGTCTCACGTATTGGGGA
TGAGGGTCAGGAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGGTGACTCCGGATTTGACTT
TTGACTACTGGGGTCAGGGAACCCTGGTCACCGTCTCGAGC (SEQ ID NO: 729)

BMS3h-168
GAGGTGCAGCTGTTGGAGTCTGGGGGAGGCTTGGTACAGCCTGGGGGTCCCTGCGTCTCTCCTGTGCAGCCTCCGGAT
TCACCTTTAGTAGTAGTTCGATGTCTTGGGTCCGCCAGGCTCCAGGGAAGGGTCTAGAGTGGGTCTCAGCGATTGGGTC
TGATGGTCCGAGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGCGTATTCCTACTCTTCATT
TTGACTACTGGGGTCAGGGAACCCTGGTCACCGTCTCGAGC (SEQ ID NO: 730)

TABLE 4-continued

Human Anti-CD40 Variable Domain Encoding Nucleotide Sequences

BMS3h-169
GAGGTGCAGCTGTTGGAGTCTGGGGGAGGCTTGGTACAGCCTGGGGGGTCCCTGCGTCTCTCCTGTGCAGCCTCCGGAT
TCACCTTTAATCCTGGTGAGATGACGTGGGTCCGCCAGGCTCCAGGGAAGGGTCTAGAGTGGGTCTCAAGTATTGATGG
GTCTGGTTCTTCGACATACTACGCAGACTCCGTGAAGGGCCGGTTCACCATCTCCCGCGACAATTCCAAGAACACGCTG
TATCTGCAAATGAACAGCCTGCGTGCCGATGACACCGCGGTATATTACTGTGCGAAAGGGCGTATTCCTACTCTTCATT
TTGACTACTGGGGTCAGGGAACCCTGGTCACCGTCTCGAGC (SEQ ID NO: 731)

BMS3h-170
GAGGTGCAGCTGTTGGAGTCTGGGGGAGGCTTGGTACAGCCTGGGGGGTCCCTGCGTCTCTCCTGTGCAGCCTCCGGAT
TCACCTTTCCTGAGTCTATGATGGGGTGGGTCCGCCAGGCTCCAGGGAAGGGTCTAGAGTGGGTCTCATCGATTGGGTA
TCCTGGTGCTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGGTGGTAGTCGGGATGATAATT
TTGACTACTGGGGTCAGGGAACCCTGGTCACCGTCTCGAGC (SEQ ID NO: 732)

BMS3h-171
GAGGTGCAGCTGTTGGAGTCTGGGGGAGGCTTGGTACAGCCTGGGGGGTCCCTGCGCCTCTCCTGTGCAGCCTCCGGAT
TCACCTTTGGTCAGCATAGTATGCATTGGGTCCGCCAGGCTCCAGGGAAGGGTCTAGAGTGGGTCTCAAGTATTAGTGT
TCCGGGTCCGAAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAGTCTTAGGGATTTGCGTCCGG
GTGATAGTAAGAGTTTTGACTACTGGGGTCAGGGAACCCTGGTCACCGTCTCGAGC (SEQ ID NO: 733)

BMS3h-197
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTTCTGCTGCTATGGATTGGGTCCGCCAGGCTCCAGGGAAGGGTCTAGAGTGGGTCTCATCTATTAATGA
TATGGGFTCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACAGGGTGGTCGTTTTGACTACT
GGGGTCAGGGAACCCTGGTCACCGTCTCGAGC (SEQ ID NO: 734)

BMS3h-199
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTTATGATAGGATGGCTTGGGTCCGCCAGGCTCCAGGGAAGGGTCTAGAGTGGGTCTCATCGATTGATGG
TCCTGGTGGGGCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGGAAGGGAGGAGGGTTCCTGATTTTG
ACTACTGGGGTCAGGGAACCCTGGTCACCGTCTCGAGC (SEQ ID NO: 735)

BMS3h-200
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTGAGTATGAGATGACTTGGGTCCGCCAGGCTCCAGGGAAGGGTCTAGAGTGGGTCTCAAGGATTGATCC
GTTTGGTTCTGAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAGGTGTGGTTCCTGATTTGAATT
TTGACTACTGGGGTCAGGGAACCCTGGTCACCGTCTCGAGC (SEQ ID NO: 736)

BMS3h-201
GAGGTGCAGCTGTTGGAGTCTGGGGGAGGCTTGGTACAGCCTGGGGGGTCCCTGCGTCTCTCCTGTGCAGCCTCCGGAT
TCACCTTTGATAAGTATGTTATGGGGTGGGTCCGCCAGGCTCCAGGGAAGGGTCTAGAGTGGGTCTCAACTATTGGTAG
TTATGGTGGGGCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAGGCTTACTCTTAGTGCGACTA
AGTTTGACTACTGGGGTCAGGGAACCCTGGTCACCGTCTCGAGC (SEQ ID NO: 737)

BMS3h-203
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGGATTATGTGATGGGTTGGGTCCGCCAGGCTCCAGGGAAGGGTCTAGAGTGGGTCTCAACTATTGCGCA
TCGGGGTGATATTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACGTAGGCGTCTTAGTGATTATC
GGTTTGACTACTGGGGTCAGGGAACCCTGGTCACCGTCTCGAGC (SEQ ID NO: 738)

BMS3h-204
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGCAGTTTGATATGTATTGGGTCCGCCAGGCTCCAGGGAAGGGTCTAGAGTGGGTCTCAGCGATTAGTCC
GGCTGGTACTGGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGCGGGGGATCGGTCTAGTCTTT
TTGACTACAGGGGTCAGGGAACCCTGGTCACCGTCTCGAGC (SEQ ID NO: 739)

BMS3h-205
GAGGTGCAGCTGTTGGAGTCTGGGGGAGGCTTGGTACAGCCTGGGGGGTCCCTGCGTCTCTCCTGTGCAGCCTCCGGAT
TCACCTTTAAGGATACGGGTATGACGTGGGTCCGCCAGGCTCCAGGGAAGGGTCTAGAGTGGGTCTCAAGTATTTCTAG
TTATGGTCGTGATACATACTACGCAGACTCCGTGAAGGGCCGGTTCACCATCTCCCGCGACAATTCCAAGAACACGCTG
TATCTGCAAATGAACAGCCTGCGTGCCGAGGACGCCGCGGTATATTACTGTGCGAAATTGAATGCGGCGCTGGGTTTTG
ACTACTGGGGTCAGGGAACCCTGGTCACCGTCTCGAGC (SEQ ID NO: 740)

BMS3h-206
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTCCGTATCCGATGAGTTGGGTCCGCCAGGCTCCAGGGAAGGGTCTAGAGTGGGTCTCAGGTATTAATGC
GCCGGGTACGAGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGCAACAGATGTCTAGTGGGGTTTTG
ACTACTGGGGTCAGGGAACCCTGGTCACCGTCTCGAGC (SEQ ID NO: 741)

TABLE 4-continued

Human Anti-CD40 Variable Domain Encoding Nucleotide Sequences

BMS3h-207
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGAATCAGGATATGACTTGGGTCCGCCAGGCTCCAGGGAAGGGTCTAGAGTGGGTCTCAAGTATTGATAG
TTCTGGTCAGCTTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGTTAAGTCTCTTGCGCGGTTTG
ACTACTGGGGTCAGGGAACCCTGGTCACCGTCTCGAGC (SEQ ID NO: 742)

BMS3h-208
GAGGTGCAGCTGTTGGAGTCTGGGGGAGGCTTGGTACAGCCTGGGGGGTCCCTGCGTCTCTCCTGCGCAGCCTCCGGAT
TCACCTTTCCTGAGTCTGATATGAAGTGGGTCCGCCAGGCTCCAGGGAAGGCTCTAGAGTGGGTCTCAAGTATTAGTCC
GAATGGTTGGGATACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACCGGCTCAGGTTCTGTTTGACT
ACTGGGGTCAGGGAACCCTGGTCACCGTCTCGAGC (SEQ ID NO: 743)

BMS3h-209
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGCAGTATGTGATGGGTTGGGTCCGCCAGGCTCCAGGGAAGGGTCTAGAGTGGGTCTCAACGATTGGTAC
GTCGGGTAAGTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGCAACGTAGGTCTCTGACTCGGGTTC
ATTTTGACTACTGGGGTCAGGGAACCCTGGTCACCGTCTCGAGC (SEQ ID NO: 744)

BMS3h-210
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTGTGGAGCATATGAGTTGGGTCCGCCAGGCTCCAGGGAAGGGTCTCAGCGATTACGGG
TGATGGTGATCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAACGGTTTCGTGGAATGGTCGTT
TTGACTACTGGGGTCAGGGAACCCTGGTCACCGTCTCGAGC (SEQ ID NO: 745)

BMS3h-211
GAGGTGCAGCTGTTGGAGTCTGGGGGAGGCTTGGTACAGCCTGGGGGGTCCCTGCGTCTCTCCTGTGCAGCCTCCGGAT
TCACCTTTGCGTGGTATAATATGGGTTGGGTCCGCCAGGCTCCAGGGAAGGGTCTGGAGTGGGTCTCAAGGATTGCTCC
GTCTGGTATTATTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGTTGCGTGGTAAGTTTGACT
ACTGGGGTCAGGGAACCCTGGTCACCGTCTCGAGC (SEQ ID NO: 746)

BMS3h-212
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGAATTATGAGATGAGGTGGGTCCGCCAGGCTCCAGGGAAGGGTCTAGAGTGGGTCTCATCTATTTCTTC
GGCTGGTACTGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACAGTCGCTTAATTTTGACTACT
GGGGTCAGGGAACCCTGGTCACCGTCTCGAGC (SEQ ID NO: 747)

BMS3h-213
GAGGTGCAGCTGTTGGAGTCTGGGGGAGGCTTGGTACAGCCTGGGGGGTCCCTGCGTCTCTCCTGTGTAGCCTCCGGAT
TCACCTTTGATGAGGAGCCGATGACTTGGGTCCGCCAGGCTCCAGGGAAGGGTCTAGAGTGGGTCTCAATTATTGATCC
GGGTGGTGGGGCGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATCTAATAGTATGTTTGACTACT
GGGGGTCAGGGAACCCTGGTCACCGTCTCGAGC (SEQ ID NO: 748)

BMS3h-214
GAGGTGCAGCTGTTGGAGTCTGGGGGAGGCTTGGTACAGCCTGGGGGGTCCCTGCGTCTCTCCTGTGCAGCCTCCGGAT
TCACCTTTTCTGCGTATCCTATGCATTGGGTCCGCCAGGCTCCAGGGAAGGGTCTAGAGTGGGTCTCATCTATTGCTTC
TTCGGGTATTACGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATTTACTCGGCTGCATTTTCCTG
CGCAGTTTGACTACTGGGGTCAGGGAACCCTGGTCACCGTCTCGAGC (SEQ ID NO: 749)

BMS3h-215
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGATTATGCGATGGGTTGGGTCCGCCAGGCTCCAGGGAAGGGTCTAGAGTGGGTCTCAAGGATTTCTCC
TGAGGGTTCTAGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATTGCGGCCGTATGCGTCGAAGT
TTGACTACTGGGGTCAGGGAACCCTGGTCACCGTCTCGAGC (SEQ ID NO: 750)

BMS3h-230
GAGGTGCAGCTGTTGGAGTCTGGGGGAGGCTTGGTACAGCCTGGGGGGTCCCTGCGTCTCTCCTGTGCAGCCTCCGGAT
TCACCTTTAGGCCGTATGATATGGGTTGGGTCCGCCAGGCTCCAGGGAAGGGTCTAGAGTGGGTCTCAACGATTTCTCA
TCAGGGTAATCGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGTGTCTCATCATTTTGACTACT
GGGGGTCAGGGAACCCTGGTCACCGTCTCGAGC (SEQ ID NO: 751)

BMS3h-231
GAGGTGCAGCTGTTGGAGTCTGGGGGAGGCTTGGTACAGCCTGGGGGGTCCCTGCGTCTCTCCTGTGCAGCCTCCGGAT
TCACCTTTTCTGCGTATAATATGTGGTGGGCCCGCCAGGCTCCAGGGAAGGGTTTAGAGTGGGTCTCATGGATTAATTC
GACTGGTTCTCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAAATTGGCATCGGGGAGGTTTG
ACTACTGGGGTCAGGGAACCCTGGTCACCGTCTCGAGC (SEQ ID NO: 752)

TABLE 4-continued

Human Anti-CD40 Variable Domain Encoding Nucleotide Sequences

BMS3h-232
GAGGTGCAGCTGTTGGAGTCTGGGGGAGGCTTGGTACAGCCTGGGGGGTCCCTGCGTCTCTCCTGTGCAGCCTCCGGAT
TCACCTTTGATAGGTATCGGATGGGGTGGGTCCGCCAGGCTCCAGGGAAGGGTCTAGAGTGGGTCTCAACGATTAATCG
GCTGGGTCAGAGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGTGAAGAAGCATAAGTTTGACT
ACTGGGGTCAGGGAACCCTGGTCACCGTCTCGAGC (SEQ ID NO: 753)

BMS3h-233
GAGGTGCAGCTGTTGGAGTCTGGGGGAGGCTTGGTACAGCCTGGGGGGTCCCTGCGTCTCTCCTGTGCAGCCTCCGGAT
TCACCTTTGCGCATTATAATATGCGGTGGGTCCGCCAGGCTCCAGGGAAGGGTCTAGAGTGGGTCTCAACGATTACGAA
GACTGGTTTTCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGCGGGGCAGTTTGATTTTGACT
ACTGGGGTCAGGGAACCCTGGTCACCGTCTCGAGC (SEQ ID NO: 754)

BMS3h-234
GAGGTGCAGCTGTTGGAGTCTGGGGGAGGCTTAGTACAGCCTGGGGGGTCCCTGCGTCTCTCCTGTGCAGCCTCCGGAT
TCACCTTTTATCCTTATAGTATGCATTGGGTCCGCCAGGCTCCAGGGAAGGGTCTGGAGTGGGTCTCAACTATTGATGG
TAGTGGTATGTTTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGGAAGATTCTCTGAAGGCTTCTTTTG
ACTACTGGGGTCAGGGAACCCTGGTCACCGTCTCGAGC (SEQ ID NO: 755)

BMS3h-235
GAGGTGCAGCTGTTGGAGTCTGGGGGAGGCTTGGTACAGCCTGGGGGGTCCCTGCGTCTCTCCTGTGCAGCCTCCGGAT
TCACCTTTCCGCTTTATGGGATGTGGTGGGTCCGCCAGGCTCCAGGGAAGGGTCTAGAGTGGGTCTCATATATTGGGCC
TTATGGTCATACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAAAGCGGAAGAAGAAGTTTGACT
ACTGGGGTCAGGGAACCCTGGTCACCGTCTCGAGC (SEQ ID NO: 756)

BMS3h-236
GAGGTGCAGCTGTTGGAGTCTGGGGGAGGCTTGGTACAGCCTGGGGGGTCCCTGCGTCTCTCCTGTGCAGCCTCCGGAT
TCACCTTTCCTAGGTATCGAGTGAGTTGGGTCCGCCAGGCTCCAGGGAAGGGTCTAGAGTGGGTCTCAAGTATTACTCC
GTATGGTGCTCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATATGGTAAGTGGTATTTTGACT
ACTGGGGTCAGGGAACCCTGGTCACCGTCTCGAGC (SEQ ID NO: 757)

BMS3h-237
GAGGTGCAGCTGTTGGAGTCTGGGGGAGGCTTGGTACAGCCTGGGGGGTCCCTGCGTCTCTCCTGTGCAGCCTCCGGAT
TCACCTTTAATGAGTATGCGATGAGGTGGGTCCGCCAGGCTCCAGGGAAGGGTCTAGAGTGGGTCTCAACGATTGATCG
TCTGGGTCTTCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAGTGGGCCTTTTACGTTTGACT
ACTGGGGTCAGGGAACCCTGGTCACCGTCTCGAGC (SEQ ID NO: 758)

BMS3h-238
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGCGGTATAATATGCGTTGGGTCCGCCAGGCTCCAGGGAAGGGTCTAGAGTGGGTCTCAACGATTGATCG
GCTGGGTCTTGCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGCGGGTTCGTGGTCTTTTGACT
ACTGGGGTCAGGGAACCCTGGTCACCGTCTCGAGC (SEQ ID NO: 759)

BMS3h-239
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTATTTATGATATGAAGTGGGTCCGCCAGGCTCCAGGGAAGGGTCTAGAGTGGGTCTCAACGATTTCGTC
GTCGGGTACTCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATATCCTCAGCCTTATCCTTTTG
ACTACTGGGGTCAGGGAACCCTGGTCACCGTCTCGAGC (SEQ ID NO: 760)

BMS3h-240
GAGGTGCAGCTATTGGAGTCTGGGGGAGGCTTGGTACAGCCTGGGGGGTCCCTGCGTCTCTCCTGTGCAGCCTCCGGAT
TCACCTTTTGGGTGTATGATATGCGTTGGGTCCGCCAGGCTCCAGGGAAGGGTCTAGAGTGGGTCTCAACGATTTCTGC
GACTGGTGTGCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATATCCGCCTGCTGGTCGGTTTG
ACTACTGGGGTCAGGGAACCCTGGTCACCGTCTCGAGC (SEQ ID NO: 761)

BMS3h-241
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGACTTATGATATGATTTGGGTCCGCCAGGCTCCAGGGAAGGGTCTAGAGTGGGTCTCAGCTATTTCTCC
TAATGGTACTGGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACCTCCGCAGGTGAATACTGAGT
TTGACTACCGGGGTCAGGGAACCCTGGTCACCGTCTCGAGC (SEQ ID NO: 762)

BMS3h-243
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGAAGGAGTATAGGGTGGGTCCGCCAGGCTCCAGGGAAGGGTCTAGAGTGGGTCTCACATATTTCGCC
GAATGGTTATGCGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAGTTGGTCTAGTTTTGACTACT
GGGGTCAGGGAACCCTGGTCACCGTCTCGAGC (SEQ ID NO: 763)

TABLE 4-continued

Human Anti-CD40 Variable Domain Encoding Nucleotide Sequences

BMS3h-244
GAGGTGCAGCTGTTGGAGTCTGGGGGAGGCTTGGTACAGCCTGGGGGGTCCCTGCGTCTCTCCTGTGCAGCCTCCGGAT
TCACCTTTAGTGCTACTCCGATGGAGTGGGCCCGCCAGGCTCCAGGGAAGGGTCTAGAGTGGGTCTCAACTATTTCTGA
GAGTGGTTATAGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATGGAATTCGACTACTGGTTTTG
ACTACTGGGGTCAGGGAACCCTGGTCACCGTCTCGAGC (SEQ ID NO: 764)

BMS3h-245
GAGGTGCAGCTGTTGGAGTCTGGGGGAGGCTTGGTACAGCCTGGGGGGTCCCTGCGTCTCTCCTGTGCAGCCTCCGGAT
TCACCTTTAATACGGTGGATATGGAGTGGGTCCGCCAGGCTCCAGGGAAGGGTCTAGAGTGGGTCTCAAGTATTAGTCC
GAATGGTTGGGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGGAAGCTCCGCATCGGGCGTTTGACT
ACTGGGGTCAGGGAACCCTGGTCACCGTCTCGAGC (SEQ ID NO: 765)

BMS3h-246
GAGGTGCAGCTGTTGGAGTCTGGGGGGGGCTTGGTACAGCCTGGGGGGTCCCTGCGTCTCTCCTGTGCAGCCTCCGGAT
TCACCTTTGAGGATAAGGAGATGAGTTGGGTCCGCCAGGCTCCAGGGAAGGGTCTAGAGTGGGTCTCACGGATTGATGC
TTTGGGTGATTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGGAAGGGATGGTTCCTCGTCTGAAGT
TTGACTACTGGGGTCAGGGAACCCTGGTCACCGTCTCGAGC (SEQ ID NO: 766)

BMS3h-247
GAGGTGCAGCTGTTGGAGTCTGGGGGAGGCTTGGTACAGCCTGGGGGGTCCCTGCGTCTCTCCTGTGCAGCCTCCGGAT
TCACCTTTAGTGATCATTCGATGATGTGGGTCCGCCAGGCTCCAGGGAAGGGTCTAGAGTGGGTCTCAGATATTGAGCC
GCATGGTGTTCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAATCCTACTTTTGACTACTGGGGTC
AGGGAACCCTGGTCACCGTCTCGAGC (SEQ ID NO: 767)

BMS3h-248
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGCCGCATACTATGCATTGGGTCCGCCAGGCTCCAGGGAAGGGTCTAGAGTGGGTCTCAGGTATTGGTCC
GGATGGTACTACTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACGTTCGTATAGTTGGGATCGTG
GGTGGACGTTTGACTACTGGGGTCAGGGAACCCTGGTCACCGTCTCGAGC (SEQ ID NO: 768)

BMS3h-249
GAGGTGCAGCTGTTGGAGTCTGGGGGAGGCTTGGTACAGCCTGGGGGGTCCCTGCGTCTCTCCTGTGCAGCCTCCGGAT
TCACCTTTTATGCTTCGGATATGAAGTGGGTCCGCCAGGCTCCAGGGAAGGGTCTAGAGTGGGTCTCAAGTATTAGTCC
GAATGGTTGGGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGCTGATTATACTTATCATTCTT
TTGACTACTGGGGTCAGGGGACCCTGGTCACCGTCTCGAGC (SEQ ID NO: 769)

BMS3h-250
GAGGTGCAGCTGTTGGAGTCTGGGGGAGGCTTGGTACAGCCTGGGGGGTCCCTGCGTCTCTCCTGTGCAGCCTCCGGAT
TCACCTTTGCGCATTATAATATGCGGTGGGTCCGCCAGGCTCCAGGGAAGGGTCTAGAGTGGGTCTCAACGATTACGAA
GACTGGTTTTCGTACATACTACGCAGACTCCGTGAAGGGCCGGTTCACCATCTCCCGTGACAATTCCAAGAACACGCTG
TATCTGCAAATGAACAGCCTGCGTGCCGAGGACACCGCGGTATATTACTGTGCGAAAGCGGGGCAGTTTGATTTTGACT
ACTGGGGTCAGGGAACCCTGGTCACCGTCTCGAGC (SEQ ID NO: 770)

BMS3h-251
GAGGTGCAGCTGTTGGAGTCTGGGGGAGGCTTGGTACAGCCTGGGGGGTCCCTGCGTCTCTCCTGTGCAGCCTCCGGAT
TCACCTTTTCGCATTATCATATGGGTTGGGCCCGCCAGGCTCCAGGGAAGGGTCTAGAGTGGGTCTCAGTTATTGGGCC
GAGGGGTATTTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATCGCCTTCGCGTCATAGGTTTG
ACTACTGGGGTCAGGGAACCCTGGTCACCGTCTCGAGC (SEQ ID NO: 771)

BMS3h-252
GAGGTGCAGCTGTTGGAGTCTGGGGGAGGCTTGGTACAGCCTGGGGGGTCCCTGCGTCTCTCCTGTGCAGCCTCCGGAT
TCACCTTTAATGAGTATGCGATGAGGTGGGTCCGCCAGGCTCCAGGGAAGGGTCTAGAGTGGGTCTCAACGATTGATCG
TCTGGGTCTTCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAGTGGGCCTTTTACGTTTGACT
ACTGGGGTCAGGGAACCCTGGTCACCGTCTCGAGC (SEQ ID NO: 772)

BMS3h-253
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTAATTATAGTATGAAGTGGGCCCGCCAGGCTCCAGGGAAGGGTCTAGAGTGGGTCTCAACTATTACTCC
TGATGGTTGGTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGTGGGGATGCTGTTTGGGGGT
GGATTGGTGGGTTTGACTACTGGGGTCAGGGAACCCTGGTCACCGTCTCGAGC (SEQ ID NO: 773)

BMS3h-254
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGGATTATGGTATGAAGTGGGTCCGCCAGGCTCCAGGGAAGGGTCTAGAGTGGGTCTCAGCTATTACGTC
TAATGGTGATTTTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATCTTTGTATAAGTTTGACTACT
GGGGTCAGGGAACCCTGGTCACCGTCTCGAGC (SEQ ID NO: 774)

TABLE 4-continued

Human Anti-CD40 Variable Domain Encoding Nucleotide Sequences

BMS3h-255
GAGGTGCAGCTGTTGGAGTCTGGGGGAGGCTTGGTACAGCCTGGGGGGTCCCTGCGTCTCTCCTGTGCAGGCTCCGGAT
TCACCTTTCCTACTTATAAGATGGGGTGGGTCCGCCAGGCTCCAGGGAAGGGTCTAGAGTGGGTCTCATTTATTGATTA
TTGGGGTTGGCGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAGTCCGTATTCTTGGACTCATG
ATAGTCCTCATTTTGACTACTGGGGTCAGGGAACCCTGGTCACCGTCTCGAGC (SEQ ID NO: 775)

BMS3h-256
GAGGTGCAGCTGTTGGAGTCTGGGGGAGGCTTGGTACAGCCTGGGGGGTCCCTGCGTCTCTCCTGTGCAGCCTCCGGAT
TCACCTTTAGGCCTTATACGATGTGTTGGGCCCGCCAGGCTCCAGGGAAGGGTCTAGAGTGGGTCTCATGTATTAGTGA
TGCTGGTTCTTTTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAAGGATGTCTTCTTTTGACTACT
GGGGTCAGGGAACCCTGGTCACCGTCTCGAGC (SEQ ID NO: 776)

BMS3h-257
GAGGTGCAGCTGTTGGAGTCTGGGGGAGGCTTGGTACAGCCTGGGGGGTCCCTGCGTCTCTCCTGTGCAGCCTCCGGAT
TCACCTTTCAGAATTATCAGATGGCTTGGGTCCGCCAGGCTCCAGGGAAGGGTCTAGAGTGGGTCTCAACTATTAGTGG
GACTGGTAAGAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAACTCCTCAGAATTATTTTAGTG
TGCGTCGGTTTGACTACTGGGGTCAGGGAACCCTGGTCACCGTCTCGAGC (SEQ ID NO: 777)

BMS3h-258
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGCGTATACTATGGGGTGGGTCCGCCAGGCTCCAGGGAAGGGTCTAGAGTGGGTCTCAAAGATTTCGAC
GTCTGGTGGGCAGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACCTTTGAATTGGTGGGCGTTTG
ACTACTGGGGTCAGGGAACCCTGGTCACCGTCTCGAGC (SEQ ID NO: 778)

BMS3h-272
GAGGTGCAGCTGTTGGAGTCTGGGGGAGGCTTGGTACAGCCTGGGGGGTCCCTGCGTCTCTCCTGTGCAGCCTCCGGAT
TCACCTTTAATGCGTATCCTATGACTTGGGTCCGCCAGGCTCCAGGGAAGGGTCTAGAGTGGGTCTCACGGATTGATGG
TTATGGTCGGCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATTATTCCTAATTTTGACT
ACTGGGGTCAGGGAACCCTGGTCACCGTCTCGAGC (SEQ ID NO: 779)

BMS3h-273
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGCGGTTGATATGACGTGGGTCCGCCAGGCTCCAGGGAAGGGTCTAGAGTGGGTCTCAGCGATTTCGCC
TAGTGGTTCTGCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGCGTGTGCCGGATCTTGGTT
TTGACTACTGGGGTCAGGGAACCCTGGTCACCGTCTCGAGC (SEQ ID NO: 780)

BMS3h-274
GAGGTGCAGCTGTTGGAGTCTGGGGGAGGCTTGGTACAGCCTGGGGGGTCCCTGCGTCTCTCCTGTGCAGCCTCCGGAT
TCACCTTTGATAGTTATGCGATGGGGTGGGCCCGCCAGGCTCCAGGGAAGGGTCTAGAGTGGGTCTCAGCTATTGGGGC
TAAGGGTTTGTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGCGGCTAGGGGTAAGTTTGACT
ACTGGGGTCAGGGAACCCTGGTCACCGTCTCGAGC (SEQ ID NO: 781)

BMS3h-275
GAGGTGCAGCTGTTGGAGTCTGGGGGAGGCTTGGTACAGCCTGGGGGGTCCCTGCGTCTCTCCTGTGCAGCCTCCGGAT
TCACCTTTACTCGGTATCAGATGGGTTGGGTCCGCCAGGCTCCAGGGAAGGGTCTAGAGTGGGTCTCAGTTATTAATGT
TTGGGGTTCGAGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAATGTCTGGGAAGTTTGCCTACT
GGGGTCAGGGAACCCTGGTCACCGTCTCGAGC (SEQ ID NO: 782)

BMS3h-276
GAGGTGCAGCTGTTGGAGTCTGGGGGAGGCTTGGTACAGCCTGGGGGGTCCCTGCGTCTTTCCTGTGCAGCCTCCGGAT
TCACCTTTGGGAATTATAGTATGATGTGGGTCCGCCAGGCTCCAGGGAAGGGTCTAGAGTGGGTCTCAACGATTATTCC
TGCTGGTACGTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACCGTCGATTAGGTTGTTTGACT
ACTGGGGTCAGGGAACCCTGGTCACCGTCTCGAGC (SEQ ID NO: 783)

BMS3h-279
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTGCGTATGATATGGGGTGGGTCCGCCAGGCTCCAGGGAAGGGTCTAGAGTGGGTCTCATGGATTTCTCC
GAATGGTTATGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGGGTGTGAAGTTTGACTACT
GGGGTCAGGGAACCCTGGTCACCGTCTCGAGC (SEQ ID NO: 784)

BMS3h-282
GAGGTGCAGCTGTTGGAGTCTGGGGGAGGCTTGGTACAGCCTGGGGGGTCCCTGCGTCTCTCCTGTGCAGCCTCCGGAT
TCACCTTTGTTTGGTATGAGATGGCTTGGGTCCGCCAGGCTCCAGGGAAGGGTCTAGAGTGGGTCTCAACGATTCAGGC
TGATGGTGAGCAGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGCTTCGTATGCTCTTGTATC
CTCCTGAGGAGTTTGACTACTGGGGTCAGGGAACCCTGGTCACCGTCTCGAGC (SEQ ID NO: 785)

TABLE 4-continued

Human Anti-CD40 Variable Domain Encoding Nucleotide Sequences

BMS3h-287
GAGGTGCAGCTGTTGGAGTCTGGGGGAGGCTTGGTACAGCCTGGGGGGTCCCTGCGTCTCTCCTGTGCAGCCTCCGGAT
TCACCTTTACGAATTATAGGATGTCTTGGGTCCGCCAGGCTCCAGGGAAGGGTCTAGAGTGGGTCTCAGCTATTGATGA
TCTGGGTGTGTCGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATGGAGGCTTAAGAATAGTCAGC
CGACGGATTTTGACTACTGGGGTCAGGGAACCCTGGTCACCGTCTCGAGC (SEQ ID NO: 786)

BMS3h-292
GAGGTGCAGCTGTTGGAGTCTGGGGGAGGCTTGGTACAGCCTGGGGGGTCCCTGCGTCTCTCCTGTGCAGCCTCCGGAT
TCACCTTTGATCAGGCTCATATGTGGTGGGTCCGCCAGGCTCCAGGGAAGGGTCTAGAGTGGGTCTCATTTATTAATCC
TTCGGGTTATTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACCTTCGCTTAGTCCGTCTTCTT
TTGACTACTGGGGTCAGGGAACCCTGGTCACCGTCTCGAGC (SEQ ID NO: 787)

BMS3h-293
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGACTGGTCAGATGGGTTGGGCCCGCCAGGCTCCAGGGAAGGGTCTAGAGTGGGTCTCAAATATTGATGG
GTCTGGTACGTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAAGTACGCAGAATTATCGGTTTG
ACTACTGGGGTCAGGGAACCCTGGTCACCGTCTCGAGC (SEQ ID NO: 788)

BMS3h-296
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTGCTTATCCGATGTATTGGGTCCGCCAGGCTCCAGGGAAGGGTCTAGAGTGGGTCTCATCTATTCATAA
GGATGGTAGGATTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACAGGGTACGCCGGTTGATGGGT
TTGACTACTGGGGTCAGGGAACCCTGGTCACCGTCTCGAGC (SEQ ID NO: 789)

BMS3h-297
GAGGTGCAGCTGTTGGAGTCTGGGGGAGGCTTGGTACAGCCTGGGGGGTCCCTGCGTCTCTCCTGTGCAGCCTCCGGAT
TCACCTTTCCTGATGAGGGTATGACGTGGGTCCGCCAGGCTCCAGGGAAGGGTCTAGAGTGGGTCTCAACGATTGAGAC
TGGTGGTACGGTGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAATGGATGGGTCTGGTACATGGC
AGACGTTTGACTACTGGGGTCAGGGAACCCTGGTCACCGTCTCGAGC (SEQ ID NO: 790)

BMS3h-298
GAGGTGCAGCTGTTGGAGTCTGGGGGAGGCTTGGTACAGCCTGGGGGGTCCCTGCGTCTCTCCTGTGCAGCCTCCGGAT
TCACCTTTGATAGTCTGGGTATGGGTTGGGCCCGCCAGGCTCCAGGGAAGGGTCTAGAGTGGGTCTCATATATTCGGGC
TGAGGGTGCTTATACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAATATCTTGCGGATTCTGACTACT
GGGGTCAGGGAACCCTGGTCACCGTCTCGAGC (SEQ ID NO: 791)

BMS3h-299
GAGGTGCAGCTGTTGGAATCTGGGGGAGGCTTGGTACAGCCTGGGGGGTCCCTGCGTCTCTCCTGTGCAGCCTCCGGAT
TCACCTTTAGTGAGTCGTATATGGAGTGGGTCCGCCAGGCTCCAGGGAAGGGTCTAGAGTGGGTCTCAGGTATTGATCA
TATTGGTGGTGGGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGATGATGGTCGTGGTGGGTCTA
TGTTTGACTACTGGGGTCAGGGAACCCTGGTCACCGTCTCGAGC (SEQ ID NO: 792)

BMS3h-300
GAGGTGCAGCTGTTGGAGTCTGGGGGAGGCTTGGTACAGCCTGGGGGGTCCCTGCGTCTCTCCTGTGCAGCCTCCGGAT
TCACCTTTTCTGGTGGGTATATGTGGTGGGTCCGCCAGGCTCCAGGGAAGGGTCTAGAGTGGGTCTCAAGTATTGGGGC
TAGTGGTGCGTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAACGGGGGTAGGTTAGACTACT
GGGGTCAGGGAACCCTGGTCACCGTCTCGAGC (SEQ ID NO: 793)

BMS3h-301
GAGGTGCAGCTGTTGGAGTCTGGGGGAGGCTTGGTACAGCCTGGGGGGTCCCTGCGTCTCTCCTGTGCAGCCTCCGGAT
TCACCTTTGATGAGGGCATATGGGTGGGTCCGCCAGGCTCCAGGGAAGGATCTAGAGTGGGTCTCATATATTGGGAG
TCTGGGTTTGCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACGGGAGTTTAGTAATGGGGGT
TTGACTACTGGGGTCAGGGAACCCTGGTCACCGTCTCGAGC (SEQ ID NO: 794)

BMS3h-302
GAGGTGCAGCTGTTGGAGTCTGGGGGAGGCTTGGTACAGCCTGGGGGGTCCCTGCGTCTCTCCTGTGCAGCCTCCGGAT
TCACCTTTAAGACTAGTCCTATGTATTGGGTCCGCCAGGCTCCAGGGAAGGGTCTAGAGTGGGTCTCATCGATTGATCG
GACTGGTGGGCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACAGGCTCTGCTTACTGATGCGA
AGCGTTTTGACTACTGGGGTCAGGGAACCCTGGTCACCGTCTCGAGC (SEQ ID NO: 795)

BMS3h-303
GAGGTGCAGCTGTTGGAGTCTGGGGGAGGCTTGGTACAGCCTGGGGGGTCCCTGCGTCTCTCCTGTGCAGCCTCCGGAT
TCACCTTTGATGGTCGGATATGGTTTGGGTCCGCCAGGCTCCAGGGAAGGGTCTAGAGTGGGTCTCAGCTATTAGTCC
GAGTGGTCTGGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAACGTCCTCAGATGCTGGTTACTA
ATTTTGACTACTGGGGTCAGGGAACCCTGGTCACCGTCTCGAGC (SEQ ID NO: 796)

TABLE 4-continued

Human Anti-CD40 Variable Domain Encoding Nucleotide Sequences

BMS3h-304
GAGGTGCAGCTGTTGGAGTCTGGGGGAGGCTTGGTACAGCCTGGGGGGTCCCTGCGTCTCTCCTGTGCAGCCTCCGGAT
TCACCTTTGGTAATGATCCGATGAGTTGGGTCCGCCAGGCTCCAGGGAAGGGTCTAGAGTGGGTCTCAGGGATTGGTCG
GGAGGGTGATTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGATTCTATGCGGCATCAGCCGT
TTGACTACTGGGGTCAGGGAACCCTGGTCACCGTCTCGAGC (SEQ ID NO: 797)

BMS3h-305
GAGGTGCAGCTGTTGGAGTCTGGGGGAGGCTTGGTACAGCCTGGGGGGTCCCTGCGTCTCTCCTGTGCAGCCTCCGGAT
TCACCTTTGATGAGACTTATATGAAGTGGGTCCGCCAGGCTCCAGGGAAGGGTCTAGAGTGGGTCTCAGCGATTGGGGC
GTCGGGTGCTGATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATTTACGCATCTGAATGGTCGGT
TTGACTACTGGGGTCAGGGAACCCTGGTCACCGTCTCGAGC (SEQ ID NO: 798)

BMS3h-306
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGGGTGCCTATGGGGTGGGTCCGCCAGGCTCCAGGGAAGGGTCTAGAGTGGGTCTCAGGTATTGATAT
TGATGGTGCTCCGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGGAGGCGGGTTCTTGGTCTT
TTGACTACTGGGGTCAGGGAACCCTGGTCACCGTCTCGAGC (SEQ ID NO: 799)

BMS3h-307
GAGGTGCAGCTGTTGGAGTCTGGGGGAGGCTTGGTACAGCCTGGGGGGTCCCTGCGTCTCTCCTGTGCAGCCTCCGGAT
TCACCTTTAGTGATCAGGCGATGTGGTGGGCCCGCCAGGCTCCAGGGAAGGGTCTAGAGTGGGTCTCATTTATTCAGGG
TGATGGTGGTTTTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACCTAGTAAGCCGTTTGACTACT
GGGGTCAGGGAACCCTGGTCACCGTCTCGAGC (SEQ ID NO: 800)

BMS3h-308
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGACTGGTCAGATGGGTTGGGCCCGCCAGGCTCCAGGGAAGGGTCTAGAGTGGGTCTCAAATATTGATGG
GTCTGGTACGTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGCGGTGCGGAATTTTGCTTTTG
ACTACTGGGGTCAGGGAACCCTGGTCACCGTCTCGAGC (SEQ ID NO: 801)

BMS3h-309
GAGGTGCAGCTGTTGGAGTCTGGGGGAGGCTTGGTACAGCCTGGGGGGTCCCTGCGTCTCTCCTGTGCAGCCTCCGGAT
TCACCTTTAGTGGGCATGATATGTCTTGGGTCCGCCAGGCTCCAGGGAAGGGTCTAGAGTGGGTCTCAGCTATTAGTCC
TCATGGTACGCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGGGATTAGGGGTTGGATTGGTC
ATGATACGCAGCCTTTTGACTACTGGGGTCAGGGAACCCTGGTCACCGTCTCGAGC (SEQ ID NO: 802)

BMS3h-310
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGAGTAAGGATATGCTTTGGGTCCGCCAGGCTCCAGGGAAGGGTCTAGAGTGGGTCTCATCTATTTCGTC
GGATGGTACTCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGCAAGAGCTGGGTGGGTCTTGGCAGT
TTGACTACTGGGGTCAGGGAACCCTGGTCACCGTCTCGAGC (SEQ ID NO: 803)

BMS3h-311
GAGGTGCAGCTGTTGGAGTCTGGGGGAGGCTTGGTACAGCCTGGGGGGTCCCTGCGTCTCTCCTGTGCAGCCTCCGGAT
TCACCTTTGCGGATCGTGATATGGTTTGGGTCCGCCAGGCTCCAGGGAAGGGTCTAGAGTGGGTCTCAGGTATTGGGGC
GTCGGGTACGTCTACATACTACGCAGACTCCGTGAAGGGCCGGTTCACCATCTCCCGCGACAATTCCAAGAACACGCTG
TATCTGCAAATGAACAGCCTGCGTGCCGAGGACGCCGCGGTATATTACTGTGCGAAAGGTGGGACGGGTCCTACTGATT
TGTGGGATTTTGACTACTGGGGTCAGGGAACCCTGGTCACCGTCTCGAGC (SEQ ID NO: 804)

BMS3h-312
GAGGTGCAGCTGTTGGAGTCTGGGGGAGGCTTGGTACAGCCTGGGGGGTCCCTGCGTCTCTCCTGTGCAGCCTCCGGAT
TCACCTTTGATGATGAGAAGATGCTTTGGGTCCGCCAGGCTCCAGGGAAGGGTCTAGAGTGGGTCTCAAGTATTAGTGT
GAGTGGTCTGCATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGGAGGCGGGTTCTTGGTCTT
TTGACTACTGGGGTCAGGGAACCCTGGTCACCGTCTCGAGC (SEQ ID NO: 805)

BMS3h-313
GAGGTGCAGCTGTTGGAGTCCGGGGGAGGCTTGGTACAGCCTGGGGGGTCCCTGCGTCTCTCCTGTGCAGCCTCCGGAT
TCACCTTTGGGCAGGAGGATGATTTGGGTCCGCCAGGCTCCTGGGAAGGGTCTAGAGTGGGTCTCAGATATTTCGGC
TTCGGGTGGGACTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGGAGGCGGGTTCTTGGTCTT
TTGACTACTGGGGTCAGGGAACCCTGGTCACCGTCTCGAGC (SEQ ID NO: 806)

BMS3h-37-1
GAGGTGCAGCTGTTGGAGTCTGGGGGAGGCTTGGTACAGCCTGGGGGGTCTCTGCGTCTCTCCTGTGCAGCCTCCGGAT
TCACCTTTGAGTGGTATGAGATGCAGTGGGTCCGCCAGGCTCCAGGGAAGGGTCTAGAGTGGGTCTCAGCGATTTCTGG
TGATGGTTATCGTACATACTACGCAGACTCCGTGAAGGGCCGGTTCACCATCTCCCGCGACAATTCCATGAACACGCTG
TATCTGCAAATGAACAGCCTGCGTGCCGAGGACACCGCGGTATATTACTGTGCGAAAGAGCTTGGGTATTTTGACTACA
GGGGTCGGGGAACCCTGGTCACCGTCTCGAGC (SEQ ID NO: 807)

TABLE 4-continued

Human Anti-CD40 Variable Domain Encoding Nucleotide Sequences

BMS3h-37-2
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACT
GGGGTCGGGGAACCCTGGTCACCGTCTCGAGC (SEQ ID NO: 808)

BMS3h-37-3
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGTCTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACC
GGGTTCAGGGAACCCTGGTCACCGTCTCGAGC (SEQ ID NO: 809)

BMS3h-37-4
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCAAGGCTCCAGGGAAGGGTCTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACT
GGGGTCGGGGAACCCTGGTCACCGTCTCGAGC (SEQ ID NO: 810)

BMS3h-37-5
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCAGGCTCCAGGGAAGGGTCTAGAGTGGATCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACA
GGGTTCAGGGAACCCTGGTCACCGTCTCGAGC (SEQ ID NO: 811)

BMS3h-37-6
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGTCTAGAGTGGGTCTCAGCGATTTCTGG
TGATGGTTATCGTACATACTACGCAGACTCCGTGAAAGGCCGGTTCACCATCTCCCGCGACAATTCCGAGAACACGCTG
TATCTGCAAATGAACAGCCTGCGTGCCGAGGACACCGCGGTATATTACTGTGCGAAAGAGCTTGGGTATTTTGACTACT
GGGGTCGGGGAACCCTGGTCACCGTCTCGAGC (SEQ ID NO: 812)

BMS3h-37-7
GAGGTGCAGCTGTTGGAGACTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGTCTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGGACAGCCTGCGTGCCGAGGACACCGCGGTATATTACTGTGCGAAAGAGCTTGGGTATTTTGACTACT
GGGGTCGGGGAACCCTGGTCACCGTCACGAGC (SEQ ID NO: 813)

BMS3h-37-8
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCAGGCTCCAGGGAAGGGTCTAGAGTGGGTCTCAGCGATTTCTGG
TGATGGTTATCGTACATACTACGCAGACTCCGTGAAAGGCCGGTTCACCATCTCACGCGACAATTCCAAGAACACGCTG
TATCTGCAAATGAACAGCCTGCGTGCCGAGGACACCGCGGTATATTACTGTGCGAAAGAGCTTGGGTATTTTCACTACT
GGGGTCGGGGAACCCTGGTCACCGTCTCGAGC (SEQ ID NO: 814)

BMS3h-37-9
GAGGTGCAGCTGTTGGAGTCTGGGGGAGGCTTGGTACAGCCTGGGGGGTCCCTGCGTCTCTCCTGTGTAGCCTCCGGAT
TCACCTTTGAGTGGTATGAGATGCAGTGGGTCCGCCAGGCTCCAGGGAATGGTCTAGAGTGGATCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACT
GGGGTCGGGGAACCCTGGTCACCGTCTCGAGC (SEQ ID NO: 815)

BMS3h-37-10
GAGGTGCAGCTGTTGGAGTCTGGGGGAGGCTTGGTACAGCCTGGGGGGTCCCTGCGTCTCTCCTGTGCAGCCTCTGGAT
TCACCTTTGAGTGGTATGAGATGCAGTGGGTCCGCCGGGCTCCAGGGAAGGGTCTAGAGTGGGTCTCAGCGATATCTGG
TGATGGTCATCGTACATACTACGCAGACTCCGTGAAAGGCCGGTTCACCATCTCCCGCGACAATTCCAAGAACACGCTG
TATCTGCTAATGAACAGCCTGCGTGCCGAGGACACCGCGGTATATTACTGTGCGAAAGAGCTTGGGTATTTCGACTACT
GGGGTCGGGGAACCCTCGTCACCGTCTCGAGC (SEQ ID NO: 816)

BMS3h-37-11
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCAAGGCTCCAGGGAAGGGTCTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACA
GGGGTCGGGGAACCCTGGTCACCGTCTCGAGC (SEQ ID NO: 817)

BMS3h-37-12
GAGGTGCAGCTGTTGGAGTCTGGGGGAGGCTTGGTACAGCCTGGGGGGTCCATGCGTCTCTCCTGTGCAGCCTCCGGAT
TCACCTTTGAGTGGTATGAGATGCAGTGGGTCCGCCGGGCTCCAGGGAAGGGTCTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACA
GGGGTCGGGGAACCCTGGTCACCGTCTCGAGC (SEQ ID NO: 818)

TABLE 4-continued

Human Anti-CD40 Variable Domain Encoding Nucleotide Sequences

BMS3h-37-201
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGATTAGAGTGGGTCTCAATGATTTCCGG
GGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACT
GGGGTCGGGGAACCCTGGTCACCGTCTCGAGC (SEQ ID NO: 819)

BMS3h-37-202
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGACGGTTGGCGCACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTTGGGTATTTTGACTACT
GGGGTCGGGGAACCCTGGTCACCGTCTCGAGC (SEQ ID NO: 820)

BMS3h-37-203
GAGGTGCAGCTGTTGGAGTCTGGGGGAGGCTTGGTACAGCCTGGGGGGTCCCTGCGTCTCTCCTGTGCAGCCTCCGGAT
TCACCTTTGGGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTGCTCTACTTTGACTACT
GGGGTCGGGGAACCCTGGTCACCGTCTCGAGC (SEQ ID NO: 821)

BMS3h-37-204
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTGGGGTTCTTTGACTACT
GGGGTCGGGGAACCCTGGTCACCGTCTCGAGC (SEQ ID NO: 822)

BMS3h-37-205
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGTTGGAGTATTTTGACTACT
GGGGTCGGGGAACCCTGGTCACCGTCTCGAGC (SEQ ID NO: 823)

BMS3h-37-206
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGATACCGCGGTATATTACTGTGCGAAAGGGTTGGAGTATTTTGACTACT
GGGGTCGGGGAACCCTGGTCACCGTCTCGAGC (SEQ ID NO: 824)

BMS3h-37-207
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTGGCCTTCTTTGACTACT
GGGGTCGGGGAACCCTGGTCACCGTCTCGAGC (SEQ ID NO: 825)

BMS3h-37-208
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTCTTGTACTTTGACTACT
GGGGTCGGGGAACCCTGGTCACCGTCTCGAGC (SEQ ID NO: 826)

BMS3h-37-209
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGTTGGAGTTCTTTGACTACT
GGGGTCGGGGAACCCTGGTCACCGTCTCGAGC (SEQ ID NO: 827)

BMS3h-37-210
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCTGCAGTTCTTTGACTACT
GGGGTCGGGGAACCCTGGTCACCGTCTCGAGC (SEQ ID NO: 828)

BMS3h-37-211
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCTGCTCTTCTTTGACTACT
GGGGTCGGGGAACCCTGGTCACCGTCTCGAGC (SEQ ID NO: 829)

TABLE 4-continued

Human Anti-CD40 Variable Domain Encoding Nucleotide Sequences

BMS3h-37-212
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGATACCGCGGTATATTACTGTGCGAAAGAGTTGGAGTTCTTTGACTACT
GGGGTCGGGGAACCCTGGTCACCGTCTCGAGC (SEQ ID NO: 830)

BMS3h-37-213
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGTTGCTCTTCTTTGACTACC
GGGGTCGGGGAACCCTGGTCACCGTCTCGAGC (SEQ ID NO: 831)

BMS3h-37-214
GAGGTGCAGCTGTTGGAGTCTGGGGGAGGCTTGGTACAGCCTGGGGGGTCCCTGCGTCTCTCCTGTGCAGCCTCCGGAT
TCATCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGATACCGCGGTATATTACTGTGCGAAAAACTTGGAGTATTTTGACTACT
GGGGTCGGGGAACCCTGGTCACCGTCTCGAGC (SEQ ID NO: 832)

BMS3h-37-215
GAGGTGCGGCTGTTGGAGTCTGGGGGAGGCTTGGTACAGCCTGGGGGGTCCCTGCGTCTCTCCTGTGCAGCCTCCGGAT
TCACCTTTGAGTGGTATGAGATGCAGTGGGTCCGCCGGGCTCCAGGGAAGGGACTAGAGTGGGTCTCAGCGATTTCTGG
TGATGGTTATCGTACATACTACGCAGACTCCGTGAAAGGCCGGTTCACCATCTCCCGCGACAATTCCAAGAACACGCTG
TATCTGCAAATGAACAGCCTGCGTGCCGAGGACACCGCGGTATATTACTGTGCGAAAGAGTTGCAGTTCTTTGACTACT
GGGGTCGGGGAACCCTGGTCACCGTCTCGAGC (SEQ ID NO: 833)

BMS3h-38-1
GAGGTGCAGCTGTTGGGGTCTGGGGGAGGCTTGGTACAGCCTGGGGGGTCCCTGCGTCTCTCCTGTGCAGCCTCCGGAT
TCACCTTTGAGGAGGAGGAGATGATTTGGGTCCGCCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTTCGAAAGAGCCGTTTCGTTTTGACTACT
GGGGTCAGGGAACCCTGGTCACCGTCTCGAGC (SEQ ID NO: 834)

BMS3h-38-2
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 835)

BMS3h-38-3
GAGGTGCAGCTGTTGGCGTCTGGGGGAGGCTTGGTACAGCCTGGGGGGTCCCTGCGTCTCTCCTGTGCAGCCTCCGGAT
TCACCTTTGAGGAGGAGGAGATGATTTGGGTCCGCCAGGCTCCAGGGAAGGGTCTAGAGTGGATCTCAGCTATTAGTGG
AAGTGGTGGTAGCACATACTACGCAGACTCCGTGAAGGGCCGGTTTACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTTTGACTACT
GGGGTCAGGGAACCCTGGTCACCGTCTCGAGC (SEQ ID NO: 836)

BMS3h-38-4
GAGGTGCAGCTGTTGGATCCTGGGGGAGGCTTGGTACAGCCTGGGGGGTCCCTGCGTCTCTCCTGTGCAGCCTCCGGAT
TCACCTTTGGGAAGGAGGAGATGATTTGGGTCCGCCAGGCTCCAGGGAAGGGTCTAGAGTGGGTCTCATCTATTAGTGG
TAGTGGTGGTAGCACATACTACGCAGACTCCGTGAAGGGCCGGTTCACCATCTCCCGCGACAATTCCAGGAACACGCTG
TATCTGCAAATGAACAGCCTGCGTGCCGAGGATACCGCGGTATATTACTGTGGGAAAGAGCCGTTTCGTTTTGACTACT
GGGGTCAGGGAACCCTGGTCACCGTCTCGAGC (SEQ ID NO: 837)

BMS3h-38-5
GAGGTGCAGCTGTTGGGGTCTGGGGGAGGCTTGGTACAGCCTGGGGGGTCCCTGCGTCTCTCCTGTGCAGCCTCCGGAT
TCACCTTTGAGGAGGAGGAGATGATTTGGGTCCGCCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTTTGACTACT
GGGGTCAGGGAACCCTGGTCACCGTCTCGAGC (SEQ ID NO: 838)

BMS3h-38-6
GAGGTGCAGCTGTTGGAGCCTGGGGGAGGCTTGGTACAGCCTGGGGGCTCCCTGCGTCTCTCCTGTGCAGCCTCCGGAT
TCACCTTTGAGGAGGAGGAGATGATTTGGGTCCGCCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCTAATGAACAGCCTGCGTGCCGAGGATACCGCGGTATATTACTGTTCGAAAGAGCCGTTTCGTTTTGACTACT
GGGGTCAGGGAGCCCTGGTCACCGTCTCGAGC (SEQ ID NO: 839)

BMS3h-38-7
GAGGTGCAGCTGTTGGATCCTGGGGGAGGCTTGGTACAGCCTGGGGGGTCCCTGCGTCTCTCCTGTGCAGCCTCCGGAT
TCACCTTTGGGAAGGAGGAGATGATTTGGGTCCGCCAGGCTCCAGGGAAGGGTCTAGAGTGGGTCTCATCTATTAGTGG
TAGTGGTGGTAGCACATACTACGCAGACTCCGTTAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGTTACGTTTTGACTACT
GGGGTCAGGGAACCCTGGTCACCGTCTCGAGC (SEQ ID NO: 840)

TABLE 4-continued

Human Anti-CD40 Variable Domain Encoding Nucleotide Sequences

BMS3h-38-8
GAGGTGCAGCTGTTGGAGTCTGGGGGAGGCTTGGTACAGCCTGGGGGGTCCCTGCGTCTCTCCTGTGCAGCCTCCGGAT
TCACCTTTGAGGAGGAGGAGATGATCTGGGTCCGCCAGGCTCCTGGGAAGGGTCTAGAGTGGATCTCAGCTATTAGTGG
TAGTGGTGGTAGCACATACTACGCAGACTCCGTGAAGGGCCGGTTCACCATCCACCGCGACAATTCTAAGAACACTCTG
TATCTGCAAATGAACAGCCTGCGTGCCGAGGATACCGCGGTATATTACTGTTCGAAAGAGCCGTTTCGTTTTGACTACA
GGGGTCTGGGAACCTTGGTCACCGTCTCGAGC (SEQ ID NO: 841)

BMS3h-38-9
GAGGTGCAGCTGTTGGATCCTGGGGGAGGCTTGGTACAGCCTGGGGGGTCCCTGCGTCTCTCCTGTGCAGCCTCCGGAT
TCACCTTTGGGAAGGAGGAGATGATTTGGGTCCGCCAGGCTCCAGGGAAGGGTCTAGAGTGGGTCTCATCTATTAGTGG
TAGTGGTGGTAGCACATACTACGCAGACTCCGTGAAGGGCCGGTTCACCATCTCCCGCGACAATTCCAGGAACACGCTG
TATCTGCAAATGAACAGCCTGCGTGCCGAGGATACCGCGGTATATTACTGTGCGAAAGAGCCGTTACGTTTTGACTACT
GGGGTCAGGGGACCCTGGTCACCGTCTCGAGC (SEQ ID NO: 842)

BMS3h-38-10
GAGGTGCAGCTGTTGGATTCTGGGGGAGGCTTTGTACAGCCTGGGGGGTCCCTGCGTCTCTCCTGTGCAGCCTCCGGAT
TCACCTTTGAGGAGGAGGAGATGATTTGGGTCCGCCAGGCTCCAGGGAAGGGTCTAGAGTGGATCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTGTATTACTGTGCGAAAGAGCCGTTTCGTTTTGACTACT
GGGGTCAGGGAACCCTGGTCACCGTCTCGAGC (SEQ ID NO: 843)

BMS3h-38-11
GAGGTGCAGCTGTTGGATCCTGGGGGAGGCTTGGTACAGCCTGGGGGGTCCCTGCGTCTCTCCTGTGCAGCCTCCGGAT
TCACCTTTGAGGAGGAGGAGATGATTTGGGTCCGCCAGGCTCCAGGGAAGGGTCTAGAGTGGATCTCAGCTATTAGTGG
TAGTGGTGGTAGCACATACTACGCAGACTCCGTGAAGGGCCGGTTCACCATCTCCCGCGACAATTCCAATAACACGCTG
TATCTGCAAATGAACAGCCTGCGTGCCGAGGATACCGCGGTATATTACTGTGGGAGAGAGCCGTTTCGTTTTGACTACT
GGGGTCAGGGAACCCTGGTCACCGTCTCGAGC (SEQ ID NO: 844)

BMS3h-38-12
GAGGTGCGGCTGTTGGAGTCTGGGGAAGGCTTGGTACAGCCTGGGGGGTCCCTGCGTCTCTCCTGTGCAGCCTCCGGAT
TCACCTTTGAGGAGGAGGAGATGATTTGGGTCCGCCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCACGCGACAATTCCAAGAACACGCTG
TATCTGCAAATGAACAGCCTGCGTGCCGAGGATACCGCGGTATATTACTGTGGGAAAGAGCCGTTTCGTTTTGACTACT
GGGGTCAGGGAACCCTGGTCACCGTCTCGAGC (SEQ ID NO: 845)

BMS3h-38-13
GAGGTGCAGCAGTTGGAGTCTGGGGGAGGCCTGGTACAGCCTGGGGGGTCCCTGCGTCTCTCCTGTGCAGCCTCCGGAT
TCACCTTTGAGGAGGAGGAGATGATTTGGGTCCGCCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTTTGACTACT
GGGGTCAGGGAACCCTGGTCACCGTCTCGAGC (SEQ ID NO: 846)

BMS3h-38-201
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTCTACTACGACTACT
GGGGTCAGGGAACCCTGGTCACCGTCTCGAGC (SEQ ID NO: 847)

BMS3h-38-202
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTCTACTTCGACTACT
GGGGTCAGGGAACCCTGGTCACCGTCTCGAGC (SEQ ID NO: 848)

BMS3h-38-203
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGAAGGAGATGATTTGGGTCCGTCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTCTTCTACGACTACT
GGGGTCAGGGAACCCTGGTCACCGTCTCGAGC (SEQ ID NO: 849)

BMS3h-38-204
GAGGTGCAGCTGTTGGCGTCTGGGGGAGGCTTGGTACAGCCTGGGGGGTCCCTGCGTCTCTCCTGCGCAGCCTCCGGAT
TCACCTTTCCCCAGGAGGAGATGATTTGGGTCCGTCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 850)

BMS3h-38-205
GAGGTGCAGCTGTTGGCGTCTGGGGGAGGCTTGGTACAGCCTGGGGGGTCCCTGCGTCTCTCCTGCGCAGCCTCCGGAT
TCACCTTTTTCGCGCCAGATGATTTGGGTCCGCCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 851)

TABLE 4-continued

Human Anti-CD40 Variable Domain Encoding Nucleotide Sequences

BMS3h-38-206
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTAG
GCCCGGTACGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 852)

BMS3h-38-207
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
GATGGGTTTCAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 853)

BMS3h-38-208
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
GTGGGGTCACAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 854)

BMS3h-38-209
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
CCTCGGTTGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 855)

BMS3h-38-210
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTCG
CTGGGGTGCCAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 856)

BMS3h-38-211
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGAGATGATTTGGGTCCGTCAGGCTCCAGGGAAGGGTCTAGAGTGGGTCTCAGCTATTAGTAG
GCAGGGTGGGAGCACATACTACGCAGACTCCGTGAAGGGCCGGTTCACCATCTCCCGTGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 857)

BMS3h-38-212
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTGT
GTCCGGTTGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 858)

BMS3h-38-213
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
GTGGGGTTGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 859)

BMS3h-38-214
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
GAACGGTCTGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 860)

BMS3h-38-215
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTGG
GCTGGGTTGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 861)

BMS3h-38-216
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
GTTGGGTTGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 862)

TABLE 4-continued

Human Anti-CD40 Variable Domain Encoding Nucleotide Sequences

BMS3h-38-217
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
CAGGGGTTACAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 863)

BMS3h-38-218
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTAG
GCACGGTTGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 864)

BMS3h-38-219
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAAGCATTAGCAG
GAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 865)

BMS3h-38-220
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
GATCGGTAACAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 866)

BMS3h-38-221
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTGG
GCACGGTTGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 867)

BMS3h-38-222
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTTCGAG
GTGGGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 868)

BMS3h-38-223
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTCATGTATGACTACT
GGGGTCAGGGAACCCTGGTCACCGTCTCGAGC (SEQ ID NO: 869)

BMS3h-38-224
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTCCCGTACGACTACT
GGGGTCAGGGAACCCTGGTCACCGTCTCGAGC (SEQ ID NO: 870)

BMS3h-38-225
GAGGTGCAGCTGTTGGCGTCTGGGGGAGGCTTGGTGCAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTGG
TAGTGGTGGTGGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 871)

BMS3h-38-226
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTGTACTATGACTACT
GGGGTCAGGGAACCCTGGTCACCGTCTCGAGC (SEQ ID NO: 872)

BMS3h-38-227
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGTCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCCATGTACTATGACTACT
GGGGTCAGGGAACCCTGGTCACCGTCTCGAGC (SEQ ID NO: 873)

TABLE 4-continued

Human Anti-CD40 Variable Domain Encoding Nucleotide Sequences

BMS3h-38-228
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTAG
GAACGGTTTCAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 874)

BMS3h-38-229
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
CACGGGTGGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 875)

BMS3h-38-230
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
GGAGGGTGGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 876)

BMS3h-38-231
GAGGTGCAGCTGTTGGCGTCTGGGGGAGGCTTGGTACAGCCTGGGGGGTCCCTGCGTCTCTCCTGCGCAGCCTCCGGGT
TCCCCTTTGAGGAGGAGGAGATGATTTGGGTCCGCCAGGCTCCAGGGAAGGGTCTAGAGTGGGTCTCAGCTATTAGTCG
GCAGGGTTGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 877)

BMS3h-38-232
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTAG
GGGCGGTGGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 878)

BMS3h-38-233
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
CACGGGTTACAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 879)

BMS3h-38-234
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTAG
GAACGGTAGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 880)

BMS3h-38-235
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTAG
GAACGGTTACAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 881)

BMS3h-38-236
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTAG
GAAGGGTAGCACACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 882)

BMS3h-38-237
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
GGGCGGTTGGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 883)

BMS3h-38-238
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTCG
CTCGGGTTACAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 884)

TABLE 4-continued

Human Anti-CD40 Variable Domain Encoding Nucleotide Sequences

BMS3h-38-239
GAGGTGCAGCTGTTGGCGTCTGGGGGAGGCTTGGTACAGCCTGGGGGGTCCCTGCGTCTCTCCTGCGCAGCCTCCGGAT
TCACCTTTGAGGAGGAGGAGATGATTTGGGTCCGCCAGGCTCCAGGGAAGGGTCTAGAGTGGGTCTCAGCTATTAGTAG
GAACGGTTATGAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 885)

BMS3h-38-240
GAGGTGCAGCTGTTGGAGTCTGGGGGAGGCTTGGTACAGCCTGGGGGGTCCCTGCGTCTCTCCTGCGCAGCCTCCGGAT
TCACCTTTGAGGAGGAGAGATGATTTGGGTCCGCCAGGCTCCAGGGAAGGGTCTAGAGTGGGTCTCAGCTATTAGTAG
GAACGGTTACAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 886)

BMS3h-41-1
GAGGTGCAGCTGTTGGAGTCTGGGGAAGGCTTGGTACAGCCTGGGGGGTCCCTGCGTCTCTCCTGTGCAGCCTCCGGAT
TCACCTTTACTGAGCATGAGATGATTTGGGTCCGCCAGGCTCCAGGGAAGGGTCTGGAGTGGGTCTCATCTATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTCCCGAGGACACCGCGGTATATTACTGTGCGAAAGAGCCGCTTAGGTTTGACTACT
GGGGCCAGGGAACCCTGGTCACCGTCTCGAGC (SEQ ID NO: 887)

BMS3h-41-2
GAGGTGCAGCTGTTGGAGTCTGGGGGAGGCTTGGTACAGCCTGGGGGGTCCCTGCGTCTCTCCTGTGCAGCCTCCGGAT
CCACCTTTACTGAGTATGAGATGATTTGGGTCCGCCAGGCTCCAGGGAAGGGTCTGGAGTGGATCTCATCTATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTTCTGTGCGAAAGAGCCGCTTAGGTTTGACTACA
GGGGTCAGGGAACCCTGGTCACCGTCTCGAGC (SEQ ID NO: 888)

BMS3h-41-3
GAGGTGCAGCTGTTGGAGCCTGGGGGAGGCTTGGTACAGCCTGGGGGGTCCCTGCGTCTCTCCTGTGCAGCCTCCGGAT
TCACCTTTACTGAGTATGAGATGATTTGGGTCCGCCAAGGCTCCAGGGAAGGGTATGGAGTGGGTCTCATCTATTTCGGG
TAATGGTGCTAATACATACTACGCAGACTCCGTGAAGGGCCGGTTCACCATCTCCCGCGACAATTCCAAGAACATGCTG
TATCTGCAAATGAACAGCCTGCGTGCCGAGGACACCGCGGTATATTACTGTGCGAAAGAGCCGCTTAGGTTTGGCTACT
GGGGTCAGGGTACCCTGGTCACCGTCTCGAGC (SEQ ID NO: 889)

BMS3h-41-4
GAGGTGCAGCTGTTGGATTCTGGGGGAGGCTTGGTACAGCCTGGGGGGTCACTGCGTCTCTCCTGTGCAGCCTCCGGAT
TCACCTTTACTGAGTATGAGATGATTTGGGTCCGCCAGGCTCCAGGGAAGGGTCTGGAGTGGGTCTCATCTATTTCGGG
TAATGGTGCTAATACATACTACGCAGACTCCGTGAAGGGCCGGTTCACCATCTCCCGCGACAATTCCAAGAACACGCTG
TATCTACAAATGAACAGCCTGCGTGCCGAGGACACCGCGGTATATTACTGTGCGAAAGAGCCGCTTAGGTTTGACTACT
GGGGTCGGGAACCCTGGTCACCGTCTCGAGC (SEQ ID NO: 890)

BMS3h-41-5
GAGGTGCAGCTGTTGGGGTCAGGGGGAGGCTTGGTACAGCCTGGGGGGTCCCTGCGTCTCTCCTGTGCAGCCTCCGGAT
TCACCTTTACTGAGTATGAGATGATTTGGGTCCGCCAGGCTCCAGGGAAGAGTCTGGAGTGGGTCTCATCTATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGCTTAGGTATGACGACT
GGGGTCAGGGAACCCTGGTCACCGTCTCGAGC (SEQ ID NO: 891)

BMS3h-41-6
GAGGTGCAGCCGTTGGAGTCTGGGGGAGGCTTGGTACAGCCTGGGGGGTCCCTGCGTCTCTCCTGTTCAGCCTCCGGAT
TCACCTTTAATGAGTATGAGATGATTTGGGTCCGCCAGGCTCCAGGGAAGGGTCTGGAGTGGGTCTCATCTATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGCTTAGGTTTGACTACT
GGGGTCAGGGAACCCTGGTCACCGTCTCGAGC (SEQ ID NO: 892)

BMS3h-41-7
GAGGTGCAGCTGTTGGAGTCTGGGGAAGGCTTGGTACAGCCTGGGGGGTCCCTGCGTCTCTCCTGTGCAGCCTCCGGAT
TCACCTTTGCTGAGTATGAGATGATTTGGGTCCGCCAGGCTCCAGGGAAAGGTCTGGAGTGGGTCTCATCTATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGCTTAGGTTTGACTACT
GGGGTCAGGGAACCCTGGTCACCGTCTCGAGC (SEQ ID NO: 893)

BMS3h-41-8
GAGGTGCAGCTGTTGGACCCTGGGGGAGGCTTGGTACAGCCTGGGGGGTCCCTGCGTCTCTCCTGTGCAGCCTCCGGAT
TCACCTTTACTGAGTCTGAGATGATTTGGGTCCGCCAGGCTCCAGGGAAGGGTCTGGAGTGGGTCTCATCTATTTCGGG
AAATGGTGCTAATACATACTACGCGGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGCTTAGGTTTGACTACT
GGGGTCAGGGAACCCTGGTCACCGTCTCGAGC (SEQ ID NO: 894)

BMS3h-41-9
GAGGTGCAGCTGTTGGAGCCTGGGGGAGGCTTGGTACAGCCTGGGGGGTCCCTGCGTCTCTCCTGTGCAGCCTCCGGAT
TCACCTTTACTGAGTATGAGATGATTTGGGTCCGCAAGGCTCCAGGGAAGGGTATGAGTGGGTCTCATCTATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTCCCGAGGACACCGCGGTATATTACTGTGCGAAAGAGCCGCTTAGGTTTGACGACT
GGGGTCAGGGAACCCTGGTCACCGTCTCGAGC (SEQ ID NO: 895)

TABLE 4-continued

Human Anti-CD40 Variable Domain Encoding Nucleotide Sequences

BMS3h-41-10
GAGGTGCAGCTGTTGGAGTCTGGGGTAGGCTTGGTACAGCCTGGGGGGTCCCTGCGTCTCTCCTGTGCAGCCTCCGGAT
TCACCTTTACTGAGTATGAGATGATTTGGGTCCGCAAGGCCCCAGGGAAGGGTCTGGAGTGGGTCTCATCTATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAACCGCTTAGGTTTGACAACT
GGGGTCAGGGAACCCTGGTCACCGTCTCGAGC (SEQ ID NO: 896)

BMS3h-41-11
GAGGTGCAGTTGTTGGAGTCTCGGGGAGGCTTGGTACAGCCTGGGGGTCCCTGCGTCTCTCCTGTGCAGCCTCCGGAT
TCACCTTTACTGAGCATGAGATGATTTGGGTCCGCCAGGCTCCAGGGAAGGGTCTGGAGTGGGTCTCATCTATTTCGGG
TAATGGTGCTAATACATACTACGCAGACTCCGTGAAGGGCCGGTTCTCCGTCTCCCGCGACAATTCCAAGAACACGCTG
TATCTGCAAATGAACAGCCTGCGTGCCGAGGACACCGCGGTATATTACTGTGCGAAAGAGCCGCTTAGGTTTGACTACT
GGGGTCAGGGAACCCTGGTCACCGTCTCGAGC (SEQ ID NO: 897)

BMS3h-41-12
GAGGTGCAGCCGTTGGAGTCTGGGGGAGGCTTGGTACAGCCTGGGGGTCCCTGCGTCTCTCCTGTGCTGCCTCCGGAT
TCACCTTTACTGAGTATGAGATGATTTGGGTCCGCCAGGCTCCAGGGAAGGGTCTGGAGTGGGTCTCATCTATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGCTTAGGTTTGACTACT
GGGGTCAGGGAACCCTGGTCACCGTCTCGAGC (SEQ ID NO: 898)

BMS3h-41-13
GAGGTGCAGCTGTTGGAGTCTGCGGGAGGCTTGGTACAGCCTGGGGGGTCCCTGCGTCTCTCCTGTGCAGCCTCCGGAT
TCACCTTTGCTGAGTATGAGATGATTTGGGTCCGCCAGGCTCCAGGGAAGGGTCTGGAGTGGGTCTCATCAATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGCTTAGGTTTGACTACT
GGGGTCAGGGAGCCCTGGTCACCGTCTCGAGC (SEQ ID NO: 899)

BMS3h-41-14
GAGGtGCAGCtGTTGGAGCCTGGGGGAGGCTTGGTACAGCCTGGGGGGTCGCTGCGTCTCTCCTGTGCAGCCTCCGGAT
TCACCTTTACTGAGTATGAGATGATTTGGGTCCGCCAGGCTCCAGGGAAGGGTCTGGAGTGGGTCTCATCTATTTCGGG
TAATGGTGCTAATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGCTTAGGTTTGACAACT
GGGGTCAGGGAACCCTGGTCACCGTCTCGAGC (SEQ ID NO: 900)

BMS3h-43-1
GAGGTGCAGCTGTTGGAGTCTGGGGGAGGCTTGGTACAGCCTGGGGGGTCTCTGCGTCTCTCCTGTACAGCCTCCGGAT
TCACCTTTAATATGTATGAGATGTCGTGGGTCCGCCAGGCTCCAGGGAAGGGTCTAGAGTGGGTCTCAGGTATTAGTAG
ACGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGATTTGA
GGTATGCGCGTTTTGACTACTCGGGTCAGGGAACCCTGGTCACCGTCTCGAGC (SEQ ID NO: 901)

BMS3h-43-2
GAGGTGCAGCTGTTGGAGTCTGGGGGAGGCTTGGTACAGCCTGGGGGGTCCCTGCGTCTCTCCTGTACAGCCTCCGGAT
GAGGAGCAGCTGTTGGAGTCTGGGGGAGGCTTGGTACAGCCTGGGGGGTCCCTGCGTCTCTCCTGTACAGCCTCCGGAT
TCACCTTTAATATGTATGAGATGTCGTGGGTCCGCCAGGCTCCAGGGAAGGGTCTAGAGTGGGTCTCAGGTATTAGTAG
ACGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGCTACGA
GGTATGCGCGTTTTGACTACTGGGGTCAGGGAACCCTGGTCACCGTCTCGAGC (SEQ ID NO: 902)

BMS3h-43-3
GAGGTGCAGCTGTTGGAGTCTGGGGGAGGCTTGGTACAGCCTGGGGGGTCCCTGCGTCTCTCCTGTACAGCCTCCGGAT
TCACCTTTAATATGTATGAGATGTCGTGGGTCCGCCAGGCTCCAGGGAAGGGTCTAGAGTGGGTCTCAGGTATTAGTAG
GCGTGGTTTTACTACATACTACGCAGACTCCGTGAAGGGCCGGTTCACCATCTCCCGCGACAATTTCAAGAACACGCTG
TATCTGCAAATGAACAGCCTGCGTGCCGAGGATACCGCGGTATATTACTGTGCGAAAGAGCCGATTACGTATGATATGA
GGTATGCGCGTTTTGACTACGGGGGTCAGGGAACCCTGGTCACCGTCTCGAGC (SEQ ID NO: 903)

BMS3h-43-4
GAGGTGCAGCTGTTGGAGTCTGGGGGAGGCTTGGTACAGCCTGGGGGGTCCCTGCGTCTCTCCTGTACAGCCTCCGGAT
TCACCTTTAATATGTATGAGATGTCGTGGGTCCGCCAGGCTCCAGGGAAGGGTCTAGAGTGGGTCTCAGGTATTAGTAG
GCGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGATATGA
GGTATGCGCGTTTTGACAACTGGGGTCAGGGAACCCTGGTCACCGTCTCGAAC (SEQ ID NO: 904)

BMS3h-43-5
GAGGTGCAGCTGTTGGAGTCTGGGGGAGGCTTGGTACAGCCTGGGGGGTCCCTGCGTCTCTCCTGTACAGCCTCCGGAT
TCACCTTTAATACGTATGAGATGTCGTGGGTCCGCCAGGCTCCAGGGAAGGGTCTAGAGTGGGTCTCAGGTATTGGTAG
GCGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGATTTGA
GGTATGCGCGTTTTGACTACTCGGGTCAGGGAACCCTGGTCACCGTCTCGAGC (SEQ ID NO: 905)

BMS3h-43-6
GAGGTGCAGCTGATGGAGTCAGGGGGAGGCTTGGTACAGCCTGGGGGGTCCCTGCGTCTCTCCTGTACAGCCTCCGGAT
TCTCCTTTAATATGTATGAGATGTCGTGGGTCCGCCAGGCTCCAGGGAAAGGTCTAGAGTGGGTCTCAGGTATTAGTAG
GCGTGGTTATACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGATATGA
GGTATGCGCGTTTTGACTACTGGGGTCGGGAACCCTGGTCACCGTCTCGAGC (SEQ ID NO: 906)

TABLE 4-continued

Human Anti-CD40 Variable Domain Encoding Nucleotide Sequences

BMS3h-43-7
GAGGTGCAGCTGTTGGAGTCTGGGGGAGGCTTGGTGCAGCCTGGGGGGTCCCTGCGTCTCTCCTGTACAGCCTCCGGAT
TCGCCTTTAATATGTATGAGATGTCGTGGGTCCGCCAGGCTCCAGGGAAGGGACTAGAGTGGGTCTCAGGTATTAGTAG
GCATGGTTTTACTACGTACTACGCAGACTCCGTGAAGGGCCGGTTCACCGTCTCCCGCGACAATTCCAAGAACACGCTG
TATCTGCAAATGAACAGCCTGCGTGCCGAGGATACCGCGGTATATTACTGTGCGAAAGAGCCGATTACGTATGATATGC
GGTATGCGCGTTCTGACTACTGGGGTCAGGGAACCCTGGTCACCGTCTCGAGC (SEQ ID NO: 907)

BMS3h-43-8
GAGGTGCAGCTGTTGGAGTCTGGGGGAGGCTTGGTACAGCCTGGGGGGTCCCTGCGTCTCTCCTGTACAGCCTCCGGAT
TCACCTTTAATATGTATGAGATGTCGTGGGTCCGCCAGGCTCCAGGGAAGGGACTAGAGTGGGTCTCAGGTATTAGTAG
GCGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTTCTGTGCGAAAGAGCCGATTACGTATGATATGA
GGTATGCGCGTTCTGACTACTGGGGTCAGGGAACCCTGGTCACCGTCTCGAGC (SEQ ID NO: 908)

BMS3h-43-9
GAGGTGCAGCTGTTGGAGTCTGGGGGGGGCTTGGTTCAGCCTGGGGGGTCCCTGCGTCTCTCCTGTACAGCCTCCGGGT
TCACCTTTAATATGTATGAGATGTCGTGGGTCCGCCAGGCTCCAGGGAAGGGTCTAGAGTGGGTCTCAGGTATTAGTAG
GCGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATTCTATGA
GGTATGCGCGTTTTGACTACTCGGGTCTGGGAACCATGGTCACCGTCTCGAGC (SEQ ID NO: 909)

BMS3h-43-10
GAGGTGCAGCTGCTGGAGTCTGGGGGAGGCTTGGTACAGCCTGGGGGGTCCCTTCGTCTCTCCTGTACAGCCTCCGGAT
TCACCTTTAATATGTATGAGATGTCGTGGGTCCGCCAGGCTCCAGGGAAGGGTCTAGAGTGGGTCTCAGGTATTAGTAG
GCGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGATATGA
GGTATGCGCGTTTTGACTACAGTGGTCAGGGAACCCTGGTCACCGTCTCGAGC (SEQ ID NO: 910)

BMS3h-43-11
GAGGTGCAGCTGTTGGAGTCTGGAGGAGGCTTGGTACAGCCTGGGGGGTCCCTGCGTCTCTCCTGTACAGCCTCCGGAT
TCACCTTTAATATGTATGAGATGTCGTGGGTCCGCAAGGCTCCAGGGAAGGGTCTAGAGTGGGTCTCAGGTATTAGTAG
GCATGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGATATGA
GGTATGCGCGTTTTGACTACTGGGGTCAGGGAACCCTGGTCACCGTCTCGAGC (SEQ ID NO: 911)

BMS3h-43-12
GAGGTGCAGCTGTTCGAGTCTGGGGGAGGCTTGGTACAGCCTGGGGGGTCCCTGCGTCTCTCCTGTACAGCCTCCGGAT
TCACCTTTAATATGTATGAGATGTCGTGGGTCCGCCAGGCTCCAGGGAAGGGTCTAGAGTGGGTCTCAGGTATTAGTAG
GCGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAGGAGCCGATTACGTATGATATGA
GGTATGCGCGTTTTGACTACTGGGGTCGGGAACCCTGGTCACCGTCTCGAGC (SEQ ID NO: 912)

BMS3h-43-13
GAGGTGCAGCTGTTGGAGTCTGGGGGAGGCTTGGTACAGCCTGGGGGATCCCTGCGTCTCTCCTGTACAGCCTCCGGTT
TCACCTTTAATATGTATGAGATGTCGTGGGTCCGCCAGGCTCCAGGGAAGGGTCTAGAGTGGGTCTCAGGTATTAGTAG
GCGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGATATGA
GGTATGCGCGTTTTGACTACTGGGGTCGGGAACCCTGGTCACCGTCTCGAGC (SEQ ID NO: 913)

BMS3h-43-14
GAGGTGCAGCTGTTGGAGTCTGGGGGAGGCTCGGTACAGCCTGGGGGGTCCCTGCGTCTCTCCTGTACAGCCTCCGGAT
TCTCCTTTAATATGTATGAGATGTCGTGGGTCCGCCAGGCTCCAGGGAAGGGTCTAGAGTGGGTCTCAGGTATTAGTAG
GCGTGGTTTTACTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGAGCCGATTACGTATGATATGA
GGTATGCGCGTTTTGACTACTGGGGTCAGGGAACCCTGGTCACCGTCTCGGGC (SEQ ID NO: 914)

BMS3h-43-15
GAGGTGCAGCTGTTGGAGTCTGGGGGAGGCTTGGTACAACCTGGGGGGTCCCTGCGTCTCTCCTGTACAGCCTCCGGAT
TCACCTTTAATATGTATGAGATGTCGTGGGTCCGCAAGGCTCCAGGGAAGGGTCTAGAGTGGGTCTCAGGTATTAGTAG
GCGTGGTTTTACTACATACTACGCAGACTCCGTGAAGGGCCGGTTCACCATCTCCCGTGACAATTCCAAGAACACGCTG
TATCTGCAAATGAACAGCCTGCGTGCCGAGGATACCGCGGTATATTACTGTGCGAAAGAGCCGATTACGTATGATATGA
GGTATGCGCGTTTTGACTACTGGGGTCAGGGAACCCTGGTCACCGTCTCGAGC (SEQ ID NO: 915)

BMS3h-56-1
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 916)

BMS3h-56-2
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 917)

TABLE 4-continued

Human Anti-CD40 Variable Domain Encoding Nucleotide Sequences

BMS3h-56-3
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCAGAGGATACCGCGGTATATTACTGTACGAAACTTCCGTTTATTTTGAATACT
GGGGTCAGGGAACCCTGGTCACCGTCTCGAGC (SEQ ID NO: 918)

BMS3h-56-4
GAGGTGCAGCTGTTGGAGTCCGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTATGTTTGACGACC
GGGGTCAGGGAACCCTGGTCACCGTCTCGAGC (SEQ ID NO: 919)

BMS3h-56-5
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 920)

BMS3h-56-6
GAGGTGCAGCTGTTGGAGTCTGGGGGAGGCTTGGTACAGCCTGGGGGGTCCCTGCGTCTCTCCTGTGCAGCCTCCGGAT
TCTCCTTTCGGGATTATGAGATGTGGTGGTACCGCCAGGCTCCAGGGAAGGGTCTAGAGCGGGTCTCAGCTATTAATCC
GCAGGGTACGCGTACATATTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTATTTTGACAACC
GGGGTCAGGGAACCCTGGTCACCGTCTCGAGC (SEQ ID NO: 921)

BMS3h-56-7
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCTCGGTATATCACTGTGCGAAACCTCCGTTTATTTTTGGCGACT
GGGGTCCGGGAACCCTGGTCACCGTCTCGAGC (SEQ ID NO: 922)

BMS3h-56-8
GAGGTGCAGCTGTTGGAGTCTGGGGGAGGCTTGGTACAGCCTGGGGGTCCCGGCGTCTCTCCTGTGCAGCCTCCGGAT
TCACCTTTCGGGATTATGAGATGTGGTGGGTCCGCCAGGCTCCGGGGAAGGGTCTAGAGCGGGTCTCAGCTATTAATCC
GCAGGGTACGCGTACATACTACGCAGACTCCGTGAAGGGCCGGTTCACGATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 923)

BMS3h-56-9
GAGGTGCAGCTGTTGGAGTCTGGGGGAGGCTTGGTACAGCCTGGGGGGTCCCTGCGTCTATCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACTGCGGTATATTACTGTGCGAAACTTCCGTTTATGTTTGACGACC
GGGGTCAGGGAACCCTGGTCACCGTCTCGAGC (SEQ ID NO: 924)

BMS3h-56-10
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGTTCTAGAGCGGGTCTCAGCTATTAATCC
GCAGGGTACGCGTACATACTACGCAGACTCCGTGAAGGGCCGGTTCACCATCTCCCGCGACAATTCCAAGAACATGCTG
TATCTGCAAATGAACAGCCTGCGTGCCGAGGATACTGCGGTATATTACTGTGCGAAACTTCCGTTTATGTTTGACGACC
GGGGTCAGGGAACCCTGGTCACCGTCTCGAGC (SEQ ID NO: 925)

BMS3h-56-11
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGAGCCGAGGATACTGCGGTATATTACTGTGCGAAACTTCCGTTTATGTTTGACGACC
GGGGTCAGGGAACCCTGGTCACCGTCTCGAGC (SEQ ID NO: 926)

BMS3h-56-12
GAGGTGCAGCTGTTGGAGTCTGGGGGAGGCTTGATACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTTTGAAACTTCCGTTTATTTTCGACTACT
GGGGTCAGGGAACCCTGGTCACCGTCTCGAGC (SEQ ID NO: 927)

BMS3h-56-13
GAGGTGCAGCTGTTGGAGTCTGGGGGAGGCTTGGTACAGCCTGGGGGGTCCCTGCGTCTATCCTGTGCAGCCTCCGGAT
TCACCTTTCGGGATTATGAGATGTGGTGGGTCCGCCAGGCTCCAGGGAAGGGTCTAGAGCGGGTCTCAGCTATTAACCC
GCAGGGTACGCGTACATACTATGCAGACTCCGTGAAGGGCCGGTTCACCATCTCCCGCGACAATTCCAAGAACACGCTG
TATCTGCAAATGAACAGCCTGCGTGCCGATGATACCGCGGTATATCACTGTACGAAACTTCCGTTTATTTTGACTACT
GGGGTCAGGGAACCCTGGTCACCGTCTCGAGC (SEQ ID NO: 928)

TABLE 4-continued

Human Anti-CD40 Variable Domain Encoding Nucleotide Sequences

BMS3h-56-14
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGATGGTTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTA
TATCTGCAAATGAACAGCCTGCGTGCCGAGGATACCGCGGTATATTACTGTGCGAAACTTCCGTTTTTTTTTGACTCCA
GGGGTCAGGGAACCCTGGTCACCGTCTCGAGC (SEQ ID NO: 929)

BMS3h-56-15
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCGGGCTCCAGGGAAGGGTCTAGAGCGGGTCTCAGCTATTAATCC
GCAGGGTACGCGTACATACTACGCAGACTCTGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 930)

BMS3h-56-16
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTACTTTTGAGGACT
GGGGTCAGGGAACCCTGGTCACCGTCTCGAGC (SEQ ID NO: 931)

BMS3h-56-17
GAGGTGCAGCTGTTGGAGTCTGGGGGAGGCTTGGTACAGCCTGGGGGGTCCCTGCGTCTCTCCTGTGCAGCCTCCGGAT
TCTCCTTTCGGGATTATGAGATGTGGTGGTACCGCCAGGCTCCAGGGAAGGGTCTAGAGCGGGTCTCAGCTATTAATCC
GCAGGGTACGCGTACATATTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTACTTTTGAGGACT
GGGGTCAGGGAACCCTGGTCACCGTCTCGAGC (SEQ ID NO: 932)

BMS3h-56-18
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTTCTAGAGCGGGTCTCAGCTATTAATCC
GCAGGGTACGCGTACATACTACGCAGACTCCGTGAAGGGCCGGTTCACCATCTCCCGCGACAATTCCAAGAACATGCTG
TATCTGCAAATGAACAGCCTGCGTGCCGAGGACACCGCGGTATATTACTGTGCGAAACTTCCGTTTACTTTTGAGGACT
GGGGTCAGGGAACCCTGGTCACCGTCTCGAGC (SEQ ID NO: 933)

BMS3h-56-19
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATCACTGTGCGAAACTTCCGTTTACTTTTGAGGACT
GGGGTCAGGGAACCCTGGTCACCGTCTCGAGC (SEQ ID NO: 934)

BMS3h-56-20
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTACGAAACTTCCGTTTACTTTTGAGGACT
GGGGTCAGGGAACCCTGGTCACCGTCTCGAGC (SEQ ID NO: 935)

BMS3h-56-21
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTTTGAAACTTCCGTTTACTTTTGAGGACT
GGGGTCAGGGAACCCTGGTCACCGTCTCGAGC (SEQ ID NO: 936)

BMS3h-56-22
GAGGTGCAGCTGTTGGAGTCTGGGGGAGGCTTGGTACAGCCTGGGGGGTCCCTGCGTCTATCCTGTGCAGCCTCCGGAT
TCACCTTTCGGGATTATGAGATGTGGTGGGTCCGCCAGGCTCCAGGGAAGGGTCTAGAGCGGGTCTCAGCTATTAACCC
GCAGGGTACGCGTACATACTATGCAGACTCCGTGAAGGGCCGGTTCACCATCTCCCGCGACAATTCCAAGAACACGCTG
TATCTGCAAATGAACAGCCTGCGTGCCGATGATACCGCGGTATATCACTGTACGAAACTTCCGTTTATTTTTGAATACT
GGGGTCAGGGAACCCTGGTCACCGTCTCGAGC (SEQ ID NO: 937)

BMS3h-56-23
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGACACCGCGGTATATTACTGTGCGAAAGAACCTTATAGTTTTGACTCCT
GGGGTCAGGGAACCCTGGTCACCGTCTCGAGC (SEQ ID NO: 938)

BMS3h-56-24
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACCGCGGTATATCACTGTGCGAAAGAACCTTATAGTTATGACTACT
GGGGTCAGGGAACCCTGGTCACCGTCTCGAGC (SEQ ID NO: 939)

TABLE 4-continued

Human Anti-CD40 Variable Domain Encoding Nucleotide Sequences

BMS3h-56-25
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCGGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 940)

BMS3h-56-26
GAGGTGCAGCTGTTGGAGTCTGGGGGAGGCTTGGTACAGCCTGGGGGGTCCCTGCGTCTATCCTGTGCAGCCTCCGGAT
TCACCTTTCGGGATTATGAGATGTGGTGGGTCCGCCGGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACTGCGGTATATTACTGTGCGAAACTTCCGTTTATGTTTGACGACC
GGGGTCAGGGAACCCTGGTCACCGTCTCGAGC (SEQ ID NO: 941)

BMS3h-56-27
GAGGTGCAGCTGTTGGAGTCTGGGGGAGGCTTGGTACAGCCTGGGGGGTCCCTGCGTCTATCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACTGCGGTATATTACTGTGCGAAACTTCCGTTTATGTTTGACGACT
GGGGTCAGGGAACCCTGGTCACCGTCTCGAGC (SEQ ID NO: 942)

BMS3h-56-28
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGTTGTGGTGGGTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 943)

BMS3h-56-29
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGTTGTGGTGGGTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACTGCGGTATATTACTGTGCGAAACTTCCGTTTATGTTTGACGACC
GGGGTCAGGGAACCCTGGTCACCGTCTCGAGC (SEQ ID NO: 944)

BMS3h-56-30
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGTTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 945)

BMS3h-56-31
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGTTCCGCCAGGCTCCAGGGAAGGGTCTAGAGCGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACTGCGGTATATTACTGTGCGAAACTTCCGTTTATGTTTGACGACC
GGGGTCAGGGAACCCTGGTCACCGTCTCGAGC (SEQ ID NO: 946)

BMS3h-56-32
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGTGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 947)

BMS3h-56-33
GAGGTGCAGCTGTTGGAGTCTGGGGGAGGCTTGGTACAGCCTGGGGGGTCCCTGCGTCTATCCTGTGCAGCCTCCGGAT
TCACCTTTCGGGATTATGAGATGTGGTGGGTCCGCCAGGCTCCAGGGAAGGGTCTAGAGTGGGTCTCAGCTATTAATCC
GCAGGGTACGCGTACATACTACGCAGACTCCGTGATGGGCCGGTTCACCATCTCCCGCGACAATTCCAAGAACACGCTG
TATCTGCAAATGAACAGCCTGCGTGCCGAGGATACTGCGGTATATTACTGTGCGAAACTTCCGTTTATGTTTGACGACC
GGGGTCAGGGAACCCTGGTCACCGTCTCGAGC (SEQ ID NO: 948)

BMS3h-56-202
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGACCTACTTTTCCGACC
GGGGTCAGGGAACCCTGGTCACCGTCTCGAGC (SEQ ID NO: 949)

BMS3h-56-203
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTCTTTGAGGAGT
GGGGTCAGGGAACCCTGGTCACCGTCTCGAGC (SEQ ID NO: 950)

TABLE 4-continued

Human Anti-CD40 Variable Domain Encoding Nucleotide Sequences

BMS3h-56-204
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGACGTACTTTAAGGACT
GGGGTCAGGGAACCCTGGTCACCGTCTCGAGC (SEQ ID NO: 951)

BMS3h-56-205
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTACTTTTCCGAGT
GGGGTCAGGGAACCCTGGTCACCGTCTCGAGC (SEQ ID NO: 952)

BMS3h-56-206
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATCACTGTGCGAAACTTCCGATGTTCTTTGAGGACT
GGGGTCAGGGAACCCTGGTCACCGTCTCGAAC (SEQ ID NO: 953)

BMS3h-56-207
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTCCGTTTTCGGAGT
GGGGTCAGGGAACCCTGGTCACCGTCTCGAGC (SEQ ID NO: 954)

BMS3h-56-208
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGGACAGCCTGCGTGCCGAGGACACCGCGGTATATTACTGTGCGAAACTTCCGTTTTACTTTTCCGAGT
GGGGTCAGGGAACCCTGGTCACCGTCTCGAGC (SEQ ID NO: 955)

BMS3h-56-209
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTACGGTAACCTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 956)

BMS3h-56-210
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCCCGGTACCTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACC
GGGGTCAGGGAACCCTGGTCACCGTCTCGAGC (SEQ ID NO: 957)

BMS3h-56-211
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGCTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 958)

BMS3h-56-212
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GATGGGTGGGTTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 959)

BMS3h-56-213
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTTCGCACACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 960)

BMS3h-56-214
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTCCGGTGGGCTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACC
GGGGTCAGGGAACCCTGGTCACCGTCTCGAGC (SEQ ID NO: 961)

TABLE 4-continued

Human Anti-CD40 Variable Domain Encoding Nucleotide Sequences

BMS3h-56-215
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCACGGTTCGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 962)

BMS3h-56-216
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GGCCGGTCGGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 963)

BMS3h-56-217
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTAGCTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 964)

BMS3h-56-218
GAGGTGCAGCTGTTGGAGTCTGGGGGAGGCTTGGTACAGCCTGGGGGGTCCCTGCGTCTCTCCTGTGCAGCCTCCGGAT
TCACCTTTCCCGACTACGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATCACTGTGCGAAACTTCCGTTTACTTTTGACGACT
GGGGTCAGGGAACCCTGGTCACCGTCTCGAGC (SEQ ID NO: 965)

BMS3h-56-219
GAGGTGCAGCTGTTGGAGTCTGGGGGAGGCTTGGTACAGCCTGGGGGGTCCCTGCGTCTCTCCTGTGCAGACTCCGGAT
TCACCTTTCCGCCCGTGGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 966)

BMS3h-56-220
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTACGGTGGGCTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 967)

BMS3h-56-221
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTAACCACACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 968)

BMS3h-56-222
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCACGGTGGCTACACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 969)

BMS3h-56-223
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAGGGGTCTAGAGCGGGTCTCAGCTATTAATCC
GCCCGGTATGCTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 970)

BMS3h-56-224
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTCAGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 971)

BMS3h-56-225
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGCTACACATACTACGCAGACTCCGTGAAGGGCCGATTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 972)

TABLE 4-continued

Human Anti-CD40 Variable Domain Encoding Nucleotide Sequences

BMS3h-56-226
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTCGGGTGGGCTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 973)

BMS3h-56-227
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTCGGGTGGGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 974)

BMS3h-56-228
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTCGGGTACGCTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 975)

BMS3h-56-229
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTACGGTTCGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 976)

BMS3h-56-230
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGCTACACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 977)

BMS3h-56-231
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTGGGCTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 978)

BMS3h-56-232
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTTCCCACACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 979)

BMS3h-56-233
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTACCTTGACATACTACGCAGACTCCGTGAAGGGCCGGTTCACCATCTCCCGCGACAATTCCAGGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 980)

BMS3h-56-234
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GAACGGTCGGCTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGCGGACT
GGGGTCAGGGAACCCTGGTCACCGTCTCGAGC (SEQ ID NO: 981)

BMS3h-56-235
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTCAGCTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 982)

BMS3h-56-236
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCACGGTGGCCTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 983)

TABLE 4-continued

Human Anti-CD40 Variable Domain Encoding Nucleotide Sequences

BMS3h-56-237
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTGGAGCGGGTCTCAGCTATTAATCC
GGCGGGTATGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 984)

BMS3h-56-238
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCACGGTACCTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 985)

BMS3h-56-239
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTTCGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 986)

BMS3h-56-240
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTACGGTGGCCTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 987)

BMS3h-56-241
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTACGAGATGTGGTGGGTCCGCCAGGCTCCAGGGAAGGGTCTAGAGCGGGTCTCAGCTATTAATCC
GGCCGGTTTCTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 988)

BMS3h-56-242
GAGGTGCAGCTGTTGGAGTCTGGGGGAGGCTTGGTACGGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTGGAGCGGGTCTCAGCTATTAATCC
GTACGGTGGCCTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 989)

BMS3h-56-243
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 990)

BMS3h-56-244
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 991)

BMS3h-56-245
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTACGGTGGGCTGACATACTACGCAGACTCCGTGAAGGGCCGGTTCACCATCTCCCGCGACAATTCCAAGAACACGCTG
TATCTGCAAATGGACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 992)

BMS3h-56-246
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTACGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 993)

BMS3h-56-247
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGCTACACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCGGGGAACCCTGGTCACCGTCTCGAGC (SEQ ID NO: 994)

TABLE 4-continued

Human Anti-CD40 Variable Domain Encoding Nucleotide Sequences

BMS3h-56-248
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTACGGTAACCTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 995)

BMS3h-56-249
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCACGGTGGGTTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 996)

BMS3h-56-250
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GGCCGGTTTCTACACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 997)

BMS3h-56-251
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GGCGGGTGGCCTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGACGACT
GGGGTCAGGGAACCCTGGTCACCGTCTCGAGC (SEQ ID NO: 998)

BMS3h-56-252
GAGGTGCAGCTGTTGGAGTCTGGGGGAGGCTTGGTACAGCCTGGGGGGTCCCTGCGTCTCTCCTGTGCAGCCTCCGGAT
TCGCCTTTCGGGATTATGAGATGTGGTGGGTCCGCCAGGCTCCAGGGAAGGGTCTAGAGCGGGTCTCAGCTATTAATCC
GCACGGTTCCCTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTACTTTTGAGGACT
GGGGTCAGGGAACCCTGGTCACCGTCTCGAGC (SEQ ID NO: 999)

BMS3h-56-253
GAGGTGCAGCTGTTGGAGTCTGGGGGAGGCTTGGTACAGCCTGGGGGGTCCCTGCGTCTCTCCTGTGCAGCCTCCGGAT
TCACCTTTCGTGATTATGAGATGTGGTGGGTCCGCCAGGCTCCAGGGAAGGGTCTAGAGCGGGTCTCAGCTATTAATCC
GGCCGGTGGGTACACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATCACTGTGCGAAACTTCCGTTTACTTTTGAGGACT
GGGGTCAGGGAACCCTGGTCACCGTCTCGAGC (SEQ ID NO: 1000)

BMS3h-56-254
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTGGTTTACGGAGT
GGGGTCAGGGAACCCTGGTCACCGTCTCGAGC (SEQ ID NO: 1001)

BMS3h-56-255
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTCATGTTTTCCGACC
GGGGTCAGGGAACCCTGGTCACCGTCTCGAGC (SEQ ID NO: 1002)

BMS3h-56-256
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTGTTTCAGGAGT
GGGGTCAGGGAACCCTGGTCACCGTCTCGAGC (SEQ ID NO: 1003)

BMS3h-56-257
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGACGCGGTTTGAGGACT
GGGGTCAGGGAACCCTGGTCACCGTCTCGAGC (SEQ ID NO: 1004)

BMS3h-56-258
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTACTTTCACGAGT
GGGGTCAGGGAACCCTGGTCACCGTCTCGAGC (SEQ ID NO: 1005)

TABLE 4-continued

Human Anti-CD40 Variable Domain Encoding Nucleotide Sequences

BMS3h-56-259
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGGGAAAGAGCCGTTTCGTTATGACTACT
GGGGTCAGGGAACCCTGGTCACCGTCTCGAGC (SEQ ID NO: 1006)

BMS3h-56-260
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGACGTTCTTTAAGGACT
GGGGTCAGGGAACCCTGGTCACCGTCTCGAGC (SEQ ID NO: 1007)

BMS3h-56-261
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACACGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTTTCTTTCAGGAGT
GGGGTCAGGGAACCCTGGTCACCGTCTCGAGC (SEQ ID NO: 1008)

BMS3h-56-262
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGCAGTTGTTTCACGACC
GGGGTCAGGGAACCCTGGTCACCGTCTCGAGC (SEQ ID NO: 1009)

BMS3h-56-263
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGCAGCTCTTTGAGGACT
GGGGTCAGGGAACCCTGGTCACCGTCTCGAGC (SEQ ID NO: 1010)

BMS3h-56-264
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATCACTGTGCGAAACTTCCGTTTGGGTTTTCCGAGT
GGGGTCAGGGAACCCTGGTCACCGTCTCGAGC (SEQ ID NO: 1011)

BMS3h-56-265
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGCAGTTGTTTCAGGACT
GGGGTCAGGGAACCCTGGTCACCGTCTCGAGC (SEQ ID NO: 1012)

BMS3h-56-266
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTTCTTTCACGAGT
GGGGTCAGGGAACCCTGGTCACCGTCTCGAGC (SEQ ID NO: 1013)

BMS3h-56-267
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGCACTACTTTAAGGACT
GGGGTCAGGGAACCCTGGTCACCGTCTCGAGC (SEQ ID NO: 1014)

BMS3h-56-268
GAGGTGCAGCTGTTGGAGTCTGGGGGAGGCTTGGTACAGTCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTTACTTTGAGGAGT
GGGGTCAGGGAACCCTGGTCACCGTCTCGAGC (SEQ ID NO: 1015)

BMS3h-56-269
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTAGGTTTTCCGACC
GGGGTCAGGGAACCCTGGTCACCGTCTCGAGC (SEQ ID NO: 1016)

TABLE 4-continued

Human Anti-CD40 Variable Domain Encoding Nucleotide Sequences

BMS3h-56-270
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGACGCTGTTTCAGGACT
GGGGTCAGGGAACCCTGGTCACCGTCTCGAGC (SEQ ID NO: 1017)

BMS3h-56-271
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTACTTTTCCGAGT
GGGGTCAGGGAACCCTGGTCACCGTCTCGAAC (SEQ ID NO: 1018)

BMS3h-56-272
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTGGTTTCAGGAGT
GGGGTCAGGGAACCCTGGTCACCGTCTCGAGC (SEQ ID NO: 1019)

BMS3h-56-273
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTTCGTTGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTACTTTCAGGAGT
GGGGTCAGGGAACCCTGGTCACCGTCTCGAGC (SEQ ID NO: 1020)

BMS3h-56-274
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTTCGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATCACTGTGCGAAACTTCCGATGTTCTTTGAGGACT
GGGGTCAGGGAACCCTGGTCACCGTCTCGAAC (SEQ ID NO: 1021)

BMS3h-56-275
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTTCGTTGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTACTTTCACGAGT
GGGGTCAGGGAACCCTGGTCACCGTCTCGAGC (SEQ ID NO: 1022)

BMS3h-56-276
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTTCGTTGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTTCTTTCAGGAGT
GGGGTCAGGGAACCCTGGTCACCGTCTCGAGC (SEQ ID NO: 1023)

BMS3h-56-277
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTTCGTTGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTTCTTTCACGAGT
GGGGTCAGGGAACCCTGGTCACCGTCTCGAGC (SEQ ID NO: 1024)

BMS3h-56-278
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTTACTTTCAGGAGT
GGGGTCAGGGAACCCTGGTCACCGTCTCGAGC (SEQ ID NO: 1025)

BMS3h-56-279
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATCACTGTGCGAAACTTCCGATGTTCTTTGAGGACT
GGGGTCAGGGAACCCTGGTCACCGTCTCGAAC (SEQ ID NO: 1026)

BMS3h-56-280
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTCACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTACTTTCACGAGT
GGGGTCAGGGAACCCTGGTCACCGTCTCGAGC (SEQ ID NO: 1027)

TABLE 4-continued

Human Anti-CD40 Variable Domain Encoding Nucleotide Sequences

BMS3h-56-281
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTCACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTTCTTTCAGGAGT
GGGGTCAGGGAACCCTGGTCACCGTCTCGAGC (SEQ ID NO: 1028)

BMS3h-56-282
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTTTCTTTCACGAGT
GGGGTCAGGGAACCCTGGTCACCGTCTCGAGC (SEQ ID NO: 1029)

BMS3h-56-283
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTTACTTTCAGGAGT
GGGGTCAGGGAACCCTGGTCACCGTCTCGAGC (SEQ ID NO: 1030)

BMS3h-56-284
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATCACTGTGCGAAACTTCCGATGTTCTTTGAGGACT
GGGGTCAGGGAACCCTGGTCACCGTCTCGAAC (SEQ ID NO: 1031)

BMS3h-56-285
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTGACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAACTTCCGTTTTACTTTCACGAGT
GGGGTCAGGGAACCCTGGTCACCGTCTCGAGC (SEQ ID NO: 1032)

BMS3h-56-286
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTTTCTTTCAGGAGT
GGGGTCAGGGAACCCTGGTCACCGTCTCGAGC (SEQ ID NO: 1033)

BMS3h-56-287
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GTGGGGTGGGTTGACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAACTTCCGTTTTTCTTTCACGAGT
GGGGTCAGGGAACCCTGGTCACCGTCTCGAGC (SEQ ID NO: 1034)

BMS3h-56-288
GAGGTGCAGCTGTTGGAGTCTGGGGGAGGCTTGGTACAGCCTGGGGGGTCCCTGCGTCTCTCCTGTGCAGCCTCCGGAT
TCACCTTTCGGGATTATGAGATGTGGTGGGTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATCACTGTGCGAAACTTCCGATGTTCTTTGAGGACT
GGGGTCAGGGAACCCTGGTCACCGTCTCCAGC (SEQ ID NO: 1035)

BMS3h-106-1
GAGGTGCAGCTGTTGGAGACTGGGGGAGGCTTGGTACAGCCTGGGGGGTCCCTGCGTCTCTCCTGTGCAGCCTCCGGAT
TCACCTTTTCGACTTATCATATGCAGTGGGTCCGCCGGGCTCCAGGGAAGGGCCTGGAGTGGGTCTCAATGATTGATGC
GGATGGTCTTGGGACATACTACGCAGACCCCGTGAAGGGCCGGTTCACCATCTCCCGCGACAATTCCAAGAACACGCTG
TATCTGCAAATGAACAGCCTGCGTGCCAAGGACACCGCGGTATATTACTGTGCGAGACCGGGTCCGCAGTTTGGTCAGT
TTGACTACTTGGGTCAGGGAACCCTGGTCACCGTCTCGAGC (SEQ ID NO: 1036)

BMS3h-106-2
GAGGTGCAGCTGTTTGAGTCTGGGGGAGGCTTGGTACAGACTGGGGGGTCCCTGCGTCTCTCCTGTGCAGCCTCCGGAT
TCACCTTTTCGACTTATCATATGCAGTGGGTCCGCCAGGCTCCAGGGAAGGGTCTGGAGTGGGTCTCAATGATTGATGC
GGATGGTCTTGGGAAATACTACGCAGACCCCGTGAAGGGCCGGTTCACCATCTCCCGCGACAATTCCAAGAACACGCTG
TATCTGCAAATGAACAGCCTGCGTGCCGAGGACACCGCGGTATATTACTGTGTGAAACCGGGTCCGCAGTTTGGTCAGT
ATGACTACTGGGGTCAGGGAACCCTGGTCACCGTCTCGAGC (SEQ ID NO: 1037)

BMS3h-107-1
GAGGTGCAGCTGTTGGAGTCAGGGGGAGGCTTGGTACAGCCTGGGGGGTCCCTGCGGCTCTCCTGTTCAGCTTCCGGAT
TCACCTTTTCGGGTATGATATGCAGTGGGTCCGCCAGGCTCCAGGGAAGGGTCTAGAGTGGGTCTCAACGATTAGTGC
GTCGGGTGTTTATACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAATATCCTAATCGTTTTGCGCTTA
ATAGTTTTGACTACAGGGGTCGGGGAACCCTGGTCACCGTCTCGAGC (SEQ ID NO: 1038)

TABLE 4-continued

Human Anti-CD40 Variable Domain Encoding Nucleotide Sequences

BMS3h-107-2
GAGGTGCAGCTGTTGGAGTCTGGGGGAGGCTTGGTACAGCCTGGGGGGTCCCTGCGTCTCTCCTGTGCAGCTTCCGGAT
TCACCTTTTCGGGGTATGATATGCAGTGGGTCCGCCAGGCTCCAGGGAGGGGTCTAGAGTGGGTCTCAACGATTAGTGC
GTCGGGTGTTTATACATACTACACAGACTCCGTGAAGGGCCGGTTCACCACCTCCCGCGACAATTCCAAGAACACGCTG
TATCTGCAAATGAACAGCCTGCGTGCCGAGGACACCGCGGTATATTACTGTACGAAATATCCAAATCGTTTTGCGCGTA
ATAATTTTGACTACTGGGGTCAGGGAACCCTGGTCACCGTCTCGAGC (SEQ ID NO: 1039)

BMS3h-131-1
GACATCCTGATGACCCAGTCTCCATCCTCCCTGTCTGCATCTGTAGGAGACCGTGTCACCATCACTTGCCGGGCAAATA
GTTCTATTTTGTGGGCGTTAGCTTGGTACCAGCAGAAACCAGGGGAAGCCCCTAAGCTCCTGATCGAGAGTTCTTCCGG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCAGCCAAGGGACCAAGGTGGAAA
TCAAACGG (SEQ ID NO: 1040)

BMS3h-131-2
GACATCCAGATGACCCAGTCTCCATCCTCCCTGTCTGCATCTGTAGGAGACCGTGTCACCATCACTTGCCGGGCAGACA
GTTCTATTTTGTGGGCGTTAGCTTGGTACCAGCAGAAACCAGGGAAAGCCCCTAAGCTCCTGATCGAGAGTTCATCCGG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAAA
TCAAACGG (SEQ ID NO: 1041)

BMS3h-131-3
GACATCCAGATGACCGTGTCTCCATCCTCCCTGTCTGCATCTGTAGGAGACCGTGTCACCATCACTTGCCGGGCAGATA
GTTCTATTTTGTGGGCGTTAGCTTGGTACCAGCAGAAACCAGGGAAAGCCCCTAAGCTCCTGATCGAGAGTTCTTCCGG
ATTGCAAAGCGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAAA
TCAAACGG (SEQ ID NO: 1042)

BMS3h-131-4
GACATCCAGATGACCCAGTCTCCATCCTCCCTGTCTGCATCTGTAGGAGACCGTGTCACCATCACTTGCCGGGCAAATA
GTTCTATTTTGTGGGCGTTAGCTTGGTACCAGCAGAAACCAGGGAAAGCCCCTAAGCTCCTGATCGAGAGTTCTTCCGG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGACCAAGGGACCAAGGTGGAAA
TCAAACGG (SEQ ID NO: 1043)

BMS3h-131-5
GACATCCAGATGACCCAGTCTCCATCCTCCCTGTCTGCATCTGTAGGAGACCGTGTCACCATCACTTGCCGGGCAAATA
GTTCTATTTTGTGGGCGTTAGCTTGGTACCAGCAGAAACCAGGGAAAGCCCCTAAGCTCCTGATCGAGAGTTCTACCGG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAAA
TCAAACGG (SEQ ID NO: 1044)

BMS3h-131-6
GACATCCAGATGACCGTGTCTCCATCCTCCCTGTCTGCATCTGTAGGAGACCGTGTCACCATCACTTGCCGGGCAAATA
GTTCTATTTTGTGGGCGTTAGCTTGGTACCAGCAGAAACCAGGGAAAGCCCCTAAGCTCCTGATCGAGAGTTCTTCCGG
ATTGCAAAGCGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAAA
TCAAACGG (SEQ ID NO: 1045)

BMS3h-131-7
GACATCCAGATGACCCAGTCTCCATCCTCCCTGTCTGCATCTGTAGGAGACCGTGTCACCATCACTTGCCGGGCAGATA
GTTCTATTTTGTGGGCGTTAGCTTGGTACCAGCAGAAACCAGGGAAAGCCCCTAAGCTCCTGATCGAGAGTTCTTCCGG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGACCAAGGGACCAAGGTGGAAA
TCAAACGG (SEQ ID NO: 1046)

BMS3h-131-8
GACATCCAGATGACCCAGTCTCCATCCTCACTGTCTGCATCTGTAGGAGACCGTGTCACCATCACTTGCCGGGCAAATA
GTTCTATTTTGTGGGCGTTAGCTTGGTACCAGCAGAAACCAGGGAAAGCCCCTGAGCTCCTGATCGAGAGTTCTTCCGG
TCTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAAA
TCAAACGG (SEQ ID NO: 1047)

BMS3h-131-9
GACATCCAGATGACCCAGTCTCCATCCTCCCTGTCTGCATCTGTAGGAGACCGTGTCACCATCACTTGCCGGGCGAATA
GTTCTATATTGTGGGCGTTGGCTTGGTACCAGCAGAAACCAGGGAAAGCCCCTAAGCTCCTGATCGAGAGTTCTTCCGG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAAA
ACAAACGG (SEQ ID NO: 1048)

BMS3h-131-10
GACATCCAGATGACCCAGTCTCCATCCTCCCTGTCTGCATCTGTAGGAGACCGTGTCACCATCACTTGCCGGGCAAATA
GTTCTATTCTGTGGGCGTTAGCTTGGTACCAGCAGAAACCTGGGAAAGCCCCTAAGCTCCTGATCGAGAGTTCTTCCGG
TTTGCAAAGTGGGGTCCCATCACGTTTCAGTGGCAGTGGATCTGGGACAGATTTCACTCTCACCATCAGCAGTCTGCAA
CCCGAAGATTTTGCTACGTACTACTGTGTTCAGAATGCGGTTTGGCCTGGTACGTTCGGCCAAGGGACCAAGGTGGAAA
TCAAACGG (SEQ ID NO: 1049)

TABLE 4-continued

Human Anti-CD40 Variable Domain Encoding Nucleotide Sequences

BMS3h-131-11
GACATCCAGATGACCCAGTCTCCATCCTCCCTGTCTGCTTCTGTAGGAGACCGTGTCACCATCACTTGCCGGGCAAATA
GTTCTATTTTGTGGGCGTTAGCTTGGTACCAGCAGAAACCAGGGAAAGCCCCTAAGCTCCTGATCGAGAGTTCTTCCGG
TTTGCAAAGTGGGATCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAAA
TCAAACGG (SEQ ID NO: 1050)

BMS3h-131-12
GACATCCAGATGACCCAGTCTCCATCCTCCCTGTCTGCATCTGTTGGAGACCGTGTCACCATCACTTGCCGGGCAAATA
GTTCTATTTTGTGGGCGTTAGCTTGGTACCAGCAGAAACCAGGGAAAGCCCCTAAGCTCCTGATCGAGAGTTCTTCCGG
ATTGCAAAGCGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAAA
TCAAACGG (SEQ ID NO: 1051)

BMS3h-131-13
GACATCCTGTTGACCCAGTCTCCATCCTCCCTGTCTGCATCTGTAGGAGACCGTGTCACCATCACTTGCCGGGCAAATA
GTTCTATTTTGTGGGCGTTAGCTTGGTACCAGCAGAAACCAGGGAAAGCCCCTAAGCTCCTGATCGAGAGTTCTTCCGG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAAA
TCAAACGG (SEQ ID NO: 1052)

BMS3h-131-14
GACATCCAGATGACCCAGTCTCCATCCTCCCTGTCTGCATCTGTAGGAGACCGTGTCACCATCACTTGCCGGGCAAATA
GTTCTATTTTGTGGGCGTTAGCTTGGTACCAGCAGAAACCAGGGAAAGCCCCTAAGCTCCTGATCGAGAGTTCTTCCGG
TTTGCAAAGTGGGGTCCCATCACGTTTCAGTGGAAGTGGAACTGGGACAGATTTCACTCTCACCATCAGCGGTCTGCAA
CCTGAAGATTTTGCTACGTACTACTGTGTTCAGAATGCGGTTTGGCCTGGTACGTTCGACCAAGGGACCAAGGTGGAAA
TCAAACGG (SEQ ID NO: 1053)

BMS3h-131-15
GACATCCAGATGACCCAGTCTCCATCCTCCCTGTCTGCATCTGTAGGAGACCGTGTCACCATCCCTTGCCGGGCAAATA
GTTCTATTTTGTGGGCGTTAGCTTGGTACCAGCAGAAACCAGGGAAAGCCCCTAAGCTCCTGATCGAGAGTTCTTCCGG
TTTGCAAAGTGGGGTCCCATCACGTTTCAGTGGCAGTGCATCTGGGACAGATTTCACTCTCACCATCAGCAGTCTGCAA
CCTGAAGATTTTGCTACGTACTACTGTGTTCAGAATGCGGTTTGGCCTGGTACGTTCGGCCAAGGGACCAAGGTGGAGA
TCAAACGG (SEQ ID NO: 1054)

BMS3h-193-1
GACATCCAGATGGCCCAGTCTCCATCCTCCCTGTCTGCATCTGTAGGAGACCGTGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGCGAGTCCACCTTTGACGTTAGGCCAAGGGACCAAAGTGGAAA
TCAAACGG (SEQ ID NO: 1055)

BMS3h-193-2
GACATCCAGATGACCCAGTCTCCATCCTCCCTGTCTGCATCTGTAGGAGACAGTGTCACCATCACTTGCCGGGCAAGTC
AGACGATTGAGCGTCGTTTAAATTGGTATCAGCAGAAACCAGGGAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGCCATCAGTATGCGAGTCCACCTTTGACGTTCGGCCAAGGGACCAATGTGGAAA
TCAAACGG (SEQ ID NO: 1056)

BMS3h-193-3
GACATCCAGATGACCCAGTCTCCATCCTCCCTATCTGCATCTGTAGGAGACCGTGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTGCGTACTACTGTCATCAGTACGAGAGTCCACCTTTGACGTTTGGCCAAGGGACCAAAGTGGAAA
TCAAACGG (SEQ ID NO: 1057)

BMS3h-193-4
GACATCCAGATGACCCAGTCTCCATCCTCCCTGTCTGCATCTGTAGGAGACCGTGTCACCATCACTTGCCGGGCAAGTC
GGACGATTGAGCGTCGTTTAAATTGGTATCAGCAGAAACCAGGGAAAGCCCCTAAGCTCCTGATCTATCTTGCTTCGCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1058)

BMS3h-193-5
GACATCCAGATGACCCAGTCTCCATCCTCCCTGTCTGCATCTGTAGGAGAACGTGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAATCTGCAA
CCTGAAGATTCTGCTACGTACTACTGTCATCAGTATGCGAGTCCACCTTTGACGTTAGGCCAAGGGACCAAAGTGGAAA
TCAAACGG (SEQ ID NO: 1059)

BMS3h-193-6
GACATCCAGATGACCCAGTCTCCATCCTCCCTGTCTGCATCTGTAGGAGACCGTGTCACCATCACTTGCCGGGCAAGCC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGCGAGTCCACCTTTGACGTTAGGCCAAGGGACCAAAGTGGAAA
TCAAACGG (SEQ ID NO: 1060)

TABLE 4-continued

Human Anti-CD40 Variable Domain Encoding Nucleotide Sequences

BMS3h-193-7
GACATCCAGATAACCCAGTCTCCATCCTCCCTGTCTGCATCTGTAGGAGACCGTGTCACCATCACTTGCCGGGCAAGTC
AGACGATTGAGCGTCGTTTAAATTGGTATCAGCAGAAACCAGGGAAAGACCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCTCCTTTGACGTTCGGCCAAGGGACCAAAGTGGAAA
TCAAACGG (SEQ ID NO: 1061)

BMS3h-193-8
GACATCCAGATGACCCAGTCTCCATCCTCCCTGTCTGCATCTGTAGGAGACCGTGTCACCATCACTTGCCGGGCAAGTC
AGACGATTGAGCGTCGTTTAAATTGGTATCAGCAGAAACCAGGGGAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAATGG (SEQ ID NO: 1062)

BMS3h-193-9
GACATCCAGTTGACCCAGTCTCCATCCTCCCTGTCTGCATCTGTAGGAGACCGAGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGAATTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1063)

BMS3h-193-10
GACATCCAGATGTCCCAGTCTCCATCCACCCTGTCTGCATCTGTAGGAGACCGTGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
CTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGATGTTCGGCCAAGGGACCAAAGTGGAAA
TCAAACGG (SEQ ID NO: 1064)

BMS3h-193-11
GACATCCAGATGACCCAGTCTCCATCCTCCCTGTCTGCATCTGTAGGAGACCGTGTCACCATTACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCAGAAGATTTTGCTACGTACTACTGTCATCAGTATGAGAGTCCACCTTTGACGTTCGGCCAAGGGACCAAAGTGGAAA
TCAAACGG (SEQ ID NO: 1065)

BMS3h-193-12
GACATCCAGATGACCCAGTCTCCATCCTCCCTGTCTGCATCCGTAGGAGACCGTGTCACCATCACTTGCCGGGCAAGTC
AGACGATTGAGCGTCGTTTAAACTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1066)

BMS3h-193-13
GACATCCAGATGACCCAGTCTCCATCCTCCCTGTTTGCATCTGTAGGGGACCGTGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1067)

BMS3h-193-14
GACATCCAGATGACCCAGTATCCATCCTCCCTGTCTGCATCTGTAGGAGACCGTGTCACCATCACTTGCCGGGCAAGTC
AGTCGATTGAGCGTCGTTTAAATTGGTATCAGCAGAAACCAGGGGAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACTAAAGTGGAAA
TCAAACGG (SEQ ID NO: 1068)

BMS3h-193-15
GACATCCAGATGACCCAGTCTCCATCCTCCCTGTCTGCATCTGTAGGAGACCGTGTCACCATCACTTGCCGGGCAAGTC
GGACGATTGAGCGTCGTTTAAATTGGTATCAGCAGAAACCAGGGAAAGCCCCTAAGCTCCTGATCTATCTTGCTTCGCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCCGTATGAGAGTCCACCTTTGACGTTCGGCCAAGGGACCAAAGTGGAAA
TCAAACGG (SEQ ID NO: 1069)

BMS3h-193-16
GACATCCAGATGACCCAGTCTCCATCCTCCCTGTCTGCATCTGTAGGAGACCGTGTCACCATCACTTGCCGGGCAAGTC
AGGCGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCTCGTTTCAGTGGCAGTGGATCTGGGACAGATTTCACTCTCACCATCAGCAGTCTGCAG
CCAGAAGATTTTGCTACGTACTACTGTCATCAGTATGCGAGTCCACCTTTGACGCTCGGCCAAGGGACCAAAGTGGAAA
TCAAACGG (SEQ ID NO: 1070)

BMS3h-193-17
AACATCCAGATGACCCAGTCTCCATCCTCCCTGTCTGCATCTGTAGGAGACCGTGTCACCATCACTTGCCGGGCAAGTC
AGGCGATTGAGCGTCGTTTAAATTGGTATCAGCAGAAACCAGGGAAAGCCCCTAAGCTCCTGATCTATCTTGCTTCTCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1071)

TABLE 4-continued

Human Anti-CD40 Variable Domain Encoding Nucleotide Sequences

BMS3h-193-18
GACATCCAGATGACCCAGTCTCCATCCTCCCTGTCTGCATCTGTAGGAGACCGTGTCACCATCACTTGCCGGGCAAGTC
AGACGATTGGGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGTCAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1072)

BMS3h-193-19
GACATCCAGATGACCCAGTCTCCATCCTCCCTTTCTGCATCTGTAGGAGACCGTGTCACCATCACTTGCCGAGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGAATTTACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1073)

BMS3h-193-20
GACATCCAGATGACCCAGACTCCATCCTCCCTGTCTGCATCTGTAGGAGACCGTGTCACCATCACTTGCCGGGCAAGTC
AGACGATTGAGCGTCGTTTAAATTGGTATCAGCAGAAACCAGGGGAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCCACGTACTACTGTCATCAGTATGAGAGTCCACCTTTGACGTTCGGCCAAGGGACCAAAGTGAAAA
TCAAACGG (SEQ ID NO: 1074)

BMS3h-193-21
GACATCCAGATGACCCAGTCTCCATCCTCCCTGTCTGCATCTGTAGGAGACAGTGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCCGAAGATTTTGCTACGTACTACTGTCATCAGTATGAGAGTCCACCTTTGACGTTCGGCCAAGGGACCAAAGTGGAAA
TCAAACGG (SEQ ID NO: 1075)

BMS3h-193-22
CACATCCAGATGACCCAGTCTCCATCCTCCCTGTCTGCATCTGTAGGAGACCGTGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGCCATCAGTATGAGAGTCCACCTTTGACGTTCGGCCAAGGGACCAAAGTGGAAA
TCAAACGG (SEQ ID NO: 1076)

BMS3h-193-23
GACGTCCAGATGACCCAGTCTCCATCCTCCCTGTCTGCATCTGTAGGAGACCGTGTCACCATCACTTGCCGGGCAAGTC
AGACGATTGAGCGTCGTTTAAATTGGTATCAGCAGAAACCAGGGGAAGCCCCTAAGCTCCTGATCTATCTTACTTCCCG
TTTGCAAAGCGGGGTCCCATCACGTTTCAGTGGTAGTGGATCTGGGACAGATTTCACTCTCACCATCAGCAGTCTGCAA
CCTGAAGATTTTGCTACGTACTACTGCCATCAGTATGCGAGTCCACCTTTGACGTTCGGCCAAGGGACCAAGGTGGAAA
TCAAACGG (SEQ ID NO: 1077)

BMS3h-193-24
GACATCCAGATGACCCAGTCGCCATCCTCCCTGTCTGCATCTGTAGGAGACCGTGTCACCATCACTTGCCGGGCAAGTC
AGACGATTGAGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCACCAGTATGAGAGTCCACCTTTGACGTTCGGCCAAGGGACCAAAGTGGTAA
TCAAACGG (SEQ ID NO: 1078)

BMS3h-193-25
GACATCCAGATGACCCAGTCTCCATCCTCCCTGTCTGCATCTGTAGGAGACCGAGTCACCATCACTTGCCGGGCAAGTC
AGACGATTGAGCGTCGTTTAAATTGGTATCAGCAGAAACCTGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1079)

BMS3h-193-26
GACATCCAGATGACCCAGTCTCCATCCTCCCTGTCTGCATCTGTAGGAGACCGTGTCACCATCACTTGCCGGGCAAGTC
AGCCGATTGAGCGTCGTTTAAATTGGTATCAGCAGAAGCCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACATACTACTGTCATCAGTATGAGAGTCCACCTTTGACGTTCGGCCAAGGGACCAAAGTGGAAA
TCAAACGG (SEQ ID NO: 1080)

BMS3h-193-27
GACATCCAGATGACCCAGTCTCCATCCTCCCTGTCTGCATCTGTAGGAGACCGTGTCACCATCACTTGCCGGGCAAGTC
AGACGATTGGGCGTCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1081)

BMS3h-193-28
GACATCCAGATGACCCAGTCTCCATCCTCCCTGTCTGCATCTGTAGGAGACCGTGTCACCATCACTTGCCGGGCAAGTC
AGTCGATTGAGCGCCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCTCCTTTGACGTTCGGCCAAGGGACCAAAGTGGAAA
TCATACGG (SEQ ID NO: 1082)

TABLE 4-continued

Human Anti-CD40 Variable Domain Encoding Nucleotide Sequences

BMS3h-193-29
GACATCCAGATGACCCAGTCTCCATCCTCCCTGTCTGCATCTGTAGGAGACCGAGTCACCATCACTTGCCGGGCAAGTC
AGACGATTGAGCGTCGTTTAAATTGGTATCAGCAGAAACCTGGGAAAGCCCCTAAGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1083)

BMS3h-193-30
GACATCCAGATGACCCAGTCTCCATCCTCCCTGTCTGCATCTGTAGGAGACCGTGTCACCATCACTTGCCGGGCAAGTC
AGTCGATTGAGCGCCGTTTAAATTGGTATCAGCAGAAACCAGGGAAAGCCCCTAAGCTCCTGATCTATCTTGCTTCCCG
TTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTCATCAGTATGAGAGTCCTCCTTTGACGTTCGGCCAAGGGACCAAAGTGGAAA
TCAAACGG (SEQ ID NO: 1084)

BMS3h-193-2501
GACATCCAGATGACCCAGTCTCCATCCTCCCTGTCTGCATCTGTAGGAGACCGAGTCACCATCACTTGCCGGGCAAGTC
AGACGATTGAGCGTCGTTTAAATTGGTATCAGCAGAAACCTGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTTCGAGCACCCACCTTTGACGTTCGGCCAAGGGACCAAAGTGGAAA
TCAAACGG (SEQ ID NO: 1085)

BMS3h-193-2502
GACATCCAGATGACCCAGTCTCCATCCTCCCTGTCTGCATCTGTAGGAGACCGAGTCACCATCACTTGCCGGGCAAGTT
TCCCCATTGACCGTCGTTTAAATTGGTATCAGCAGAAACCTGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1086)

BMS3h-193-2503
GACATCCAGATGACCCAGTCTCCATCCTCCCTGTCTGCATCTGTAGGAGACCGAGTCACCATCACTTGCCGGGCAAGTT
CCACCATTGGCCGTCGTTTAAATTGGTATCAGCAGAAACCTGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1087)

BMS3h-193-2504
GACATCCAGATGACCCAGTCTCCATCCTCCCTGTCTGCATCTGTAGGAGACCGAGTTACCATCACTTGCCGGGCAAGTT
CCCGAGATTGGGCGTCGTTTAAATTGGTACCAGCAGAAACCAGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1088)

BMS3h-193-2505
GACATCCAGATGACCCAGTCTCCATCCTCCCTGTCTGCATCTGTAGGAGACCGAGTCACCATCACTTGCCGGGCAAGTG
AGCGGATTGGGCGTCGTTTAAATTGGTATCAGCAGAAACCAGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1089)

BMS3h-193-2506
GACATCCAGATGACCCAGTCTCCATCCTCCCTGTCTGCATCTGTAGGAGACCGAGTCACCATCACTTGCCGGGCAAGTC
AGCAGATTGGCCGCCGTTTAAATTGGTATCAGCAGAAACCTGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1090)

BMS3h-193-2507
GACATCCAGATGACCCAGTCTCCATCCTCCCTGTCTGCATCTGTAGGAGACCGAGTCACCATCACTTGCCGGGCAAGTC
AGCCGATTGCCCGGCGTTTAAATTGGTACCAGCAGAAACCAGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1091)

BMS3h-193-2508
GACATCCAGATGACCCAGTCTCCATCCTCCCTGTCTGCATCTGTAGGAGACCGAGTCACCATCACTTGCCGGGCAAGTG
GGAACATTGGCCGTCGTTTAAATTGGTACCAGCAGAAACCAGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAGCGG (SEQ ID NO: 1092)

BMS3h-193-2509
GACATCCAGATGACCCAGTCTCCATCCTCCCTGTCTGCATCTGTAGGAGACCGAGTCACCATCACTTGCCGGGCAAGTC
GGAACATTGACCGTCGTTTAAATTGGTACCAGCAGAAACCAGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1093)

TABLE 4-continued

Human Anti-CD40 Variable Domain Encoding Nucleotide Sequences

BMS3h-193-2510
GACATCCAGATGACCCAGTCTCCATCCTCCCTGTCTGCATCTGTAGGAGACCGAGTCACCATCACTTGCCGGGCAAGTC
AGAGCATTGGGCGTCGTTTAAATTGGTACCAGCAGAAACCTGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1094)

BMS3h-193-2511
GACATCCAGATGACCCAGTCTCCATCCTCCCTGTCTGCATCTGTAGGAGACCGAGTCACCATCACTTGCCGGGCAAGTC
AGAACATTGGGACGCGTTTAAATTGGTACCAGCAGAAACCAGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1095)

BMS3h-193-2512
GACATCCAGATGACCCAGTCTCCATCCTCCCTGTCTGCATCTGTAGGAGACCGAGTCACCATCACTTGCCGGGCAAGTG
AGGTCATTGGGCGTCGTTTAAATTGGTACCAGCAGAAACCAGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1096)

BMS3h-193-2513
GACATCCAGATGACCCAGTCTCCATCCTCCCTGTCTGCATCTGTAGGAGACCGAGTCACCATCACTTGCCGGGCAAGTG
AGGCGATTGGCCGTCGTTTAAATTGGTATCAGCAGAAACCAGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1097)

BMS3h-193-2514
GACATCCAGATGACCCAGTCTCCATCCTCCCTGTCTGCATCTGTAGGAGACCGAGTCACCATCACTTGCCGGGCAAGTA
CCAGCATTGCGCGTCGTTTAAATTGGTATCAGCAGAAACCTGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1098)

BMS3h-193-2515
GACATCCAGATGACCCAGTCTCCATCCTCCCTGTCTGCATCTGTAGGAGACCGAGTCACCATCACTTGCCGGGCAAGTT
TGAACATTGGGCGTCGTTTAAATTGGTACCAGCAGAAACCAGGGAAAGCCCCTAGGCTCCTGATCTATCTTGCTACCCG
TTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1099)

BMS3h-193-2516
GACATCCAGATGACCCAGTCTCCATCCTCCCTGTCTGCATCTGTAGGAGACCGAGTCACCATCACTTGCCGGGCAAGTC
AGACGATTGAGCGTCGTTTAAATTGGTACCAGCAGAAACCAGGGAAAGCCCCTAGGCTCCTGATCTATCTTTCGTCGAA
GTTGCAAAGTGGGGTCCCATCACGCTTCAGTGGCAGTGGATCTGGGACAGATTTCACTCTCACCATCAGCAGTCTGCAA
CCTGAAGATTTTGCTACGTACTACTGTCATCAGTATGAGAGTCCACCTTTGACGTTCGGCCAAGGGACCAAAGTGGAAA
TCAAACGG (SEQ ID NO: 1100)

BMS3h-198-1
GAGGTGCAGCTGTTGGAGTCTGGGGGAGGCTTGGTTCAGCCTGGGGGGTCCCTGCGTCTCTCCTGTGCAGCCTCCGGAT
CCACCATTGCTGGGTATGAGATGTGGTGGGTCCGCCAGGCTCCAGGGAAGGGTCTAGAGCGTGTCTCAGCTATTAGTGG
TAGTGGTGGTAGCACATACTACGCAGACTCCGTGAAGGGCCGGTTCACCATCTCCCGAGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCAGGGAACCCTGGTCACCGTCTCGAGC (SEQ ID NO: 1101)

BMS3h-198-2
GAGGTGCAGCCGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGATCTCAGCTATTAGCGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCAGGGAACCCTGGTCACCGTCTCGAGC (SEQ ID NO: 1102)

BMS3h-198-3
GAGGTGCAGCTGTTGGAGTCTGGGGGAGGCTCGGTACAGCCTGGGGGGTCCCTGCGTCTCTCCTGTGCAGCCACCGGAT
CCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTACAGTTATGACTACT
GGGGTCAGGGAACCCTGGTCTCCGTCTCGAGC (SEQ ID NO: 1103)

BMS3h-198-4
GAGGTGCAGCTGTTGGAGTCTGGGGGAGGCTTGGTACAGCCTGGGGGGTCCCTGCGTCTCTCCTGTGCAGCCTCCGGAC
TCACCTTTGCTGGGTATGAGATGTGGTGGGTCCGCCAGGCACCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCAGTATATCACTGTGCGAGAGATCCTTATAGTTTTGACTACT
GGGGTCAGGGAACCCTGGTCACCGTCTCGAGC (SEQ ID NO: 1104)

TABLE 4-continued

Human Anti-CD40 Variable Domain Encoding Nucleotide Sequences

BMS3h-198-5
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCTGTGAAGGGCCGGTTCACCATCTCCCGCGACGATTCCAAGAACACGCTG
TATCTGCAAATGAACAGCCTGCGTGCCGAGGATACCGCGGTATATCACTGTGCGAAAGAACCTTATAGTTATGACTACT
GGGGTCAGGGAACCCTGGTCACCGTCTCGAGC (SEQ ID NO: 1105)

BMS3h-198-6
GAGGTGCAGCTGTTGGAGTCTGGGGGAGGCTTGGTACAGCCTGGGGGGTCCCTGCGTCTCTCCTGTGCAGCCTCCGGAT
CCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTCCCGAGGATACCGCGGTATATTACTGTGCGAAAGATCCTTATAGTTTTGACTACT
GGGGTCAGGGAACCCTGGTCACCGTCTCGAGC (SEQ ID NO: 1106)

BMS3h-198-7
GAGGTGCAGCTGTTGGAGTCTGGGGGAGGCTTGGTACAGCCTGGGGGGTCCCTGCGTCTCTCCTGTGCAGCCTCCGGAT
CCACCATTGCCGGGTATGAGATGTGGTGGGTCCGCCAGGCTCCGGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCAGGGAACCCCGGTCACCGTCTCGAGC (SEQ ID NO: 1107)

BMS3h-198-8
GAGGTGCAGCTGATGGAGTCTGGGGGAGGCTTGGTACAGCCTGGGGGGTCCCTGCGTCTCTCCTGTGCAGCCTCCGGAT
CCACCTTTGCTGGGTATGAGATGTGGTGGTACCGCCAGGCTCCAGGGAAGGGTCTAGAGCGGGTCTCAGCTATTAGTGG
AAGTGGTAGAAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGATCCTTATAGTTTTGACTACT
GGGGTCAGGGAACCCTGGTCACCGTCTCGAGC (SEQ ID NO: 1108)

BMS3h-198-9
GAGGTGCAGCTGCTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAGCACGTACTACGCAGACTCCGTGAAGGGCCGGTTCACCATCTCCCGCGACGATTCCAAGAACACGCTG
TATCTGCAAATGAACAGCCTGCGTGCCGAGGATACCGCAGTATATTACTGTGCGAAAGAACCTTATAGTTTTGACTACT
GGGGTCAGGGAACCCTGGTCACCGTCTCGAGC (SEQ ID NO: 1109)

BMS3h-198-10
GAGGTGCAGCTGTTGGAGTCTGGGGGAGGCTTGGTACAGCCTGGGGGGTCCCTGCGTCTCTCCTGTGCAGCCTCCGGAT
CCACCATTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGATCCATATAGTTTTGACTACT
GGGGTCAGGGAACCCTGGTCACCGTCTCGAGC (SEQ ID NO: 1110)

BMS3h-198-11
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGACCCTTATAGTTTTGACTACT
GGGGTCAGGGAACCCTGGTCTCCGTCTCGAGC (SEQ ID NO: 1111)

BMS3h-198-12
GAGGTGCAGCTGTTGGAGTCTGGGGGAGGCTTGGTACAGCCTGGGGGGTCCCTGCGTCTCTCCTGTGCAGCCTCCGGAT
TCACCATTGCTGGGTATGAGATGTGGTGGGTCCGCCAGGCTCCAGGGAAGGGTCTAGAGCGGGTCTCCGCTATTAGTGG
TAGTGGTGGTAGCACATACTACGCGGACTCCGTGAAGGGCCGGTTCACCATCTCCCGCGACGATTCCAAGAACACGCTG
TATCTGCAAATGAACAGCCTGCGTGCCGAGGATACCGCGTATATTACTGTGCGAAAGATCCTTATAGTTTTGACTACT
GGGGTCAGGGAACCCTGGTCACCGTTTCGAGC (SEQ ID NO: 1112)

BMS3h-198-13
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGTGTCTCAGCTATTAGTGG
TAGTGGTGGTAGCACATACTACGCAGACTCCGTGAAGGGCCGGTTCACCATCACCCGCGACGATTCCAAGAACACGCTG
TATCTGCAAATGAACAGCCTGCGTGCCGAGGATACCGCGGTATATTACTGTGCGAAAGAGCCTTATAGTTTTGACTACT
GGGGTCAGGGAACCCTGGTCACCGTCTCGAGC (SEQ ID NO: 1113)

BMS3h-198-14
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGTTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATACCAAGAACACGCTG
TATCTGCAAATGAACAGCCTGCGTGCCGAGGATACCGCGGTATATTACTGTGCGAAAGATCCTTATAGTTTTGACTACT
GGCGTCAGGGAACCCTGGTCACCGTCTCGAGC (SEQ ID NO: 1114)

BMS3h-198-15
GAGGTGCAGCTGTTGGAGTCTGGGGGAGGCTTGGTACAGCCTGGGGGGTCCCTGCGTCTCTCCTGTGCAGCCTCCGGAT
CCACCTTTGCTGGGTATGAGGTGTGGTGGGTCCGCCAGGCTCCAGGGAAGGGTCTGGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCAGGGAACCCTGGTCACCGTCTCGAGC (SEQ ID NO: 1115)

TABLE 4-continued

Human Anti-CD40 Variable Domain Encoding Nucleotide Sequences

BMS3h-198-16
GAGGTGCAGCTGTTGGAGTCTGGGGGAGGCTTGGTACAGCCTGGGGGGTCCCTGCGTCTCTCCTGTGCAGCCTCCGGAT
CCACCTTTGCTGGGTATGAGATGTGGTGGGTCCGCCAGGCTCCAGGGAAGGGTCTAGAGCGGATCTCAGCTATTAGTGG
TAGTGGTGGTAGCACATACTACGCAGACTCCGTGAAGGGCCGGTTCACCATCTCCCGCGACGATTCCAAGAACACGCTG
TATCTGAAAATGAACAGCCTGCGTGCCGAGGATACCGCGGTATATTACTGTGCGAAAGATCCTTATAGTTTTGACTACT
GGGGTCAGGGAACCCTGGTCACCGTCTCGAGC (SEQ ID NO: 1116)

BMS3h-198-17
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCAGGGAACCCTGGTCACCGTCTCGAGC (SEQ ID NO: 1117)

BMS3h-198-18
GAGGTGCAGCTGTTGGAGTCTGGGGGAGGCTTGGTACAGCCTGGGGGGTCCCTGCGTCTCTCCTGTGCAGCCTCCGGAC
TCACCTTTGCTGGGTATGAGATGTGGTGGGTCCGCCGGGCTCCAGGGAAGGGTCTAGAGCGGGTCGCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCAGGGAACCCTGGTCACCGTCTCGAGC (SEQ ID NO: 1118)

BMS3h-198-19
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGTTGTGGTGGGTCCGCCAGGCCCCAGGGAAGGGTCTAGAGCGGGTCTCAGCTATTAGTGG
AAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACC
GGGGTCAGGGAACCCTGGTCACCGTCTCGAGC (SEQ ID NO: 1119)

BMS3h-198-20
GAGGTGCAGCTGTTGGAGTCTGGGGGAGGCTTGGTACAGCCTGGGGGGTCCCTGCGTCTCTCCTGTGCAGCCCCCGGAT
TCACCTTAGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGAACCTTATAGTTTTGACTACT
GGGGTCAGGGAACCCTGGTCACCGTCTCGAGC (SEQ ID NO: 1120)

BMS3h-198-21
GAGGTGCAGCTGTTGGAGTCTGGGGGAGGCTTGGTACAGCCTGGGGGGTCCCTGCGTCTCTCCTGTGCAGCCTCCGGAC
TCACCTTTGCTGGGTATGAGATGTGGTGGGTCCGTCGGGCTCCAGGGAAGGGTCTAGAGCGGGTCTCAGCTATTAGTGG
TAGTGGTGGTAGCACATACTACGCAGACTCCGTGAAGGGCCGGTTCACCACCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCGGGGAACCCTGGTCACCGTCTCGAGC (SEQ ID NO: 1121)

BMS3h-198-22
GAGGTGCAGCTGTTGGAGTCTGGGGGAGGCTTGGTACAGCCCGGGGGGTCCCTGCGTCTCTCCTGTGCCGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGCGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGAACCTTATAGTTATGACTACT
GGGGTCATGGAACCCTGGTTACTGTCTCGAGC (SEQ ID NO: 1122)

BMS3h-198-23
GAGGTGCAGCCGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAACACATACTACGCAGACTCCGTGAAGGGCCGGTTCACCATCTCCCGCGACGATTCCAAGAACACGCTG
TATCTGCAAATGAACAGCCTGCGTGCCGAGGATACCGGGGTATATTACTGTGCGAGAGATCCTTATAGTTTTGACTACT
GGGGTCAGGGTACCCTGGTCACCGTCTCGAGC (SEQ ID NO: 1123)

BMS3h-198-24
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGAACCTTATAGTTTTGACTCCT
GGGGTCAGGGAACCCTGGTCACCGTCTCGAGC (SEQ ID NO: 1124)

BMS3h-198-25
GAGGCGCAGCTGTTGGAGTCTGGGGGAGGCTTGGTACAGCCTGGGGGGTCCCTGCGTCTCTCCTGTGCAGCCTCCGGAT
TAACCTTCGCTGGGTATGAGATGTGGTGGGTCCGCCAGGCTCCAGGGAAGGGTCTAGAGCGCGTCTCAGCTATTAGTGG
TAGTGGCGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCAGGGAACCCTGGTCACCGTCTCGAGC (SEQ ID NO: 1125)

BMS3h-198-26
GAGGTGCAGCTGTTGGAGTCTGGGGGAGGCTTGGTACAGCCTGGGGGGTCCCTGCGTCTCTCCTGTGCAGCCTCCGGAT
CCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCTCCATCTCCCGCGACGATTCCAAGAACACGCTG
TATCTGCAAATGAACAGCCTGCGTGCCGAGGATACCGCGGTATATTACTGTGCGAAAGAACCTTATAGTTTTGACCACT
GGGGTCAGGGAACCCTGGTCACCGTCTCGAGC (SEQ ID NO: 1126)

TABLE 4-continued

Human Anti-CD40 Variable Domain Encoding Nucleotide Sequences

BMS3h-198-27
GAGGTGCAGCTGTTGGAGTCTGGGGGAGGCTTGGTACAGCCTGGGGGGTCCCTGCGTCTCTCCTGTGCAGCCTCGGAT
CCACCTTTGCTGGGTATGAGATGTGGTGGGTCCGCAGGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCAGGGAACCCTGGTCACCGTCTCGAGC (SEQ ID NO: 1127)

BMS3h-198-28
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGTTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGATCCTTATAGTTTTGACAACT
GGGGTCAGGGAACCCTGGTCACCGTCTCGAGC (SEQ ID NO: 1128)

BMS3h-198-29
GAGGTGCAGCTGTTGGAGTCTGGGGGAGGCTTGGTAGAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGAACCTTATAGTTTTGACCACC
GGGGTCAGGGAACCCTGGTCACCGTCTCGAGC (SEQ ID NO: 1129)

BMS3h-198-30
GAGGTGCAGCTGTTGGAGTCTGGGGGAGGCTTGGTACAGCCTGGGGGGTCCCTGCGTCTCTCCTGTGCAGCCTCCGGAT
ACACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGAACCTTATAGTTTTGACCACC
GGGGTCAGGGAACCCTGGTCACCGTCTCGAGC (SEQ ID NO: 1130)

BMS3h-198-31
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCTGTGAAGGGCCGGTTCACCATCTCCCGCGACAATTCCAAGAACACGCTG
TATCTGCAAATGAACAGCCTGCGTGCCGAGGATACCGCGGTATATCACTGTGCGAAAGAACCTTATAGTTATGACTACT
GGGGTCAGGGAACCCTGGTCACCGTCTCGAGC (SEQ ID NO: 1131)

BMS3h-198-32
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGTTCCGCCAGGCTCCAGGGAAGGGTCTAGAGCGGGTCTCAGCTATTAGTGG
TAGTGGTGGTAGCACATACTACGCAGACTCCGTGAAGGGCCGGTTCACCATCTCCCGCGACAATTCCAAGAACACGCTG
TATCTGCAAATGAACAGCCTGCGTGCCGAGGATACCGCGGTATATTACTGTGCGAAAGATCCTTATAGTTTTGACAACT
GGGGTCAGGGAACCCTGGTCACCGTCTCGAGC (SEQ ID NO: 1132)

BMS3h-198-33
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGCGGGTCTCAGCTATTAGTGG
TAGTGGTGGTAGCACATACTACGCAGACTCTGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGAACCTTATAGTTATGACTACT
GGGGTCAGGGAACCCTGGTCACCGTCTCGAGC (SEQ ID NO: 1133)

BMS3h-198-34
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCGGGAAGGGTCTAGAGCGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGATCCTTATAGTTTTGACAACT
GGGGTCAGGGAACCCTGGTCACCGTCTCGAGC (SEQ ID NO: 1134)

BMS3h-198-35
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGGTCCGCCAGGCTCCAGGGAAGGGTCTAGAGTGGGTCTCAGCTATTAGTGG
TAGTGGTGGTAGCACATACTACGCAGACTCTGTGAAGGGCCGGTTCACCATCTCCCGCGACGATTCCAAGAACACGCTG
TATCTGCAAATGAACAGCCTGCGTGCCGAGGATACCGCGGTATATCACTGTGCGAAAGAACCTTATAGTTATGACTACT
GGGGTCAGGGAACCCTGGTCACCGTCTCGAGC (SEQ ID NO: 1135)

BMS3h-198-36
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGATGTGGTGGTTCCGCCAGGCTCCAGGGAAGGGTCTAGAGTGGGTCTCAGCTATTAGTGG
TAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGATCCTTATAGTTTTGACAACT
GGGGTCAGGGAACCCTGGTCACCGTCTCGAGC (SEQ ID NO: 1136)

BMS3h-198-37
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGTTGTGGTGGGTCCGCCAGGCCCAGGGAAGGGTCTAGAGCGGGTCTCAGCTATTAGTGG
AAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAAAGATCCTTATAGTTTTGACTACC
GGGGTCAGGGAACCCTGGTCACCGTCTCGAGC (SEQ ID NO: 1137)

TABLE 4-continued

Human Anti-CD40 Variable Domain Encoding Nucleotide Sequences

BMS3h-198-38
GAGGTGCAGCTGTTGGAGTCTGGGGGAGGCTTGGTACAGCCTGGGGGGTCCCTGCGTCTCTCCTGTGCAGCCTCCGGAT
TCACCTTTGCTGGGTATGAGTTGTGGTGGGTCCGCCAGGCCCCAGGGAAGGGTCTAGAGCGGGTCTCAGCTATTAGTGG
AAGTGGTGGTAGCACATACTACGCAGACTCCGTGAAGGGCCGGTTCACCATCTCCCGCGACGATTCCAAGAACACGCTG
TATCTGCAAATGAACAGCCTGCGTGCCGAGGATACCGCGGTATATTACTGTGCGAGAGATCCTTATAGTTTTGACTACT
GGGGTCAGGGAACCCTGGTCACCGTCTCGAGC (SEQ ID NO: 1138)

BMS3h-202-1
GAGGTGCAGCTGTTGGAGTCTGGGGGGGGCTTGGTACAGCCTGGGGGGTCCCTGCGTCTCTCCTGTGCAGCCTCCGGAT
TCACCTTTCCGACTGCTGAGATGCTGTGGGTCCGCAAGGCTCCAGGGAAGGGTCTAGAGTGGGTCTCATCTATTTCGGC
TAGTGGTGGTTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGGTGAGTTATGTGGCGA
CGTTTGACTACTGGGGTCAGGGAACCCTGGTCACCGTCTCGAGC (SEQ ID NO: 1139)

BMS3h-202-2
GAGGTGCAGCTGTTGGTGTCTGGGGGAGGCTTGGTACAGCCTGGGGGGTCCCTGCGTCTCTCCTGTGCAGCCTCCGGAT
TCACCTTTCCGACTGCTGAGATGTTGTGGGTCCGCCAGGCTCCAGGGAAGGGTCCAGAGTGGGTCTCATCAATTTCGGC
TAGTGGTGGTTCTACATACTATGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGGTGAGTTATGTGGCGA
CGTTTGACTACTGGGGTCAGGGAACCCTGGTCACCGTCTCGAGC (SEQ ID NO: 1140)

BMS3h-202-3
GAGGTGCAGCTGTTGGAGTCTGGGGGAGGCTTGGTACAGCCTGGGGGGTCCCTGCGTCTCTCGTGTGCAGCCTCCGGAT
TCACCTTTCCGACTGCCGAGATGGTGTGGGTCCGCAAGGCTCCAGGGATGGGTCTAGAGTGGGTCTCATCTATTTCGGC
TAGTGGTGGTTATACATACTACGCAGACTCCGTGAAGGGCCGGTTCACCATCTCCCGCGACAATTCCAAGAACATGCTG
TATCTGCAAATGAACAGCCTGCGTGCCGAGGACACCGCGGTATATTACTGTGCGAAAGAGCCGGTGAGTTATGTGGCGA
CGTTTGACTACTGGGGTCAGGGAGCCCTGGTCACCGTCACGAGC (SEQ ID NO: 1141)

BMS3h-202-4
GAGGTGCAGCTGTTGGTGTCTGGGGGAGGCTTGGTACAGCCTGGGGGGTCCCTGCGTCTCTCCTGTGCAGCCTCCGGAT
TCACCTTTCCGACTGCTGAGATGGTGTGGGTCCGCCAGGCTCCAGGGAAGGGTCTAGAGTGGGTCTCATCTATTTCGGC
TAGTGGTGGTTCTACATACTACGCAGACTCCGTGAAGGGCCGGTTCTCCATCTCCCGCGACGATTCCAAGAACACGCTG
TATCTGCAAATGAACAGCCTGCGTGCCGAGGACACCGCGGTATATTACTGTGCGAAAGAGCCGGTGAGTTATGTGGCGA
CGTTTGACTACTGGGGTCATGGAGCCCTGGTCACCGTCTCGAGC (SEQ ID NO: 1142)

BMS3h-202-5
GAGGTGCAGCTGTTGGAGTCTGGGGGAGGCTTGGTACAGCCTGGGGGGTCCCTGCGTCTCTCCTGTGCAGCCTCCGGAT
TCACATTTCCGACTGCTGAGATGTTGTGGGTCCGCCAGGCTCCAGGGAAGGGTCTAGAGTGGGTCTCATCTATTTCGGC
TAGTGGTGGTTCTACATACTACGCAGACTCCGTGAAGGGCCGGTTCACCATCTCCCGCGACAATTCCAAGAACACGCTG
TATCTGCAAATGAACAGCCTGCGAGCCGAGGACACCGCGGTATATTACTGTGCGAAAGAGCCGGTGAGTTATGTGGCAA
CGTTTGACTACTGGGGTCAGGGAACCCTGGTCACCGTCTCGAGC (SEQ ID NO: 1143)

BMS3h-202-6
GAGGCGCAGCTGTTGGAGTCTGGGGGTGGCTTGGTACAGCCTGGGGGGTCCCTGCGTCTCTCCTGTGCAGCCTCCGGAT
TCACCTTTCCGACTGCTGAGATGGTGTGGGTCCGCCAGGCTCCAGGGAAGGGTCTAGAGTGGATCTCATCTATTTCGGC
TAGTGGTGGTTCTACATACTACGCAGACTCCGTGAAGGGCCGGTTCACCATCTCCCGCGACAATTCCAAGAACACGCTG
TATCTGCAATTGAACAGCCTGCGTGCCGAGGACACCGCGGTATATTACTGTGCGAAAGAGCCGGTGAGTTATGTGGCGA
CGTTTGACTACTGGGGTCGGGGAACCCTGGTCACCGTCTCGAGC (SEQ ID NO: 1144)

BMS3h-202-7
GAGGTGCAGCTGTTGGAGTCTGGGGGAGGCTTGGTACAGCCTGGGGGGTCCCTGCGTCTCTCCTGTGCAGCCTCCGGAT
TCACATTTCCGACTGCTGAGATGTTGTGGGTCCGCCAGGCTCCAGGGAAGGGTCTAGAGTGGGTCTCATCTATTTCGGC
TAGTGGTGGTTCTACATACTACGCAGACTCCGTGAAGGGCCGGTTCACCATCTCCCGCGACAATTCCAAGAGCACGCTG
TATCTGCAAATGAACAGCCTGCGTGCCGAGGACACCGCGGTATATTACTGTGCGAAAGAGCCGGTGAGTTATGTGGCGA
CGTTTGACTACTGGGGTCCAGGAGCCCTGGTCACCGTCTCGAGC (SEQ ID NO: 1145)

BMS3h-202-8
GAGGTGCAGCTGTTGGAGTCCGGGGGAGGCTTGGTACAGCCTGGGGGGTCCCTGCGTCTCTCCTGTGCAGCCTCCGGAT
TCACCTTTCCGACTGCTGAGATGCTGTGGGTCCGCAAGGCTCCAGGGAAGGGTCTAGAGTGGGTCTCATCTATTTCGGC
TAGTGGTGGTTCTACATACTACGCAGACTCCGTGAAGGGCCGGTTCACCATCTCCCGCGACAATTCCAAGAACACGCTG
TTTCTGCAAATGAACAGCCTGCGTGCCGAGGACACCGCGGTATATTACTGTGCCAAAGAGCCGGTGAGTTATGTGGCGA
CGTTTGACTACTGGGGTCAGGGAACCCTGGTCACCGTCTCGAGC (SEQ ID NO: 1146)

BMS3h-202-9
GAGGTGCAGCTGTTGGAGTCTGGGGGAGGCTTGGTACAGCCTGGGGGGTCCCTGCGTCTCTCCTGTGCAGCCTCCGGAT
TCACATTTCCGACTGCTGAGATGTTGTGGGTCCGCCAGGCTCCAGGGAAGGGTCTAGAGTGGGTCTCATCTATTTCGGC
TAGTGGTGGTTCTACATACTACGCAGACTCCGTGAAGGGCCGGTTCACCATCTCCCGCGACAATTCCAAGAACACGCTG
TATCTGCAAATGAACAGCCTGCGTGCCGAGGACACCGCGGTATATTACTGTGCGAAAGAGCCGGTGAGTTATGTGGCGA
CGTTTGACTACTGGGGTCCAGGAGCCCTGGTCACCGTCTCGAGC (SEQ ID NO: 1147)

BMS3h-202-10
GAGGTGCAGCTGTTGGAGTCTGGGGGAGGCTTGGTACAGCCTGGGGGGTCCCTGCGTCTCTCCTGTGCAGCCTCCGGAT
TCACCTTTCCGACTGCTGAGATGCTGTGGGTCCGCCAGGCTCCAGGGAAGGGTCTAGAGTGGGTCTCATCTATTTCGGC
TAGTGGTGGTTCTACATACTACGCAGACTCCGTGAAGGGCCGGTTCACCATCTCCCGCGACAATTCCAAGAACACGCTG
TATTTGCAAATGAACAGCCTGCGTGCCGAGGACACCGCGGTATATTACTGTGCGAAAGAGCCGGTGTATTATGTGGCGA
CGTTTGACTACTGGGGTCAGGGAACCCTGGTCACCGTCTCGAGC (SEQ ID NO: 1148)

TABLE 4-continued

Human Anti-CD40 Variable Domain Encoding Nucleotide Sequences

BMS3h-202-11
GAGGTGCAGCTGTTGGAGTCCGGGGGAGGCTTGGTACAGCCTGGGGGGTCCCTGCGTCTCTCCTGTGCAGCCTCCGGAT
TCACCTTTCCGACTGCTGAGATGCTGTGGGTCCGCAAGGCTCCAGGGAAGGGTCTAGAGTGGGTCTCATCTATTTCGGC
TAGTGGTGGTTCTACATACTACGCAGACTCCGTGAAGGGCCGGTTCACCATCTCCCGCGACAATTCCAAGAACACGCTG
TATCTGCAAATGAACAGCCTGCGTGCCGAGGACGCCGCGGTATATTACTGTGCGAAAGAGCCGGTGAGTTATGTGGCGA
CGTTTGACTACTGGGGTCAGGGAACCCTGGTCACCGTCTCGAGC (SEQ ID NO: 1149)

BMS3h-217-1
AACATCCAGATGACCCAGTCTCCATCCTCCCTGTCTGCATCTGTAGGAGACCGTGTCACCATCACTTGCCGGGCAAGTC
ATTTTATTGGTACTCTGTTAACTTGGTACCAGCATAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1150)

BMS3h-217-2
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCAGAAACCACGGAAAGCCCCTAAACTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAT
CCTGAAGATTTTGCTACGTACTACTGTGGTCAGGGGGTGCTGTGGCCTCCGACGTTCGGTCAAGGGACCAAGGTGGAAA
TCAAACGG (SEQ ID NO: 1151)

BMS3h-217-3
GACATCCAGATGACCCAGTCTCCGTCCTCCCTGACTGCATCTGTAGGAGACCGTGTCACCATCACTTGCCGGGCAAGTC
ATTTTATTGGTACTCTGTTATCTTGGTACCAGCAGAAACCAGGGAAAGCCCCTAAGCTCCTGGTCACTTATGGTTCCTT
GTTGCAAAGTGGGGTCCCATCACGTTTCAGTGGCAGTGGATCTGGGACAGATTTCACTCTCACCATCAGCAATCTGCAA
CCTGAAGATTTTGCTACGTACTACTGTGGTCAGGGGGTGCTGTGGCCTCCTACGTTCGGCCAAGGGACCAAGGTGGAAA
ACATACGG (SEQ ID NO: 1152)

BMS3h-217-4
GACATCCAGATGACCCAGTCTCCATCCTCCCTGTCTGCATCTGTAGGAGACCGTGTCACCATCACTTGCCGGGCAAGTC
ATTTTATTGCTACTCTGTTATCTTGGTACCAGCAGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTCCGACGTTCGGCCAAGGGACCAAGGTGGAAA
TCAAACGG (SEQ ID NO: 1153)

BMS3h-217-5
GACATCCAGATGACCCAGTCTCCATCCTTCCTGTCTGCATCTGTAGGAGACCGTGTCACCATCACTTGCCGGGCAAGTC
ATTTTATTGCTACTCTGTTATCTTGGTACCAGCAGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTCCGACGTTCGGCCAAGGGACCAAGGTGGAAA
TCAAACGG (SEQ ID NO: 1154)

BMS3h-217-6
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCAGAAACCAGGGAAAGCCACTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGACTTTGCTACGTACTACTGTGGTCAGGGGGTGCTGTGGCCCCCGACGTTCGGCCAGGGGACCAAGGTGGAAA
TCAAACGT (SEQ ID NO: 1155)

BMS3h-217-7
GACATCCAGATGACCCAGTCTCCATCCTCCCTGTCTGCATCTGTAGGAGACCGTGTCACCATCACTTGCCGGGCAAGTC
ATTTTATTGGTTCTCTGTTATCTTGGTACCAGCATAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1156)

BMS3h-217-8
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCATAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1157)

BMS3h-217-9
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCATAAACCAGGGAAAGCCCCTAAGCTCCTGATCACTTATGGTTCCAT
GTTGCAAAGTGGGGTCCCATCACGTTTCAGTGGCAGTGGATCTGGGACAGATTTCACTCTCACCATCAGCAGTCTGCAA
CCTGAAGATTTTGCAACGTACTACTGTGGTCAGGGGGTGCTGTGGCCTGCGACGTTCGGCCAAGGGACCAAGGTGGAAA
TCAAACGG (SEQ ID NO: 1158)

BMS3h-217-10
GACATCCAGATGACTCAGTCTCCATCCTCCCTGTCTGCATCTGTAGGAGACCGAGTCACCATCACTTGCCGGGCAAGTC
ATTTTATTGGTACTCTGTTATCCTGGTACCAGCATAAACCAGGGAAAGCCCCTAAGCTCCTGATCACCTATGGTTCCTT
GTTGCAAAGTGGGGTCCCATCACGTTTCAGTGGCAGTGGATCTGGGACAGAATTCACTCTCACCATCAGCAGTCTGCAA
CCTGAAGATTTTGCTACGTACTACTGTGGTCAGGGAGTGCTGTGGCCTGCGACGTTCGGCCAAGGGACCAAGGTGGAAA
TCAAACGG (SEQ ID NO: 1159)

TABLE 4-continued

Human Anti-CD40 Variable Domain Encoding Nucleotide Sequences

BMS3h-217-11
GACATCCAGATGACCCAGTCTCCATCCTCCCTGACTGCATCTGTAGGAGACCGTGTCACCATCACTTGCCGGGCAAGTC
ATTTTATTGGTACTCTGTTATCTTGGTACCAGCATAAACCAGGGAAAGCCCCTAAGCTCCTGATCACTTATGGTTCCTT
GTTGCAAAGTGGGGTCCCATCACGTTTCAGTGGCAGTGGATCTGGGACAGAATTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1160)

BMS3h-217-12
AACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCATAAACCAGGGAAAGCCCCTAAGCTCCTGATCACTTATGGTTCCTT
GTTGCAAAGTGGGGTCCCATCACGTTTCAGTGGCAGTGGATCTGGGACAGATTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1161)

BMS3h-217-13
GACATCCAGATGACCCAGTCTCCATCCTCCCTGTCTGCATCTGTAGGAGACCGTGTCACCATCAATTGCCGGGCAAGTC
ATTTTATTGGTACTCTGTTATCTTGGTACCAGCATAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1162)

BMS3h-217-14
GACATCCAGTTGACCCAGTCACCATCCTCCCTGTCTGCATCTGTAGGAGACCGTGTCACCATCACTTGCCGGGCAAGTC
ATTTTATTGGTACTCTGTTATCTTGGTACCAGCAGAAACCAGGGAAAGCCACTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTCCGACGTTCGGCCAAGGGACCAAGGTGGAAA
TCAAACGG (SEQ ID NO: 1163)

BMS3h-217-15
GACATCCAGATGACACAGTCTCCATCCTCCCTGTATGCATCTGTAGGAGACCGTGTCACCATCACTTGCCGGGTAAGTC
ATTTTATTGGTACTCTGTTATCTTGGTACCAGCAGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCAGCATCAGCAGTCTGCAA
CCTGAAGATTTTGCTACGTACTACTGTGGTCAGGGGGTGCTGTGGCCCCCGACGTTCGGACAAGGGACCAAGGTGGAAA
TCAAACAG (SEQ ID NO: 1164)

BMS3h-217-16
GACATTCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCAGAAACCAAGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTCCGACGTTCGGCCAAGGGACCAAGGTGGAAA
TCAAACGG (SEQ ID NO: 1165)

BMS3h-217-17
GACATCCAGATTATCCAGTCTCCATCCTCCCTTTCTGCATCTGTAGGAGACCGTGTCACCATCACTTGCCGGGCAAGTC
ATTTTATTGGTACTCTGTTATCTTGGTACCAGCAGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTCCGACGTTCGGCCAAGGGACCAAGGTGGAAA
TCAAACGG (SEQ ID NO: 1166)

BMS3h-217-18
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1167)

BMS3h-217-19
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCTGAAACCAGGGAAAGCCCCAAAGCTCCTGATCACTTATGGTTCCTG
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTAGAAA
ACAAACGG (SEQ ID NO: 1168)

BMS3h-217-20
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCTTAAACCAGGGAAAGCCCCTAAGCTCCTGATCACTTATGGTTCCTT
GTTGCAACGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1169)

BMS3h-217-21
GACATCCAGATGACCCAGGCTCCATCCTCCCTGTCTGCATCTGTAGGAGACCGTGTCACCATCACTTGCCGGGCAAGTC
ATTTTATTGGTACTCTGTTATCTTGGTACCAGCTGAAACCAGGGAAAGCCCCTAAGCTCCTGATCACTTATGGTTCCTT
GTTGCAGAGTGGGGTCCCATCACGTTTCAGTGGTAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTTGAAA
ACAAACGG (SEQ ID NO: 1170)

TABLE 4-continued

Human Anti-CD40 Variable Domain Encoding Nucleotide Sequences

BMS3h-217-22
GACATCCAGATGACCCAGTCTCCATCCTCCCTGTCTGCATCTGTAGGAGACCGTGTCACCATCACTTGCCGGGCAAGTC
ATTTTATTGGTTCTCTGTTATCTTGGTACCAGCAGAAACCAGGGAAAGCCCCAAAGCTCCTGATCACTTATGGTTCCTT
GTTGCAAAGTGGGGTCCCATCACGTTTCAGTGGCAGTGGATCTGGGACAGATTTCGCTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1171)

BMS3h-217-23
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1172)

BMS3h-217-24
GACATCCTGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGCAGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1173)

BMS3h-217-25
GACATCCAGATGACCCAGTCTCCATCCTCCCTGTCTGCATCTGTAGGAGACCGTGTCACCATCACTTGCCGGGCAAGTC
ATTTTATTGGTACTCTGGTATCTTGGTACCAGCAGAAACCGGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTACGGCCAAGGGACCAAGGTGGAAA
TCAAACGG (SEQ ID NO: 1174)

BMS3h-217-26
GACATCCAGATGACCCAGTCTCCATCCTCTCTGTCTGCATCTGTAGGAGACCGTGTCACCATCACTTGCCGGGCAAGTC
ATTTTATTGGTACTCTGGTATCTTGGTACCAGCAGAAACAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACTTTCGGCCAAGGGACCAAGGTGGAAA
ACAAACGG (SEQ ID NO: 1175)

BMS3h-217-27
GACATCAAGATGACCCAGTCTCCATCCTCCCTGTCTGCATCTGTAGGAGACCGTGTCACCATCACTTGCCGGGCGAGTC
ATTTTATTGGTACTCTGGTATCTTGGTACCAGCAGAAACCAGGGAAAGCCCCAAAGCTCCTGATCACTTATGGTTCCAT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1176)

BMS3h-217-28
GACATCCAGATGACCCAGTCTCCATCCTCCCTGTCTGCATCTGTAGGAGACCGTGTCACCATCACTTGCCAGGCAAGTC
ATTTTATTGGTACTCTGGTATCCTGGTACCAGCAGAAACAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCCGCGACGTTCGGCCAAGGGACCAAGGTGGAAA
TCAAACGG (SEQ ID NO: 1177)

BMS3h-217-29
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCAGAAACAGGGAAAGCCCCTAAGCTCCTGATCACTTATGGTTCCTG
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1178)

BMS3h-217-30
GACATCCAGATGACCCAGTCTCCATCCTCCCTGTCTGCATCTGTTGGAGACCGTGTCACCATCACTTGCCGGGCAAGTC
ATTTTATTGGTACTCTGTTATCTTGGTACCAGCTGAAACCAGGGAAAGCCCCTAAGCTCCTGATCACTTATGGTTCCTG
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1179)

BMS3h-217-31
GACATCCAGATGACCCAGTCTCCATCCTCCCTGTCTGCATCTGTAGGAGACCGTGTCACCATCACTTGCCGGGCAAGTC
ATTTTATTGGTACTCTGTTATCTTGGTACCAGCAGAAACCGGGGAAAGCCCCTAAGCTCCTGATCACTTATGGTTCCTT
GTTGCAAAGTGGGGTCCCATCACGTTTCAGTGGCAGTGGATTTGGGACAGATTTCACTCTCACCATCAGCAGTCTGCAA
CCTGAAGATTTTGCTACGTACTACTGTGGTCAGGAGGTGCTGTGGCCTGCGACGTTCGGCCAAGGGACTAAGGTGGAAA
TCAAACGG (SEQ ID NO: 1180)

BMS3h-217-32
GACATCCAGATGACCCAGTCTCCATCCTCCCTGTCTGCATCTGTAGGAGACCGTGTCTCCATCACTTGCCGAGCAAGTC
ATTTTATTGGTACTCTGTTATCTTGGTACCAGCAGAAACCAGGGAAAGCCCCTAAGCTCCTGATCACTTATGGTTCCTT
GTTGCAAAGTGGGGTCCCATCACGTTTCAGTGGCAGTGGATTTGGGACAGATTTCACTCTCACCATCAGCAGTCTGCAA
CCTGAAGATCTTGCTACGTACTACTGTGGTCAGGAGGTGCTGTGGCCTGCGACGTTCGGCCAAGGGACCAAGGTGGAAA
TCAAACGG (SEQ ID NO: 1181)

TABLE 4-continued

Human Anti-CD40 Variable Domain Encoding Nucleotide Sequences

BMS3h-217-33
GACATCCAGATGACCCAGTCTCCATCCTCCCTGTCTGCATCTGTAGGAGACCGTGTCACCATCACTTGCCAGGCAAGTC
ATTTTATTGGTACTCTGTTATCTTGGTACCAGCAGAAACCAGGGAAAGCCCCTAAGCTCCTGATCACTTATGGTTCCTT
GTTGCAAAGTGGGGTCCCATCACGTTTCAGTGGCAGTGGATTTGGGACAGATTTCACTCTCACCATCAGCAGTCTGCAA
CCCGAAGATTTTGCTACGTACTACTGTGGTCAGGAGGTGCTGTGGCCTGCGACGTTCGGCCAAGGGACCAAGGTGGAAA
TCAAACGG (SEQ ID NO: 1182)

BMS3h-217-34
GACATCCAGATGACCCAGTCTCCATCCTCCCTGTCTGCATCAGTAGGAGACCGTGTCACCATCACTTGCCGGGCAAGTC
ATTTTATTGGTACTCTGTTATCTTGGTACCAGCAGAAACCTGGGAAAGCCCCTAAGCTCCTGATCACTTATGGTTCCTT
GTTGCAAAGTGGGGTCCCATCACGTTTCAGTGGCAGTGGATTTGGGACAGAATTCACTCTCACCATCGGCAGTCTGCAA
CCTGAAGATTTTGCTACGTACTACTGTGGTCAGGGGGTGCTGTGGCCTGCGACGTTCGGCCAAGGGACCAAGGTGGAAA
TCAAACGG (SEQ ID NO: 1183)

BMS3h-217-35
GACATCCAGATGACCCAGTCACCATCCTCCCTGTCTGCATCTGTAGGAGACCGTGTCACCATCACTTGCCGGGCAAGTC
ATTTTATTGGTACTCTGTTATCTTGGTACCAGCAGAAACCAGGGAAAGCCACTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTCCGACGTTCGGCCAAGGGACCAAGGTGGAAA
TCAAACGG (SEQ ID NO: 1184)

BMS3h-217-2301
GACATCCAGATGACCCAGTCTCCATCCTCCCTGTCTGCATCTGTAGGAGACCGTGTCACCATCACTTGCCGGGCAAGTC
ACTTCATTGCCAGTCTGTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1185)

BMS3h-217-2302
GACATCCAGATGACCCAGTCTCCATCCTCCCTGTCTGCATCTGTAGGAGACCGTGTCACCATCACTTGCCGGGCAAGTC
ATTTCATTGCCCAGCTGTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1186)

BMS3h-217-2303
GACATCCAGATGACCCAGTCTCCATCCTCCCTGTCTGCATCTGTAGGAGACCGTGTCACCATCACTTGCCGGGCAAGTC
ATTTCATTGCCCAGCTGTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAGACGG (SEQ ID NO: 1187)

BMS3h-217-2304
GACATCCAGATGACCCAGTCTCCATCCTCCCTGTCTGCATCTGTAGGAGACCGTGTCACCATCACTTGCCGGGCAAGTC
ATTACATTGCCTCCCTGTTATCTTGGTACCAGGTGAAACCAGGGAAAGCCCCTAAGCTCCTGATCACTTATGGTTCCTT
GTTGCAGAGTGGGGCCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1188)

BMS3h-217-2305
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTGGGCCTCCTA
CTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1189)

BMS3h-217-2306
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTGGACGTCCTA
CTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1190)

BMS3h-217-2307
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTGGTCGTCCTA
CTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1191)

BMS3h-217-2308
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTGGGGGTCCTG
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1192)

TABLE 4-continued

Human Anti-CD40 Variable Domain Encoding Nucleotide Sequences

BMS3h-217-2309
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTGGGCGTCCTG
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1193)

BMS3h-217-2310
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTGGAGCTCCTG
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1194)

BMS3h-217-2311
GACATCCAGATGACCCAGTCTCCATCCTCCCTGTCTGCATCTGTAGGAGACCGTGTCACCATCACTTGCCGGGCAAGTC
ATTGGATTGCCCAGCTGTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1195)

BMS3h-217-2312
GACATCCAGATGACCCAGTCTCCATCCTCCCTGTCTGCATCTGTAGGAGACCGTGTCACCATCACTTGCCGGGCAAGTC
ATTTTATTGGTTCGCTCTTACGCTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1196)

BMS3h-217-2313
GACATCCAGATGACCCAGTCTCCATCCTCCCTGTCTGCATCTGTAGGAGACCGTGTCACCATCACTTGCCGGGCAAGTC
ATCGGATTGCCCAGCTGTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1197)

BMS3h-217-2314
GACATCCAGATGACCCAGTCTCCATCCTCCCTGTCTGCATCTGTAGGAGACCGTGTCACCATCACTTGCCGGGCAAGTC
ATTACATTGCCTCCCTGTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1198)

BMS3h-217-2315
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCCGGTTCGGCTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1199)

BMS3h-217-2316
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTACAAGTCCTA
CTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1200)

BMS3h-217-2317
GACATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTGGGGCTCCTA
CTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1201)

BMS3h-217-2318
GACATCCAGATGACCCAGTCTCCATCCTCCCTGTCTGCATCTGTAGGAGACCGTGTCACCATCACTTGCCGGGCAAGTC
ATTTTATTTGGGGGCCCTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTCTGCTACGTACTACTGTGGTCAGGGGGTGCTGTGGCCTGCGACGTTCGGCCAAGGGACAACGGTGGAAA
TCAAACGG (SEQ ID NO: 1202)

BMS3h-217-2319
GACATCCAGATGACCCAGTCTCCATCCTCCCTGTCTGCATCTGTAGGAGACCGTGTCACCATCACTTGCCGGGCAAGTC
ATTGGATTGCCACCCTGTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1203)

TABLE 4-continued

Human Anti-CD40 Variable Domain Encoding Nucleotide Sequences

BMS3h-217-2320
GACATCCAGATGACCCAGTCTCCATCCTCCCTGTCTGCATCTGTAGGAGACCGTGTCACCATCACTTGCCGGGCAAGTC
ATTTTATTTGGGGGCCCTTATCTTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1204)

BMS3h-217-2321
GACATCCAGATGACCCAGTCTCCATCCTCCCTGTCTGCATCTGTAGGAGACCGTGTCACCATCACTTGCCGGGCAAGTC
ATTTTATTGGTAGCCTCTTAAACTGGTACCAGGTGAAACCAGGGAAAGCCCCTAAGCTCCTGATCACTTATGGTTCCTT
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1205)

BMS3h-217-2322
GGCATCCAGATGACCCAGTCTCCATCCTCCCTGTCTGCATCTGTAGGAGACCGTGTCACCATCACTTGCCGGGCAAGTC
ATTTTATTGGTAGTCTGTTATCTTGGTACCAGGTGAAACCAGGGAAAGCCCCTAAGCTCCTGATCACTTACGGGTCCTG
GTTGCAAAGTGGGGTCCCATCACGTTTCAGTGGCAGTGGATCTGGGACAGATTTCACTCTCACCATCAGCAGTCTGCAA
CCTGAAGATTTTGCTACGTACTACTGTGGTCAGGGGGTGCTGTGGCCTGCGACGTTCGGCCAAGGGACAACGGTGGAAA
TCAAACGG (SEQ ID NO: 1206)

Example 1

Generation of Human Anti-CD40 Variable Domains BMS3h-1 Through BMS3h-225

The following example describes the generation of a series of anti-human CD40 variable domains, designated BMS3h-1 through BMS3h-225. Following recombinant expression of a repertoire of single immunoglobulin variable domains on the surface of phage, selection is performed by contacting the phage repertoire with immobilized target antigen, washing to remove unbound phage, and propagating the bound phage. This process frequently referred to as "panning." It is applicable to the screening of single immunoglobulin variable domains, as well as other antibody fragments that can be expressed on a display library, e.g., scFv, Fab, and Fab'. Alternatively, phage may be pre-selected for the expression of properly folded member variants by panning against an immobilized generic ligand (e.g., protein A or protein L) that is only bound by folded members. This has the advantage of reducing the proportion of non-functional members, thereby increasing the proportion of members likely to bind a target antigen. Pre-selection with generic ligands is taught in WO 99/20749, for example. The screening of phage antibody libraries is generally described, for example, by Harrison et al., Meth. Enzymol. 267: 83-109 (1996).

Screening is commonly performed using purified antigen immobilized on a solid support, for example, plastic tubes or wells, or on a chromatography matrix, for example Sepharose™ (Pharmacia). Screening or selection can also be performed on complex antigens, such as the surface of cells (Marks et al., BioTechnology 11: 1145 (1993); de Kruif et al., Proc. Natl. Acad. Sci. USA 92: 3938 (1995)). Another alternative involves selection by binding biotinylated antigen in solution, followed by capture on streptavidin-coated beads.

Clones BMS3h-1 to BMS3h-69:

Three rounds of selections using decreasing concentrations of antigen (100 nM at round 1; 10 nM at round 2; 1 nM at round 3) were performed in parallel against both biotinylated human CD40 monomer (supplied by BMS, 1.5 moles biotin/mole CD40) and biotinylated human CD40-Ig (supplied by BMS, 3.3 moles biotin/mole CD40-Ig). Phage from the naïve 4G and 6G Domantis dAb libraries were combined as follows before initiating selections:
1) 4G+6G VH CDR3 lengths between 7-9 amino acids.
2) 4G+6G VH CDR3 lengths between 10-12 amino acids.
3) 4G+6G VH CDR3 lengths between 13-15 amino acids.
4) 4G VK
5) 6G VK Each round of selection involved adding the desired concentration of antigen to a mixture of 750 µl of phage from one of the nave library pools or subsequent selection output phage and 750 µl of PBS+2% Marvel (Phosphate Buffered Saline containing 2% (w/v) Marvel [Premier Foods, UK]) and incubating at room temperature for 1 hour by mixing end-over-end. The biotinylated antigen phage complex was then captured by adding 100 µl of resuspended Dynabeads® M-280 Streptavidin [Invitrogen, UK] and incubated for 5 minutes with mixing end-over-end at room temperature. The Dynabeads® were then recovered using a KingFisher™ magnetic separator [Thermo Fisher Scientific, UK] and washed 7×1 ml PBS+0.1% Tween 20 (PBS containing 0.1% (v/v) polyoxyethylenesorbitan monolaurate [Sigma-Aldrich, UK], PBST) followed by 1×1 ml PBS. Bound phage retained on the washed Dynabeads® were eluted by incubation with 500 µl of trypsin-PBS (50 µl of 10 mg/ml trypsin [Sigma-Aldrich, UK] dissolved in 50 mM Tris-HCl pH 7.4, 1 mM $CaCl_2$ added to 450 µl PBS). The phage-containing solution was recovered and 250 µl used to infect 1.75 ml of logarithmic growth phase E. coli TG1 (at an $OD_{600}$ of 0.4) for 30 minutes at 37° C. The E. coli TG1 phage infected culture was centrifuged at 11,600 g in a micro centrifuge for 1 minute. The resulting cell pellet was resuspended in 1 ml 2×TY (16 g Tryptone, 10 g Yeast Extract and 5 g NaCl in 1 liter, autoclaved for 15 minutes at 121° C.) and plated onto a 9 cm Petri dish containing TY supplemented with 15 µg/ml tetracycline. The plates were incubated overnight at 37° C. Then 2 ml of 2×TY supplemented with 15% glycerol was added to each plate, and the cells were loosened with a glass spreader and mixed thoroughly. Fifty microliters of the scraped bacteria were used to inoculate 50 ml of 2×TY supplemented with 15 µg/ml tetracycline and grown overnight at 37° C. with shaking at 250 rpm. The overnight culture was centrifuged at 3,300 g for 15 min to pellet the bacteria. To precipitate phage, 10 ml PEG/NaCl (20% Polyethylene glycol 8000, 2.5 M NaCl) was added to 40 ml supernatant. The phage/PEG solution was mixed and left on ice for 1 h, then spun at 3,300 g for 30 min at 4° C., and the supernatant discarded. The pellet was resuspended in 2 ml PBS and spun at 11,600 g for 10 min in a micro centrifuge to remove the remaining bacterial debris. The resultant supernatant containing phage was then used for the next round of selection against the appropriate biotinylated CD40 antigen.

Monoclonal phage ELISAs were carried out following selection rounds 2 and 3. All washes were performed using 3 washes of 250 µl PBST followed by 3 washes of 250 µl PBS. The plates were coated overnight at 4° C. with 50 µl/well of 1 µg/ml NeutrAvidin (Thermo Scientific, UK) in 0.2 M carbonate-bicarbonate buffer, pH 9.4. The plates were washed and then blocked with 2% MPBS (2% w/v Marvel skimmed milk powder [Premier Foods] in PBS) for 1 hour at room temperature. The plates were then washed and incubated with 50 µl/well of 0.7 biotinylated human CD40 in 2% MPBS. The plates were washed, and phage supernatants were added to an equal volume of 2% MPBS. The plates were then incubated for 1 hour at room temperature. The plates were washed and bound phage detected with anti-M13-HRP conjugate (GE Healthcare, UK) diluted 1:5000 in 2% MPBS and incubated for 1 hour at room temperature. The plates were washed, and the ELISA was developed using SureBlue™ 1-Component TMB MicroWell Peroxidase solution (KPL Inc, USA). Specific phage were identified by comparison to plates coated with NeutrAvidin but without biotinylated CD40. A MidiPrep was used to isolate dAb V-genes from pDOM4 (Domantis) round 2 and round 3 outputs and cloned into pDOM5 (Domantis). pDOM4, disclosed in WO 2007/085815, is a derivative of the Fd phage vector in which the gene III signal peptide sequence is replaced with the yeast glycolipid anchored surface protein (GAS) signal peptide (WO 2005/093074). pDOM4 also contains a c-myc tag between the leader sequence and gene III, which puts the gene III back in frame.

Binding dAbs were identified as follows. Ninety-six individual colonies (in pDOM5) were picked from each output into 200 µL Terrific Broth containing OnEx Autoinduction media (Novagen, UK) overnight at 37° C. with shaking at 250 rpm in Costar™ 96 Well Cell Culture Clusters (Corning Incorporated, USA). The cultures were centrifuged to pellet the cells, and the supernatants were assayed by antigen binding ELISA for CD40 binding dAbs. MaxiSorp™ 96 well immunoplates (Nunc, USA) were coated overnight at 4° C. with 50 µl/well of 1 µg/ml NeutrAvidin in 0.2 M carbonate-bicarbonate buffer, pH 9.4. All washes were as described for the phage ELISA. The plates were blocked for 1 hour at room temperature with 200 µl of PBS containing 1% Tween 20. The plate was then washed and incubated with 50 µl/well of 0.7 µg/ml biotinylated human CD40 in 0.1% PBST. The clarified dAb-containing culture supernatant was added to the ELISA plate with an equal volume of 0.1% PBST. The plates were incubated for 1 hour at room temperature and then washed. Bound dAb was detected using a two step process: firstly 9E10 (anti-myc IgG, Sigma-Aldrich, UK) diluted 1:2000 in 0.1% PBST was added for 1 hour at room temperature then washed, followed by anti-mouse Fc-HRP (Sigma-Aldrich, UK) diluted 1:2000 in 0.1% PBST for 1 hour at room temperature. The plates were washed, and the ELISA was developed using SureBlue® 1-Component TMB MicroWell Peroxidase solution (KPL Inc, USA). The color was allowed to develop, and the colorimetric reaction was stopped by the addition of an equal volume of 1 M HCl. The ELISA plate was read at 450 nm. Specific phage were identified by comparison to plates coated with NeutrAvidin but without biotinylated CD40.

Clones specific for CD40 were tested in either the bead- or ELISA-based receptor-binding assay (RBA) to assess for inhibition of CD40 ligand binding. Domain antibodies that showed inhibition in the RBA were tested in the B-cell proliferation assay and then in a variety of other in vitro cell assays. These assays are described in greater detail below.
BMS3h-106 to -225:

BMS3h-106 to -225 were isolated from selections against biotinylated CD40 or biotinylated CD40-Fc as described for BMS3h-1 to BMS3h-69, but with the following modifications. Phage from the naïve 4G and 6G libraries were combined as follows before initiating selections:

6) 4G VH CDR3 lengths between 7-9 amino acids.
7) 4G VH CDR3 lengths between 10-12 amino acids.
8) 4G VH CDR3 lengths between 13-15 amino acids.
9) 6G VH CDR3 lengths between 7-9 amino acids.
10) 6G VH CDR3 lengths between 10-12 amino acids.
11) 6G VH CDR3 lengths between 13-15 amino acids.
12) 4G VK
13) 6G VK Round one was performed at an antigen concentration of 160 nM for CD40-Fc and 100 nM for CD40. Output titres were in the range $2.0 \times 10^4$ to $9.0 \times 10^7$ TU/ml (functional viral titre).

For round two, enriched phage from round one were combined in pairs before using in selections:

1) 4G+6G VH CDR3 lengths between 7-9 amino acids (pools 1+4 from round 1).
2) 4G+6G VH CDR3 lengths between 10-12 amino acids (pools 2+5 from round 1).
3) 4G+6G VH CDR3 lengths between 13-15 amino acids (pools 3+6 from round 1).
4) 4G+6G VK (pools 7+8 from round 1)

Selections were performed at an antigen concentration of 100 nM, and the antigen-phage complexes were captured using M-280 tosyl-activated Dynabeads® (Invitrogen) that had been coupled with NeutrAvidin (Thermo Fisher Scientific, UK). Output titres were in the range $6.5 \times 10^7$ to $7.5 \times 10^8$ TU/ml.

Round three was performed at an antigen concentration of 20 nM and, in the case of the CD40-Fc selections, in the presence of 6.7 µM free human Fc tail (BMS). Output titres were in the range $4.3 \times 10^7$ to $1.6 \times 10^9$ TU/ml.

Round four was performed as described for round two but at an antigen concentration of 2 nM and in the presence and absence of 500-fold excess unlabelled CD40-Fc. The addition of this competitor was made after the initial one hour incubation of the phage with the biotinylated antigen, and the mixture was then incubated overnight, as before. This competition step was included with the aim of enhancing selection of dAbs with a slower off-rate. Output titres were in the range $1.8 \times 10^7$ to $4.4 \times 10^7$ without competition and $1.8 \times 10^6$ to $2.3 \times 10^7$ TU/ml with competition.

To monitor the progress of the selections, monoclonal phage ELISAs were carried out following rounds 2 and 3. These were performed as described for BMS3h-1 to BMS3h-69. Binding dAbs were identified as described for BMS3h-1 to BMS3h-69 except that, in the case of the VK library screening, protein L was included at a final concentration of 0.8 µg/ml. Addition of protein L increased the signal strength by cross-linking the dAbs.
BMS3h-70 to -105:

BMS3h-70 to -105 were isolated from selections against antigen that had been passively adsorbed to immunotubes. Phage from the naïve 4G and 6G Domantis dAb libraries were combined as follows before initiating selections:

1) 4G VH CDR3 lengths between 7-9 amino acids.
2) 4G VH CDR3 lengths between 10-12 amino acids.
3) 4G VH CDR3 lengths between 13-15 amino acids.

4) 6G VH CDR3 lengths between 7-9 amino acids.
5) 6G VH CDR3 lengths between 10-12 amino acids.
6) 6G VH CDR3 lengths between 13-15 amino acids.
7) 4G VK
8) 6G VK For the first round of selection, 1 ml of 10 µg/ml human CD40-Fc fusion (BMS) in 0.2 M carbonate-bicarbonate buffer, pH 9.4, was added to a Nuns MaxiSorp™ immunotube and then incubated overnight at 4° C. with rolling. The tube was then emptied and washed three times with phosphate buffered saline (PBS). The tube was then blocked by filling to the brim with MPBS and incubating for 1 h at room temperature. The tube was then emptied and washed three times with PBS. Library phage in 4 ml MPBS Were added to the tube and incubated for 1 hour with rotation end-over-end at room temperature.

The tube was emptied and washed 10 times with PBST (PBS with 0.1% (v/v) Tween 20). Bound phage retained on the washed tube were eluted by incubation with 500 µl of trypsin-PBS (50 µl of 10 mg/ml trypsin [Sigma-Aldrich, UK] dissolved in 50 mM Tris-HCl pH 7.4, 1 mM $CaCl_2$ added to 450 µl PBS) with rotation end-over-end for 10 min at room temperature. The phage-containing solution was recovered, and 250 µl were used to infect 1.75 ml of logarithmic growth phase E. coli TG1 (at an $OD_{600}$ of 0.4) for 30 minutes at 37° C. The E. coli TG1 phage infected culture was centrifuged at 11,600 g in a microcentrifuge for 1 min, and the resulting cell pellet was re-suspended in 1 ml 2×TY (16 g Tryptone, 10 g Yeast Extract, and 5 g NaCl in 1 liter. The suspension was autoclaved for 15 minutes at 121° C.) and plated onto a 9 cm Petri dish containing LB agar supplemented with 15 µg/ml tetracycline. The plates were incubated overnight at 37° C. Two milliliters of 2×TY supplemented with 15% glycerol was then added to each plate, and the cells were loosened with a glass spreader and mixed thoroughly.

Fifty microliters of the scraped bacteria were used to inoculate 50 ml of 2×TY supplemented with 15 µg/ml tetracycline and grown overnight at 37° C. with shaking at 250 rpm. The overnight culture was centrifuged at 3,300 g for 15 min to pellet the bacteria. To precipitate phage, 10 ml PEG/NaCl (20% Polyethylene glycol 8000, 2.5 M NaCl) was added to 40 ml supernatant. The phage/PEG solution was mixed and left on ice for 1 h. The solution was then spun at 3,300 g for 30 min at 4° C., and the supernatant was discarded. The pellet was re-suspended in 2 ml PBS and spun at 11,600 g for 10 min in a micro centrifuge to remove the remaining bacterial debris. The resultant supernatant containing phage was then used for the next round of selection against CD40-Fc antigen. Output titres from round one were in the range $7.5 \times 10^4$ to $1.5 \times 10^7$ TU/ml (transforming units per ml).

A second round of selection was performed using enriched phage recovered from the first round of selection. This was performed exactly as described above and the output titres were in the range $2.5 \times 10^7$ to $1.2 \times 10^8$ TU/ml.

A third round of selection was performed using enriched phage recovered from the second round of selection. These were performed as described above but with an antigen concentration of 1 µg/ml. Output titres were in the range $5.1 \times 10^7$ to $7.5 \times 10^8$ TU/ml.

To monitor the progress of the selections, monoclonal phage ELISAs were carried out following rounds 2 and 3. A sample of individual colonies were picked into 200 µl. 2×TY supplemented with 15 µg/ml tetracycline and incubated overnight at 37° C. with shaking at 250 rpm in Costar® 96 Well Cell Culture Clusters (Corning Incorporated, USA). The cultures were centrifuged to pellet the cells, and the supernatants were assayed by antigen binding ELISA for CD40-binding phage dAbs. All washes were performed using 3 washes of 250 µl PBST followed by 3 washes of 250 µl PBS MaxiSorp™ 96 well immunoplates (Nunc, USA) were coated overnight at 4° C. with 50 µl/well of 0.5 µg/ml CD40-Fc (BMS) in 0.2 M carbonate-bicarbonate buffer, pH 9.4. The plates were washed and then blocked with 250 µl of 2% MPBS for 1 hour at room temperature. The plates were washed, and phage supernatants were added to an equal volume of 2% MPBS and incubated for 1 hour at room temperature. The plates were washed, and bound phage were detected with anti-M13-HRP conjugate (GE Healthcare, UK) diluted 1:5000 in 2% MPBS and incubated for 1 hour at room temperature. The plates were washed, and the ELISA was developed using SureBlue™ 1-Component TMB Micro ell Peroxidase solution (KPL Inc, USA). Specific phage dAbs were identified by comparison to plates coated with free Fc.

The dAb genes from each of the above rounds two and three selection outputs were sub-cloned, as a pool, into soluble expression vector pDOM5 in E. coli strain HB2151. This vector allowed expression of free dAb with a c-myc tag (Roche Diagnostics GmbH) in E. coli and secretion to the supernatant.

CD40-binding dAbs from passive selections were identified as follows. Ninety-six individual colonies (in pDOM5) were picked from each output into 200 µL Terrific Broth containing OnEx Autoinduction media (Novagen, UK) overnight at 37° C. with shaking at 250 rpm in Costar® 96 Well Cell Culture Clusters (Corning incorporated, USA). The cultures were centrifuged to pellet the cells, and the supernatants were assayed by antigen binding ELISA for CD40 binding dAbs. MaxiSorp™ 96 well immunoplates (Nunc, USA) were coated overnight at 4° C. with 50 µl/well of 0.5 µg/ml CD40-Fc (BMS) in 0.2 M carbonate-bicarbonate buffer, pH 9.4. All washes were as described for the phage ELISA. The plates were blocked for 1 hour at room temperature with 250 µl of PBS containing 1% Tween 20 (PBST). The clarified dAb-containing culture supernatant was added to the ELISA plate with an equal volume of 0.1% PBST. The plates were incubated for 1 hour at room temperature and then washed. Bound dAb was detected using a two step process: firstly biotinylated 9E10 (anti-myc IgG, Sigma-Aldrich, UK) diluted 1:2000 in 0.1% PBST was added for 1 hour at room temperature then washed, followed by streptavidin-HRP (Bender MedSystems, Austria) diluted 1:5000 in 0.1% PBST for 1 hour at room temperature. The plates were washed and the ELISA developed using SureBlue™ 1-Component TMB. Specific dAbs were identified by comparison to plates coated with free Fc.

Clones specific for CD40 were tested in either the bead- or ELISA-based receptor-binding assay (RBA) to assess for inhibition of CD40 ligand binding. The potency measurements obtained from the RBA are given in Table 5 (Primary Screening effort). Domain antibodies that showed inhibition in the RBA were tested in the B-cell proliferation assay and then in a variety of other in vitro cell assays.

BMS3h-210 to -225

BMS3h-210 to -225 were isolated from selections against whole cells. Phage from the naïve 4G and 6G Domantis dAb libraries were combined as follows before initiating selections:

1) 4G+6G VH CDR3 lengths between 7-9 amino acids.
2) 4G+6G VH CDR3 lengths between 10-12 amino acids.
3) 4G+6G VH CDR3 lengths between 13-15 amino acids.
4) 4G and 6G VK For round one a DG44 CHO cell line stably transfected with cell-surface expressed human CD40 (supplied by BMS) was used as antigen. Prior to selection against these cells, the library pools outlined above were incubated with non-transfected CHO cells to deplete them of phage displaying dAbs specific for cell surface antigens other than CD40. Both types of cells were harvested by incubation with Versene (Invitrogen) before assessing for viability. Six million viable non-transfected CHO cells were re-suspended in 4 ml PBS with 2% (w/v) BSA (PBS/BSA) and rotated end-over-end at 4° C. for 1 hour to block. All subsequent steps were performed at 4° C. unless otherwise noted. The cells were centrifuged at 185 g for 5 min and the supernatant, containing the depleted library phage, transferred to a fresh tube. To this were added $6 \times 10^6$ viable CHO-CD40 cells in 1 ml PBS/BSA and the mixture was rotated for 1 hour. The cells were then washed five times by centrifuging at 185 g for 5 min and re-suspending in 10 ml PBS/BSA. After the final wash, the cells were pelleted as previously and were then re-suspended in 0.5 ml of 1 mg/ml trypsin type XIII from bovine pancreas (Sigma Aldrich, UK) in PBS supplemented with 5 mM Tris-HCl pH 7.4, 0.1 mM $CaCl_2$ and transferred to a microcentrifuge tube. The cells were rotated at room temperature for 10 min before centrifuging at 16000 g for 5 min. Eluted phage in the supernatant were used to infect E. coli and the output phage titres were determined to be between $5.1 \times 10^3$ and $2.7 \times 10^6$ TU/ml (transforming units per ml).

A second round of selection was performed using enriched phage recovered from the first round of selection. These were performed as above but without the initial depletion (de-selection) step and using RAMOS human B cells (ATCC) instead of CHO-CD40. Output titres were in the range $2.3 \times 10^5$ to $7.5 \times 10^3$ TU/ml.

A third round of selection was performed as for the second round. Output titres were in the range $1.9 \times 10^8$ to $3.5 \times 10^8$ TU/ml.

The dAb genes from each of the above rounds two and three selection outputs were sub-cloned, as a pool, into soluble expression vector pDOM5 in E. coli strain HB2151. This vector allowed expression of free dAb with a c-myc tag in E. coli and secretion to the supernatant.

Clones specific for CD40 were tested in either the CHO cell receptor-binding assay (RBA) to assess for inhibition of CD40 ligand binding. Domain antibodies that showed inhibition in the RBA were tested in the B-cell proliferation assay and then in a variety of other in vitro cell assays.

Affinity Maturation by Error-Prone PCR

Error-prone phage libraries were constructed for 13 BMS3h dAbs that showed neutralization activity in the B-cell proliferation assay described below in Example 6 (See TABLE 17). This was performed by using Mutazyme II polymerase (part of the GeneMorph II kit from Agilent Technologies) to randomly introduce errors into the dAb gene during amplification by polymerase chain reaction (PCR). The mutated dAb genes were cloned as a genetic fusion with the fd phage gene III protein under the control of the GAS 1 leader sequence in pDOM4 vector, which contained all the fd genes necessary to generate infective phage particles. These libraries were approximately $1 \times 10^8$ CFU (colony forming units) in size, with an error-rate of 2-5 amino acids per dAb gene.

Phage generated from these libraries were subjected to three rounds of selection against soluble biotinylated human CD40. The first round of phage selection was performed by premixing the phage library with 2% MPBS (phosphate buffered saline supplemented with 2% (w/v) Marvel dried skimmed milk powder) and adding biotinylated human CD40 (BMS) to a final concentration of 20 nM in a final volume of 1 ml. The mixture was incubated for at least one hour at room temperature with mixing end-over-end. The antigen-phage complexes were then captured using 50 μl of M-280 streptavidin Dynabeads® (Invitrogen) and washed 7 times with 1 ml PBST followed by a single wash in 1 ml PBS. The washed phage were eluted from the antigen/bead complex by incubating with 0.5 ml of 1 mg/ml trypsin type XIII from bovine pancreas (Sigma Aldrich, UK) in PBS supplemented with 5 mM Tris-HCl pH 7.4, 0.1 mM $CaCl_2$. Eluted phage were used to infect E. coli and the output phage titres were determined to be between $2 \times 10^5$ and $9 \times 10^7$ TU/ml (transforming units per ml).

A second round of selection was performed using enriched phage recovered from the first round of selection, with a final concentration of 2 nM biotinylated CD40 followed by capture using streptavidin beads as described above. Output titres were in the range $3 \times 10^4$ to $5 \times 10^6$ TU/ml.

A third round of selection using 2 nM biotinylated CD40 followed by capture using streptavidin beads was performed. The eluted phage titres were in the range $8 \times 10^4$ to $4 \times 10^6$ TU/ml.

BIAcore™ Screening

The dAb genes from each of the above round three selection outputs were sub-dozed, as a pool, into soluble expression vector pDOM13 (Domantis) in E. coli HB2151. The pDOM13 vector is also known as pDOM33 and is disclosed in WO/2008/149143. This vector allowed expression of free dAb in E. coli and secretion to the supernatant. Forty-seven individual colonies were picked from each of the outputs and expressed in 200 μl Terrific Broth (TB) containing Novagen Overnight Express Autoinduction media (Merck Chemicals, UK) overnight at 37° C. with shaking at 250 rpm in Costar® 96 Well Cell Culture Clusters (Corning Incorporated, USA). In the same plate, a single well was inoculated with E. coli expressing the appropriate parental (wild-type) dAb. The cultures were centrifuged to pellet the cells and the supernatants screened on a BIAcore™ 3000 instrument (GE Healthcare) for improvements in "off-rate" (i.e. dissociation rate constant, $k_d$) compared to parental dAb.

Approximately 1600 response units (RU) of biotinylated human CD40 (BMS) were immobilized on one flow-cell of a streptavidin (SA) BIAcore™ chip. A second flow cell without any ligand immobilized served as a reference flow-cell for inline referencing. Each dAb supernatant to be analyzed was diluted 1:3 in HBS-EP buffer (0.01 M HEPES pH 7.4 with 0.15 M NaCl, 3 mM EDTA and 0.005% v/v Surfactant P20, GE Healthcare). Ten microliters of each dAb supernatant were injected, using the instrument's KINJECT function, across the CD40-immobilized and reference flow-cells in series, with inline subtraction of the signal from the reference cell. The experiment was performed at 25° C. and with a flow rate of 10 μl/min of HBS-EP. After each injection had been completed, the dAb was allowed to dissociate from the ligand in buffer for 120 s before regeneration with a 5 μl injection of 10 mM glycine pH 2.0. BIAevaluation 4.1 software (GE Healthcare) was used to subtract the reference flow-cell trace from each analyte trace. The same software was used to perform an approximate fit of a 1:1 (Langmuir) kinetic model to the dissociation phase of the analyte traces. This model yielded approximate dissociation rate constants ("off-rate" or $k_d$) for each clone and allowed relative comparisons to be made with the wild type dAb.

Clones with improved off-rates were identified for all lineages except BMS3h-129 and -197. Clones with improved off-rates were tested in either the bead- or ELISA-based receptor-binding assay (RBA) to assess for improved potency as described above. The potency measurements obtained from the RBA are given in the Tables labeled "Error-Prone-Matured Clones." Clones that were more potent in the RBA were subsequently tested in a B-cell proliferation assay to assess for enhanced biological potency and these measurements obtained are given in TABLE 17. Domain antibodies that had improved potency in the B-cell proliferation assay were also tested in a variety of other in vitro cell assays.

Affinity Maturation by Triplet Scanning Diversification

Five improved-potency dAbs isolated from the error-prone maturation, BMS3h-37-2, -38-2, -56-2, -193-25 and -217-23, were chosen to be further affinity matured by triplet scanning diversification. Phage libraries were constructed based on these parents as described above for the error-prone libraries except that, instead of using error-prone PCR, a series of overlapping degenerate triplet oligonucleotides were used to diversify the complementarity determining (CDR) regions of each dAb. For each dAb to be affinity matured, oligonucleotides containing NNS codon triplets (see Arkin et al. (1992) Proc. Nat'l Acad. Sci. USA 89:7811-7815) were used to make a number of libraries for each CDR by slicing by overlap extension (SOE) PCR. The triplets diversified by the oligonucleotides for a given CDR overlapped by two codons, resulting in two to four libraries per CDR. The amino acid residues diversified in the BMS3h-37-2 libraries were at positions 30, 31, 32, 33, 35, 50, 52, 53, 55, 56, 95, 96, 97, and 98 (Kabat numbering). The residues diversified in the BMS3h-38-2 libraries were as for 37-2, but with the addition of position 100. The residues diversified in the BMS3h-56-2 libraries were as for 37-2, but with the addition of positions 100 and 101. The residues diversified in the BMS3h-193-25 and -217-23 libraries were at positions 27, 28, 30, 31, 32, 34, 49, 50, 51, 53, 89, 91, 92, 93, 94, and 96.

Phage generated from these libraries were pooled by CDR and selections performed as described above, except that, for BMS3h-37-2, -38-2, -56-2 and -193-25, the concentrations of antigen used were 10, 1 and 0.1 nM for rounds one, two and three, respectively. For BMS3h-217-23 the concentrations of antigen used were 20, 2 and 0.2 nM for rounds one, two and three, respectively. For BMS3h-193-25, which is cross-reactive for cynomolgus CD40, selections were also performed against cyno CD40 in parallel. Additionally, selection rounds two and three were performed in the presence and absence of 100- or 1000-fold excess unlabelled CD40, respectively. The addition of this competitor was made after the initial one hour incubation of the phage with the biotinylated antigen and the mixture was then incubated, as before, for a further hour. This competition step was included with the aim of enhancing selection of dAbs with a slower off-rate. Round one titres were in the range $1.4 \times 10^6$ to $1.4 \times 10^9$. Titres in round 2 were $1.3 \times 10^5$ to $4.0 \times 10^8$ without competition and $8.6 \times 10^4$ to $1.3 \times 10^8$ with competition. Titres in round 3 were $1.2 \times 10^5$ to $1.9 \times 10^8$ without competition and $6.0 \times 10^5$ to $1.2 \times 10^8$ with competition.

These selection outputs were sub-cloned and screened as described for the error-prone affinity maturation. Clones with improved off-rates were identified for all lineages except BMS3h-193-25. Clones with improved off-rates were tested in the ELISA receptor-binding assay (RBA) to assess for improved potency. The potency measurements obtained from the RBA are given in the Tables labeled "Further-Matured Clones." Clones that were more potent in the RBA were subsequently tested in a B-cell proliferation assay to assess for enhanced biological potency and these measurements obtained are given in TABLE 17. Domain antibodies that had improved potency in the B-cell proliferation assay were also tested in a variety of other in vitro cell assays.

Example 2

Screening Using Receptor Binding Assays (RBA)

Several in vitro receptor binding assays (RBA) were used to determined CD40 affinity of the anti-human CD40 variable domain amino acid sequences generated in Example 1. Three RBA formats were used: (1) a bead RBA, (2) an ELISA RBA, and (3) a CHO cell RBA.

Bead RBA:

Phosphate buffered saline (PBS) washed Sphero streptavidin polystyrene particles (Saxon Europe, UK) were coated with 0.5 µg/ml biotinylated human IZ-CD40L (BMS). After coating, biotinylated CD40L particles were washed in PBS and diluted 1:10 in 0.1% (w/v) bovine serum albumin (BSA) (Sigma-Aldrich, UK) in PBS assay buffer. In a 384-well clear bottom, black walled plate (Applied Biosystems) a dilution range of purified dAb, 0.25 µg/ml human CD40 (BMS, CY24FEB06-01), 1 in 5000 mouse anti-human IgG (Fc) mAb clone GG-7 (Sigma-Aldrich, UK), 0.25 µg/ml goat anti-mouse ALEXA Fluor® 647 (Invitrogen, Molecular probes, UK) and the biotinylated CD40L polystyrene particles were combined equally and allowed to incubate at room temperature for 6 hours in the absence of light. Following incubation, competitive binding of dAb vs. human CD40 to biotinylated CD40L particles was assessed using relative fluorescence with the AB8200 cellular detection mechanism (Applied Biosystems).

ELISA RBA:

Clear walled High Bind, 384-well plates (Corning, UK) were coated with 25 µl of 1 µg/ml Neutravidin in 0.2 M carbonate-bicarbonate buffer, pH 9.4 overnight at 4° C. The following day, assay plates were washed with 0.1% (v/v) Tween PBS buffer, blocked with 1% (w/v) BSA in PBS for 1 hour at room temperature and washed again. Following removal of excess washing buffer, 25 µl 1 µg/ml of biotinylated human IZ-CD40L (BMS) was incubated with the assay plates for 1 hour at room temperature. Simultaneously, a dilution range of purified dAb and 1 µg/ml of human CD40 (BMS, CY24FEB06-01) were complexed in a 1:1 ratio, Following washing of the assay plate, the dAb:human CD40 complex was incubated in the assay plate at room temperature for 2 hours with gentle agitation. Competitive binding of dAb vs. human CD40 to biotinylated CD40L was detected with sequential incubations of 1 in 5000 mouse anti-human IgG (Fc) mAb clone GG-7 (Sigma-Aldrich, UK) followed by 1 in 10,000 horse radish peroxidase (HRP) conjugated goat anti-mouse IgG (Fc) secondary detection antibody (Sigma-Aldrich, UK). Absorbance signal was measured using a SpectraMax® M5e plate reader (Molecular Devices) at 450 nm following neutralization with 1 M HCl solution.

Cell Assays: CD40 CHO Cell RBA:

Stably transfected human CD40 expressing CHO-DG44 cells or native CHO-DG44 cells (both BMS) were detached from cell culture flasks using Versene (Invitrogen). Forty thousand cells per well were seeded into 96-well High Bind, black walled, clear bottom plates (Corning, UK) in 0.1% (w/v) BSA PBS assay buffer with a dilution range of dAb, 0.25 µg/ml of biotinylated human IZ-CD40L (BMS), and 0.25 µg/ml of streptavidin ALEXA Fluor® 647 (Invitrogen, Molecular probes, UK). The mixture was incubated in the absence of light for 6 hours. Following incubation, competitive binding of dAb vs. human CD40 CHO cells to soluble biotinylated IZ-CD40L was assessed using relative fluorescence with the AB8200 cellular detection mechanism (Applied Biosystems).

TABLES 5-7 respectively show the results from a primary screening effort ("naïve clones") and subsequent rounds of affinity maturation ("error-prone matured clones" and "further-matured clones") for the tested anti-human CD40 dAbs.

TABLE 5

Primary Screening Effort:

| Naïve Clone | $EC_{50}$ Bead RBA (nM) | $EC_{50}$ ELISA RBA-(nM) | $EC_{50}$ cell RBA (CHO-CD40) (nM) |
|---|---|---|---|
| BMS3h-37 | 100, 200 | | |
| BMS3h-38 | 600, 650 | | >10000 |
| BMS3h-41 | 2000, 1600 | | >10000 |
| BMS3h-43 | 100, 50, 50 | | 5000 |
| BMS3h-56 | 1000, 500 | | |
| BMS3h-106 | 300, 1000, 500, 400 | | >10000 |
| BMS3h-129 | 5000 | | |
| BMS3h-131 | 500, >1000 | | |
| BMS3h-193 | 1000 | | |
| BMS3h-197 | 30 | | |
| BMS3h-198 | 80 | | 600 |
| BMS3h-202 | 3000, 3700 | | >10000 |
| BMS3h-217 | 800 | | 1400 |
| BMS3h-231 | | 670, 870 | |
| BMS3h-233 | | 2770 | |
| BMS3h-257 | | 3210, 1340 | |
| BMS3h-242 | | 390, 210 | |
| BMS3h-262 | | 1770, 1160 | |
| BMS3h-263 | | 3130 | |
| BMS3h-271 | | 370, 210 | |
| BMS3h-285 | | 168, 258 | |
| BMS3h-287 | | >10000, 6758 | |
| BMS3h-289 | | 2390, >10000 | |

TABLE 6

Error-Prone-Matured Clones:

| Clone | $EC_{50}$ ELISA RBA (nM) | $EC_{50}$ cell RBA (CHO-CD40) (nM) |
|---|---|---|
| BMS3h-37-2 | | 32 |
| BMS3h-37-4 | | 45 |
| BMS3h-37-11 | | 27 |
| BMS3h-38-5 | | 1000 |
| BMS3h-38-8 | | 2800 |
| BMS3h-41-3 | | 200 |
| BMS3h-41-10 | | 4300 |
| BMS3h-43-3 | | 320 |
| BMS3h-43-5 | | 90 |
| BMS3h-56-1 | 7.1 | |
| BMS3h-56-2 | 17.0 | |
| BMS3h-56-5 | 4.9, 7.5, 4.7 | 18, 28 |
| BMS3h-56-7 | 5.5 | |
| BMS3h-56-8 | 6.2 | |
| BMS3h-56-9 | 4.4, 5.5 | |
| BMS3h-56-16 | 7.0 | |
| BMS3h-56-17 | 66 | |
| BMS3h-56-18 | 6.5 | |
| BMS3h-56-19 | 5.5, 5.1 | |
| BMS3h-56-20 | 6.8 | |
| BMS3h-56-21 | 6.5, 6.2 | |
| BMS3h-56-22 | 6.5 | |
| BMS3h-56-23 | 24.5 | |
| BMS3h-56-24 | 11.7 | |

TABLE 6-continued

Error-Prone-Matured Clones:

| Clone | $EC_{50}$ ELISA RBA (nM) | $EC_{50}$ cell RBA (CHO-CD40) (nM) |
|---|---|---|
| BMS3h-56-25 | 5.5 | |
| BMS3h-56-26 | 5.0 | |
| BMS3h-56-27 | 16.3 | |
| BMS3h-56-28 | 8.9 | |
| BMS3h-56-29 | 9.7 | |
| BMS3h-56-30 | 24.2 | |
| BMS3h-56-31 | 61.0 | |
| BMS3h-193-5 | >300 | |
| BMS3h-193-7 | 300 | |
| BMS3h-193-10 | 200 | |
| BMS3h-193-11 | 300 | |
| BMS3h-193-12 | 200 | |
| BMS3h-193-15 | | 300 |
| BMS3h-193-18 | 100 | |
| BMS3h-193-19 | 100 | |
| BMS3h-193-25 | 140 | |
| BMS3h-193-26 | 100 | |
| BMS3h-193-27 | 100 | |
| BMS3h-193-29 | 360, 114 | |
| BMS3h-193-30 | 290, 116 | |
| BMS3h-198-1 | 12 | 70 |
| BMS3h-198-2 | | 115 |
| BMS3h-198-3 | | 330 |
| BMS3h-198-9 | 20 | |
| BMS3h-198-10 | 35 | |
| BMS3h-198-11 | 20 | |
| BMS3h-198-14 | 9 | |
| BMS3h-198-17 | 20 | |
| BMS3h-198-19 | 7.9 | |
| BMS3h-198-22 | 10 | |
| BMS3h-198-31 | 6.1 | |
| BMS3h-198-32 | 24.7 | |
| BMS3h-198-33 | 8.7 | |
| BMS3h-198-34 | 32.6 | |
| BMS3h-198-37 | 15.1 | |
| BMS3h-198-38 | 7.2 | |
| BMS3h-202-10 | | 7200 |
| BMS3h-202-11 | | 8300 |
| BMS3h-217-1 | 23 | |
| BMS3h-217-2 | 78 | |
| BMS3h-217-3 | 32 | |
| BMS3h-217-4 | partial, 15 | |
| BMS3h-217-5 | 65 | |
| BMS3h-217-6 | 26 | |
| BMS3h-217-7 | 39 | |
| BMS3h-217-8 | 6 | |
| BMS3h-217-9 | 53 | |
| BMS3h-217-14 | 8 | |
| BMS3h-217-15 | 21 | |
| BMS3h-217-16 | 9 | |
| BMS3h-217-17 | 60 | |
| BMS3h-217-23 | 16 | |

TABLE 7

Further-Matured Clones:

| Clone | $EC_{50}$ ELISA RBA (nM) | $EC_{50}$ ICAM1 cell assay (nM) | $EC_{50}$ cell RBA (CHO-CD40) (nM) |
|---|---|---|---|
| BMS3h-37-202 | 4.1, 35 | | |
| BMS3h-37-205 | 3.1, 4.4 | | |
| BMS3h-37-206 | 3.2, 8.9 | | |
| BMS3h-37-207 | 2.5, 6.6 | | |
| BMS3h-37-212 | 24 | | |
| BMS3h-37-213 | 16 | | |
| BMS3h-38-201 | 3.4, inactive | | |
| BMS3h-38-202 | 4.8 | | |
| BMS3h-38-203 | 5.5 | | |
| BMS3h-38-204 | 4.8 | | |

TABLE 7-continued

Further-Matured Clones:

| Clone | EC$_{50}$ ELISA RBA (nM) | EC$_{50}$ ICAM1 cell assay (nM) | EC$_{50}$ cell RBA (CHO-CD40) (nM) |
|---|---|---|---|
| BMS3h-38-205 | 4.5, 11.1 | | |
| BMS3h-38-209 | 10.2 | | |
| BMS3h-38-211 | 2.3, 13.8 | | |
| BMS3h-38-215 | 2.3, 3.6 | | |
| BMS3h-38-217 | 1.8, 2.2 | | |
| BMS3h-38-218 | 3.0 | | |
| BMS3h-38-219 | 1.8, 7.1 | | |
| BMS3h-38-223 | 5.7 | | |
| BMS3h-38-224 | 6.3 | | |
| BMS3h-38-225 | 8.8 | | |
| BMS3h-38-226 | 18.1 | | |
| BMS3h-38-228 | 4 | | |
| BMS3h-38-231 | 4.4 | | |
| BMS3h-38-235 | 1.5 | | |
| BMS3h-38-237 | 2 | | |
| BMS3h-38-238 | 5.1 | | |
| BMS3h-56-201 | 3.7, 2.3 | 10.0 | |
| BMS3h-56-202 | 3.4, 3.2 | 80.0 | |
| BMS3h-56-203 | 5.2, 4.3 | 70.0 | |
| BMS3h-56-204 | 4.5 | | |
| BMS3h-56-205 | 9.0 | | |
| BMS3h-56-206 | 2.9, 2.3 | 5.0 | |
| BMS3h-56-207 | 7.3 | | |
| BMS3h-56-215 | 3.2, 4.6 | 40.0 | |
| BMS3h-56-217 | 2.1, 12.6 | | |
| BMS3h-56-220 | 4.2 | | |
| BMS3h-56-223 | 5.0 | | |
| BMS3h-56-224 | 2.1, 4.2 | | |
| BMS3h-56-225 | 2.9 | | |
| BMS3h-56-229 | 4.1 | | |
| BMS3h-56-232 | 2.8, 3.7 | | |
| BMS3h-56-239 | 2.7 | | |
| BMS3h-56-243 | 9.9 | | |
| BMS3h-56-244 | 6.0 | | |
| BMS3h-56-246 | 11.1 | | |
| BMS3h-56-248 | 0.7 | | |
| BMS3h-56-253 | 1.3 | | |
| BMS3h-56-258 | 5.2 | 23.0 | 15 |
| BMS3h-56-261 | 5.7 | 42.4 | 17 |
| BMS3h-56-262 | 4.0 | 135.0 | 42 |
| BMS3h-56-265 | 18.8 | 289.0 | 88 |
| BMS3h-56-266 | 3.8 | 31.9 | 27 |
| BMS3h-56-269 | 3.3 | 34.2 | 24 |
| BMS3h-56-270 | 11.3 | 93.8 | 91 |
| BMS3h-193-2501 | 114 | | |
| BMS3h-193-2502 | 170 | | |
| BMS3h-193-2503 | 3000 | | |
| BMS3h-193-2504 | 140 | | |
| BMS3h-193-2505 | 500 | | |
| BMS3h-193-2506 | 180 | | |
| BMS3h-193-2507 | 160 | | |
| BMS3h-193-2510 | 170 | | |
| BMS3h-193-2511 | 270 | | |
| BMS3h-193-2512 | 600 | | |
| BMS3h-193-2513 | 130 | | |
| BMS3h-193-2514 | 525 | | |
| BMS3h-193-2515 | 100 | | |
| BMS3h-193-2516 | 100 | | |

Example 3

CD40 Binding Kinetics

The binding kinetics were determined for anti-human CD40 dAbs identified in the primary screening effort ("naïve clones") and subsequent rounds of affinity maturation ("error-prone matured clones"). The methods used directly measure the affinity of the dAbs for CD40.

A BIAcore™ 3000 instrument (GE Healthcare) was used to analyze the binding kinetics of CD40-specific dAbs to CD40. Approximately 600 response units (RU) of biotinylated human CD40 (BMS) were immobilized on one flow-cell of a streptavidin (SA) BIAcore™ chip. A second flow cell without any ligand immobilized served as a reference flow-cell for inline referencing. An appropriate doubling dilution series of each dAb to be analyzed was prepared in HBS-EP buffer (0.01 M HEPES pH 7.4 with 0.15 M NaCl, 3 mM EDTA and 0.005% v/v Surfactant P20, GE Healthcare). One hundred and eighty microliters of each dAb were injected in duplicate using the instrument's KINJECT function. Each dAb was injected across the CD40-immobilised and reference flow-cells in series with inline subtraction of the signal from the reference cell. The experiment was performed at 25° C. and a flow rate of 30 µl/min of HBS-EP. After each injection had been completed, the dAb was allowed to dissociate from the ligand in buffer for 300 s before regeneration with a 10 µl injection of 10 mM glycine pH 2.0. A reference injection of HBS-EP buffer blank (containing no analyte) was also injected under the same conditions, to serve as a second reference for subtraction from each analyte trace. BIAevaluation 4.1 software (GE Healthcare) was used to subtract both the reference flow-cell trace and the buffer blank trace from each analyte trace. The same software was used to perform a simultaneous, global fit of a 1:1 (Langmuir) kinetic model to the association and dissociation phases of the analyte dilution series traces. This model yielded association and dissociation rate constants ($k_a$ and $k_d$, respectively) and the equilibrium dissociation constant ($K_D$) of the interaction; these are detailed in TABLES 8 and 9.

TABLE 8

Naïve Clones:

| Clone | BIAcore™ $k_a$ (M$^{-1}$s$^{-1}$) | BIAcore™ $k_d$ (s$^{-1}$) | BIAcore™ $K_D$ (M) |
|---|---|---|---|
| BMS3h-37 | 1.9E+04 | 3.6E−03 | 1.9E−07 |
| BMS3h-38 | 2.1E+04 | 6.2E−03 | 3.0E−07 |
| BMS3h-41 | 9.9E+03 | 8.3E−03 | 8.4E−07 |
| BMS3h-43 | 1.4E+03 | 3.1E−03 | 2.1E−06 |
| BMS3h-56 | 2.3E+04 | 4.0E−03 | 1.8E−07 |
| BMS3h-106 | 1.3E+05 | 4.6E−02 | 3.5E−07 |
| BMS3h-107 | 2.0E+05 | 1.7E−01 | 8.5E−07 |
| BMS3h-129 | 4.7E+05 | 5.1E−01 | 1.1E−06 |
| BMS3h-131 | 2.4E+04 | 2.2E−02 | 9.3E−07 |
| BMS3h-197 | 8.1E+04 | 1.4E−02 | 1.8E−07 |
| BMS3h-198 | 1.6E+03 | 3.8E−04 | 2.4E−07 |
| BMS3h-202 | 1.7E+03 | 3.5E−03 | 2.0E−06 |

TABLE 9

Error-Prone Matured Clones:

| Clone | BIAcore™ $k_a$ (M$^{-1}$s$^{-1}$) | BIAcore™ $k_d$ (s$^{-1}$) | BIAcore™ $K_D$ (M) |
|---|---|---|---|
| BMS3h-37-2 | 1.0E+05 | 4.1E−04 | 4.0E−09 |
| BMS3h-37-5 | 3.9E+04 | 2.2E−04 | 5.5E−09 |
| BMS3h-37-9 | 1.5E+04 | 1.8E−04 | 1.2E−08 |
| BMS3h-38-1 | 3.2E+04 | 1.1E−03 | 3.3E−08 |
| BMS3h-38-2 | 6.1E+04 | 7.5E−04 | 1.2E−08 |
| BMS3h-38-3 | 7.5E+04 | 4.1E−04 | 5.5E−09 |
| BMS3h-41-1 | 5.1E+04 | 5.6E−04 | 1.1E−08 |
| BMS3h-43-1 | 4.4E+03 | 6.3E−04 | 1.4E−07 |
| BMS3h-43-3 | 3.1E+04 | 5.9E−04 | 1.9E−08 |
| BMS3h-56-1 | 9.8E+04 | 5.4E−04 | 5.5E−09 |
| BMS3h-56-2 | 1.1E+05 | 6.0E−04 | 5.3E−09 |
| BMS3h-56-5 | 1.1E+05 | 6.3E−04 | 5.9E−09 |
| BMS3h-56-7 | 1.3E+05 | 4.7E−04 | 3.5E−09 |
| BMS3h-56-9 | 1.5E+05 | 3.9E−04 | 2.6E−09 |
| BMS3h-131-2 | 7.9E+04 | 1.7E−03 | 2.1E−08 |

TABLE 9-continued

Error-Prone Matured Clones:

| Clone | BIAcore™ $k_a$ (M$^{-1}$s$^{-1}$) | BIAcore™ $k_d$ (s$^{-1}$) | BIAcore™ $K_D$ (M) |
|---|---|---|---|
| BMS3h-193-25 | 4.6E+05 | 3.7E−02 | 8.1E−08 |
| BMS3h-198-1 | 1.5E+04 | 1.8E−04 | 1.3E−08 |
| BMS3h-202-5 | 4.4E+03 | 1.3E−03 | 3.0E−07 |

Example 4

Biophysical Characterization

Anti-human CD40 dAbs identified in the primary screening effort ("naïve clones") and subsequent rounds of affinity maturation ("error-prone matured clones" and "further-matured clones") were further characterized by analysis of biophysical parameters. To measure the relative stability of the dAbs, their melting point was determined by differential scanning calorimetry (DSC). dAbs with a higher melting temperature are more stable. To determine whether the dAbs form multimeric aggregates in solution, the dAbs were assayed by size exclusion chromatography/multiangle laser light scattering (SEC-MALLS). The results are shown in TABLES 10-12.

TABLE 10

Naïve clones:

| Clone | DSC (Tm/° C.) | SEC-MALS solution state |
|---|---|---|
| BMS3h-38 | 59 | Monomer and dimer (<5%) |
| BMS3h-41 | 59 | Monomer and monomer-dimer equilibrium (<5%) |
| BMS3h-43 | | Dimer and trimer |
| BMS3h-56 | 57 | Monomer and dimer (<10%) |
| BMS3h-106 | | Monomer |
| BMS3h-107 | 63 | Monomer |
| BMS3h-129 | 59 | Monomer |
| BMS3h-193 | 56 | Monomer |
| BMS3h-197 | 62 & 53 | Monomer and dimer (<5%) |
| BMS3h-198 | 61 | Monomer |
| BMS3h-202 | 60 | Monomer and monomer-dimer equilibrium (<2%) |
| BMS3h-207 | | Dimer and tetramer |
| BMS3h-208 | | Monomer and dimer |
| BMS3h-217 | 57 | Dimer |
| BMS3h-233 | | Monomer |
| BMS3h-242 | | Monomer and monomer-dimer |
| BMS3h-262 | | Monomer |
| BMS3h-265 | | Dimer |
| BMS3h-271 | | Dimer |
| BMS3h-285 | | Monomer |

TABLE 11

Error-Prone-Matured Clones:

| Clone | DSC Tm/° C. | SEC-MALS solution state |
|---|---|---|
| BMS3h-37-1 | 57.2 | |
| BMS3h-37-2 | 56.2 | |
| BMS3h-37-9 | 59.7 | |
| BMS3h-37-11 | 60.0 | |
| BMS3h-56-1 | 49.6 | Monomer |
| BMS3h-56-2 | 63.0 | Monomer and dimer (<2%) |
| BMS3h-56-3 | 64.0 | Monomer (>98%) |
| BMS3h-56-5 | 51.2 | |
| BMS3h-41-1 | 56 | Monomer (~99%) |
| BMS3h-41-2 | 53.4 | |
| BMS3h-41-3 | 51.8 | |
| BMS3h-41-9 | 61 | Monomer and Monomer/Dimer rapid equilibrium (<2%) |
| BMS3h-41-12 | 49.8 | Monomer/Dimer |
| BMS3h-41-13 | | Monomer/Dimer |
| BMS3h-43-1 | 53 | Monomer (~99%) |
| BMS3h-43-3 | 51.2 | |
| BMS3h-43-5 | 48.2 | Monomer/Dimer |
| BMS3h-43-10 | 51.8 | |
| BMS3h-43-11 | 54.8 | |
| BMS3h-43-12 | | Dimer (60%) and Monomer (40%) |
| BMS3h-56-1 | 59.2 | Monomer/Dimer |
| BMS3h-56-2 | 60.1 | Monomer/Dimer |
| BMS3h-56-5 | 57 | Monomer (>95%) |
| BMS3h-56-6 | 57.5 | Monomer/Dimer |
| BMS3h-56-7 | 61 | Monomer + Monomer/Dimer rapid equilibrium (<5%) |
| BMS3h-56-8 | 58 | Monomer (>98%) |
| BMS3h-56-9 | 61 | Monomer + dimer (<5%) |
| BMS3h-56-14 | 60.1 | Monomer |
| BMS3h-193-8 | 60 | |
| BMS3h-193-12 | 52 | |
| BMS3h-193-16 | 54.5 & 65.7 | Monomer |
| BMS3h-193-19 | 56.8 | Monomer |
| BMS3h-193-25 | 55.8 | Monomer |
| BMS3h-193-29 | 60 | Monomer |
| BMS3h-193-30 | 58 | |
| BMS3h-198-1 | 52.5 | Monomer |
| BMS3h-198-2 | | Monomer |
| BMS3h-198-3 | 59 | |
| BMS3h-198-5 | 55.6 | |
| BMS3h-198-19 | 60.7 | |
| BMS3h-198-24 | 59.9 | Monomer |
| BMS3h-198-28 | 60.3 | Monomer |
| BMS3h-202-1 | 56.8 | Monomer |
| BMS3h-202-5 | 55.5 | Trimer (60%) and Monomer/Dimer (40%) |
| BMS3h-202-10 | 58.3 | Trimer (60%) and Monomer/Dimer (40%) |
| BMS3h-217-1 | | Monomer/Dimer |
| BMS3h-217-2 | | Dimer |
| BMS3h-217-3 | | Dimer |
| BMS3h-217-4 | | Monomer/Dimer |
| BMS3h-217-5 | | Dimer |
| BMS3h-217-6 | | Dimer |
| BMS3h-217-8 | | Dimer |
| BMS3h-217-14 | | Monomer/Dimer |
| BMS3h-217-15 | | Dimer |
| BMS3h-217-16 | | Dimer |
| BMS3h-217-17 | | Monomer/Dimer |
| BMS3h-217-23 | | Dimer |

TABLE 12

Further-Matured Clones:

| Clone | DSC Tm/° C. | SEC-MALS solution state |
|---|---|---|
| BMS3h-37-206 | | Monomer (73%) and dimer (20%) + HMW |
| BMS3h-37-212 | | Dimer |
| BMS3h-38-201 | | Monomer (75%) and Dimer (15%) |
| BMS3h-38-228 | | Monomer (90%) and Trimer (10%) |
| BMS3h-38-231 | | Monomer (90%) and Dimer (10%) |
| BMS3h-38-235 | | Monomer (90%) and Trimer-Dimer |
| BMS3h-38-237 | | Monomer (90%) and Tetramer (10%) |
| BMS3h-38-238 | | Monomer (95%) and Dimer-Monomer |
| BMS3h-56-201 | 57.4 + 61.8 | Monomer and Dimer (15%) |
| BMS3h-56-202 | | Monomer |
| BMS3h-56-203 | | Monomer and Trimer |
| BMS3h-56-206 | | Monomer |

TABLE 12-continued

Further-Matured Clones:

| Clone | DSC Tm/° C. | SEC-MALS solution state |
|---|---|---|
| BMS3h-56-215 | | Monomer, Dimer (2%) and Trimer (9%) |
| BMS3h-56-217 | 52.8 + 54.6 | |
| BMS3h-56-232 | 51.0 + 56.1 | Monomer (95%) and Dimer (5%) |
| BMS3h-56-239 | 53.5 | Monomer |
| BMS3h-56-243 | 51.9 | Monomer and Pentamer |
| BMS3h-56-244 | | Monomer (90%) and Trimer (10%) |
| BMS3h-56-248 | | Monomer (60%), Dimer and Tetramer |
| BMS3h-56-253 | | Monomer |
| BMS3h-56-258 | 62.5 + 57.5 | |
| BMS3h-56-261 | 58.6 + 61.5 | |
| BMS3h-56-266 | 61.3 + 62.3 | |
| BMS3h-56-269 | 64.5 + 67.2 | |

Example 5

Competition Analysis

A BIAcore™ 3000 instrument (GE Healthcare) was used to analyze whether CD40-specific dAbs bound the same CD40 epitope. Approximately 600 response units (RU) of biotinylated human CD40 (BMS) were immobilized on one flow-cell of a streptavidin (SA) BIAcore™ chip. A second flow-cell without any ligand immobilized served as a reference flow-cell for inline referencing. An appropriate dilution of each dAb or Fab to be analyzed was prepared in HBS-EP buffer (0.01 M HEPES pH 7.4 with 0.15 M NaCl, 3 mM EDTA and 0.005% v/v Surfactant P20, GE Healthcare). The dilution chosen was one which when injected as described below resulted in >80% of the maximum possible bound RU for the particular inhibitor, typically 1-10 µM. Next, a mixture of the same dAb or Fab as above (at the same final concentration) was prepared with a second dAb or Fab to be analyzed for competition. The COINJECT function of the instrument was used to inject 60 µl of the single-inhibitor dilution across the CD40-immobilized and reference flow-cells in series, followed immediately by a 60 µl injection of the two-inhibitor mixture. Inline subtraction of the signal from the reference cell was performed by the instrument's control software. The experiment was performed at 25° C. and a flow rate of 30 µl/min of HBS-EP. After each co-injection had been completed, the inhibitors were allowed to dissociate from the ligand in buffer for 60 s before regeneration with a 10 µl injection of 10 mM glycine pH 2.0. The maximum RU obtained for the second injection (the mixture of the two inhibitors) was noted and expressed as a percentage of the RU obtained for the same inhibitor when injected alone.

If the second inhibitor retained at least 100% of the RU usually bound when it was injected alone, then this implied that the two inhibitors bind to discrete epitopes. If less than 100% binding of the second inhibitor was observed, then this was indicative of competition between the two inhibitors for binding to CD40. There are several possible reasons for this competition: the two inhibitors may bind to the same or overlapping epitopes, there may be steric inhibition of binding, or binding of the first inhibitor may induce a conformational change in the antigen that prevents or reduces binding of the second inhibitor.

An example clone from each lineage (except BMS3h-217) was tested for competition with other dAbs in overlapping groups. All the dAbs tested appear to compete with each other for binding to CD40, as shown in TABLES 13 and 14. This data suggests that all antibody polypeptides selected from the group consisting of lineage BMS3h-37, BMS3h-38, BMS3h-41, BMS3h-43, BMS3h-56, BMS3h-131, BMS3h-198, and BMS3h-202 should compete with the binding of a dAb from any of these lineages to human CD40.

TABLE 13

Competition BIAcore ™:

| | RU first | Second Injection (% of single dAb RU) | | | | |
|---|---|---|---|---|---|---|
| First injection | dAb alone | BMS3h-56-5 | BMS3h-37-11 | BMS3h-131-2 | BMS3h-198-1 | BMS3h-202-11 |
| BMS3h-56-5 | 245 | | −15 | 17 | 0.6 | 7.3 |
| BMS3h-37-11 | 158 | 15 | | 25 | 16 | 0.3 |
| BMS3h-131-2 | 220 | 22 | −3.7 | | 23.2 | 10.3 |
| BMS3h-198-1 | 176 | 28 | 6.4 | 41 | | 18 |
| BMSSh-202-11 | 124 | 50 | 42 | 57 | 39 | |

TABLE 14

| | RU first | Second Injection (% of single dAb RU) | | | |
|---|---|---|---|---|---|
| First injection | dAb alone | BMS3h-38-2 | BMS3h-41-9 | BMS3h-43-1 | BMS3h-56-5 |
| BMS3h-38-2 | 170 | | 11 | 29 | 29 |
| BMS3h-41-9 | 150 | 27 | | 44 | 47 |
| BMS3h-43-1 | 210 | 20 | 19 | | 39 |
| BMS3h-56-5 | 190 | 4 | 0 | 22 | |

Similarly, various dAbs were tested for competition with Chi220 Fab', as shown in TABLES 15 and 16. In this case, all the dAbs do not compete with Chi220 Fab', except BMS3h-217, which shows competition. BMS3h-56-5 and BMS3h-193-12 dAbs bound with at least 100% of single dAb RU in the presence of bound Chi220 or G28-5 Fab', suggesting that the Fab's bind a different epitope(s) than the dAbs. Chi220 Fab' showed a reduction of bound RU in the presence G28-5. The same result was observed in the opposite order of binding. This suggests that G28-5 Fab' binds the same epitope as Chi220 Fab'.

TABLE 15

| | RU first | Second Injection (% of single dAb/Fab RU) | | | |
|---|---|---|---|---|---|
| First injection | dAb/Fab alone | BMS3h-56-5 | Chi220 Fab | G28-5 Fab | BMS3h-193-12 |
| BMS3h-56-5 | 193 | | 98 | 94 | 64 |
| Chi220 Fab | 1089 | 105 | | 11 | 109 |
| G28-5 Fab | 730 | 125 | 39 | | 116 |
| BMS3h-193-12 | 282 | 44 | 98 | 93 | |

TABLE 16

| Clone name | μM dAb or Fab tested | Single dAb RU | % of single dAb RU (Chi220 + dAb) |
|---|---|---|---|
| BMS3h-38-2 | 5 | 156 | 121 |
| BMS3h-41-13 | 5 | 162 | 109 |
| BMS3h-43-3 | 5 | 300 | 101 |
| BMS3h-38-2 | 5 | 175 | 114 |
| BMS3h-56-5 | 5 | 193 | 105 |
| BMS3h-106 | 10 | 165 | 111 |
| BMS3h-107 | 10 | 35 | 146 |
| BMS3h-129 | 10 | 156 | 121 |
| BMS3h-193-12 | 5 | 282 | 98 |
| BMS3h-197 | 1 | 177 | 116 |
| BMS3h-217 | 10 | 85 | 25 |
| G28-5 Fab | 1 | 730 | 11 |

Example 6

CD40 Activity Assays

Anti-human CD40 dAbs were assayed functionally for their ability to antagonize CD40 activities. The CD40 activities tested were B cell proliferation and cytokine production by hCD40L-driven activation of primary human monocyte-derived dendritic cells (DCs). Unless otherwise noted, all assays were performed in RPMI media supplemented with 10% fetal calf serum (FCS). The results using the various assays are shown in TABLE 17.

Soluble IZ-hCD40L-Driven Primary Human B Cell Proliferation:

$1 \times 10^5$ tonsillar human B cells were incubated with 0.6 μg/ml of IZ-hCD40L along with varying titrations of antibody polypeptide in a final volume of 200 Owen in a 96-well round bottom plate. The plates were incubated at 37° C. for 72 hours, then thymidine ($^3$H; 0.5 μci/well) was added for 6 hours. B cell proliferation was quantified based on thymidine incorporation.

CHO-hCD40L-Driven Primary Human B Cell Proliferation:

CHO cells were transfected with human CD40L to generate a stable cell line expressing high levels of CD40L on the cell surface. CHO-CD40L cells were irradiated at 10,000 Rads before incubation with human B cells. $1 \times 10^5$ tonsillar human B cells were incubated with $1 \times 10^3$ CHO-CD40L cells (1:100 ratio of CHO-CD40L: human B cells) along with varying titrations of antibody polypeptide in a final volume of 200 μl/well in a 96-well round bottom plate. The plates were incubated at 37° C. for 72 hours following which $^3$H-thymidine (0.5 μci/well) was added for 6 hours. B cell proliferation was quantified based on thymidine incorporation.

Soluble IZ-hCD40L-Driven Cyno Splenic Human B Cell Proliferation:

$1 \times 10^5$ cyno splenic B cells were incubated with 0.5 μg/ml of IZ-hCD40L along with varying titrations of antibody polypeptide in a final volume of 200 μl/well in a 96-well round bottom plate. The plates were incubated at 37° C. for 72 hours following which $^3$H-thymidine (0.5 μci/well) was added for 6 hours. B cell proliferation was quantified based on thymidine incorporation.

Primary T Cell-Driven Human B Cell Proliferation:

T cells were isolated from human peripheral blood mononuclear cells (PBMC) and enriched using sheep red blood cell (SRBC) rosetting. Human tonsillar B cells were isolated by homogenizing tonsil tissue to a single-cell suspension. Leukocytes were obtained by ficoll separation, then B cells were negatively selected busing SRBC resetting and enriched by discarding the rosetted cells.

Enriched human T cells were cultured with PM-LCLs (an EBV-transformed B cell line; irradiated at 10,000 Rads) at a 5:1 ratio (T:LCL) for 6 days at 37° C. to generate a population of allogeneic T cells. At day 6, the expanded T cells were isolated and irradiated at 3000 Rads, and then cultured ($5 \times 10^4$ T cells/well) with primary human tonsillar B cells ($1 \times 10^5$ B cells/well) at a 1:2 ratio in 96-well flat bottom plated coated with anti-CD3 mAb (OKT3). Varying titrations of antibody polypeptides were added to each well; the final volume in each well was 200 μl. Test plates were incubated at 37° C. for 3 days. Human B cell proliferation was determined via the addition of $^3$H-thymidine (0.5 μci/well) to the cultures for the last 18 hours.

CHO-hCD40L-Driven Activation of Primary Human Monocyte-Derived Dendritic Cells (DCs):

Human PBMCs were enriched for monocytes by depleting T cells via SRBC rosetting. The monocyte-enriched PBMCs were cultured with 10 ng/ml GM-CSF and 5 ng/ml IL-4 in 6-well plates for 6 days at 37° C. The cultured plates were replenished with fresh media (with GM-CSF and IL-4) on days 2 and 5. The immature dendritic cells (DCs) were used in cell assays on day 6. $8 \times 10^4$ immature DCs were cultured with $4 \times 10^3$ CHO-hCD40L cells (irradiated at 10,000 Rads) along with varying titrations of antibody polypeptides in a 96-well flat bottom plate. After 24 hours, supernatants were harvested and tested for the presence of various cytokines (IL-12. TNF, IL-23). DC activation was determined by the levels of cytokine production.

TABLE 17

| Clone | hIZCD40L-driven Human B Cell Proliferation EC50 (nM) | hIZCD40L-driven Cyno B Cell Proliferation EC50 (nM) | CHO-hCD40L-driven Human B Cell Proliferation EC50 (nM) | T-B cell MLR EC50 (nM) | CHO-hCD40L-driven DC Activation IL-12 EC50 (nM) |
|---|---|---|---|---|---|
| 3h-5 | >7000 | | >7000 | | |
| 3h-8 | >7000 | | >7000 | | |
| 3h-28 | >7000 | | >7000 | | |
| 3h-33 | >7000 | | >7000 | | |
| 3h-48 | >7000 | | >7000 | | |
| 3h-52 | >7000 | | >7000 | | |
| 3h-57 | >7000 | | >7000 | | |
| 3h-61 | >7000 | | >7000 | | |
| 3h-88 | >7000 | | | | |
| 3h-102 | >7000 | | | | |
| 3h-106 | 437.0 ± 214.0 | >7000 | | | |
| 3h-107 | >7000 | >7000 | | | |

TABLE 17-continued

| Clone | hIZCD40L-driven Human B Cell Proliferation EC50 (nM) | hIZCD40L-driven Cyno B Cell Proliferation EC50 (nM) | CHO-hCD40L-driven Human B Cell Proliferation EC50 (nM) | T-B cell MLR EC50 (nM) | CHO-hCD40L-driven DC Activation IL-12 EC50 (nM) |
|---|---|---|---|---|---|
| 3h-112 | >7000 | | | | |
| 3h-129 | 2100.0 ± 1000.0 | | | | |
| 3h-197 | 360.0 ± 500.0 | >7000 | | | |
| 3h-207 | >7000 | | | | |
| 3h-208 | >7000 | | | | |
| 3h-37 | 3400.0 ± 2900.0 | >7000 | | | |
| 3h-37-1 | 250.0 ± 100.0 | | | | |
| 3h-37-2 | 5.0 ± 2.0 | >7000 | | 198 ± 35 | 13.0 ± 7.3 |
| 3h-37-202 | 0.6 ± 0.2 | | | 83 ± 18 | 10.0 |
| 3h-37-205 | 2.0 ± 1.0 | | | | 6.6 |
| 3h-37-206 | 5.0 ± 0.8 | | | | 23.0 |
| 3h-37-207 | 4.0 ± 2.0 | | | | 15.5 ± 8.0 |
| 3h-37-212 | 1.0 ± 0.05 | | | | |
| 3h-37-213 | 0.7 ± 0.2 | | | | |
| 3h-37-11 | 8.0 ± 7.0 | | | | |
| 3h-38 | 2800.0 ± 400.0 | >7000 | | | |
| 3h-38-1 | 142.0 ± 86.0 | | | | |
| 3h-38-2 | 10.0 ± 6.0 | >7000 | 723.0 ± 185.0 | 986 ± 383 | 289.0 ± 315.0 |
| 3h-38-201 | >70.0 | | >7000 | | >800.0 |
| 3h-38-205 | 4.0 ± 2.0 | | 1100.0 ± 141.0 | | 29.0 |
| 3h-38-211 | 2.0 ± 1.0 | | 82.0 ± 4.0 | 200 ± 1 | 18.0 ± 19.0 |
| 3h-38-215 | 1.0 ± 0.0 | | 65.0 ± 1.0 | 163 ± 14 | 6.0 ± 4.0 |
| 3h-38-217 | 0.8 ± 0.2 | | 34.0 ± 6.0 | 74 ± 22 | 1.7 ± 0.4 |
| 3h-38-219 | 2.0 ± 0.5 | | 93.0 ± 26.0 | 164 ± 3 | 9.0 ± 5.0 |
| 3h-38-228 | 0.7 ± 0.05 | | | | |
| 3h-38-231 | 0.66 ± 0.2 | | | | |
| 3h-38-235 | 0.4 ± 0.2 | | | | |
| 3h-38-237 | 0.4 ± 0.2 | | | | |
| 3h-38-238 | 0.7 ± 0.03 | | | | |
| 3h-38-3 | 10.0 ± 7.0 | | | | |
| 3h-41 | >7000 | | | | |
| 3h-41-1 | 104.0 ± 56.0 | | | | |
| 3h-41-2 | 47.0 ± 67.0 | | | | |
| 3h-41-3 | 12.0 ± 7.0 | >7000 | | | |
| 3h-41-9 | 148.0 ± 98.0 | | | | |
| 3h-41-12 | 104.0 ± 50.0 | | | | |
| 3h-41-13 | 208.0 ± 90.0 | | | | |
| 3h-43 | 83.0 ± 40.0 | >7000 | | | |
| 3h-43-1 | 53.0 ± 20.0 | | | | |
| 3h-43-3 | 87.0 ± 19.0 | | | | |
| 3h-43-5 | 180.0 ± 130.0 | | | | |
| 3h-43-10 | 143.0 ± 131.0 | | | | |
| 3h-43-11 | 30.0 ± 19.0 | | | | |
| 3h-43-12 | 12.0 ± 6.0 | | | | |
| 3h-56 | 713.0 ± 133.0 | >7000 | | | |
| 3h-56-1 | 7.0 ± 5.0 | | | | |
| 3h-56-2 | 3.0 ± 1.0 | | 326.0 ± 79.0 | 276 ± 29 | 444.0, >2000.0 |
| 3h-56-201 | 0.12 ± 0.04 | | 11.0 ± 6.0 | 7.25 ± 0.96 | 0.93 ± 0.7 |
| 3h-56-202 | 0.6 ± 0.2 | | 39.0 ± 16.0 | 50 ± 9.8 | 2.9 ± 2.6 |
| 3h-56-203 | 0.45 ± 0.1 | | 51.0 ± 29.0 | 52 ± 23 | 3.7 ± 4.0 |
| 3h-56-206 | 0.1 ± 0.01 | | 6.0 ± 2.0 | 5.25 ± 0.5 | 0.7 ± 0.4 |
| 3h-56-215 | 0.2 ± 0.03 | | 41.0 ± 15.0 | 31 ± 7 | 11.0 ± 12.0 |
| 3h-56-217 | 0.1 ± 0.04 | | 13.0 ± 5.0 | 16 ± 6.7 | 9.4 ± 8.0 |
| 3h-56-224 | 0.5 ± 0.2 | | 26.0 ± 5.0 | 47 ± 11 | 18.0 ± 22.0 |
| 3h-56-232 | 0.27 ± 0.1 | | 37.0 ± 0.7 | 42 ± 10 | 7.3 ± 6.6 |
| 3h-56-239 | 0.11 ± 0.0 | | 18.0 ± 4.0 | 13.5 ± 4.76 | 5.8 ± 6.5 |
| 3h-56-243 | 0.15 ± 0.007 | | 13.5 ± 2.0 | 14.2 ± 4.6 | 8.8 ± 10.0 |
| 3h-56-244 | 0.17 ± 0.02 | | 26.0 ± 3.0 | 21 ± 4.1 | 12.6 ± 16.0 |
| 3h-56-246 | 0.24 ± 0.06 | | 34.0 ± 14.0 | 23.8 ± 6.2 | 23.2 ± 22.0 |
| 3h-56-248 | 0.36 ± 0.1 | | | | |
| 3h-56-253 | 0.4 ± 0.2 | | | | |
| 3h-56-258 | 0.079 ± 0.003 | | 11.0 ± 3.0 | 8.7 ± 1.9 | 1.52 ± 1.6 |
| 3h-56-261 | 0.17 ± 0.09 | | 25.5 ± 6.0 | 17 ± 5.4 | 3.0 ± 1.8 |
| 3h-56-262 | 0.31 ± 0.007 | | | | |
| 3h-56-265 | 0.36 ± 0.06 | | | | |
| 3h-56-266 | 0.19 ± 0.04 | | 19.5 ± 6.0 | 13.8 ± 2.4 | 2.8 ± 2.3 |
| 3h-56-269 | 0.14 ± 0.02 | | 15.0 ± 5.0 | 9.7 ± 1.9 | 1.8 ± 1.2 |
| 3h-56-270 | 0.31 ± 0.1 | | | | |
| 3h-56-5 | 6.0 ± 4.0 | >7000 | | | |

TABLE 17-continued

| Clone | hIZCD40L-driven Human B Cell Proliferation EC50 (nM) | hIZCD40L-driven Cyno B Cell Proliferation EC50 (nM) | CHO-hCD40L-driven Human B Cell Proliferation EC50 (nM) | T-B cell MLR EC50 (nM) | CHO-hCD40L-driven DC Activation IL-12 EC50 (nM) |
|---|---|---|---|---|---|
| 3h-56-6 | 4.0 ± 3.0 | | | | |
| 3h-56-7 | 8.0 ± 6.0 | | | | |
| 3h-56-8 | 5.0 ± 2.0 | | | | |
| 3h-56-9 | 3.0 ± 0.6 | | | | |
| 3h-56-15 | 2.0 ± 0.9 | | | | |
| 3h-56-19 | 3.0 ± 2.0 | | | | |
| 3h-56-21 | 2.0 ± 1.0 | | | | |
| 3h-131 | 2700.0 ± 1000.0 | >7000 | | | |
| 3h-131-2 | 55.0 ± 53.0 | >7000 | | | |
| 3h-131-6 | 141.0 ± 37.0 | | | | |
| 3h-131-14 | 24.0 ± 4.0 | | | | |
| 3h-193 | >7000 | | | | |
| 3h-193-12 | 277.0 ± 167.0 | | | | |
| 3h-193-16 | 387.0 ± 173.0 | | | | |
| 3h-193-19 | 233.0 ± 110.0 | | | | |
| 3h-193-25 | 303.0 ± 214.0 | 2200.0 ± 1200.0 | | | |
| 3h-193-29 | 1380.0 ± 721.0 | | | | |
| 3h-198 | 554.0 ± 186.0 | >7000 | | | |
| 3h-198-1 | 64.0 ± 47.0 | | | | |
| 3h-198-2 | 207.0 ± 158.0 | | | | |
| 3h-198-5 | 9.0 ± 6.0 | | | | |
| 3h-198-19 | 19.0 ± 14.0 | | | | |
| 3h-198-24 | 34.0 ± 37.0 | | | | |
| 3h-198-28 | 20.0 ± 9.0 | | | | |
| 3h-202 | 6400.0 ± 1300.0 | >7000 | | | |
| 3h-202-1 | 192.0 ± 77.0 | >7000 | | | |
| 3h-202-5 | 6500.0 ± 1000.0 | | | | |
| 3h-202-10 | 289.0 ± 158.0 | | | | |
| 3h-202-11 | 201.0 ± 103.0 | | | | |
| 3h-217 | 3200.0 ± 2030.0 | >7000, 5300, 1690 | | | |
| 3h-217-1 | 45.0 ± 26.0 | 35.0 ± 8.0 | | | |
| 3h-217-2 | 8.0 ± 4.0 | 7.0 | | | 335.0 |
| 3h-217-4 | 61.0 ± 20.0 | 27.0 | | | |
| 3h-217-5 | 13.0 ± 5.0 | 15.0 | | | |
| 3h-217-6 | 11.0 ± 3.0 | 10.0 | | | |
| 3h-217-7 | 220.0 ± 20.0 | | | | |
| 3h-217-8 | 33.0 ± 10.0 | 14.0 | | | |
| 3h-217-9 | 380.0 ± 170.0 | | | | |
| 3h-217-14 | 26.0 ± 10.0 | 8.0 | | | |
| 3h-217-15 | 47.0 ± 21.0 | 20.0 | | | |
| 3h-217-16 | 5.0 ± 2.0 | 7.0 | | | 1125.0 |
| 3h-217-17 | 1950.0 ± 110.0 | | | | |
| 3h-217-23 | 16.0 ± 6.0 | 15.0 | | | |
| 3h-217-2305 | 11.0 ± 4.0 | | | | |
| 3h-217-30 | 80.0 ± 9.0 | | | | >7700 |
| 3h-217-31 | >700.0 | | | | |
| 3h-231 | 328.0 ± 144.0 | >7000 | | | |
| 3h-233 | 184.0 ± 75.0 | >7000 | | | 1492.0, >2000 |
| 3h-240 | >7000 | >7000 | | | |
| 3h-242 | 219.0 ± 53.0 | 435.0 ± 62.0 | | | 2050.0 |
| 3h-257 | 135.0 ± 28.0 | >7000 | | | 704.0 ± 445.0 |
| 3h-262 | 548.0 ± 121.0 | >700 | | | 998.0 |
| 3h-263 | >700.0 | >700 | | | |
| 3h-264 | 1200.0 ± 400.0 | >7000 | | | >2000 |
| 3h-265 | 2400.0 ± 1000.0 | >7000 | | | >2000 |
| 3h-271 | 295.0 ± 92.0 | 446.0 | | | >2000 |
| 3h-274 | 1200, >7000 | >7000 | | | |
| 3h-275 | 157.0 ± 11.0 | >7000 | | | |
| 3h-285 | 49.0 ± 0.7 | 155.0 | | | |
| 3h-287 | 287.0 ± 156.0 | 918.0 | | | |
| 3h-289 | 2300.0 ± 1200.0 | 4300.0 | | | |
| 3h-290 | >7000 | 5650.0 | | | |
| 3h-294 | >7000 | >7000 | | | |
| 3h-295 | >7000 | >7000 | | | |
| 3h-296 | 306.0 ± 55.0 | >7000 | | | |
| 3h-309 | 648.0 ± 268.0 | 838.0 | | | |
| 3h-312 | 1100.0 ± 346.0 | >7000 | | | |

Example 7

Dual Specific dAbs Binding CD40 and Serum Albumin

Dual specific dAbs that specifically bind CD40 and human serum albumin (HSA) or cynomolgus serum albumin (CSA) were constructed and tested for activity in cell-based assays. The albumin-specific dAbs are called "AlbudAbs." In this example, AlbudAb fusions comprise a BMS3h dAb that binds CD40 and another domain antibody, DOM7h, that recognizes HSA. The two dAbs are fused in frame to the amino and carboxyl termini of an amino acid linker to form an inline fusion (ILF) polypeptide. The ILF polypeptide is expressed recombinantly as a single fusion protein. RBAs demonstrating activity of the AlbudAb ILFs are described below, and the results are shown in TABLE 18. TABLE 19 summarizes the linker sequences used in the tested AlbudAb ILFs. Kinetic binding data determined by a BIAcore™ assay are shown in TABLE 20.

Human CD40 CHO Cell ELISA for the Detection of dAbs in a Supernatant:

Stably transfected human CD40 expressing CHO-DG44 cells or native CHO-DG44 cells (both BMS) were detached from cell culture flasks using 0.25% trypsin EDTA, and 100,000 cells per well were seeded in growth media into 96 well tissue culture treated plates (NUNC). The cells were allowed to adhere overnight in a humidified atmosphere at 37° C., 5% $CO_2$. On the day of assay, the cell sheet was washed with PBS prior to being fixed with 2% paraformaldehyde (Sigma-Aldrich) for 20 minutes. Following fixing, the cell sheet was washed again in PBS prior to a 1 hr blocking step with 15% fetal bovine serum (FBS, PAA) in PBS. Plates were washed once more prior to addition of 100 μl/well of dAb supernatant and incubated for 2 h at room temperature. Following incubation of dAb supernatants with cells, the plates were washed and dAb binding was detected with incubation of horse radish peroxidase (HRP) conjugate anti-protein A or L, depending on whether dAbs are $V_H$ or $V_L$ domains. Absorbance signal was measured using a SpectraMax® M5e plate reader (Molecular Devices) at 450 nm following neutralization with 1 M HCl.

ICAM-1 Up-Regulation Cell Assay:

Stably transfected human CD40L expressing COS cells were detached from cell culture flasks using Versene (invitrogen). 20,000 cells per well were seeded into 96 well Highbind, black walled, clear bottom plates (Corning, UK) in assay buffer (RPMI 1640 without phenol red (Sigma-Aldrich, UK)+1% penicillin/streptomycin+10% FBS Gold (both PAA Laboratories, UK). The cells were left to adhere overnight in a humidified atmosphere at 37° C. with 5% $CO_2$. The following day, exhausted assay buffer containing non attached cells was replenished with 100 μl of fresh assay buffer. To this, 20,000 RAMOS cells/well were added in assay buffer in addition to a dilution range of dAb. The assay plate was returned to a humidified atmosphere at 37° C. with 5% $CO_2$ for a further 24 hours. For negative control wells, no RAMOS cells were added. The ability of dAb to inhibit the up-regulation of ICAM-1 on the cell surface of RAMOS cells in response to exposure to CD40L on the cell surface of COS cells was assessed by addition of 0.5 μg/ml mouse anti human ICAM-1 antibody (R&D systems) and 0.2 μg/ml goat anti mouse ALEXA Fluor® 647 (Invitrogen, Molecular probes, UK). Following a 3 hour incubation period in the absence of light, relative fluorescence was detected as measured by the AB8200 cellular detection platform (Applied Biosystems).

Analysis of Inline Fusion (ILF) Kinetics of Binding to Serum Albumin:

A BIAcore™ 3000 instrument (GE Healthcare) was used to analyze the binding kinetics of anti-CD40-AlbudAb ILFs to human and cynomolgus serum albumin. Approximately 400 response units (RU) of human serum albumin (HSA) or cynomolgus serum albumin (CSA) were immobilized on a flow-cell of a CM5 BIAcore™ chip using an Amine Coupling Kit (GE Healthcare). A second flow cell without any ligand immobilized served as a reference flow-cell for inline referencing. An appropriate doubling dilution series of each dAb to be analyzed was prepared in HBS-EP buffer (0.01 M HEPES pH 7.4 with 0.15 M NaCl, 3 mM EDTA and 0.005% v/v Surfactant P20, GE Healthcare). Two hundred microliters of each ILF were injected in duplicate using the instrument's KINJECT function. The injections were made across the serum albumin-immobilized and reference flow-cells in series, with inline subtraction of the signal from the reference cell. The experiment was performed at 25° C. and a flow rate of 40 μl/min of HBS-EP. After each injection had been completed, the dAb was allowed to dissociate from the ligand in buffer for 120 s before regeneration with a 10 μl injection of 10 mM glycine pH 2.0. A reference injection of HBS-EP buffer blank (containing no analyte) was also injected under the same conditions to serve as a second reference for subtraction from each analyte trace. BIAevaluation 4.1 software (GE Healthcare) was used to subtract both the reference flow-cell trace and the buffer blank trace from each analyte trace. The same software was used to perform a simultaneous, global fit of a 1:1 (Langmuir) kinetic model to the association and dissociation phases of the analyte dilution series traces. This model yielded association and dissociation rate constants ($k_a$ and $k_d$, respectively) and the equilibrium dissociation constant ($K_D$) of the interaction. The parameter values are shown in TABLE 20.

TABLE 18

Activity Assays

| | | | | CHO-CD40 Cell RBA | | ICAM-1 Cell Assay $EC_{50}$ (nM) | |
|---|---|---|---|---|---|---|---|
| | | | | $EC_{50}$ (nM) | | 10% | 10% |
| DMS No. | N-term. dAb | Linker | C-term. dAb | 0.1% BSA | 50 μM HSA | bovine serum | human serum |
| DMS0654 | BMS3h-56-201 | AST | DOM7h-11-3 | 15 | 8.6 | | |
| DMS0655 | BMS3h-56-201 | AST | DOM7h-11-87 | 6.3 | 2.7 | | |
| DMS0656 | BMS3h-56-258 | AST | DOM7h-11-3 | 11.8 | 26.8 | | |
| DMS0657 | BMS3h-56-258 | AST | DOM7h-11-87 | 6.8 | 16.6 | | |
| DMS0658 | DOM7h-11-3 | TVAAPS | BMS3h-56-201 | 12.2 | 9.1 | | |

TABLE 18-continued

Activity Assays

| DMS No. | N-term. dAb | Linker | C-term. dAb | CHO-CD40 Cell RBA EC$_{50}$ (nM) 0.1% BSA | CHO-CD40 Cell RBA EC$_{50}$ (nM) 50 µM HSA | ICAM-1 Cell Assay EC$_{50}$ (nM) 10% bovine serum | ICAM-1 Cell Assay EC$_{50}$ (nM) 10% human serum |
|---|---|---|---|---|---|---|---|
| DMS0659 | DOM7h-11-87 | TVAAPS | BMS3h-56-201 | 7.2 | 3.3 | | |
| DMS0660 | DOM7h-11-3 | TVAAPS | BMS3h-56-258 | 21.8 | 13.1 | | |
| DMS0661 | DOM7h-11-87 | TVAAPS | BMS3h-56-258 | 4.1 | 5.7 | | |
| DMS0662 | DOM7h-11-90 | TVAAPS | BMS3h-56-201 | | | 33.5 | >1000 |
| DMS0663 | DOM7h-11-86 | TVAAPS | BMS3h-56-201 | | | 21.4 | >1000 |
| DMS0664 | DOM7h-11-69 | TVAAPS | BMS3h-56-201 | | | 16.5 | >1000 |
| DMS0677 | DOM7h-11-90 | TVA | BMS3h-56-258 | | | 21.7 | 20.35 |
| DMS0679 | DOM7h-11-90 | G$_4$S | BMS3h-56-258 | | | 21.7 | 39.2 |
| DMS0680 | DOM7h-11-90 | (G$_4$S)$_3$ | BMS3h-56-258 | | | 39.3 | 74.2 |
| DMS0681 | DOM7h-11-90 | (G$_4$S)$_5$ | BMS3h-56-258 | | | 43.6 | 53.3 |
| DMS0682 | BMS3h-56-258 | TVA | DOM7h-11-90 | | | 10.2 | 94.8 |
| DMS0683 | BMS3h-56-258 | ASTSGPS | DOM7h-11-90 | | | 32.4 | 50.9 |
| DMS0684 | BMS3h-56-258 | G$_4$S | DOM7h-11-90 | | | 37.9 | 74.3 |
| DMS0685 | BMS3h-56-258 | (G$_4$S)$_3$ | DOM7h-11-90 | | | 31.9 | 62.4 |
| DMS0686 | BMS3h-56-258 | (G$_4$S)$_5$ | DOM7h-11-90 | | | 48.3 | 66.6 |

TABLE 19

Representative Linker Sequences

| | |
|---|---|
| AST | SEQ ID NO: 5 |
| TVAAPS | SEQ ID NO: 6 |
| TVA | SEQ ID NO: 7 |
| GGGGS | SEQ ID NO: 1207 |
| (GGGGS)$_3$ | SEQ ID NO: 1208 |
| (GGGGS)$_5$ | SEQ ID NO: 1209 |
| ASTSGPS | SEQ ID NO: 8 |

TABLE 20

BIAcore™ Analysis

| DMS No. | N-Term dAb | Linker ("TVAAPS" disclosed as SEQ ID NO: 6) | C-Term dAb | Human Serum Albumin k$_a$ (1/Ms) x10$^{-6}$ | Human Serum Albumin k$_d$ (1/s) x10$^3$ | Human Serum Albumin K$_D$ (nM) | Cyno Serum Albumin k$_a$ (1/Ms) x10$^{-6}$ | Cyno Serum Albumin k$_d$ (1/s) x10$^3$ | Cyno Serum Albumin K$_D$ (nM) |
|---|---|---|---|---|---|---|---|---|---|
| DMS0659 | DOM7h-11-87 | TVAAPS | BMS3h-56-201 | 0.85, 2.85, 2.6 | 1.17, 1.69, 1.2 | 1.37, 0.60, 0.45 | 0.85, 2.79, 2.9 | 2.37, 3.37, 2.4 | 2.79, 1.21, 0.83 |
| DMS0662 | DOM7h-11-90 | TVAAPS | BMS3h-56-201 | 1.1, 1.19 | 1.33, 1.47 | 1.21, 1.23 | 1.01, 1.10 | 2.52, 2.66 | 2.5, 2.42 |
| DMS0663 | DOM7h-11-86 | TVAAPS | BMS3h-56-201 | 1.25, 1.32 | 1.40, 1.60 | 1.12, 1.21 | 1.18, 1.18 | 2.81, 2.96 | 2.38, 2.52 |
| DMS0664 | DOM7h-11-69 | TVAAPS | BMS3h-56-201 | 2.5, 0.93 | 1.42, 1.49 | 0.57, 1.59 | 2.51, 0.92 | 2.73, 2.72 | 1.09, 2.97 |

TABLE 21 lists amino acid sequences of representative AlbudAb ILFs that can specifically bind CD40 and HSA or CSA. The designation of each ILF identifies the particular linker sequence: "GxS" means the linker has "x" residues of glycine followed by serine, and "(GxS)y" means the linker has y repeating units of GxS. TABLE 22 discloses representative nucleic acids that encode the ILF sequences listed in TABLE 21. As is known in the art, multiple codons can encode the same amino acid. Nucleic acids encoding a protein sequence thus include nucleic acids having codon degeneracy.

TABLE 21

Dual Specificity dAb Amino Acid Sequences

DMS0654 BMS3h-56-201-AST-DOM7h-11-3
EVQLLESGGGLVQPGGSLRLSCAASGFTFRDYEMWWVRQAPGKGLERVSAINPQGTRTYY
ADSVKGRFTISRDNSKNTLYLQMNSLRAEDTAVYYCAKLPFYFQEWGQGTLVTVSSASTD
IQMTQSPSSLSASVGDRVTITCRASRPIGTTLSWYQQKPGKAPKLLILWNSRLINGVPSR
FSGSGSGTDFTLTISSLQPEDFATYYCAQAGTHPTTFGQGTKVEIKR (SEQ ID NO:
1210)

DMS0655 BMS3h-56-201-AST-DOM7h-11-87
EVQLLESGGGLVQPGGSLRLSCAASGFTFRDYEMWWVRQAPGKGLERVSAINPQGTRTYY
ADSVKGRFTISRDNSKNTLYLQMNSLRAEDTAVYYCAKLPFYFQEWGQGTLVTVSSASTD
IQMTQSPSSLSASVGDRVTITCRASRPIGTMLSWYQQKPGKAPKLLILAFSRLQSGVPSR
FSGSGSGTDFTLTISSLQPEDFATYYCAQAGTHHTTFGQGTKVEIKR (SEQ ID NO:
1211)

DMS0656 BMS3h-56-258-AST-DOM7h-11-3
EVQLLESGGGLVQPGGSLRLSCAASGFTFRDYEMWWVRQAPGKGLERVSAINPQGTRTYY
ADSVKGRFTISRDNSKNTLYLQMNSLRAEDTAVYYCAKLPFYFHEWGQGTLVTVSSASTD
IQMTQSPSSLSASVGDRVTITCRASRPIGTTLSWYQQKPGKAPKLLILWNSRLQSGVPSR
FSGSGSGTDFTLTISSLQPEDFATYYCAQAGTHPTTFGQGTKVEIKR (SEQ ID NO:
1212)

DMS0657 BMS3h-56-258-AST-DOM7h-11-87
EVQLLESGGGLVQPGGSLRLSCAASGFTFRDYEMWWVRQAPGKGLERVSAINPQGTRTYY
ADSVKGRFTISRDNSKNTLYLQMNSLRAEDTAVYYCAKLPFYFHEWGQGTLVTVSSASTD
IQMTQSPSSLSASVGDRVTITCRASRPIGTMLSWYQQKPGKAPKLLILAFSRLQSGVPSR
FSGSGSGTDFTLTISSLQPEDFATYYCAQAGTHHTTFGQGTKVEIKR (SEQ ID NO:
1213)

DMS0658 DOM7h-11-3-TVAAPS-BMS3h-56-201
DIQMTQSPSSLSASVGDRVTITCRASRPIGTTLSWYQQKPGKAPKLLILWNSRLQSGVPS
RFSGSGSGTDFTLTISSLQPEDFATYYCAQAGTHPTTFGQGTKVEIKRTVAAPSEVQLLE
SGGGLVQPGGSLRLSCAASGFTFRDYEMWWVRQAPGKGLERVSAINPQGTRTYYADSVKG
RFTISRDNSKNTLYLQMNSLRAEDTAVYYCAKLPFYFQEWGQGTLVTVSS (SEQ ID
NO: 1214)

DMS0659 DOM7h-11-87-TVAAPS-BMS3h-56-201
DIQMTQSPSSLSASVGDRVTITCRASRPIGTMLSWYQQKPGKAPKLLILAFSRLQSGVPS
RFSGSGSGTDFTLTISSLQPEDFATYYCAQAGTHHTTFGQGTKVEIKRTVAAPSEVQLLE
SGGGLVQPGGSLRLSCAASGFTFRDYEMWWVRQAPGKGLERVSAINPQGTRTYYADSVKG
RFTISRDNSKNTLYLQMNSLRAEDTAVYYCAKLPFYFQEWGQGTLVTVSS (SEQ ID
NO: 1215)

DMS0660 DOM7h-11-3-TVAAPS-BMS3h-56-258
DIQMTQSPSSLSASVGDRVTITCRASRPIGTTLSWYQQKPGKAPKLLILWNSRLQSGVPS
RFSGSGSGTDFTLTISSLQPEDFATYYCAQAGTHPTTFGQGTKVEIKRTVAAPSEVQLLE
SGGGLVQPGGSLRLSCAASGFTFRDYEMWWVRQAPGKGLERVSAINPQGTRTYYADSVKG
RFTISRDNSKNTLYLQMNSLRAEDTAVYYCAKLPFYFHEWGQGTLVTVSS (SEQ ID
NO: 1216)

DMS0661 DOM7h-11-87-TVAAPS-BMS3h-56-258
DIQMTQSPSSLSASVGDRVTITCRASRPIGTMLSWYQQKPGKAPKLLILAFSRLQSGVPS
RFSGSGSGTDFTLTISSLQPEDFATYYCAQAGTHHTTFGQGTKVEIKRTVAAPSEVQLLE
SGGGLVQPGGSLRLSCAASGFTFRDYEMWWVRQAPGKGLERVSAINPQGTRTYYADSVKG
RFTISRDNSKNTLYLQMNSLRAEDTAVYYCAKLPFYFHEWGQGTLVTVSS (SEQ ID
NO: 1217)

DMS0662 DOM7h-11-90-TVAAPS-BMS3h-56-201
DIQMTQSPSSLSASVGDRVTITCRASRPIGTMLSWYQQKPGKAPKLLILAFSRLQSGVPS
RFSGSGSGTDFTLTISNLQPEDFATYYCAQAGTHPTTFGQGTKVEIKRTVAAPSEVQLLE
SGGGLVQPGGSLRLSCAASGFTFRDYEMWWVRQAPGKGLERVSAINPQGTRTYYADSVKG
RFTISRDNSKNTLYLQMNSLRAEDTAVYYCAKLPFYFQEWGQGTLVTVSS (SEQ ID
NO: 1218)

DMS0663 DOM7h-11-86-TVAAPS-BMS3h-56-201
DIQMTQSPSSLSASVGDRVTITCRASRPIGTMLSWYQQKPGKAPKLLILAFSRLQSGVPS
RFSGSGSGTDFTLTISSLQPEDVATYYCAQAGTHPTTFGQGTKVEIKRTVAAPSEVQLLE
SGGGLVQPGGSLRLSCAASGFTFRDYEMWWVRQAPGKGLERVSAINPQGTRTYYADSVKG
RFTISRDNSKNTLYLQMNSLRAEDTAVYYCAKLPFYFQEWGQGTLVTVSS (SEQ ID
NO: 1219)

DMS0664 DOM7h-11-69-TVAAPS-BMS3h-56-201
DIQMTQSPSSLSASVGDRVTITCRASRPIGTMLSWYQQKPGKAPKLLILAFSRLQSGVPS
RFSGSGSGTDFTLTISSLQPEDFATYYCAQAGVHPTTFGQGTKVEIKRTVAAPSEVQLLE
SGGGLVQPGGSLRLSCAASGFTERDYEMWWVRQAPGKGLERVSAINPQGTRTYYADSVKG
RFTISRDNSKNTLYLQMNSLRAEDTAVYYCAKLPFYFQEWGQGTLVTVSS (SEQ ID
NO: 1220)

TABLE 21-continued

Dual Specificity dAb Amino Acid Sequences

DMS0667 DOM7h-11-3-TVAAPS-BMS3h-38-240
DIQMTQSPSSLSASVGDRVTITCRASRPIGTTLSWYQQKPGKAPKLLILWNSRLQSGVPS
RFSGSGSGTDFTLTISSLQPEDFATYYCAQAGTHPTTFGQGTKVEIKRTVAAPSEVQLLE
SGGGLVQPGGSLRLSCAASGFTFEEEEMIWVRQAPGKGLEWVSAISRNGYSTYYADSVKG
RFTISRDNSKNTLYLQMNSLRAEDTAVYYCGKEPFRYDYWGQGTLVTVSS (SEQ ID
NO: 1221)

DMS0668 BMS3h-38-240-AST-DOM7h-11-3
EVQLLESGGGLVQPGGSLRLSCAASGFTFEEEEMIWVRQAPGKGLEWVSAISRNGYSTYY
ADSVKGRFTISRDNSKNTLYLQMNSLRAEDTAVYYCGKEPFRYDYWGQGTLVTVSSASTD
IQMTQSPSSLSASVGDRVTITCRASRPIGTTLSWYQQKPGKAPKLLILWNSRLQSGVPSR
FSGSGSGTDFTLTISSLQPEDFATYYCAQAGTHPTTFGQGTKVEIKR (SEQ ID NO:
1222)

DMS0669 DOM7h-14-10-TVAAPS-BMS3h-38-240
DIQMTQSPSSLSASVGDRVTITCRASQWIGSQLSWYQQKPGKAPKLLIMWRSSLQSGVPS
RFSGSGSGTDFTLTISSLQPEDFATYYCAQGLRHPKTFGQGTKVEIKRTVAAPSEVQLLE
SGGGLVQPGGSLRLSCAASGFTFEEEEMIWVRQAPGKGLEWVSAISRNGYSTYYADSVKG
RFTISRDNSKNTLYLQMNSLRAEDTAVYYCGKEPFRYDYWGQGTLVTVSS (SEQ ID
NO: 1223)

DMS0670 BMS3h-38-240-AST-DOM7h-14-10
EVQLLESGGGLVQPGGSLRLSCAASGFTFEEEEMIWVRQAPGKGLEWVSAISRNGYSTYY
ADSVKGRFTISRDNSKNTLYLQMNSLRAEDTAVYYCGKEPFRYDYWGQGTLVTVSSASTD
IQMTQSPSSLSASVGDRVTITCRASQWIGSQLSWYQQKPGKAPKLLIMWRSSLINGVPSR
FSGSGSGTDFTLTISSLQPEDFATYYCAQGLRHPKTFGQGTKVEIKR (SEQ ID NO:
1224)

DMS0671 BMS3h-38-235-AST-DOM7h-11-3
EVQLLASGGGLVQPGGSLRLSCAASGFTFEEEEMIWVRQAPGKGLEWVSAISRNGYSTYY
ADSVKGRFTISRDNSKNTLYLQMNSLRAEDTAVYYCGKEPFRYDYWGQGTLVTVSSASTD
IQMTQSPSSLSASVGDRVTITCRASRPIGTTLSWYQQKPGKAPKLLILWNSRLINGVPSR
FSGSGSGTDFTLTISSLQPEDFATYYCAQAGTHPTTFGQGTKVEIKR (SEQ ID NO:
1225)

DMS0672 BMS3h-38-235-AST-DOM7h-11-90
EVQLLASGGGLVQPGGSLRLSCAASGFTFEEEEMIWVRQAPGKGLEWVSAISRNGYSTYY
ADSVKGRFTISRDNSKNTLYLQMNSLRAEDTAVYYCGKEPFRYDYWGQGTLVTVSSASTD
IQMTQSPSSLSASVGDRVTITCRASRPIGTMLSWYQQKPGKAPKLLILAFSRLQSGVPSR
FSGSGSGTDFTLTISNLQPEDFATYYCAQAGTHPTTFGQGTKVEIKR (SEQ ID NO:
1226)

DMS0674 DOM7h-11-3-TVAAPS-BMS3h-38-235
DIQMTQSPSSLSASVGDRVTITCRASRPIGTTLSWYQQKPGKAPKLLILWNSRLQSGVPS
RFSGSGSGTDFTLTISSLQPEDFATYYCAQAGTHPTTFGQGTKVEIKRTVAAPSEVQLLA
SGGGLVQPGGSLRLSCAASGFTFEEEEMIWVRQAPGKGLEWVSAISRNGYSTYYADSVKG
RFTISRDNSKNTLYLQMNSLRAEDTAVYYCGKEPFRYDYWGQGTLVTVSS (SEQ ID
NO: 1227)

DMS0675 DOM7h-11-90-TVAAPS-BMS3h-38-235
DIQMTQSPSSLSASVGDRVTITCRASRPIGTMLSWYQQKPGKAPKLLILAFSRLQSGVPS
RFSGSGSGTDFTLTISNLQPEDFATYYCAQAGTHPTTFGQGTKVEIKRTVAAPSEVQLLA
SGGGLVQPGGSLRLSCAASGFTFEEEEMIWVRQAPGKGLEWVSAISRNGYSTYYADSVKG
RFTISRDNSKNTLYLQMNSLRAEDTAVYYCGKEPFRYDYWGQGTLVTVSS (SEQ ID
NO: 1228)

DMS0677 DOM7h-11-90-TVA-BMS3h-56-258
DIQMTQSPSSLSASVGDRVTITCRASRPIGTMLSWYQQKPGKAPKLLILAFSRLQSGVPS
RFSGSGSGTDFTLTISNLQPEDFATYYCAQAGTHPTTFGQGTKVEIKRTVAEVQLLESGG
GLVQPGGSLRLSCAASGFTERDYEMWWVRQAPGKGLERVSAINPQGTRTYYADSVKGRFT
ISRDNSKNTLYLQMNSLRAEDTAVYYCAKLPFYFHEWGQGTLVTVSS (SEQ ID NO:
1229)

DMS0678 DOM7h-11-90-ASTSGPS-BMS3h-56-258
DIQMTQSPSSLSASVGDRVTITCRASRPIGTMLSWYQQKPGKAPKLLILAFSRLQSGVPS
RFSGSGSGTDFTLTISNLQPEDFATYYCAQAGTHPTTFGQGTKVEIKRASTSGPSEVQLL
ESGGGLVQPGGSLRLSCAASGFTERDYEMWWVRQAPGKGLERVSAINPQGTRTYYADSVK
GRFTISRDNSKNTLYLQMNSLRAEDTAVYYCAKLPFYFHEWGQGTLVTVSS (SEQ ID
NO: 1230)

DMS0679 DOM7h-11-90-G4S-BMS3h-56-258
DIQMTQSPSSLSASVGDRVTITCRASRPIGTMLSWYQQKPGKAPKLLILAFSRLQSGVPS
RFSGSGSGTDFTLTISNLQPEDFATYYCAQAGTHPTTFGQGTKVEIKRGGGGSEVQLLES
GGGLVQPGGSLRLSCAASGFTERDYEMWWVRQAPGKGLERVSAINPQGTRTYYADSVKGR
FTISRDNSKNTLYLQMNSLRAEDTAVYYCAKLPFYFHEWGQGTLVTVSS (SEQ ID
NO: 1231)

TABLE 21-continued

Dual Specificity dAb Amino Acid Sequences

DMS0680 DOM7h-11-90-(G4S)3-BMS3h-56-258
DIQMTQSPSSLSASVGDRVTITCRASRPIGTMLSWYQQKPGKAPKLLILAFSRLQSGVPS
RFSGSGSGTDFTLTISNLQPEDFATYYCAQAGTHPTTFGQGTKVEIKRGGGGSGGGGSGG
GGSEVQLLESGGGLVQPGGSLRLSCAASGFTERDYEMWWVRQAPGKGLERVSAINPGTR
TYYADSVKGRFTISRDNSKNTLYLQMNSLRAEDTAVYYCAKLPFYFHEWGQGTLVTVSS
(SEQ ID NO: 1232)

DMS0681 DOM7h-11-90-(G4S)5-BMS3h-56-258
DIQMTQSPSSLSASVGDRVTITCRASRPIGTMLSWYQQKPGKAPKLLILAFSRLQSGVPS
RFSGSGSGTDFTLTISNLQPEDFATYYCAQAGTHPTTFGQGTKVEIKRGGGGSGGGGSGG
GGSGGGGSGGGGSEVQLLESGGGLVQPGGSLRLSCAASGFTERDYEMWWVRQAPGKGLER
VSAINPGTRTYYADSVKGRFTISRDNSKNTLYLQMNSLRAEDTAVYYCAKLPFYFHEWG
QGTLVTVSS (SEQ ID NO: 1233)

DMS0682 BMS3h-56-258-TVA-DOM7h-11-90
EVQLLESGGGLVQPGGSLRLSCAASGFTFRDYEMWWVRQAPGKGLERVSAINPGTRTYY
ADSVKGRFTISRDNSKNTLYLQMNSLRAEDTAVYYCAKLPFYFHEWGQGTLVTVSSTVAD
IQMTQSPSSLSASVGDRVTITCRASRPIGTMLSWYQQKPGKAPKLLILAFSRLINGVPSR
FSGSGSGTDFTLTISNLQPEDFATYYCAQAGTHPTTFGQGTKVEIKR (SEQ ID NO:
1234)

DMS0683 BMS3h-56-258-ASTSGPS-DOM7h-11-90
EVQLLESGGGLVQPGGSLRLSCAASGFTFRDYEMWWVRQAPGKGLERVSAINPGTRTYY
ADSVKGRFTISRDNSKNTLYLQMNSLRAEDTAVYYCAKLPFYFHEWGQGTLVTVSSASTS
GPSDIQMTQSPSSLSASVGDRVTITCRASRPIGTMLSWYQQKPGKAPKLLILAFSRLING
VPSRFSGSGSGTDFTLTISNLQPEDFATYYCAQAGTHPTTFGQGTKVEIKR (SEQ ID
NO: 1235)

DMS0684 BMS3h-56-258-G4S-DOM7h-11-90
EVQLLESGGGLVQPGGSLRLSCAASGFTFRDYEMWWVRQAPGKGLERVSAINPGTRTYY
ADSVKGRFTISRDNSKNTLYLQMNSLRAEDTAVYYCAKLPFYFHEWGQGTLVTVSSGGGG
SDIQMTQSPSSLSASVGDRVTITCRASRPIGTMLSWYQQKPGKAPKLLILAFSRLQSGVP
SRFSGSGSGTDFTLTISNLQPEDFATYYCAQAGTHPTTFGQGTKVEIKR (SEQ ID
NO: 1236)

DMS0685 BMS3h-56-258-(G4S)3-DOM7h-11-90
EVQLLESGGGLVQPGGSLRLSCAASGFTFRDYEMWWVRQAPGKGLERVSAINPGTRTYY
ADSVKGRFTISRDNSKNTLYLQMNSLRAEDTAVYYCAKLPFYFHEWGQGTLVTVSSGGGG
SGGGGSGGGGSDIQMTQSPSSLSASVGDRVTITCRASRPIGTMLSWYQQKPGKAPKLLIL
AFSRLQSGVPSRFSGSGSGTDFTLTISNLQPEDFATYYCAQAGTHPTTFGQGTKVEIKR
(SEQ ID NO: 1237)

DMS0686 BMS3h-56-258-(G4S)5-DOM7h-11-90
EVQLLESGGGLVQPGGSLRLSCAASGFTFRDYEMWWVRQAPGKGLERVSAINPGTRTYY
ADSVKGRFTISRDNSKNTLYLQMNSLRAEDTAVYYCAKLPFYFHEWGQGTLVTVSSGGGG
SGGGGSGGGGSGGGGSGGGGSDIQMTQSPSSLSASVGDRVTITCRASRPIGTMLSWYQQK
PGKAPKLLILAFSRLQSGVPSRFSGSGSGTDFTLTISNLQPEDFATYYCAQAGTHPTTFG
QGTKVEIKR (SEQ ID NO: 1238)

DMS0688 DOM7h-11-90-TVAAPS-BMS3h-56-258
DIQMTQSPSSLSASVGDRVTITCRASRPIGTMLSWYQQKPGKAPKLLILAFSRLQSGVPS
RFSGSGSGTDFTLTISNLQPEDFATYYCAQAGTHPTTFGQGTKVEIKRTVAAPSEVQLLE
SGGGLVQPGGSLRLSCAASGFTFRDYEMWWVRQAPGKGLERVSAINPGTRTYYADSVKG
RFTISRDNSKNTLYLQMNSLRAEDTAVYYCAKLPFYFHEWGQGTLVTVSS (SEQ ID
NO: 1239)

(Table 21 discloses "AST," "TVAAPS," "TVA," "G4S," "(G4S)3," "(G4S)5," and "ASTSGPS" disclosed as SEQ ID NOS 5-7, 1207-1209 and 8, respectively)

TABLE 22

Polynucleotides Encoding Dual Specificity dAbs
(Table 22 discloses "AST," "TVAAPS," "TVA," "G4S," "(G4S)3," "(G4S)5," and "ASTSGPS" disclosed as SEQ ID NOS 5-7, 1207-1209 and 8, respectively)

DMS0654 BMS3h-56-201-AST-DOM7h-11-3
GAGGTGCAGCTGTTGGAGTCTGGGGGAGGCTTGGTACAGCCTGGGGGGT
CCCTGCGTCTCTCCTGTGCAGCCTCCGGATTCACCTTTCGGGATTATGA
GATGTGGTGGGTCCGCCAGGCTCCAGGGAAGGGTCTAGAGCGGGTCTCA
GCTATTAATCCGCAGGGTACGCGTACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGAAA
CTTCCGTTTTACTTTCAGGAGTGGGGTCAGGGAACCCTGGTCACCGTCT
CGAGCGCTAGCACCGACATCCAGATGACCCAGTCTCCATCCTCCCTGTC
TGCATCTGTAGGAGACCGTGTCACCATCACTTGCCGGGCAAGTCGTCCG
ATTGGGACGACGTTAAGTTGGTACCAGCAGAAACCAGGGAAAGCCCCTA
AGCTCCTGATCCTTTTGGAATTCCCGTTTGCAAAGTGGGGTCCCATCACG
TTTCAGTGGCAGTGGATCTGGGACAGATTTCACTCTCACCATCAGCAGT
CTGCAACCTGAAGATTTTGCTACGTACTACTGTGCGCAGGCTGGGACGC
ATCCTACGACGTTCGGCCAAGGGACCAAGGTGGAAATCAAACGG
(SEQ ID NO: 1240)

DMS0655 BMS3h-56-201-AST-DOM7h-11-87
GAGGTGCAGCTGTTGGAGTCTGGGGGAGGCTTGGTACAGCCTGGGGGGT
CCCTGCGTCTCTCCTGTGCAGCCTCCGGATTCACCTTTCGGGATTATGA

TABLE 22-continued

Polynucleotides Encoding Dual Specificity dAbs
(Table 22 discloses "AST," "TVAAPS," "TVA," "G4S,"
"(G4S)3,"
"(G4S)5," and "ASTSGPS" disclosed as SEQ ID NOS
5-7, 1207-1209 and 8, respectively)

GATGTGGTGGGTCCGCCAGGCTCCAGGGAAGGGTCTAGAGCGGGTCTCA
GCTATTAATCCGCAGGGTACGCGTACATACTACGCAGACTCCGTGAAGG
GCCGGTTCACCATCTCCCGCGACAATTCCAAGAACACGCTGTATCTGCA
AATGAACAGCCTGCGTGCCGAGGACACCGCGGTATATTACTGTGCGAAA
CTTCCGTTTTACTTTCAGGAGTGGGGTCAGGGAACCCTGGTCACCGTCT
CGAGCGCTAGCACCGACATCCAGATGACCCAGTCTCCATCCTCCCTGTC
TGCATCTGTAGGAGACCGTGTCACCATCACTTGCCGGGCAAGTCGTCCG
ATTGGGACGATGTTAAGTTGGTACCAGCAGAAACCAGGGAAAGCCCCTA
AGCTCCTGATCCTTGCTTTTTCCCGTTTGCAAAGTGGGGTCCCATCACG
TTTCAGTGGCAGTGGATCTGGGACAGATTTCACTCTCACCATCAGCAGT
CTGCAACCTGAAGATTTTGCTACGTACTACTGTGCGCAGGCTGGGACGC
ATCATACGACGTTCGGCCAAGGGACCAAGGTGGAAATCAAACGG
(SEQ ID NO: 1241)

DMS0656 BMS3h-56-258-AST-DOM7h-11-3
GAGGTGCAGCTGTTGGAGTCTGGGGGAGGCTTGGTACAGCCTGGGGGGTC
CCTGCGTCTCTCCTGTGCAGCCTCCGGATTCACCTTTCGGGATTATGAGA
TGTGGTGGGTCCGCCAGGCTCCAGGGAAGGGTCTAGAGCGGGTCTCAGCT
ATTAATCCGCAGGGTACGCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTCCG
TTTTACTTTCACGAGTGGGGTCAGGGAACCCTGGTCACCGTCTCGAGCGC
TAGCACCGACATCCAGATGACCCAGTCTCCATCCTCCCTGTCTGCATCTG
TAGGAGACCGTGTCACCATCACTTGCCGGGCAAGTCGTCCGATTGGGACG
ACGTTAAGTTGGTACCAGCAGAAACCAGGGAAAGCCCCTAAGCTCCTGAT
CCTTTGGAATTCCCGTTTGCAAAGTGGGGTCCCATCACGTTTCAGTGGCA
GTGGATCTGGGACAGATTTCACTCTCACCATCAGCAGTCTGCAACCTGAA
GATTTTGCTACGTACTACTGTGCGCAGGCTGGGACGCATCCTACGACGTT
CGGCCAAGGGACCAAGGTGGAAATCAAACGG (SEQ ID NO: 1242)

DMS0657 BMS3h-56-258-AST-DOM7h-11-87
GAGGTGCAGCTGTTGGAGTCTGGGGGAGGCTTGGTACAGCCTGGGGGGTC
CCTGCGTCTCTCCTGTGCAGCCTCCGGATTCACCTTTCGGGATTATGAGA
TGTGGTGGGTCCGCCAGGCTCCAGGGAAGGGTCTAGAGCGGGTCTCAGCT
ATTAATCCGCAGGGTACGCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTCCG
TTTTACTTTCACGAGTGGGGTCAGGGAACCCTGGTCACCGTCTCGAGCGC
TAGCACCGACATCCAGATGACCCAGTCTCCATCCTCCCTGTCTGCATCTG
TAGGAGACCGTGTCACCATCACTTGCCGGGCAAGTCGTCCGATTGGGACG
ATGTTAAGTTGGTACCAGCAGAAACCAGGGAAAGCCCCTAAGCTCCTGAT
CCTTGCTTTTTCCCGTTTGCAAAGTGGGGTCCCATCACGTTTCAGTGGCA
GTGGATCTGGGACAGATTTCACTCTCACCATCAGCAGTCTGCAACCTGAA
GATTTTGCTACGTACTACTGTGCGCAGGCTGGGACGCATCATACGACGTT
CGGCCAAGGGACCAAGGTGGAAATCAAACGG (SEQ ID NO: 1243)

DMS0658 DOM7h-11-3-TVAAPS-BMS3h-56-201
GACATCCAGATGACCCAGTCTCCATCCTCCCTGTCTGCATCTGTAGGAGA
CCGTGTCACCATCACTTGCCGGGCAAGTCGTCCGATTGGGACGACGTTAA
GTTGGTACCAGCAGAAACCAGGGAAAGCCCCTAAGCTCCTGATCCTTTGG
AATTCCCGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAGGCTGGGACGCATCCTACGACGTTCGGCCAA
GGGACCAAGGTGGAAATCAAACGTACGGTGGCTGCACCATCTGAGGTGCA
GCTGTTGGAGTCTGGGGGAGGCTTGGTACAGCCTGGGGGGTCCCTGCGTC
TCTCCTGTGCAGCCTCCGGATTCACCTTTCGGGATTATGAGATGTGGTGG
GTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCA
TCTCCCGCGACAATTCCAAGAACACGCTGTATCTGCAAATGAACAGCCTG
CGTGCCGAGGACACCGCGGTATATTACTGTGCGAAACTTCCGTTTTACTT
TCAGGAGTGGGGTCAGGGAACCCTGGTCACCGTCTCCAGC
(SEQ ID NO: 1244)

DMS0659 DOM7h-11-87-TVAAPS-BMS3h-56-201
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAGGCTGGGACGCATCATACGACGTTCGGCCAA
GGGACCAAGGTGGAAATCAAACGTACGGTGGCTGCACCATCTGAGGTGCA
GCTGTTGGAGTCTGGGGGAGGCTTGGTACAGCCTGGGGGGTCCCTGCGTC
TCTCCTGTGCAGCCTCCGGATTCACCTTTCGGGATTATGAGATGTGGTGG
GTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCA
TCTCCCGCGACAATTCCAAGAACACGCTGTATCTGCAAATGAACAGCCTG
CGTGCCGAGGACACCGCGGTATATTACTGTGCGAAACTTCCGTTTTACTT
TCAGGAGTGGGGTCAGGGAACCCTGGTCACCGTCTCCAGC
(SEQ ID NO: 1245)

DMSC660 DOM7h-11-3-TVAAPS-BMS3h-56-258
GACATCCAGATGACCCAGTCTCCATCCTCCCTGTCTGCATCTGTAGGAGA
CCGTGTCACCATCACTTGCCGGGCAAGTCGTCCGATTGGGACGACGTTAA
GTTGGTACCAGCAGAAACCAGGGAAAGCCCCTAAGCTCCTGATCCTTTGG
AATTCCCGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAGGCTGGGACGCATCCTACGACGTTCGGCCAA
GGGACCAAGGTGGAAATCAAACGTACGGTGGCTGCACCATCTGAGGTGCA
GCTGTTGGAGTCTGGGGGAGGCTTGGTACAGCCTGGGGGGTCCCTGCGTC
TCTCCTGTGCAGCCTCCGGATTCACCTTTCGGGATTATGAGATGGTGGTGG
GTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCA
TCTCCCGCGACAATTCCAAGAACACGCTGTATCTGCAAATGAACAGCCTG
CGTGCCGAGGACACCGCGGTATATTACTGTGCGAAACTTCCGTTTTACTT
TCACGAGTGGGGTCAGGGAACCCTGGTCACCGTCTCCAGC
(SEQ ID NO: 1246)

DMS0661 DOM7h-11-87-TVAAPS-BMS3h-56-258
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAGGCTGGGACGCATCATACGACGTTCGGCCAA
GGGACCAAGGTGGAAATCAAACGTACGGTGGCTGCACCATCTGAGGTGCA
GCTGTTGGAGTCTGGGGGAGGCTTGGTACAGCCTGGGGGGTCCCTGCGTC
TCTCCTGTGCAGCCTCCGGATTCACCTTTCGGGATTATGAGATGTGGTGG
GTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCA
TCTCCCGCGACAATTCCAAGAACACGCTGTATCTGCAAATGAACAGCCTG
CGTGCCGAGGACACCGCGGTATATTACTGTGCGAAACTTCCGTTTTACTT
TCACGAGTGGGGTCAGGGAACCCTGGTCACCGTCTCCAGC
(SEQ ID NO: 1247)

DMS0662 DOM7h-11-90-TVAAPS-BMS3h-56-201
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGTGCGCGCAGGCTGGGACGCATCCTACGACGTTCGGCCAA
GGGACCAAGGTGGAAATCAAACGTACGGTGGCTGCACCATCTGAGGTGCA
GCTGTTGGAGTCTGGGGGAGGCTTGGTACAGCCTGGGGGGTCCCTGCGTC
TCTCCTGTGCAGCCTCCGGATTCACCTTTCGGGATTATGAGATGTGGTGG
GTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCA
TCTCCCGCGACAATTCCAAGAACACGCTGTATCTGCAAATGAACAGCCTG
CGTGCCGAGGACACCGCGGTATATTACTGTGCGAAACTTCCGTTTTACTT
TCAGGAGTGGGGTCAGGGAACCCTGGTCACCGTCTCCAGC
(SEQ ID NO: 1248)

DMS0663 DOM7h-11-86-TVAAPS-BMS3h-56-201
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAGTCTGCAACCTGAAGATTGTG
CTACGTACTACTGTGCGCAGGCTGGGACGCATCCTACGACGTTCGGCCAA
GGGACCAAGGTGGAAATCAAACGTACGGTGGCTGCACCATCTGAGGTGCA
GCTGTTGGAGTCTGGGGGAGGCTTGGTACAGCCTGGGGGGTCCCTGCGTC
TCTCCTGTGCAGCCTCCGGATTCACCTTTCGGGATTATGAGATGTGGTGG
GTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCA
TCTCCCGCGACAATTCCAAGAACACGCTGTATCTGCAAATGAACAGCCTG
CGTGCCGAGGACACCGCGGTATATTACTGTGCGAAACTTCCGTTTTACTT
TCAGGAGTGGGGTCAGGGAACCCTGGTCACCGTCTCCAGC
(SEQ ID NO: 1249)

TABLE 22-continued

Polynucleotides Encoding Dual Specificity dAbs
(Table 22 discloses "AST," "TVAAPS," "TVA," "G4S,"
"(G4S)3,"
"(G4S)5," and "ASTSGPS" disclosed as SEQ ID NOS
5-7, 1207-1209 and 8, respectively)

DMS0664 DOM7h-11-69-TVAAPS-BMS3h-56-201
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAGGCTGGGGTGCATCCTACGACGTTCGGCCAA
GGGACCAAGGTGGAAATCAAACGTACGGTGGCTGCACCATCTGAGGTGCA
GCTGTTGGAGTCTGGGGGAGGCTTGGTACAGCCTGGGGGGTCCCTGCGTC
TCTCCTGTGCAGCCTCCGGATTCACCTTTCGGGATTATGAGATGTGGTGG
GTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCA
TCTCCCGCGACAATTCCAAGAACACGCTGTATCTGCAAATGAACAGCCTG
CGTGCCGAGGACACCGCGGTATATTACTGTGCGAAACTTCCGTTTTACTT
TCAGGAGTGGGGTCAGGGAACCCTGGTCACCGTCTCCAGC
(SEQ ID NO: 1250)

DMS0667 DOM7h-11-3-TVAAPS-BMS3h-38-240
GACATCCAGATGACCCAGTCTCCATCCTCCCTGTCTGCATCTGTAGGAGA
CCGTGTCACCATCACTTGCCGGGCAAGTCGTCCGATTGGGACGACGTTAA
GTTGGTACCAGCAGAAACCAGGGAAAGCCCCTAAGCTCCTGATCCTTTGG
AATTCCCGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCAGGCTGGGACGCATCCTACGACGTTCGGCCAA
GGGACCAAGGTGGAAATCAAACGTACGGTGGCTGCACCATCTGAGGTGCA
GCTGTTGGAGTCTGGGGGAGGCTTGGTACAGCCTGGGGGGTCCCTGCGTC
TCTCCTGCGCAGCCTCCGGATTCACCTTTGAGGAGGAGGAGATGATTTGG
GTCCGCCAGGCTCCAGGGAAGGGTCTAGAGTGGGTCTCAGCTATTAGTAG
GAACGGTTACAGCACATACTACGCAGACTCCGTGAAGGGCCGGTTCACCA
TCTCCCGCGACAATTCCAAGAACACGCTGTATCTGCAAATGAACAGCCTG
CGTGCCGAGGATACCGCGGTATATTACTGTGGGAAAGAGCCGTTTCGTTA
TGACTACTGGGGTCAGGGAACCCTGGTCACCGTCTCCAGC
(SEQ ID NO: 1251)

DMS0668 BMS3h-38-240-AST-DOM7h-11-3
GAGGTGCAGCTGTTGGAGTCTGGGGGAGGCTTGGTACAGCCTGGGGGGTC
CCTGCGTCTCTCCTGCGCAGCCTCCGGATTCACCTTTGAGGAGGAGGAGA
TGATTTGGGTCCGCCAGGCTCCAGGGAAGGGTCTAGAGTGGGTCTCAGCT
ATTAGTAGGAACGGTTACAGCACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGGGAAAGAGCCG
TTTCGTTATGACTACTGGGGTCAGGGAACCCTGGTCACCGTCTCGAGCGC
TAGCACCGACATCCAGATGACCCAGTCTCCATCCTCCCTGTCTGCATCTG
TAGGAGACCGTGTCACCATCACTTGCCGGGCAAGTCGTCCGATTGGGACG
ACGTTAAGTTGGTACCAGCAGAAACCAGGGAAAGCCCCTAAGCTCCTGAT
CCTTTGGAATTCCCGTTTGCAAAGTGGGGTCCCATCACGTTTCAGTGGCA
GTGGATCTGGGACAGATTTCACTCTCACCATCAGCAGTCTGCAACCTGAA
GATTTTGCTACGTACTACTGTGCGCAGGCTGGGACGCATCCTACGACGTT
CGGCCAAGGGACCAAGGTGGAAATCAAACGG (SEQ ID NO: 1252)

DMS0669 DOM7h-14-10-TVAAPS-BMS3h-38-240
GACATCCAGATGACCCAGTCTCCATCCTCCCTGTCTGCATCTGTAGGAGA
CCGTGTCACCATCACTTGCCGGGCAAGTCAGTGGATTGGGTCTCAGTTAT
CTTGGTACCAGCAGAAACCAGGGAAAGCCCCTAAGCTCCTGATCATGTGG
CGTTCCTCGTTGCAAAGTGGGGTCCCATCACGTTTCAGTGGCAGTGGATC
TGGGACAGATTTCACTCTCACCATCAGCAGTCTGCAACCTGAAGATTTTG
CTACTACTACTGTGCTCAGGGTTTGAGGCATCCTAAGACGTTCGGCCAA
GGGACCAAGGTGGAAATCAAACGTACGGTGGCTGCACCATCTGAGGTGCA
GCTGTTGGAGTCTGGGGGAGGCTTGGTACAGCCTGGGGGGTCCCTGCGTC
TCTCCTGCGCAGCCTCCGGATTCACCTTTGAGGAGGAGGAGATGATTTGG
GTCCGCCAGGCTCCAGGGAAGGGTCTAGAGTGGGTCTCAGCTATTAGTAG
GAACGGTTACAGCACATACTACGCAGACTCCGTGAAGGGCCGGTTCACCA
TCTCCCGCGACAATTCCAAGAACACGCTGTATCTGCAAATGAACAGCCTG
CGTGCCGAGGATACCGCGGTATATTACTGTGGGAAAGAGCCGTTTCGTTA
TGACTACTGGGGTCAGGGAACCCTGGTCACCGTCTCCAGC
(SEQ ID NO: 1253)

DMS0670 BMS3h-38-240-AST-DOM7h-14-10
GAGGTGCAGCTGTTGGAGTCTGGGGGAGGCTTGGTACAGCCTGGGGGGTC
CCTGCGTCTCTCCTGCGCAGCCTCCGGATTCACCTTTGAGGAGGAGGAGA
TGATTTGGGTCCGCCAGGCTCCAGGGAAGGGTCTAGAGTGGGTCTCAGCT
ATTAGTAGGAACGGTTACAGCACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGGGAAAGAGCCG
TTTCGTTATGACTACTGGGGTCAGGGAACCCTGGTCACCGTCTCGAGCGC
TAGCACCGACATCCAGATGACCCAGTCTCCATCCTCCCTGTCTGCATCTG
TAGGAGACCGTGTCACCATCACTTGCCGGGCAAGTCAGTGGATTGGGTCT
CAGTTATCTTGGTACCAGCAGAAACCAGGGAAAGCCCCTAAGCTCCTGAT
CATGTGGCGTTCCTCGTTGCAAAGTGGGGTCCCATCACGTTTCAGTGGCA
GTGGATCTGGGACAGATTTCACTCTCACCATCAGCAGTCTGCAACCTGAA
GATTTTGCTACTACTGTGCTCAGGGTTTGAGGCATCCTAAGACGTT
CGGCCAAGGGACCAAGGTGGAAATCAAACGG (SEQ ID NO: 1254)

DMS0671 BMS3h-38-235-AST-DOM7h-11-3
GAGGTGCAGCTGTTGGCGTCTGGGGGAGGCTTGGTACAGCCTGGGGGGTC
CCTGCGTCTCTCCTGCGCAGCCTCCGGATTCACCTTTGAGGAGGAGGAGA
TGATTTGGGTCCGCCAGGCTCCAGGGAAGGGTCTAGAGTGGGTCTCAGCT
ATTAGTAGGAACGGTTACAGCACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGGGAAAGAGCCG
TTTCGTTATGACTACTGGGGTCAGGGAACCCTGGTCACCGTCTCGAGCGC
TTCAACCGACATCCAGATGACCCAGTCTCCATCCTCCCTGTCTGCATCTG
TAGGAGACCGTGTCACCATCACTTGCCGGGCAAGTCGTCCGATTGGGACG
ACGTTAAGTTGGTACCAGCAGAAACCAGGGAAAGCCCCTAAGCTCCTGAT
CCTTTGGAATTCCCGTTTGCAAAGTGGGGTCCCATCACGTTTCAGTGGCA
GTGGATCTGGGACAGATTTCACTCTCACCATCAGCAGTCTGCAACCTGAA
GATTTTGCTACGTACTACTGTGCGCAGGCTGGGACGCATCCTACGACGTT
CGGCCAAGGGACCAAGGTGGAAATCAAACGG (SEQ ID NO: 1255)

DMS0672 BMS3h-38-235-AST-DOM7h-11-90
GAGGTGCAGCTGTTGGCGTCTGGGGGAGGCTTGGTACAGCCTGGGGGGTC
CCTGCGTCTCTCCTGCGCAGCCTCCGGATTCACCTTTGAGGAGGAGGAGA
TGATTTGGGTCCGCCAGGCCCCAGGGAAGGGTCTAGAGTGGGTCTCAGCT
ATTAGTAGGAACGGTTACAGCACATACTACGCAGACTCCGTGAAGGGCCG
GTTCACCATCTCCCGCGACAATTCCAAGAACACGCTGTATCTGCAAATGA
ACAGCCTGCGTGCCGAGGATACCGCGGTATATTACTGTGGGAAAGAGCCG
TTTCGTTATGACTACTGGGGTCAGGGAACCCTGGTCACCGTCTCGAGCGC
TTCAACCGACATCCAGATGACCCAGTCTCCATCCTCCCTGTCTGCATCTG
TAGGAGACCGTGTCACCATCACTTGCCGGGCAAGTCGTCCGATTGGGACG
ATGTTAAGTTGGTACCAGCAGAAACCAGGGAAAGCCCCTAAGCTCCTGAT
CCTTGCTTTTTCCCGTTTGCAAAGTGGGGTCCCATCACGTTTCAGTGGCA
GTGGATCTGGGACAGATTTCACTCTCACCATCAGCAATCTGCAACCTGAA
GATTTTGCTACGTACTACTGTGCGCAGGCTGGGACGCATCCTACGACGTT
CGGCCAAGGGACCAAGGTGGAAATCAAACGG (SEQ ID NO: 1256)

DMS0674 DOM7h-11-3-TVAAPS-BMS3h-38-235
GACATCCAGATGACCCAGTCTCCATCCTCCCTGTCTGCATCTGTAGGAGA
CCGTGTCACCATCACTTGCCGGGCAAGTCGTCCGATTGGGACGACGTTAA
GTTGGTACCAGCAGAAACCAGGGAAAGCCCCTAAGCTCCTGATCCTTTGG
AATTCCCGTTTGCAAAGTGGGGTCCCATCACGTTTCAGTGGCAGTGGATC
TGGGACAGATTTCACTCTCACCATCAGCAGTCTGCAACCTGAAGATTTTG
CTACGTACTACTGTGCGCAGGCTGGGACGCATCCTACGACGTTCGGCCAA
GGGACCAAGGTGGAAATCAAACGACCGTGGCGGCCGAGTGAGGTGCA
GCTGTTGGCGTCTGGGGGAGGCTTGGTACAGCCTGGGGGGTCCCTGCGTC
TCTCCTGCGCAGCCTCCGGATTCACCTTTGAGGAGGAGGAGATGATTTGG
GTCCGCCAGGCTCCAGGGAAGGGTCTAGAGTGGGTCTCAGCTATTAGTAG
GAACGGTTACAGCACATACTACGCAGACTCCGTGAAGGGCCGGTTCACCA
TCTCCCGCGACAATTCCAAGAACACGCTGTATCTGCAAATGAACAGCCTG
CGTGCCGAGGATACCGCGGTATATTACTGTGGGAAAGAGCCGTTTCGTTA
TGACTACTGGGGTCAGGGAACCCTGGTCACCGTCTCCAGC
(SEQ ID NO: 1257)

DMS0675 DOM7h-11-90-TVAAPS-BMS3h-38-235
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGTGCGCAGGCTGGGACGCATCCTACGACGTTCGGCCAA
GGGACCAAGGTGGAAATCAAACGACCGTGGCGGCCGAGTGAGGTGCA
ACTGTTGGCGTCTGGGGGAGGCTTGGTACAGCCTGGGGGGTCCCTGCGTC
TCTCCTGCGCAGCCTCCGGATTCACCTTTGAGGAGGAGGAGATGATTTGG
GTCCGCCAGGCTCCAGGGAAGGGTCTAGAGTGGGTCTCAGCTATTAGTAG
GAACGGTTACAGCACATACTACGCAGACTCCGTGAAGGGCCGGTTCACCA
TCTCCCGCGACAATTCCAAGAACACGCTGTATCTGCAAATGAACAGCCTG
CGTGCCGAGGATACCGCGGTATATTACTGTGGGAAAGAGCCGTTTCGTTA
TGACTACTGGGGTCAGGGAACCCTGGTCACCGTCTCCAGC
(SEQ ID NO: 1258)

TABLE 22-continued

Polynucleotides Encoding Dual Specificity dAbs
(Table 22 discloses "AST," "TVAAPS," "TVA," "G4S,"
"(G4S)3,"
"(G4S)5," and "ASTSGPS" disclosed as SEQ ID NOS
5-7, 1207-1209 and 8, respectively)

DMS0677 DOM7h-11-90-TVA-BMS3h-56-258
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGCGCGCAGGCTGGGACGCATCCTACGACGTTCGGCCAA
GGGACCAAGGTGGAAATCAAACGTACGGTGGCGGAGGTGCAGCTGTTGGA
GTCTGGGGGAGGCTTGGTACAGCCTGGGGGGTCCCTGCGTCTCTCCTGTG
CAGCCTCCGGATTCACCTTTCGGGATTATGAGATGTGGTGGGTCCGCAG
GCTCCAGGGAAGGGTCTAGAGCGGGTCTCAGCTATTAATCCGCAGGGTAC
GCGTACATACTACGCAGACTCCGTGAAGGGCCGGTTCACCATCTCCCGCG
ACAATTCCAAGAACACGCTGTATCTGCAAATGAACAGCCTGCGTGCCGAG
GACACCGCGGTATATTACTGTGCGAAACTTCCGTTTTACTTTCACGAGTG
GGGTCAGGGAACCCTGGTCACCGTCTCCAGC (SEQ ID NO: 1259)

DMS0678 DOM7h-11-90-ASTSGPS-BMS3h-56-258
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGCGCGCAGGCTGGGACGCATCCTACGACGTTCGGCCAA
GGGACCAAGGTGGAAATCAAACGGGCTAGCACCTCAGGTCCATCGGAGGT
GCAGCTGTTGGAGTCTGGGGGAGGCTTGGTACAGCCTGGGGGGTCCCTGC
GTCTCTCCTGTGCAGCCTCCGGATTCACCTTTCGGGATTATGAGATGTGG
TGGGTCCGCCAGGCTCCAGGGAAGGGTCTAGAGCGGGTCTCAGCTATTAA
TCCGCAGGGTACGCGTACATACTACGCAGACTCCGTGAAGGGCCGGTTCA
CCATCTCCCGCGACAATTCCAAGAACACGCTGTATCTGCAAATGAACAGC
CTGCGTGCCGAGGACACCGCGGTATATTACTGTGCGAAACTTCCGTTTTA
CTTTCACGAGTGGGGTCAGGGAACCCTGGTCACCGTCTCCAGC
(SEQ ID NO: 1260)

DMS0679 DOM7h-11-90-G4S-BMS3h-56-258
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGCGCGCAGGCTGGGACGCATCCTACGACGTTCGGCCAA
GGGACCAAGGTGGAAATCAAACGGGGTGGAGGTGGCTCTGAGGTGCAGCT
GTTGGAGTCTGGGGGAGGCTTGGTACAGCCTGGGGGGTCCCTGCGTCTCT
CCTGTGCAGCCTCCGGATTCACCTTTCGGGATTATGAGATGTGGTGGGTC
CGCCAGGCTCCAGGGAAGGGTCTAGAGCGGGTCTCAGCTATTAATCCGCA
GGGTACGCGTACATACTACGCAGACTCCGTGAAGGGCCGGTTCACCATCT
CCCGCGACAATTCCAAGAACACGCTGTATCTGCAAATGAACAGCCTGCGT
GCCGAGGACACCGCGGTATATTACTGTGCGAAACTTCCGTTTTACTTTCA
CGAGTGGGGTCAGGGAACCCTGGTCACCGTCTCCAGC
(SEQ ID NO: 1261)

DMS0680 DOM7h-11-90-(G4S)3-BMS3h-56-258
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGCGCGCAGGCTGGGACGCATCCTACGACGTTCGGCCAA
GGGACCAAGGTGGAAATCAAACGGGGTGGAGGTGGCTCTGGAGGTGGCGG
TAGCGGCGGAGGCGGTTCAGAGGTGCAGCTGTTGGAGTCTGGGGGAGGCT
TGGTACAGCCTGGGGGGTCCCTGCGTCTCTCCTGTGCAGCCTCCGGATTC
ACCTTTCGGGATTATGAGATGTGGTGGGTCCGCCAGGCTCCAGGGAAGGG
TCTAGAGCGGGTCTCAGCTATTAATCCGCAGGGTACGCGTACATACTACG
CAGACTCCGTGAAGGGCCGGTTCACCATCTCCCGCGACAATTCCAAGAAC
ACGCTGTATCTGCAAATGAACAGCCTGCGTGCCGAGGACACCGCGGTATA
TTACTGTGCGAAACTTCCGTTTTACTTTCACGAGTGGGGTCAGGGAACCC
TGGTCACCGTCTCCAGC (SEQ ID NO: 1262)

DMS0681 DOM7h-11-90-(G4S)5-BMS3h-56-258
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGCGCGCAGGCTGGGACGCATCCTACGACGTTCGGCCAA
GGGACCAAGGTGGAAATCAAACGGGGTGGAGGTGGCTCTGGAGGTGGCGG
TAGCGGCGGTGGCGGTTCAGGTGGCGGAGGTTCTGGAGGCGGTGGATCTG
AGGTGCAGCTGTTGGAGTCTGGGGGAGGCTTGGTACAGCCTGGGGGGTCC
CTGCGTCTCTCCTGTGCAGCCTCCGGATTCACCTTTCGGGATTATGAGAT
GTGGTGGGTCCGCCAGGCTCCAGGGAAGGGTCTAGAGCGGGTCTCAGCTA
TTAATCCGCAGGGTACGCGTACATACTACGCAGACTCCGTGAAGGGCCGG
TTCACCATCTCCCGCGACAATTCCAAGAACACGCTGTATCTGCAAATGAA
CAGCCTGCGTGCCGAGGACACCGCGGTATATTACTGTGCGAAACTTCCGT
TTTACTTTCACGAGTGGGGTCAGGGAACCCTGGTCACCGTCTCCAGC
(SEQ ID NO: 1263)

DMS0682 BMS3h-56-258-TVA-DOM7h-11-90
GAGGTGCAGCTGTTGGAGTCTGGGGGAGGCTTGGTACAGCCTGGGGGGTC
CCTGCGTCTCTCCTGTGCAGCCTCCGGATTCACCTTTCGGGATTATGAGA
TGTGGTGGGTCCGCCAGGCTCCAGGGAAGGGTCTAGAGCGGGTCTCAGCT
ATTAATCCGCAGGGTACGCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTCCG
TTTTACTTTCACGAGTGGGGTCAGGGAACCCTGGTCACCGTCTCGAGCAC
GGTGGCGGACATCCAGATGACCCAGTCTCCATCCTCCCTGTCTGCATCTG
TAGGAGACCGTGTCACCATCACTTGCCGGGCAAGTCGTCCGATTGGGACG
ATGTTAAGTTGGTACCAGCAGAAACCAGGGAAAGCCCCTAAGCTCCTGAT
CCTTGCTTTTTCCCGTTTGCAAAGTGGGGTCCCATCACGTTTCAGTGGCA
GTGGATCTGGGACAGATTTCACTCTCACCATCAGCAATCTGCAACCTGAA
GATTTTGCTACGTACTACTGCGCGCAGGCTGGGACGCATCCTACGACGTT
CGGCCAAGGGACCAAGGTGGAAATCAAACGG (SEQ ID NO: 1264)

DMS0683 BMS3h-56-258-ASTSGPS-DOM7h-11-90
GAGGTGCAGCTGTTGGAGTCTGGGGGAGGCTTGGTACAGCCTGGGGGGTC
CCTGCGTCTCTCCTGTGCAGCCTCCGGATTCACCTTTCGGGATTATGAGA
TGTGGTGGGTCCGCCAGGCTCCAGGGAAGGGTCTAGAGCGGGTCTCAGCT
ATTAATCCGCAGGGTACGCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTCCG
TTTTACTTTCACGAGTGGGGTCAGGGAACCCTGGTCACCGTCTCGAGCGC
TAGCACCTCAGGTCCATCGGAGGTGCAGCTGTTGGAGTCTCCATCCTCCC
TGTCTGCATCTGTAGGAGACCGTGTCACCATCACTTGCCGGGCAAGTCGT
CCGATTGGGACGATGTTAAGTTGGTACCAGCAGAAACCAGGGAAAGCCCC
TAAGCTCCTGATCCTTGCTTTTTCCCGTTTGCAAAGTGGGGTCCCATCAC
GTTTCAGTGGCAGTGGATCTGGGACAGATTTCACTCTCACCATCAGCAAT
CTGCAACCTGAAGATTTTGCTACGTACTACTGCGCGCAGGCTGGGACGCA
TCCTACGACGTTCGGCCAAGGGACCAAGGTGGAAATCAAACGG
(SEQ ID NO: 1265)

DMS0684 BMS3h-56-258-G4S-DOM7h-11-90
GAGGTGCAGCTGTTGGAGTCTGGGGGAGGCTTGGTACAGCCTGGGGGGTC
CCTGCGTCTCTCCTGTGCAGCCTCCGGATTCACCTTTCGGGATTATGAGA
TGTGGTGGGTCCGCCAGGCTCCAGGGAAGGGTCTAGAGCGGGTCTCAGCT
ATTAATCCGCAGGGTACGCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTCCG
TTTTACTTTCACGAGTGGGGTCAGGGAACCCTGGTCACCGTCTCGAGCGC
TGGAGGCGGCTCTGACATCCAGATGACCCAGTCTCCATCCTCCCTGTCTG
CATCTGTAGGAGACCGTGTCACCATCACTTGCCGGGCAAGTCGTCCGATT
GGGACGATGTTAAGTTGGTACCAGCAGAAACCAGGGAAAGCCCCTAAGCT
CCTGATCCTTGCTTTTTCCCGTTTGCAAAGTGGGGTCCCATCACGTTTCA
GTGGCAGTGGATCTGGGACAGATTTCACTCTCACCATCAGCAATCTGCAA
CCTGAAGATTTTGCTACGTACTACTGCGCGCAGGCTGGGACGCATCCTAC
GACGTTCGGCCAAGGGACCAAGGTGGAAATCAAACGG
(SEQ ID NO: 1266)

DMS0685 BMS3h-56-258-(G4S)3-DOM7h-11-90
GAGGTGCAGCTGTTGGAGTCTGGGGGAGGCTTGGTACAGCCTGGGGGGTC
CCTGCGTCTCTCCTGTGCAGCCTCCGGATTCACCTTTCGGGATTATGAGA
TGTGGTGGGTCCGCCAGGCTCCAGGGAAGGGTCTAGAGCGGGTCTCAGCT
ATTAATCCGCAGGGTACGCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTCCG
TTTTACTTTCACGAGTGGGGTCAGGGAACCCTGGTCACCGTCTCGAGCGC
TGGAGGTGGCTCTGGAGGTGGCGGTAGCGGCGGTGGCGGTTCAGACATCC
AGATGACCCAGTCTCCATCCTCCCTGTCTGCATCTGTAGGAGACCGTGTC
ACCATCACTTGCCGGGCAAGTCGTCCGATTGGGACGATGTTAAGTTGGTA
CCAGGAGAAACCAGGGAAAGCCCCTAAGCTCCTGATCCTTGCTTTTTCCC
GTTTGCAAAGTGGGGTCCCATCACGTTTCAGTGGCAGTGGATCTGGGACA

TABLE 22-continued

Polynucleotides Encoding Dual Specificity dAbs
(Table 22 discloses "AST," "TVAAPS," "TVA," "G4S,"
"(G4S)3,"
"(G4S)5," and "ASTSGPS" disclosed as SEQ ID NOS
5-7, 1207-1209 and 8, respectively)

```
GATTTCACTCTCACCATCAGCAATCTGCAACCTGAAGATTTTGCTACGTA
CTACTGCGCGCAGGCTGGGACGCATCCTACGACGTTCGGCCAAGGGACCA
AGGTGGAAATCAAACGG (SEQ ID NO: 1267)

DMS0686 BMS3h-56-258-(G4S)5-DOM7h-11-90
GAGGTGCAGCTGTTGGAGTCTGGGGGAGGCTTGGTACAGCCTGGGGGGTC
CCTGCGTCTCTCCTGTGCAGCCTCCGGATTCACCTTTCGGGATTATGAGA
TGTGGTGGGTCCGCCAGGCTCCAGGGAAGGGTCTAGAGCGGGTCTCAGCT
ATTAATCCGCAGGGTACGCGTACATACTACGCAGACTCCGTGAAGGGCCG
GTTCACCATCTCCCGCGACAATTCCAAGAACACGCTGTATCTGCAAATGA
ACAGCCTGCGTGCCGAGGACACCGCGGTATATTACTGTGCGAAACTTCCG
TTTTACTTTCACGAGTGGGGTCAGGGAACCCTGGTCACCGTCTCGAGCGG
TGGAGGTGGCTCTGGAGGTGGCGGTAGCGGCGGTGGCGGTTCAGGTGGCG
GAGGTTCTGGAGGCGGTGGATCTGACATCCAGATGACCCAGTCTCCATCC
TCCCTGTCTGCATCTGTAGGAGACCGTGTCACCATCACTTGCCGGGCAAG
TCGTCCGATTGGGACGATGTTAAGTTGGTACCAGCAGAAACCAGGGAAAG
CCCCTAAGCTCCTGATCCTTGCTTTTTCCCGTTTGCAAAGTGGGGTCCCA
TCACGTTTCAGTGGCAGTGGATCTGGGACAGATTTCACTCTCACCATCAG
CAATCTGCAACCTGAAGATTTTGCTACGTACTACTGCGCGCAGGCTGGGA
CGCATCCTACGACGTTCGGCCAAGGGACCAAGGTGGAAATCAAACGG
(SEQ ID NO: 1268)

DMS0688 DOM7h-11-90-TVAAPS-BMS3h-56-258
GACATCCAGATGACCCAGTCTCCATCCTCCCTGTCTGCATCTGTAGGAGA
CCGTGTCACCATCACTTGCCGGGCAAGTCGTCCGATTGGGACGATGTTAA
GTTGGTACCAGCAGAAACCAGGGAAAGCCCCTAAGCTCCTGATCCTTGCT
TTTTCCCGTTTGCAAAGTGGGGTCCCATCACGTTTCAGTGGCAGTGGATC
TGGGACAGATTTCACTCTCACCATCAGCAATCTGCAACCTGAAGATTTTG
CTACGTACTACTGCGCGCAGGCTGGGACGCATCCTACGACGTTCGGCCAA
GGGACCAAGGTGGAAATCAAACGGACCGTAGCGGCGCCGAGTGAGGTGCA
GCTGTTGGAGTCTGGGGGAGGCTTGGTACAGCCTGGGGGGTCCCTGCGTC
TCTCCTGTGCAGCCTCCGGATTCACCTTTCGGGATTATGAGATGTGGTGG
GTCCGCCAGGCTCCAGGGAAGGGTCTAGAGCGGGTCTCAGCTATTAATCC
GCAGGGTACGCGTACATACTACGCAGACTCCGTGAAGGGCCGGTTCACCA
TCTCCCGCGACAATTCCAAGAACACGCTGTATCTGCAAATGAACAGCCTG
CGTGCCGAGGACACCGCGGTATATTACTGTGCGAAACTTCCGTTTTACTT
TCACGAGTGGGGTCAGGGAACCCTGGTCACCGTCTCCAGC
(SEQ ID NO: 1269)
```

Example 8

Anti-Cynomolgus CD40 dAbs

The methods disclosed herein to generate antibody polypeptides that specifically bind human CD40 may be used to generate antibody polypeptides that specifically bind CD40 of other species. For example, anti-cynomolgus (anti-cyno) CD40 antibody polypeptides can be produced using the presently disclosed methods. The anti-cynoCD40 antibody polypeptides can be generated using the same scheme of initial/primary screening and affinity maturation as anti-human CD40 dAbs, for example. Methods for obtaining anti-cynoCD40 dAbs are disclosed, and representative examples of anti-cynoCD40 dAbs are provided in TABLE 23 below.

ELISA RBA:
Clear walled Highbind, 384 well plates (Corning, UK) were coated with 25 μl of 1 μg/ml neutravidin in carbonate buffer overnight at 4° C. The following day, assay plates were washed with 0.1% Tween PBS buffer, blocked with 1% BSA in PBS for 1 hour at room temperature, and washed again. Following removal of excess washing buffer, 25 μl of 1 μg/ml of biotinylated human IZ-CD40L (BMS, 1.2 mg/ml stock concentration) was incubated with the assay plates for 1 hour at room temperature. Simultaneously, a dilution range of purified dAb and 1 μg/ml of cynoCD40 (BMS) were complexed in a 1:1 ratio. Following washing of the assay plate, the dAb:cyno CD40 complex was incubated in the assay plate at room temperature for 2 hours with gentle agitation. Competitive binding of dAb vs. cynoCD40 to biotinylated CD40L was detected with horse radish peroxidase (HRP) conjugated anti human (Fc) secondary antibody (Sigma-Aldrich, UK). Absorbance signal was measured using a Spectromax M5e plate reader (Molecular Devices) at 450 nm following neutralization with 1M HCl.

cynoCD40 CHO Cell RBA Using AB8200 FMAT:
Stably transfected cynoCD40-expressing CHO-DG44 cells or native CHO-DG44 cells (BMS) were detached from cell culture flasks using Versene (Invitrogen). 40,000 cells per well were seeded into 96 well Highbind, black walled, clear bottom plates (Corning, UK) in 0.1% BSA PBS assay buffer with a dilution range of dAb, 0.25 μg/ml of biotinylated human IZ-CD40L (BMS, 1.2 mg/ml stock concentration), and 0.25 μg/ml of streptavidin Alexa Fluor® 647 (Invitrogen, Molecular probes, UK). The mixture vas incubated in the absence of light for 6 hours. Following incubation, competitive binding of dAb vs. cynoCD40 CHO cells to soluble biotinylated IZ-CD40L was assessed using relative fluorescence as measured by the AB8200 cellular detection platform (Applied Biosystems).

CHO-hCD40L-Driven Primary Human B Cell Proliferation:
CHO cells (ATCC) were transfected with human CD40L to generate a stable cell line expressing high levels of CD40L on the cell surface. CHO-CD40L cells were irradiated at 10,000 Rads before incubation with human B cells. $1 \times 10^5$ tonsillar human B cells were incubated with $1 \times 10^3$ CHO-CD40L cells (1:100 ratio of CHO-CD40L: human B cells) along with varying titration of dAb or monoclonal antibody in a final volume of 200 μl/well in a 96-well round bottom plate. The plates were incubated at 37° C. for 72 hours, following which thymidine ($^3$H; 0.5 μci/well) was added for 6 hours. B cell proliferation was quantified based on thymidine incorporation. All assays, unless otherwise noted, were performed in RPMI media supplemented with 10% fetal calf serum (FCS).

Soluble IZ-hCD40L-Driven Cyno Splenic B Cell Proliferation:
$1 \times 10^5$ B cells isolated from cynomolgous monkey spleens were incubated with 0.5 μg/ml of IZ-hCD40L along with varying titration of dAb or mAb in a final volume of 200 μl/well in a 96-well round bottom plate. The plates were incubated at 37° C. for 72 hours, following which $^3$H-thymidine (μci/well) was added for 6 hours. B cell proliferation was quantified based on thymidine incorporation. All assays, unless otherwise noted, were performed in RPMI media supplemented with 10% fetal calf serum (FCS).

TABLE 23

| Clone | ELISA RBA (nM) | Cell RBA (nM) | B cell proliferation assay (EC50 nM) | |
|---|---|---|---|---|
| | | | Human | Cyno |
| BMS5c8 | | | | 8, 10, 12, 8, 8 |
| BMS3c-85 | 370 | | >7000, >7000 | 747, 2700, 7000, 7000 |

TABLE 23-continued

| Clone | ELISA RBA (nM) | Cell RBA (nM) | B cell proliferation assay (EC50 nM) | |
|---|---|---|---|---|
| | | | Human | Cyno |
| BMS3c-85-1 | 52, 8 | 12 | 2600, 1100 | 18, 39, 47 |
| BMS3c-85-2 | 12, 4 | 4, 17 | 1800, 800 | 2, 5, 6, 1 |
| BMS3c-85-3 | 7 | 23 | >7000, >7000 | 33, 31, 21, 31 |
| BMS3c-85-8 | 22 | 17.2 | >7000, >7000 | 33, 33, 25 |
| BMS3c-85-9 | 10 | | >7000, >7000 | >70, >70, 104 |
| BMS3c-85-21 | 11 | 18 | | 24 |
| BMS3c-85-24 | 8 | 13, 14 | | |
| BMS3c-85-25 | 62 | | | |
| BMS3c-85-26 | 3 | | 3300, 3900 | >70, >70, 385 |
| BMS3c-85-27 | 13 | 23 | | 39 |
| BMS3c-85-31 | 13 | 11, 9 | | |
| BMS3c-85-32 | 21 | 56 | | 111 |
| BMS3c-85-33 | 15 | 10, 21.3 | | 17 |
| BMS3c-85-34 | 48 | | | |
| BMS3c-85-35 | — | 19, 1.5 | >700 | 2 |
| BMS3c-85-36 | — | 28 | | |
| BMS3c-85-37 | — | 71 | | |
| BMS3c-85-38 | — | 17 | | |
| BMS3c-85-47 | — | 2.9 | >700 | <2, 0.5 |
| BMS3c-85-49 | — | 10 | >700 | 3, 3 |
| BMS3c-85-51 | — | 2.5 | >700 | 3 |
| BMS3c-85-52 | — | 8.5 | | |
| BMS3c-85-55 | — | 13.3, 6.7 | >700 | 3, 3 |
| BMS3c-85-56 | — | no convergence | | |
| BMS3c-85-57 | — | 13.8, 5.3 | >700 | 2, 4 |
| BMS3c-85-62 | — | 9.9, 2.7, 2.0 | >700 | <2, 0.63 |
| BMS3c-85-63 | — | 80.9 | | |
| BMS3c-85-64 | — | 16.1 | | |
| BMS3c-85-65 | — | 13.9, 7.4 | >700 | 3, 2 |
| BMS3c-85-67 | — | 1.5 | | 0.17 |
| BMS3c-85-69 | — | 1.8 | | 0.33 |
| BMS3c-85-72 | — | 2 | | 0.16 |
| BMS3c-85-73 | — | 2.3 | | |
| BMS3c-85-77 | — | 2.3 | | 0.2 |
| BMS3c-85-84 | — | 1.3 | | 0.21 |
| BMS3c-85-88 | — | 3 | | 0.25 |
| BMS3c-85-91 | — | 1.3 | | 0.26 |

Example 9

Anti-Human CD40 dAbs do not Bind CynoCD40

CynoCD40 has a Leu109 residue instead of a Trp109, as in human CD40. The amino acid sequence of *Macaca fascicularis* CD40 is reproduced below:

```
                                                (SEQ ID NO: 2)
  1    MVRLPLQCVL  WGCLLTAVYP  EPPTACREKQ  YLINSQCCSL  CQPGQKLVSD

51    CTEFTETECL  PCGESEFLDT  WNRETRCHQH  KYCDPNLGLR  VQQKGTSETD

101    TICTCEEGLH  CTSESCESCV  PHRSCLPGFG  VKQIATGVSD  TICEPCPVGF

151    FSNVSSAFEK  CRPWTSCETK  DLVVQQAGIN  KTDVVCGPQD  RQRALVVIPI

201    CLGILFVILL  LVLVFIKKVA  KKPNDKVPHP  KQEPQEINFP  DDLPGSNPAA

251    PVQETLHGCQ  PVTQEDGKES  RISVQERQ
```

Anti-human CD40 dAbs were tested for cross reactivity to B cells in cynomolgus monkey, rhesus macaque and chimpanzee blood, and lymphocytes from marmoset blood using flow cytometric methods. The procedures detailed below summarize methods used for CD40 dAb detection over multiple experiments. The results, shown in TABLE 24, suggest that anti-human CD40 dAbs do not bind cynoCD40. This is consistent with the evidence disclosed above (see FIGS. 1 and 2) that Trp109 in human CD40 (which is absent in cynoCD40) is important for complex formation between the dAbs and human CD40.

Methods:

PEGylated anti-human CD40 dAbs (BMS3h-56-5C-40L and BMS3h38-2C-P40Br) or a biotin-conjugated dAb (BMS3h38-2-biotin) were incubated with human and primate blood samples on a rotator for 1 hour at 37° C. 100 µl from each blood sample was aliquoted to 12×75 mm tubes and washed 3 times with FACS buffer (0.5% FBS/PBS/0.1% sodium azide). Tubes were centrifuged for 5 minutes at 1500 rpm, and supernatants were decanted between washes. Following the washes, tubes were placed on ice and incubated with human IgG for 5 minutes to block non-specific binding via Fc receptors.

For PEGylated dAb detection, anti-PEG antibodies (clone CH-2074. Silver Lake Research or clone 2-2, Open Biosystems) were added to tubes and incubated for 30 minutes. Samples were washed once in FACS buffer, then incubated with an APC-labeled CD20 antibody (clone 2H7, BD Biosciences) and PE labeled-anti-mouse IgG (Fcγ1 specific; Calbiochem) for an additional 30 minutes on ice.

For biotin-conjugated dAb detection, PE-labeled streptavidin (Invitrogen) and APC-labeled CD20 antibody (clone 2H7, BD Biosciences) were added to tubes and incubated 30 minutes at room temperature.

Additionally, to measure CD40 levels on human and primate blood, an aliquot of each blood sample was incubated with an APC-labeled CD20 antibody (clone 2H7, BD Biosciences) and a PE-labeled anti-human CD40 antibody that cross reacts with primate species (clone 5C3, BD Biosciences) for 30 minutes at room temperature.

To lyse red blood cells and fix white blood cells following detection antibody incubation, FACS Lysing Solution (BD Biosciences) was added to all tubes, and samples were incubated for 15 minutes at room temperature. Samples were centrifuged and resuspended in FACS Lysing Solution, and analyzed by flow cytometry on a BD FACSCanto™, gating on CD20+ B cells for analysis. For marmoset samples, the CD20 antibody was not cross reactive; therefore analysis was performed on all lymphocytes as identified by forward and side scatter properties (size).

Figure 3A:
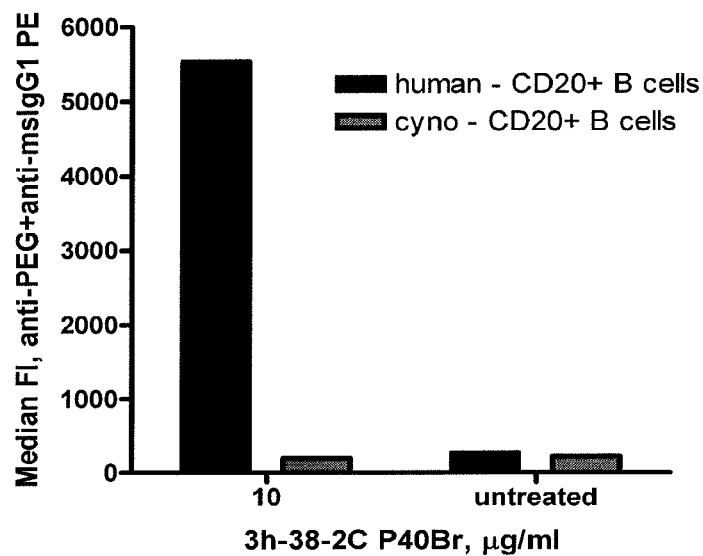
FIGS. 3A and 3B depict binding of a PEGylated anti-human CD40 dAb, BMS3h38-2C-P40Br, on blood samples from human and primate species.
Figure 3B:
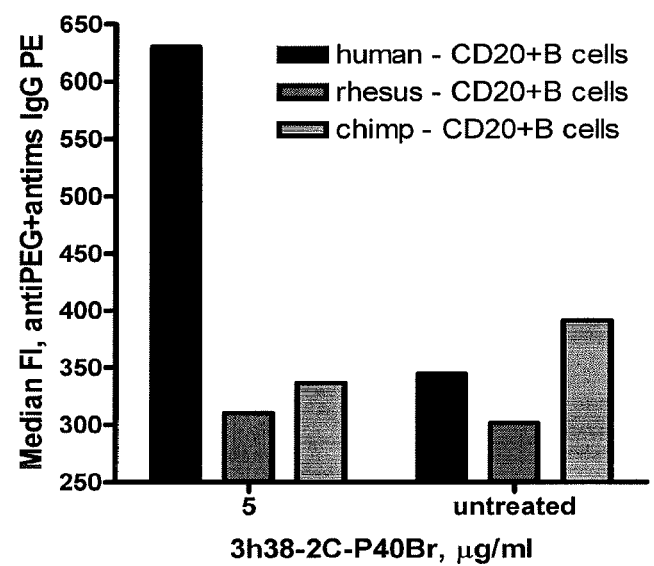

Results:

Binding of PEGylated and biotinylated anti-human CD40 dAbs was tested in human and primate blood samples according to the method above. Anti-human CD40 dAb binding to CD20+ B cells in human blood samples was detected. In contrast, the binding of PEGylated and biotinylated CD40 dAbs was not detected on CD20+ B cells in cynomolgus, rhesus, or chimp blood samples or on lymphocytes in marmoset blood samples. Results for BMS3h-38-2C-P40Br dAb are shown in FIG. 3, Panels A and B. Similar results were obtained for the other dAbs. Comparable levels of CD40 on the B cells of human and primate species were confirmed using an anti-human CD40 antibody that cross reacts with primate CD40. These data indicate that human CD40 dAbs from the BMS3h-56 and BMS3h-38 lineages are unable to bind CD40 in primate species. The data are consistent with the importance of the Trp109 residue in forming a complex between CD40 and the anti-CD40 dAbs, as shown in FIGS. 1 and 2.

Example 10

X-Ray Crystallography of a Complex Between CD40 and dAb BMS3h-56-5 Data Collection and Processing Two different crystal forms were analyzed during the structure determination of the human CD40 (SEQ ID NO: 1)/BMS3h-56-5 (SEQ ID NO: 321) complex. Data were collected from a crystal of the CD40/BMS3h56-5 complex, flash-cooled to and maintained at 100 K, and mounted on a Rigaku AFC-9 goniometer. The X-ray source was a Rigaku FR-E using a copper target with MicroMax™ confocal optics and a Saturn 92 detector. Data were collected at extremely high redundancy to enhance the sulfur anomalous diffraction signal in the hopes of using that signal to phase the data. Data were processed with HKL2000 (HKL Research; Otwinowski et al., In *Methods Enzymol. Macromolecular Crystallography* part A, Carter et al., eds., vol. 276, p. 307-326, Academic Press, Inc., New York, N.Y. (1997)). Data collection statistics for this crystal are summarized below and in Table 24:

Space Group: I222;
Unit Cell: a=156.6 Å; b=158.3 Å; c=200.7 Å;
Mosaicity 0.59-0.84; Rejected observations: 1028; 0.06%.

TABLE 24

| s09-167 | Resolution, Å | Measured | Unique | Redun. | % Complete | R value | I/σ$_I$ |
|---|---|---|---|---|---|---|---|
| Overall | 50.00-3.30 | 1603547 | 37772 | 42.5 | 99.8 | 0.137 | 33.7 |
| First Shell | 50.00-8.94 | ≥38193 | 1971 | 40.1 | 97.1 | 0.049 | 58.7 |
| Last Shell | 3.36-3.30 | ≥37054 | 1861 | 43.6 | 99.8 | 0.439 | 12.5 |

A second crystal form was collected from a crystal flash-cooled to 100 K and mounted on a Rayonix MX-225 detector at the Canadian Light Source beamline CMCF1 (08-ID-1) and the wavelength was 0.9793 Å. These data were collected by Shamrock Structures (R. Walter and G. Ranieri) and were processed with HKL2000. *Data collection statistics for this crystal are summarized below and in Table* 25:

Space Group: C2;
Unit Cell: a=199.3 Å; b=48.7 Å; c=138.8 Å; β=118.2°;
Mosaicity 0.62-0.71; Rejected observations: 70; 0.08%.

TABLE 25

| x09-275 | Resolution, Å | Measured | Unique | Redun. | % Complete | R value | I/σ$_I$ |
|---|---|---|---|---|---|---|---|
| Overall | 50.00-2.80 | 92545 | 29303 | 3.2 | 98.6 | 0.091 | 14.6 |
| First Shell | 50.00-6.03 | 9265 | 3060 | 3.0 | 98.5 | 0.052 | 18.0 |
| Last Shell | 2.90-2.80 | 8857 | 2882 | 3.1 | 98.0 | 0.421 | 3.4 |

Molecular Replacement Models:

The model of the dAb, BMS3h-56-5, was derived from PDB ID 2VYR chain E residues 1-124 with sequential residues corresponding to CDRs 31-35. 50-57, and 99-111 removed by SPLIT_PDB (which corresponds to Kabat numbering 31-35, 50-56, and 95-100G) and then run through MUTATE and finally renumbered by RENUMBER. MUTATE changes non-identical residues to the minimum identical, i.e., normally Ala or Gly, but, for example Tyr→Phe and Phe→Tyr would result in Phe. It does not build any atoms, although for Thr→Val, Val→Thr, Cys→Ser, and Ser→Cys, it will substitute the appropriate atom name, but not change the position. RENUMBER changed the numbering to Kabat numbering (Kabat et al., *Sequences of Immunological Interest*, 5$^{th}$ ed., U.S. Dept. Health & Human Services, Washington, D.C. (1991)), which is a standard numbering system for antibodies that makes description of CDRs and framework residues straight-forward.

A CD40 model was constructed from PDB IDs 1JMA (chain B), 1NCF (chain A), 1TNR (chain R), 2HEV (chain R), 2HEY (chains R, T), and 2UWI (chains A, B) using phenix.ensembler (University of Cambridge, UK) to create an ensemble of structures. The N-termini (residues 24-78) plus a six residue segment (residues 95-100) of these molecules were superimposable with an acceptable root mean square distance for Cα atoms, and that was used as a model for the N-terminal region of CD40.

Molecular Replacement Methods:

The program PHASER (McCoy et al., *J. Appl. Crystallogr.* 40: 658-674 (2007)) was used for molecular replacement. The translation function Z-score (TFZ) and the increase in the log-likelihood gain were monitored to decide whether real solutions had been found. TFZ scores of 8 and above generally represent a solution. Lesser TFZ scores accompanied by substantial increases (>50) in the log-likelihood gain also are acceptable indicators.

Model Building, Density Modification, and Crystallographic Refinement Methods:

Model-building tools for molecular graphics included the COOT program (Emsley et al., *Acta Crystallogr Sect. D* 60: 2126-2132 (2004); Emsley et al., "Features and Development of Coot," *Acta Crystallogr Sect. D* 66: 486-501 (2010)). Density modification using non-crystallographic symmetry map averaging was performed using known density modification programs and other programs to calculate the Eulerian angles and translations between molecules. Refinement was run using autoBUSTER (GlobalPhasing, Ltd.: Bricogne et al., *Acta Crystallogr. Sect. D* 60: 2210-2221 (2004); Tronrud et al., *Acta Crystallogr. Sect. A* 43: 489-501 (1987)).

Domain Antibody Numbering System:

The residue numbering system for the domain antibody follows that of Kabat.

The Kabat numbering is compared to straight sequential numbering below for BMS3h-56-5:

```
                 -2-1
                  ||
BMS-3h-56-5  ST
                                 CDR1_
Kabat             10    20    30    40    50
                - |  - |  - |  - |  - |

Sequential        10    20    30    40    50
                - |  - |  - |  - |  - |

BMS-3h-56-5
EVQLLESGGGLVQPGGSLRLSCAASGFTFRDYEMWWVRQAPGKGLERVSA

CDR2_
Kabat              60    70    80    90   100
A               - |  - |  - |  - |
Sequential         60    70    80    90   100
                - |  - |  - |  - |

BMS-3h-56-5
INPQGTRTYYADSVMGRFTISRDNSKNTLYLQMNSLRAEDTAVYYCAKLP

CDR3_
Kabat            99101   110 116
                  ||   - |  -|

Sequential              110    119
                      - |   - |
BMS-3h-56-5        FTFDDWGQGTLVTVSSAA (SEQ ID NO: 3)
```

In Kabat numbering BMS3h-56-5 has insertion residues 52A, 82A, 82B, 82C and is missing residue 100. In both numbering systems the Ser and Thr at the N-terminus that are part of the expression construct are given negative numbers.

Determination of the Structure of CD40/BMS3h-56-5 Complex:

PHASER was able to locate four BMS3h-56-5 dAb molecules in the I222 crystal form and three BMS3h-56-5 dAb molecules in the C2 crystal form. In the I222 crystal form the TFZ scores ranged from 7.6 to 41.0, and the increase in the log-likelihood gain ranged from 77 to 446. These solutions for the BMS3h-56-5 dAb molecules formed helical columns of dAb molecules through the I222 crystal that were separated from other columns by large channels. In the C2 crystal the TFZ scores ranged from 7.7 to 16.5, and the increase in the log-likelihood gain ranged from 110 to 150. The packing of the dAbs in this crystal form was not repetitive or symmetric.

Using the ensemble model for the CD40 N-terminal domain, four molecules of the N-terminal domain of CD40 could be placed in the I222 crystal form with TFZ scores ranging from 5.7 to 8.5, and the increase in the log-likelihood gain ranged from 83 to 389. The four N-terminal domains of CD40 in the I222 crystal form formed a clump equally centered between four columns of dAb molecules. However, they did not touch the BMS3h-56-5 dAb molecules. In the C2 crystal form three molecules of the N-terminal domain of CD40 could be placed with TFZ scores ranging from 5.8 to 12.1, and the increase in the log-likelihood gain ranged from 100 to 198. In this crystal form, the N-terminal domains also did not contact the BMS3h-56-5 dAb molecules.

In the I222 crystal form, the N-terminal domain of the CD40 from the CD40/Chi220 Fab complex and the N-terminal domain from 2UWI were superimposed on the CD40 N-terminal domain. The ability to associate the N-terminal with a particular BMS3h-56-5 dAb allowed the use of non-crystallographic symmetry (NCS) map averaging. The starting correlation coefficients for NCS averaging gave off-diagonal values of 0.71-0.81. The final off-diagonal values were 0.88-0.92. The electron density close to the N-terminal region was clear, and a path could be traced for CDR3 of the BMS3h-56-5 dAb. Residues 82-94 and 101-121 from the CD40/Chi220 Fab' complex were superimposed on the corresponding residues on 2UWI and then COOT was used to improve the fit manually. This position for the second domain (residues 82-94 and 101-121) of CD40 was then transformed onto the other three N-terminal domains.

A cycle of refinement was run with R-free decreasing from 0.437 to 0.380 and R-work from 0.447 to 0.381 with improvement in root mean square bond and angle deviations from ideal. The resulting electron density map showed that residue 109 had a side chain that was consistent with Trp and that density existed for at least some residues in the C-terminal 70 residues of CD40.

Since CD40 has little secondary structure, fitting the C-terminal ~70 residues to the electron proved difficult, so the Research Collaboratory for Structural Bioinformatics Protein Data Base was searched for a suitable model to help guide chain tracing. The top two hits with 16 out of 44 identities and 24 out of 44 matches were 2AW2 and 1JMA, which have the same sequence:

```
         125   130       140       150       160
           _    |    _    |    _    |    _    |    _
CD40     CSPGFGVKQIATGVSDTICEPCPVGFESNVSSAFEKCHPWTSCE

2AW2     CSPGYRVKEACGELTGTVCEPCPPGTYIAHLNGLSKCLQCQMCD
```

```
                         -continued
Consensus   CSPG* VK*    ** T CEGCP G *    *  KC       C*
            | .      | .    | .    | .    | .    .|
            23       30     40     50     60     66

| .          . |    | .    | .    .|
1JMA        19           30     40     50      62
(SEQ ID NOS 1270-1271)
```

Identical residues are noted with the appropriate single letter code on the consensus line and similar residues are noted on the consensus line as asterisks. This was the same stretch of residues as for residues 41-84 of the N-terminal domain of CD40:

```
              41        50        60        70        80
              |  _      |   _     |   _     |    _    |
CD40          CQPGQKLVSDCTEFTETECLPCGESEFLDTWNRETHCHQHKYCD

CD40          CSPGFGVKQIATGVSDTICEPCPVGFFSNVSSAFEKCHPWTSCE

Consensus     C PG  *    T  **T C PC     F * *    *CH    C*
              _   |      |      |    _   |    _   |    _
             125 130    140    150      160
(SEQ ID NOS 1272 and 1270)
```

Identical residues are noted with the appropriate single letter code on the consensus line and similar residues are noted on the consensus line as asterisks.
Matching Disulfide Bonds:
Comparison of Disulfide Linkages in Residues 41-84 and 125-168 of CD40

| Residues 41-84 | Residues 125-168 |
|---|---|
| C41-C59 | C125-C143 |
| [C38]-C51 | |
| C62-C77 | C146-C161 |
| C83[-C103] | C167[-C186] |

Residues in brackets fall outside of the residue ranges in the sequence repeat.

With the 1JMA/2AW2 model as a guide, the COOT program was used to fit one of the CD40 chains. This fitted model was then superimposed on one of the other three CD40 chains. However, it appeared that the position of this new stretch of residues was differently oriented in the other two CD40 chains, and they were not fitted at this time. A cycle of refinement was run with R-free decreasing from 0.393 to 0.366 and R-work from 0.400 to 0.349 with considerable improvement in root mean square bond and angle deviations from ideal.

The BMS3h-56-5 dAb from one of the molecules in the I222 crystal form was superimposed on each of the three dAbs in the C2 crystal form. That transformation matrix was used to orient the second and C-terminal domains of the I222 crystal form. The model was rebuilt using the COOT program. A cycle of refinement was run with R-free decreasing from 0.361 to 0.334 and R-work from 0.375 to 0.306 with improved root mean square bond and angle deviations from ideal. The resulting electron density map provided guidance for placing many more CD40 residues. Another cycle of refinement was run with R-free decreasing from 0.302 to 0.287 and R-work from 0.299 to 0.270 with improved root mean square bond and angle deviations from ideal Conventional model building and refinement then were used to complete the structure determination. Several more rounds of optimization led to a final refinement with the following statistics: R-free 0.260, R-work 0.228, root mean square bonds 0.010 Å, root mean square angles 1.4°. The real space correlation coefficients are 0.92 for main-chain atoms and 0.80 for side-chain atoms. The final model had 13 water molecules.

Using the model of the C-terminal domain from the C2 crystal form as a guide, the CD40 models in I222 crystal form were further refined. Several more cycles of model building using the COOT program and refinement with the autoBUSTER program led to the following statistics: R-free 0.323, R-work 0.292, root mean square bonds 0.011 Å, root mean square angles 1.5°. The real space correlation coefficients are 0.91 for main-chain atoms and 0.80 for side-chain atoms. The model contained no water molecules.
Overall Structure of the CD40/BMS3h-56-5 Complex:

One BMS3h-56-5 dAb binds to one CD40 molecule. As shown in FIG. 1, BMS3h-56-5 binds to an epitope that is distinct from that of the antibody Chi220, which binds in the N-terminal region. CD40 residues (SEQ ID NO: 1) are shown in green, except for epitope residues. CD40 epitope residues for Chi220 are shown in blue; BMS3h-56-5 dAb epitope residues are shown in cyan. Chi220 Fab and BMS3h-56-5 strands are shown in red, CDR residues are shown in magenta, and other loops are shown in orange. Disulfide bonds are shown for the CD40, Chi220, and BMS3h-56-5 molecules with the sulfur atoms in yellow.

The I222 crystal form contains four crystallographically independent CD40/BMS3h-56-5 complexes, and the C2 crystal for contains three crystallographically independent CD40/BMS3h-56-5 complexes. The CD40 molecule has a certain amount of flexibility, and the domains are arrayed differently in the seven unique versions of the complex, but the overall nature of the interaction is retained in all cases.
BMS3h-56-5 dAb Epitope Residues:

The minimal CD40 epitope for BMS3h-56-5 is defined as CD40 residues containing at least one atom in van der Waals or hydrogen-bond contact with a BMS3h-56-5 atom. The minimal epitope in all the complexes contains the following CD40 residues with reference to SEQ ID NO: 1: Trp109, Leu121, His122, Ser124, Ser156, Ala157, Phe158, Glu159, and His162. The following additional residues are in van der Waals or hydrogen-bond contact in some complexes: Pro85, Asn86, Leu87, Gly88, Glu106, Glu107, Gly108, His110, Thr112, Cys119, Val120, Gln133, Ile134, Ala135, Thr136, Ser155, Lys160.

A maximal CD40 epitope is defined as residues containing atoms that are buried by a 1.7 Å probe sphere. These residues include all the residues above, plus Val154 in all complexes. In some complexes, additional buried residues are: Ser118, Arg123, Thr141, Phe151, Asp153, Cys161, and Pro163.

A depiction of the surface of BMS3h-56-5 with contacting residues is shown in FIG. 2. Contacting BMS3h-56-5 residues are shown. Buried residues are. also shown. CD40 is represented as a cartoon with orange representing non-repetitive secondary structure and magenta representing the epitope residues. Also shown as sticks (carbon atoms in cyan) are CD40 residues Trp109, Ala115, Leu121, Ser126, and His162, which are five of the seven residues that differ between human and cynomolgus monkey (*Macaca fascicularis*). Ala115 and Ser126 are on the opposite side of CD40 from the BMS3h-56-5 binding site. Trp109 and Leu121 bind in a cleft of BMS-h-56-5 that lies between CDR-3 and FR-2 (BMS-3h-56-5 residues Leu45 and Arg47). His162 of CD40 interacts with Arg56 of CDR-2 of the BMS3h-56-5 dAb. Mutation of Trp109 considerably reduces or ablates BMS3h-56-5 activity.

Depending on the crystallographically independent complex, 660-740 Å$^2$ of CD40 surface area is buried with between 16-21 contacting residues represented at a finer level with contacting 46-67 atoms. For BMS3h-56-5, 660-780 Å$^2$ of surface area is buried with contacting 14-17 residues represented at a finer level with contacting 48-62 atoms. These contacts yield 3-7 hydrogen bonds and 111-142 van der Waals interactions, depending on the crystallographically independent complex.

Example 11

Identifying dAb Binding Epitopes on CD40

To identify dAb binding epitopes on CD40, dAb binding was tested against seven CD40-Fc fusion proteins containing specific amino acid residue substitutions at residues 76, 109, or 121. These CD40-Fc fusion proteins include wild type human CD40 (wt-hCD40), wild type cynomolgus monkey CD40 (wt-cCD40), and five mutant human CD40 proteins (M1-M5) with specific amino acid residues mutated to the corresponding residue from the sequence of cynomolgus monkey CD40 (M1, M2, M4, M5) or chimpanzee CD40 (M3). The amino acid substitutions are listed in Table 26.

The sequence of the wild type human CD40 extracellular domain (1-193) is from REFSEQ:accession NM_001250.3. Cynomolgous and mutant constructs were generated using site-directed mutagenesis of the wild type sequence at the positions shown in Table 26. The extracellular domains were fused with a thrombin-cleavable linker DPGGGGGR-LVPRGFGTGDP (SEQ ID NO: 1273), which was fused with human IgG1 Fc. The proteins were expressed in HEK-293-6E cells transfected with TIG-pYD7-GATE Durocher expression vectors. The supernatants were harvested after five days. Each CD40 protein was purified from conditioned media using protein A fast flow chromatography. The column was washed with PBS (20 mM sodium phosphate, 0.15 M NaCl, pH 7.2) and then eluted using 80 mM sodium acetate, pH 3, into ⅕$^{th}$ volume of 1 M Tris-HCl, pH 8. The eluate was run on a Superdex-200 column in PBS.

TABLE 26

| Name | Short name | Residue 76 | Residue 109 | Residue 121 |
|---|---|---|---|---|
| wild type human CD40 Fc fusion | wt-hCD40 | H | W | L |
| human CD40 (H76R) Fc fusion | hCD40-M1 | R | W | L |
| human CD40 (W109L) Fc fusion | hCD40-M2 | H | L | L |
| human CD40 (W109R) Fc fusion (Chimpanzee CD40) | hCD40-M3 | H | R | L |
| human CD40 (W109L, L121P) Fc fusion | hCD40-M4 | H | L | P |
| human CD40 (H76R, W109L, L121P) Fc fusion | hCD40-M5 | R | L | P |
| wild type cynomolgus monkey CD40 Fc fusion | wt-cyno-CD40 | R | L | P |

Representative dAb's from the 3h217, 3h37, 3h38, and 3h56 lineages were assayed for their binding to CD40-Fc fusion proteins listed in Table 26. Assays were performed on a BioRad ProteOn XPR36 SPR instrument. The SPR surfaces were prepared by immobilizing 8 µg/ml anti-human IgG(Fc) antibody (Biacore/GE Healthcare) in 10 mM sodium acetate pH 4.5 on a BioRad GLC sensor chip using standard ethyl(dimethylaminopropyl) carbodiimide (EDC)/N-hydroxysuccinimide (NHS) chemistry, with ethanolamine blocking. The running buffer for immobilization and kinetic binding analysis was 10 mM sodium phosphate, 130 mM sodium chloride, 0.05% tween 20, pH 7.1. CD40-Fc fusion proteins at concentrations of 20 µg/ml were captured in the vertical orientation on these surfaces via the Fc tail, and reference surfaces lacking CD40-Fc proteins were used for reference subtraction. Kinetic experiments were performed by flowing 405, 135, 45, 15, and 5 nM dAb analytes in the horizontal orientation over the captured CD40-Fc surfaces at 25° C., using a 240 s association time, and a 420 s dissociation time, at a flow rate of 30 µl/min. The surfaces were regenerated in both horizontal and vertical orientations with 30 s pulses of 3 M MgCl$_2$ followed by running buffer at 60 µl/min. Sensogram data was double-referenced and then fitted to a 1:1 Langmuir model using BioRad ProteOn Manager V.2.1.0.38 software, to determine the association rate constant (ka), the dissociation rate constant (kd), and the equilibrium dissociation constant (K$_D$).

All dAbs of the 3h-37, 3h-38, and 3h-56 lineages were found to bind with high affinity (K$_D$<10$^{-8}$ M) to CD40-Fc fusion proteins containing the human CD40 residues W109 and L121, but binding was significantly reduced or undetectable to CD40-Fc fusion proteins with the corresponding residues from cynomolgus monkey CD40 (L109, P121) or chimpanzee CD40 (R109). This indicates that dAbs from each of the 3h37, 3h38-, and 3h56-lineages bind specifically to an epitope that includes residues 109 and 121 of human CD40. In contrast, all tested members of the 3h-217 lineage bound with similar affinity to all CD40-Fc fusion proteins tested, indicating that the members of the 3h-217 lineage bind to a site on CD40 which does not include residues 76, 109, or 121. Therefore, the 3h-217 lineage binds to a different epitope than the 3h-37, 3h-38, and 3h-56 lineages. Table 27 summarizes K$_D$ values determined for dAb binding to CD40-Fc fusion proteins using SPR on a ProteOn XPR36 instrument. An "X" in Table 27 means that no evidence for binding was found under these conditions.

TABLE 27

| | wt-hCD40 | hCD40-M1 (H76R) | hCD40-M2 (W109L) | hCD40-M3 (W109R) | hCD40-M4 (W109L, L121P) | hCD40-M5 (H76R, W109L, L121P) | cyno CD40 |
|---|---|---|---|---|---|---|---|
| 3h-217-5 | 0.47, 0.48 | 0.94 | 0.99 | 0.72 | 0.93 | 1.0 | 0.9 |
| 3h-217-16 | 0.22, 0.26 | 0.35 | 0.41 | 0.27 | 0.35 | 0.5 | 0.4 |
| 3h-217-23 | 0.78, 1.5 | 1.6 | 2.0 | 1.2 | 1.6 | 2.2 | 1.9 |
| 3h-37-2 | 2.0, 2.0 | 2.6 | >1000 | X | X | X | X |
| 3h-37-11 | 1.9, 2.3 | 2.4 | >1000 | X | X | X | X |
| 3h-38-2 | 5.1, 8.0 | 7.2 | X | X | X | X | X |
| 3h-38-211 | 3.3, 6.1 | 4.0 | >1000 | X | X | X | X |
| 3h-38-215 | 2.1, 6.0 | 3.0 | >1000 | X | X | X | X |
| 3h-38-217 | 2.3, 2.4 | 3.4 | >1000 | X | X | X | X |
| 3h-56-1 | 3.0, 5.4 | 4.2 | 29 | >1000 | X | X | X |
| 3h-56-2 | 3.8, 3.2 | 6.1 | 44 | >1000 | X | X | X |
| 3h-56-5 | 5.3, 4.7 | 7.2 | 65 | >1000 | X | X | X |
| 3h-56-202 | 2.3, 1.3 | 3.3 | 160 | X | X | X | X |
| 3h-56-206 | 0.60, 1.4 | 1.0 | 55 | X | X | X | X |
| 3h-56-217 | 1.0, 1.9 | 1.4 | 2.5 | 23 | X | X | X |

Table 28 shows the association rate constant (ka), dissociation rate constant (kd), and equilibrium dissociation constant ($K_D$) determined for dAb binding to CD40-Fc fusion proteins using SPR on a ProteOn XPR36 instrument. An "X" in Table 28 means that no evidence for binding was found under these conditions.

TABLE 28

| Ligand | dAb | ka (1/Ms) | kd (1/s) | Kd (nM) |
|---|---|---|---|---|
| wt-hCD40 | 3h-217-5 | $2.71 \times 10^6$ | $1.27 \times 10^{-3}$ | 0.47 |
| wt-hCD40 (repeat) | 3h-217-5 | $2.03 \times 10^6$ | $9.81 \times 10^{-4}$ | 0.48 |
| hCD40 M1 (H76R) | 3h-217-5 | $3.17 \times 10^6$ | $2.99 \times 10^{-3}$ | 0.94 |
| hCD40 M2 (W109L) | 3h-217-5 | $2.55 \times 10^6$ | $2.51 \times 10^{-3}$ | 0.99 |
| hCD40 M3 (W109R) | 3h-217-5 | $2.73 \times 10^6$ | $1.96 \times 10^{-3}$ | 0.72 |
| hCD40 M4 (W109L, L121P) | 3h-217-5 | $2.78 \times 10^6$ | $2.59 \times 10^{-3}$ | 0.93 |
| hCD40-M5 (H76R, W109L, L121P) | 3h-217-5 | $2.44 \times 10^6$ | $2.42 \times 10^{-3}$ | 0.99 |
| wt-cCD40 | 3h-217-5 | $2.46 \times 10^6$ | $2.12 \times 10^{-3}$ | 0.86 |
| wt-hCD40 | 3h-217-16 | $4.47 \times 10^6$ | $9.91 \times 10^{-4}$ | 0.22 |
| wt-hCD40 (repeat) | 3h-217-16 | $3.30 \times 10^6$ | $8.47 \times 10^{-4}$ | 0.26 |
| hCD40 M1 (H76R) | 3h-217-16 | $4.83 \times 10^6$ | $1.68 \times 10^{-3}$ | 0.35 |
| hCD40 M2 (W109L) | 3h-217-16 | $4.06 \times 10^6$ | $1.67 \times 10^{-3}$ | 0.41 |
| hCD40 M3 (W109R) | 3h-217-16 | $3.78 \times 10^6$ | $1.04 \times 10^{-3}$ | 0.27 |
| hCD40 M4 (W109L, L121P) | 3h-217-16 | $4.39 \times 10^6$ | $1.52 \times 10^{-3}$ | 0.35 |
| hCD40-M5 (H76R, W109L, L121P) | 3h-217-16 | $3.65 \times 10^6$ | $1.70 \times 10^{-3}$ | 0.47 |
| wt-cCD40 | 3h-217-16 | $3.44 \times 10^6$ | $1.47 \times 10^{-3}$ | 0.43 |
| wt-hCD40 | 3h-217-23 | $1.64 \times 10^6$ | $1.27 \times 10^{-3}$ | 0.78 |
| wt-hCD40 (repeat) | 3h-217-23 | $1.07 \times 10^6$ | $1.63 \times 10^{-3}$ | 1.52 |
| hCD40 M1 (H76R) | 3h-217-23 | $1.64 \times 10^6$ | $2.62 \times 10^{-3}$ | 1.59 |
| hCD40 M2 (W109L) | 3h-217-23 | $1.49 \times 10^6$ | $2.91 \times 10^{-3}$ | 1.95 |
| hCD40 M3 (W109R) | 3h-217-23 | $1.53 \times 10^6$ | $1.86 \times 10^{-3}$ | 1.22 |
| hCD40 M4 (W109L, L121P) | 3h-217-23 | $1.67 \times 10^6$ | $2.68 \times 10^{-3}$ | 1.61 |
| hCD40-M5 (H76R, W109L, L121P) | 3h-217-23 | $1.30 \times 10^6$ | $2.87 \times 10^{-3}$ | 2.21 |
| wt-cCD40 | 3h-217-23 | $1.24 \times 10^6$ | $2.35 \times 10^{-3}$ | 1.90 |
| wt-hCD40 | 3h-37-2 | $2.12 \times 10^5$ | $4.17 \times 10^{-4}$ | 1.96 |
| wt-hCD40 (repeat) | 3h-37-2 | $2.13 \times 10^5$ | $4.26 \times 10^{-4}$ | 2.00 |
| hCD40 M1 (H76R) | 3h-37-2 | $2.17 \times 10^5$ | $5.62 \times 10^{-4}$ | 2.58 |
| hCD40 M2 (W109L) | 3h-37-2 | | | >1000 |
| hCD40 M3 (W109R) | 3h-37-2 | | | X |
| hCD40 M4 (W109L, L121P) | 3h-37-2 | | | X |
| hCD40-M5 (H76R, W109L, L121P) | 3h-37-2 | | | X |
| wt-cCD40 | 3h-37-2 | | | X |
| wt-hCD40 | 3h-37-11 | $2.91 \times 10^5$ | $5.60 \times 10^{-4}$ | 1.92 |
| wt-hCD40 (repeat) | 3h-37-11 | $2.81 \times 10^5$ | $6.40 \times 10^{-4}$ | 2.28 |
| hCD40 M1 (H76R) | 3h-37-11 | $3.00 \times 10^5$ | $7.17 \times 10^{-4}$ | 2.39 |
| hCD40 M2 (W109L) | 3h-37-11 | | | >1000 |
| hCD40 M3 (W109R) | 3h-37-11 | | | X |
| hCD40 M4 (W109L, L121P) | 3h-37-11 | | | X |
| hCD40-M5 (H76R, W109L, L121P) | 3h-37-11 | | | X |
| wt-cCD40 | 3h-37-11 | | | X |
| wt-hCD40 | 3h-38-2 | $1.20 \times 10^5$ | $6.08 \times 10^{-4}$ | 5.07 |
| wt-hCD40 (repeat) | 3h-38-2 | $1.42 \times 10^5$ | $1.14 \times 10^{-3}$ | 8.04 |
| hCD40 M1 (H76R) | 3h-38-2 | $1.40 \times 10^5$ | $1.00 \times 10^{-3}$ | 7.15 |
| hCD40 M2 (W109L) | 3h-38-2 | | | X |
| hCD40 M3 (W109R) | 3h-38-2 | | | X |
| hCD40 M4 (W109L, L121P) | 3h-38-2 | | | X |

TABLE 28-continued

| Ligand | dAb | ka (1/Ms) | kd (1/s) | Kd (nM) |
|---|---|---|---|---|
| hCD40-M5 (H76R, W109L, L121P) | 3h-38-2 | | | X |
| wt-cCD40 | 3h-38-2 | | | X |
| wt-hCD40 | 3h-38-211 | $1.11 \times 10^5$ | $3.62 \times 10^{-4}$ | 3.26 |
| wt-hCD40 (repeat) | 3h-38-211 | $1.20 \times 10^5$ | $7.28 \times 10^{-4}$ | 6.08 |
| hCD40 M1 (H76R) | 3h-38-211 | $1.28 \times 10^5$ | $5.10 \times 10^{-4}$ | 3.98 |
| hCD40 M2 (W109L) | 3h-38-211 | | | >1000 |
| hCD40 M3 (W109R) | 3h-38-211 | | | X |
| hCD40 M4 (W109L, L121P) | 3h-38-211 | | | X |
| hCD40-M5 (H76R, W109L, L121P) | 3h-38-211 | | | X |
| wt-cCD40 | 3h-38-211 | | | X |
| wt-hCD40 | 3h-38-215 | $1.37 \times 10^5$ | $2.88 \times 10^{-4}$ | 2.10 |
| wt-hCD40 (repeat) | 3h-38-215 | $1.36 \times 10^5$ | $8.20 \times 10^{-4}$ | 6.02 |
| hCD40 M1 (H76R) | 3h-38-215 | $1.75 \times 10^5$ | $5.30 \times 10^{-4}$ | 3.03 |
| hCD40 M2 (W109L) | 3h-38-215 | | | >1000 |
| hCD40 M3 (W109R) | 3h-38-215 | | | X |
| hCD40 M4 (W109L, L121P) | 3h-38-215 | | | X |
| hCD40-M5 (H76R, W109L, L121P) | 3h-38-215 | | | X |
| wt-cCD40 | 3h-38-215 | | | X |
| wt-hCD40 | 3h-38-217 | $1.27 \times 10^5$ | $2.96 \times 10^{-4}$ | 2.34 |
| wt-hCD40 (repeat) | 3h-38-217 | $1.44 \times 10^5$ | $3.40 \times 10^{-4}$ | 2.37 |
| hCD40 M1 (H76R) | 3h-38-217 | $1.41 \times 10^5$ | $4.81 \times 10^{-4}$ | 3.41 |
| hCD40 M2 (W109L) | 3h-38-217 | | | >1000 |
| hCD40 M3 (W109R) | 3h-38-217 | | | X |
| hCD40 M4 (W109L, L121P) | 3h-38-217 | | | X |
| hCD40-M5 (H76R, W109L, L121P) | 3h-38-217 | | | X |
| wt-cCD40 | 3h-38-217 | | | X |
| wt-hCD40 | 3h-56-1 | $2.52 \times 10^5$ | $7.50 \times 10^{-4}$ | 2.97 |
| wt-hCD40 (repeat) | 3h-56-1 | $1.93 \times 10^5$ | $1.03 \times 10^{-3}$ | 5.35 |
| hCD40 M1 (H76R) | 3h-56-1 | $2.31 \times 10^5$ | $9.67 \times 10^{-4}$ | 4.18 |
| hCD40 M2 (W109L) | 3h-56-1 | $1.92 \times 10^5$ | $5.57 \times 10^{-3}$ | 29.10 |
| hCD40 M3 (W109R) | 3h-56-1 | | | >1000 |
| hCD40 M4 (W109L, L121P) | 3h-56-1 | | | X |
| hCD40-M5 (H76R, W109L, L121P) | 3h-56-1 | | | X |
| wt-cCD40 | 3h-56-1 | | | X |
| wt-hCD40 | 3h-56-2 | $2.46 \times 10^5$ | $9.27 \times 10^{-4}$ | 3.77 |
| wt-hCD40 (repeat) | 3h-56-2 | $1.97 \times 10^5$ | $6.24 \times 10^{-4}$ | 3.17 |
| hCD40 M1 (H76R) | 3h-56-2 | $2.20 \times 10^5$ | $1.33 \times 10^{-3}$ | 6.05 |
| hCD40 M2 (W109L) | 3h-56-2 | $1.89 \times 10^5$ | $8.30 \times 10^{-3}$ | 43.90 |
| hCD40 M3 (W109R) | 3h-56-2 | | | >1000 |
| hCD40 M4 (W109L, L121P) | 3h-56-2 | | | X |
| hCD40-M5 (H76R, W109L, L121P) | 3h-56-2 | | | X |
| wt-cCD40 | 3h-56-2 | | | X |
| wt-hCD40 | 3h-56-5 | $1.78 \times 10^5$ | $9.38 \times 10^{-4}$ | 5.26 |
| wt-hCD40 (repeat) | 3h-56-5 | $1.53 \times 10^5$ | $7.19 \times 10^{-4}$ | 4.69 |
| hCD40 M1 (H76R) | 3h-56-5 | $1.69 \times 10^5$ | $1.21 \times 10^{-3}$ | 7.18 |
| hCD40 M2 (W109L) | 3h-56-5 | $1.38 \times 10^5$ | $8.89 \times 10^{-3}$ | 64.60 |
| hCD40 M3 (W109R) | 3h-56-5 | | | >1000 |
| hCD40 M4 (W109L, L121P) | 3h-56-5 | | | X |
| hCD40-M5 (H76R, W109L, L121P) | 3h-56-5 | | | X |
| wt-cCD40 | 3h-56-5 | | | X |
| wt-hCD40 | 3h-56-202 | 1.82E+05 | $4.15 \times 10^{-4}$ | 2.27 |
| wt-hCD40 (repeat) | 3h-56-202 | 1.77E+05 | $2.21 \times 10^{-4}$ | 1.25 |
| hCD40 M1 (H76R) | 3h-56-202 | 1.76E+05 | $5.79 \times 10^{-4}$ | 3.29 |
| hCD40 M2 (W109L) | 3h-56-202 | 1.35E+05 | $2.00 \times 10^{-2}$ | 155.00 |
| hCD40 M3 (W109R) | 3h-56-202 | | | X |
| hCD40 M4 (W109L, L121P) | 3h-56-202 | | | X |
| hCD40-M5 (H76R, W109L, L121P) | 3h-56-202 | | | X |
| wt-cCD40 | 3h-56-202 | | | X |
| wt-hCD40 | 3h-56-206 | 6.48E+05 | $3.89 \times 10^{-4}$ | 0.60 |
| wt-hCD40 (repeat) | 3h-56-206 | 3.27E+05 | $4.72 \times 10^{-4}$ | 1.44 |
| hCD40 M1 (H76R) | 3h-56-206 | 5.65E+05 | $5.45 \times 10^{-4}$ | 0.96 |
| hCD40 M2 (W109L) | 3h-56-206 | 3.38E+05 | $2.00 \times 10^{-2}$ | 54.70 |
| hCD40 M3 (W109R) | 3h-56-206 | | | X |
| hCD40 M4 (W109L, L121P) | 3h-56-206 | | | X |
| hCD40-M5 (H76R, W109L, L121P) | 3h-56-206 | | | X |
| wt-cCD40 | 3h-56-206 | | | X |
| wt-hCD40 | 3h-56-217 | 4.71E+05 | $4.70 \times 10^{-4}$ | 1.00 |
| wt-hCD40 (repeat) | 3h-56-217 | 2.91E+05 | $5.46 \times 10^{-4}$ | 1.87 |
| hCD40 M1 (H76R) | 3h-56-217 | 4.45E+05 | $6.35 \times 10^{-4}$ | 1.43 |
| hCD40 M2 (W109L) | 3h-56-217 | 4.25E+05 | $1.05 \times 10^{-3}$ | 2.48 |
| hCD40 M3 (W109R) | 3h-56-217 | 2.91E+05 | $6.70 \times 10^{-3}$ | 23.00 |
| hCD40 M4 (W109L, L121P) | 3h-56-217 | | | X |
| hCD40-M5 (H76R, W109L, L121P) | 3h-56-217 | | | X |
| wt-cCD40 | 3h-56-217 | | | X |

Example 12

Construction of Fc Fusion Polypeptides

Antibody polypeptides comprising dAbs can be constructed in various configurations, as disclosed herein. In this example, various dAbs were fused with a Fc domain to generate Fc fusion polypeptides of anti-human CD40 variable domain constructs such as 3h37-202, 3h37-235, 3h37-258, and 3h37-202.

In one representative example, the dAb BMS3h-56-269 (SEQ ID NO: 417) was fused with a modified IgG1 (IgG1*) Fc domain (SEQ ID NO: 1284). In the dAb-IgG1* Fc domain fusion polypeptide, the C-terminus of dAb BMS3h-56-269 was fused to a linker tripeptide having the sequence Ala-Ser-Thr, which in turn was fused with the IgG1* Fc domain (SEQ ID NO: 1284). The IgG1* Fc domain contained the modification C5S, referring to the numbering of positions in SEQ ID NO: 1284. C5 of the IgG1 Fc domain normally forms a disulfide bond with a Cys residue in the light chain of an IgG molecule. The IgG1* Fc domain also contained C11S and C14S mutations to eliminate interchain disulfide bonds in the IgG1 hinge region. Finally, the IgG1* Fc domain contained a P23S mutation to lower Fc domain effector function. The dAb-IgG1* Fc fusion polypeptide has the following sequence, where the Ala-Ser-Thr linker is in bold font and the modifications to the Fc domain are in bold italics:

```
                                               (SEQ ID NO: 1286)
  1  EVQLLESGGG LVQPGGSLRL SCAASGFTFR DYEMWWVRQA PGKGLERVSA

51  INPQGTRTYY ADSVKGRFTI SRDNSKNTLY LQMNSLRAED TAVYYCAKLP

101  FRFSDRGQGT LVTVSSASTE PKSSDKTHTS PPSPAPELLG GSSVFLFPPK

151  PKDTLMISRT PEVTCVVVDV SHEDPEVKFN WYVDGVEVHN AKTKPREEQY

201  NSTYRVVSVL TVLHQDWLNG KEYKCKVSNK ALPAPIEKTI SKAKGQPREP

251  QVYTLPPSRD ELTKNQVSLT CLVKGFYPSD IAVEWESNGQ PENNYKTTPP

301  VLDSDGSFFL YSKLTVDKSR WQQGNVFSCS VMHEALHNHY TQKSLSLSPG

351  K
```

The dAb-IgG1* Fc fusion polypeptide depicted in SEQ ID NO: 1286 is a monomer having a calculated molecular weight of 39,127 Da. It can form a dimer having a calculated molecular weight of 78,254 Da.

dAb BMS3h-56-269 (SEQ ID NO: 417) alternatively was fused with a human IgG4 Fc domain (SEQ ID NO: 1285). The C-terminus of dAb BMS3h-56-269 was again fused to the Ala-Ser-Thr linker, which was fused with the IgG4 Fc domain (SEQ ID NO: 1285). The IgG4 Fc domain contained the modification S10P, referring to the numbering of positions in SEQ ID NO: 1285. The BMS3h-56-269-IgG4 Fc fusion polypeptide has the following sequence, where the Ala-Ser-Thr linker is in bold font and the S10P modification is in bold italics:

```
                                               (SEQ ID NO: 1287)
  1  EVQLLESGGG LVQPGGSLRL SCAASGFTFR DYEMWWVRQA PGKGLERVSA

51  INPQGTRTYY ADSVKGRFTI SRDNSKNTLY LQMNSLRAED TAVYYCAKLP

101  FRFSDRGQGT LVTVSSASTE SKYGPPCPPC PAPEFLGGPS VFLFPPKPKD

151  TLMISRTPEV TCVVVDVSQE DPEVQFNWYV DGVEVHNAKT KPREEQFNST

201  YRVVSVLTVL HQDWLNGKEY KCKVSNKGLP SSIEKTISKA KGQPREPQVY

251  TLPPSQEEMT KNQVSLTCLV KGFYPSDIAV EWESNGQPEN NYKTTPPVLD

301  SDGSFFLYSR LTVDKSRWQE GNVFSCSVMH EALHNHYTQK SLSLSLGK
```

The BMS3h-56-269-IgG4 Fc fusion polypeptide depicted in SEQ ID NO: 1287 is a monomer having a calculated molecular weight of 38,867 Da. It can form a dimer having a calculated molecular weight of 77,734 Da.

The sequences of BMS3h-56-269 (SEQ ID NO: 417), BMS3h-56-269-IgG1* Fc fusion polypeptide (SEQ ID NO: 1286), and BMS3h-56-269-IgG4 Fc fusion polypeptide (SEQ ID NO: 1287) are aligned below, where the start of the Fc domain is marked by an arrow:

(SEQ ID NO: 417)
BMS3h56-269 (1)

EVQLLESGGGLVQPGGSLRLSCAASGFTFRDYEMWWVRQAPGKGLERVSA (SEQ ID NO: 1286)
BMS3h56-269-0112 (1)

EVQLLESGGGLVQPGGSLRLSCAASGFTFRDYEMWWVRQAPGKGLERVSA (SEQ ID NO: 1287)
BMS3h56-269-Ig4 (1)

EVQLLESGGGLVQPGGSLRLSCAASGFTFRDYEMWWVRQAPGKGLERVSA (SEQ ID NO: 417)
BMS3h56-269 (34)

INPQGTRTYYADSVKGRFTISRDNSKNTLYLQMNSLRAEDTAVYYCAKLP (SEQ ID NO: 1286)
BM53h56-269-CTL2 (51)

INPQGTRTYYADSVKGRFTISRDNSKNTLYLQMNSLRAEDTAVYYCAKLP (SEQ ID NO: 1287)
BMS3h56-269-Ig4 (51)

INPQGTRTYYADSVKGRFTISRDNSKNTLYLQMNSLRAEDTAVYYCAKLP (SEQ ID NO: 417)
BMS3h56-269 (84)

FRFSDRGQGYLVTVSS---------------------------------

(SEQ ID NO: 1286)
BM53h56-269-C1L2 (101)

FRFSDRGQGTLVTVSSASTEPKSSDKTHTSPPSPAPELLGGSSVFLFPPK (SEQ ID NO: 1287)
BMS3h56-269-Ig4 (101)

FRFSDRGQGTLVTVSSASTESKYG---PPCPPCPAPEFLGGPSVFLFPPK
                ↑
            Start of Fc (SEQ ID NO: 417)
BMS3h56-269 (117)

--------------------------------------------------

(SEQ ID NO: 1286)
BM53h56-269-CTL2 (151)

PKDTLMISRTPEVTCVVVDVSHEDPEVKFNWYVDGVEVHNAKTKPREEQY (SEQ ID NO: 1287)
BMS3h56-269-Ig4 (148)

PKDTLMISRTPEVTCVVVDVSQEDPEVQFNWYVDGVEVHNAKTKPREEQF (SEQ ID NO: 417)
BMS3h56-269 (117)

--------------------------------------------------

(SEQ ID NO: 1286)
BM53h56-269-CTL2 (201)

NSTYRVVSVLTVLHQDWLNGKEYKCKVSNKALPAPIEKTISKAKGQPREP (SEQ ID NO: 1287)
BMS3h56-269-Ig4 (198)

NSTYRVVSVLTVLHQDWLNGKEYKCKVSNKGLPSSIEKTISKAKGQPREP (SEQ ID NO: 417)
BMS3h56-269 (117)---------------------

---------------------------

(SEQ ID NO: 1286)
BMS3h56-269-CTL2 (251)

QVYTLPPSRDELTKNQVSLTCLVKGFYPSDIAVEWESNGQPENNYKTTPP (SEQ ID NO: 1287)
BMS3h56-269-Ig4 (248)

QVYTLPPSQEEMTKNQVSLTCLVKGFYPSDIAVEWESNGQPENNYKTTPP (SEQ ID NO: 417)
BMS3h56-269 (117)

--------------------------------------------------

(SEQ ID NO: 1286)
BM53h56-269-CTL2 (301)

VLDSDGSFFLYSKLTVDKSRWQQGNVFSCSVMHEALHNHYTQKSLSLSPG (SEQ ID NO: 1287)
BMS3h56-269-Ig4 (298)

VLDSDGSFFLYSRLTVDKSRWQEGNVFSCSVMHEALHNHYTQKSLSLSLG (SEQ ID NO: 417)
BMS3h56-269 (117)

(SEQ ID NO: 1286)
BMS3h56-269-CTL2 (351)         K (SEQ ID NO: 1287)
BMS3h56-269-Ig4 (348)          K

The Fc fusion polypeptides were expressed using the cell culture methods disclosed in Example 11. The column was washed with PBS (20 mM sodium phosphate, 0.15 M NaCl, pH 7.2) and then eluted using 80 mM sodium acetate, pH 3, into $1/5^{th}$ volume of 1 M Tris-HCl, pH 8. The eluate was run on a Superdex-200 column in PBS.

Example 13

CD40 Fc Fusion Polypeptide Activity Assays

Anti-human CD40 Fc Fusion Polypeptides were assayed functionally for their ability to antagonize CD40 activities. The CD40 activities tested were B cell proliferation and cytokine production by hCD40L-driven activation of primary human monocyte-derived dendritic cells (DCs). B cell proliferation and cytokine production were measured using the assays disclosed in Example 6. Unless otherwise noted, all assays were performed in RPMI media supplemented with 10% fetal calf serum (FCS). The dAb-Fc domain fusion polypeptides exhibited potent inhibition (i.e., antagonism) of CD40-dependent activation. There were no agonistic properties noted among any of the humanCD40-specific dAb-Fc domain fusion polypeptides. The results using the various assays are shown in TABLE 29. 3h56-269-IgG4 was assayed for its binding to immobilized human-CD40 using the assays disclosed in Example 11. For 3h56-269-IgG4, the apparent avidity influenced Kd value for binding immobilized human-CD40 is measured at 30 pM at 25 C and 40 pM at 37 C.

TABLE 29

| dAb-Fc | hIZCD40L-driven Human B Cell Proliferation EC50 (nM) | CHO-hCD40L-driven Human B Cell Proliferation EC50 (nM) | T-B cell MLR EC50 (nM) | CHO-hCD40L-driven DC Activation TNF EC50 (nM) | CHO-hCD40L-driven DC Activation IL-6 EC50 (nM) | CHO-hCD40L-driven DC Activation IL-12 EC50 (nM) |
|---|---|---|---|---|---|---|
| 3h37-202-IgG4 | 0.16 ± 0.08 | 5.0, 3.0 | 5.0, 6.0 | | | 0.53 ± 0.1 |
| 3h37-202-IgG1* | 0.27, 0.22 | 3.0, 7.0 | | | | 0.74 ± 0.2 |
| 3h38-235-IgG4 | 0.20, 0.15 | 6.0, 10.0 | 16.7 ± 5.7 | | | 0.67 ± 0.3 |
| 3h38-235-IgG1* | 0.25 ± 0.1 | 4.0 ± 1.0 | | | | 0.88 ± 0.3 |
| 3h56-258-IgG4 | 0.16 ± 0.05 | 1.0 ± 0.8 | 2.4 ± 0.99 | 0.22 ± 0.08 | 0.11 ± 0.05 | 0.3 ± 0.2 |
| 3h56-258-IgG1* | 0.063 ± 0.03 | 0.6 ± 0.4 | 2.0 ± 0.63 | | | 0.31 ± 0.1 |
| 3h56-269-IgG4 | 0.028 ± 0.01 | 0.27 ± 0.08 | 0.52 ± 0.07 | 0.16 ± 0.03 | 0.09 ± 0.02 | 0.092 ± 0.03 |
| 3h56-269-IgG1* | 0.025 ± 0.01 | 0.25 ± 0.04 | 0.53 ± 0.1 | 0.27 ± 0.06 | 0.15 ± 0.05 | 0.14 ± 0.06 |

Although the present embodiments have been described in detail with reference to examples above, it is understood that various modifications can be made without departing from the spirit of these embodiments, and would be readily known to the skilled artisan.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10544228B2). An electronic copy of the "Sequence Listing" will also be available from the USPTO upon request and payment of the fee set forth in 37 CFR 1.19(b)(3).

What is claimed is:

1. A nucleic acid encoding an antibody polypeptide comprising a single variable domain comprising three complementarity determining regions (CDR), wherein:
    (a) CDR1 region comprises the amino acid sequence of the CDR1 region of BMS3h-56-269 (amino acids 31 to 35 of SEQ ID NO: 417),
    (b) CDR2 region comprises the amino acid sequence of the CDR2 region of BMS3h-56-269 (amino acids 50 to 66 of SEQ ID NO: 417), and
    (c) CDR3 region comprises the amino acid sequence of the CDR3 region of BMS3h-56-269 (amino acids 99 to 105 of SEQ ID NO: 417),
    or
    the amino acid sequences of the CDR1, CDR2, and CDR3 regions are elected from amino acids 31 to 35, 50 to 66, and 99-105, respectively, of one of the antibody polypeptide sequences selected from the group consisting of: SEQ ID NO: 317; SEQ ID NO: 318; SEQ ID NO: 320; SEQ ID NO: 321; SEQ ID NO: 324; SEQ ID NO: 325; SEQ ID NO: 326; SEQ ID NO: 327; SEQ ID NO: 331; SEQ ID NO: 332; SEQ ID NO: 333; SEQ ID NO: 334; SEQ ID NO: 335; SEQ ID NO: 336; SEQ ID NO: 337; SEQ ID NO: 341; SEQ ID NO: 342; SEQ ID NO: 343; SEQ ID NO: 344; SEQ ID NO: 345; SEQ ID NO: 346; SEQ ID NO: 347; SEQ ID NO: 348; SEQ ID NO: 349; SEQ ID NO: 350; SEQ ID NO: 353; SEQ ID NO: 355; SEQ ID NO: 356; SEQ ID NO: 358; SEQ ID NO: 366; SEQ ID NO: 367; SEQ ID NO: 376; SEQ ID NO: 379; SEQ ID NO: 381; SEQ ID NO: 386; SEQ ID NO: 394; SEQ ID NO: 403; SEQ ID NO: 405; SEQ ID NO: 412; and SEQ ID NO: 419,
    wherein said antibody polypeptide binds CD40.

2. The nucleic acid of claim 1, wherein the single variable domain comprises:
    (a) the CDR1 region comprising the amino acid sequence of the CDR1 region of BMS3h-56-269 (amino acids 31 to 35 of SEQ ID NO: 417),
    (b) the CDR2 region comprising the amino acid sequence of the CDR2 region of BMS3h-56-269 (amino acids 50 to 66 of SEQ ID NO: 417), and
    (c) the CDR3 region comprising the amino acid sequence of the CDR3 region of BMS3h-56-269 (amino acids 99 to 105 of SEQ ID NO: 417).

3. The nucleic acid of claim 2, wherein the single variable domain comprises the amino acid sequence of BMS3h-56-269 (SEQ ID NO: 417).

4. The nucleic acid of claim 2, wherein the amino acid sequence of the single variable domain is set forth in SEQ ID NO: 417.

5. The nucleic acid of claim 2, wherein the antibody polypeptide is a fusion polypeptide comprising the single variable domain and an Fc domain.

6. The nucleic acid of claim 5, wherein the fusion polypeptide comprises an IgG4 Fc domain.

7. The nucleic acid of claim 5, wherein the fusion polypeptide comprises an IgG1 Fc domain.

8. The nucleic acid of claim 5, wherein the antibody polypeptide comprises the amino acid sequence of the BMS3h-56-269-IgG1* Fc fusion polypeptide (SEQ ID NO: 1286).

9. The nucleic acid of claim 5, wherein the amino acid sequence of the antibody polypeptide is set forth in SEQ ID NO: 1286.

10. The nucleic acid of claim 5, wherein the antibody polypeptide comprises the amino acid sequence of the BMS3h-56-269-IgG4 Fc fusion polypeptide (SEQ ID NO: 1287).

11. The nucleic acid of claim 5, wherein the amino acid sequence of the antibody polypeptide is set forth in SEQ ID NO: 1287.

12. The nucleic acid of claim 2, wherein the antibody polypeptide further comprises a second variable domain that specifically binds a second antigen, wherein the second antigen is an antigen other than human CD40.

13. The nucleic acid of claim 1, wherein the single variable domain comprises the amino acid sequence of one of the antibody polypeptides selected from the group consisting of SEQ ID NO: 317; SEQ ID NO: 318; SEQ ID NO: 320; SEQ ID NO: 321; SEQ ID NO: 324; SEQ ID NO: 325; SEQ ID NO: 326; SEQ ID NO: 327; SEQ ID NO: 331; SEQ ID NO: 332; SEQ ID NO: 333; SEQ ID NO: 334; SEQ ID NO: 335; SEQ NO: 336; SEQ ID NO: 337; SEQ ID NO: 341; SEQ ID NO: 342; SEQ ID NO: 343; SEQ ID NO: 344; SEQ ID NO: 345; SEQ ID NO: 346; SEQ ID NO: 347; SEQ ID NO: 348; SEQ ID NO: 349; SEQ ID NO: 350; SEQ ID NO: 353; SEQ ID NO: 355; SEQ ID NO: 356; SEQ ID NO: 358; SEQ ID NO: 366; SEQ ID NO: 367; SEQ ID NO: 376; SEQ ID NO: 379; SEQ ID NO: 381; SEQ ID NO: 386; SEQ ID NO: 394; SEQ ID NO: 403; SEQ ID NO: 405; SEQ ID NO: 412; and SEQ ID NO: 419.

14. A vector comprising the nucleic acid of claim 1.

15. A vector comprising the nucleic acid of claim 2.

16. An isolated host cell comprising the vector of claim 14.

17. An isolated host cell comprising the vector of claim 15.

* * * * *

UNITED STATES PATENT AND TRADEMARK OFFICE
CERTIFICATE OF CORRECTION

PATENT NO. : 10,544,228 B2
APPLICATION NO. : 15/259828
DATED : January 28, 2020
INVENTOR(S) : Anish Suri et al.

Page 1 of 1

It is certified that error appears in the above-identified patent and that said Letters Patent is hereby corrected as shown below:

In the Claims

Column 253, Claim 1, Line 16, replace "elected" with --selected--

Column 254, Claim 13, Line 34, replace "SEQ NO: 336" with --SEQ ID NO: 336--

Signed and Sealed this
Ninth Day of June, 2020

Andrei Iancu
*Director of the United States Patent and Trademark Office*